US007425631B2

(12) United States Patent
Groneberg et al.

(10) Patent No.: US 7,425,631 B2
(45) Date of Patent: Sep. 16, 2008

(54) COMPOUNDS AND METHODS OF USE

(75) Inventors: Robert D. Groneberg, Boulder, CO (US); Benny C. Askew, Jr., Newbury Park, CA (US); Derin C. D'Amico, Newbury Park, CA (US); James Zhan, Shanghai (CN); Andras Toro, Toronto (CA); Youngboo Kim, Osaka (JP); David A. Mareska, Longmont, CO (US); Nianhe Han, Thousands Oaks, CA (US); Christopher H. Fotsch, Thousands Oaks, CA (US); Qingyian Liu, Camarillo, CA (US); Babak Riahi, Woodland Hills, CA (US); Kevin Yang, San Gabriel, CA (US); Aiwen Li, Westlake Village, CA (US); Chester Chenguang Yuan, Newbury Park, CA (US); Kaustav Biswas, Calabasas, CA (US); Scott Harried, Woodland Hills, CA (US); Thomas Nguyen, Thousand Oaks, CA (US); Wenyuan Qian, Camarillo, CA (US); Jian Jeffrey Chen, Newbury Park, CA (US); Rana Nomak, Westlake Village, CA (US)

(73) Assignees: Amgen Inc., Thousand Oaks, CA (US); Array BioPharma Inc., Boulder, CO (US)

( * ) Notice: Subject to any disclaimer, the term of this patent is extended or adjusted under 35 U.S.C. 154(b) by 442 days.

(21) Appl. No.: 10/823,377

(22) Filed: Apr. 12, 2004

(65) Prior Publication Data
US 2005/0124654 A1 Jun. 9, 2005

Related U.S. Application Data

(60) Provisional application No. 60/461,888, filed on Apr. 10, 2003.

(51) Int. Cl.
C07D 215/04 (2006.01)
(52) U.S. Cl. .................. 546/192; 548/530; 548/557; 549/51; 549/58; 549/59
(58) Field of Classification Search ............. 546/192; 549/51, 58, 59; 548/530, 557
See application file for complete search history.

(56) References Cited

FOREIGN PATENT DOCUMENTS

| EP | 0035868 A | 9/1981 |
|---|---|---|
| WO | WO 92/12140 | 7/1992 |
| WO | WO 97/25315 A | 7/1997 |
| WO | WO 02/06222 A1 | 1/2002 |
| WO | WO 02/076964 A | 10/2002 |
| WO | WO 2004/054584 A1 | 7/2004 |
| WO | WO 2004/083173 A3 | 9/2004 |

OTHER PUBLICATIONS

Jessell et al., "Pain and Analgesia" in *Principles of Neural Science*, 3rd Edition, 1991, E.R. Kandel, J.H. Schwartz, T.M. Jessell, editors, pp. 385-399.
M.J. Millan, "The Induction of Pain: An Integrative Review," *Prog. Neurobiol.*, 1999, 57:1-164.
Regoli et al., "Pharmacology of Bradykinin and Related Kinins," *Pharmacological Rev.*, 1980, 32(1):1-46.
Menke et al., "Expression Cloning of a Human $B_1$ Bradykinin Receptor," *J. Biol. Chem.*, 1994, 269:21583-21586.
Hess et al., "Cloning and Pharmacological Characterization of a Human Bradykinin (BK-2) Receptor," *Biochem. Biophys. Res. Commun.*, 1992, 184:260-268.
F. Marceau et al., "Kinin $B_1$ receptors: a review," *Immunopharmacology*, 1995, 30:1-26.
E.J. Corey et al., "Highly Enantioselective Borane Reduction of Ketones Catalyzed by Chiral Oxazaborolidines. Mechanism and Synthetic Implications," *J. Am. Chem. Soc.*, 1987, v. 109, pp. 5551-5553.
T. Ohkuma et al., "Practical Enantioselective Hydrogenation of Aromatic Ketones," *J. Am. Chem Soc.*, 1995, v. 117, pp. 2575-2676.
Thompson et al., "Direct Conversion of Activated Alcohols to Azides Using Diphenyl Phosphoroazidate. A Practical Alternative to Mitsunobu Conditions," *J. Org. Chem.*, 1993, 58 (22):5886-5888.
DG Batt et al., "Disubstituted Indazoles as Potent Antagonists of the Integrin $α_vβ_3$," *Journal of Medicinal Chemistry*, 2000, 43:41-58.
G. Wagner et al., "Synthesis of 3-(p- and m-amidinophenyl-3-arylsulfonylaminopropionic acid amide hydroiodides," *Chemical Abstracts*, Mar. 29, 1982, 96(13), abstract No. 104710e.
G. Wagner et al., "Synthese von 3-(p- und m-Amidinophenyl)-3-arylsulfonylaminopropionsäureamidhydroiodiden," *Pharmazie*, 1981, 36(9):607-609.

Primary Examiner—D. Margaret Seaman
(74) Attorney, Agent, or Firm—McDonnell Boehnen Hulbert & Berghoff

(57) ABSTRACT

Selected compounds are effective for treatment of pain and diseases, such as inflammation mediated diseases. The invention encompasses novel compounds, analogs, prodrugs and pharmaceutically acceptable derivatives thereof, pharmaceutical compositions and methods for prophylaxis and treatment of diseases and other maladies or conditions involving pain, inflammation, and the like. The subject invention also relates to processes for making such compounds as well as to intermediates useful in such processes.

6 Claims, No Drawings

COMPOUNDS AND METHODS OF USE

RELATED APPLICATIONS

This application claims priority to provisional application 60/461,888, filed Apr. 10, 2003.

FIELD OF THE INVENTION

This invention is in the field of pharmaceutical agents and specifically relates to compounds, compositions, uses and methods for treating inflammation-related disorders, including pain.

BACKGROUND OF THE INVENTION

More than two million people in the United States alone are incapacitated by chronic pain on any given day (T. M. Jessell & D. D. Kelly, Pain and Analgesia in Principles of Neural Science, $3^{rd}$ edition (E. R. Kandel, J. H. Schwartz, T. M. Jessell, editors, (1991)). Unfortunately, current treatments for pain are only partially effective, and many cause life-style altering, debilitating, and/or dangerous side effects. For example, non-steroidal anti-inflammatory drugs ("NSAIDs") such as aspirin, ibuprofen, and indomethacin are moderately effective against inflammatory pain but they are also renally toxic, and high doses tend to cause gastrointestinal irritation, ulceration, bleeding, increased cardiovascular risk, and confusion. Patients treated with opioids frequently experience confusion and constipation, and long-term opioid use is associated with tolerance and dependence. Local anesthetics such as lidocaine and mixelitine simultaneously inhibit pain and cause loss of normal sensation. In addition, when used systemically, local anesthetics are associated with adverse cardiovascular effects. Thus, there is currently an unmet need in the treatment of chronic pain.

Pain is a perception based on signals received from the environment and transmitted and interpreted by the nervous system (for review, see M. J. Millan, Prog. Neurobiol. 57:1-164 (1999)). Noxious stimuli such as heat and touch cause specialized sensory receptors in the skin to send signals to the central nervous system ("CNS"). This process is called nociception, and the peripheral sensory neurons that mediate it are nociceptors. Depending on the strength of the signal from the nociceptor(s) and the abstraction and elaboration of that signal by the CNS, a person may or may not experience a noxious stimulus as painful. When one's perception of pain is properly calibrated to the intensity of the stimulus, pain serves its intended protective function. However, certain types of tissue damage cause a phenomenon, known as hyperalgesia or pronociception, in which relatively innocuous stimuli are perceived as intensely painful because the person's pain thresholds have been lowered. Both inflammation and nerve damage can induce hyperalgesia. Thus, persons afflicted with inflammatory conditions, such as sunburn, osteoarthritis, colitis, carditis, dermatitis, myositis, neuritis, inflammatory bowel disease, collagen vascular diseases (which include rheumatoid arthritis and lupus) and the like, often experience enhanced sensations of pain. Similarly, trauma, surgery, amputation, abscess, causalgia, collagen vascular diseases, demyelinating diseases, trigeminal neuralgia, cancer, chronic alcoholism, stroke, thalamic pain syndrome, diabetes, herpes infections, acquired immune deficiency syndrome ("AIDS"), toxins and chemotherapy cause nerve injuries that result in excessive pain.

As the mechanisms by which nociceptors transduce external signals under normal and hyperalgesic conditions become better understood, processes implicated in hyperalgesia can be targeted to inhibit the lowering of the pain threshold and thereby lessen the amount of pain experienced.

Bradykinin (BK) and the related peptide, kallidin (Lys-BK) mediate the physiological actions of kinins on the cardiovascular and renal systems. However, the active peptides, BK and kallidin, are quickly degraded by peptidases in the plasma and other biological fluids and by those released from a variety of cells, so that the half-life of BK in plasma is reported to be approximately 17 seconds (1). BK and kallidin are rapidly metabolized in the body by carboxypeptidase N, which removes the carboxyterminal arginine residue to generate des-Arg BK or des-Arg kallidin. Des-Arg-kallidin is among the predominant kinins in man and mediate the pathophysiological actions of kinins in man. In addition to being a very potent proinflammatory peptide, des-Arg-BK or des-Arg-kallidin is known to induce vasodilation, vascular permeability, and bronchoconstriction (for review, see Regoli and Barabe, Pharmacological Rev, 32(1):1-46 (1980)). In addition, des-Arg-BK and des-Arg-kallidin appear to be particularly important mediators of inflammation and inflammatory pain as well as being involved in the maintenance thereof. There is also a considerable body of evidence implicating the overproduction of des-Arg-kallidin in conditions in which pain is a prominent feature such as septic shock, arthritis, angina, and migraine.

The membrane receptors that mediate the pleiotropic actions of kinins are of two distinct classes, designated B1 and B2. Both classes of receptors have been cloned and sequenced from a variety of species, including man (Menke, et al, J. Biol. Chem., 269:21583-21586 (1994); Hess et al, Biochem. Biophys. Res. Commun., 184:260-268 (1992)). They are typical G protein coupled receptors having seven putative membrane spanning regions. In various tissues, BK receptors are coupled to every known second messenger. B2 receptors, which have a higher affinity for BK, appear to be the most prevalent form of bradykinin receptor. Essentially all normal physiological responses and many pathophysiological responses to bradykinin are mediated by B2 receptors.

B1 receptors, on the other hand, have a higher affinity for des-Arg-BK compared with BK, whereas des-Arg-BK is inactive at B2 receptors. In addition, B1 receptors are not normally expressed in most tissues. Their expression is induced upon injury or tissue damage as well as in certain kinds of chronic inflammation or systemic insult (Marceau, F. et al., Immunopharmacology, 30:1-26 (1995)). Furthermore, responses mediated by B1 receptors are upregulated from a null level following administration of bacterial lipopolysaccharide (LPS) or inflammatory cytokines in rabbits, rats, and pigs.

The pain-inducing properties of kinins coupled with the inducible expression of B1 receptors make the B1 receptor an interesting target in the development of anti-inflammatory, antinociceptive, antihyperalgesic and analgesic agents that may be directed specifically at injured tissues with minimal actions in normal tissues.

Clearly, there is a need for new, safe and effective treatments for inflammation and pain. Such agents are provided in the present invention.

DETAILED DESCRIPTION OF THE INVENTION

A class of compounds useful in treating inflammation and pain is defined by Formula I

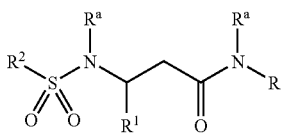

I wherein R is a 9-11 membered fused bicyclic carbocyclic or heterocyclic ring substituted with one to three basic moieties, and optionally substituted with one to three groups independently selected from halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$;

wherein R$^8$ and R$^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein R$^1$ is selected from cycloalkyl, aryl, heteroaryl and heterocyclyl, each of which is optionally substituted with one to five groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$, and (C$_2$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$;

wherein R$^2$ is selected from arylalkenyl, aryl, and heterocyclyl, wherein R$^2$ is optionally substituted with one to five groups independently selected from halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$; and wherein each R$^a$ is independently selected from H, aminocarbonylmethyl and C$_{1-4}$-alkyl, and aryl optionally substituted with one to three groups selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$—C(O)NR$^8$R$^{8'}$, and —NR$^8$C(O)R$^{8'}$;

and pharmaceutically acceptable derivatives thereof; provided the basic moiety is not 2-oxo-piperaziny-4-ylmethyl.

The invention also relates to compounds of Formula I wherein R is a partially unsaturated carbocyclic ring, such as 1,2,3,4-tetrahydronaphthyl or indanyl.

The invention also relates to compounds of Formula I wherein R is selected from 1,2,3,4-tetrahydronaphth-1-yl, 1,2,3,4-tetrahydronaphth-2-yl, indan-1-yl and indan-2-yl.

The invention also relates to compounds of Formula I wherein R is partially unsaturated heterocyclyl, such as chroman and 2,2-dioxo-3,4-dihydro-1H-2,1-benzothiazinyl.

The invention also relates to compounds of Formula I wherein R is chroman-4-yl, or 2,2-dioxo-3,4-dihydro-1H-2,1-benzothiazin-4-yl.

The invention also relates to compounds of Formula I wherein R$^1$ is selected from C$_{5-6}$ cycloalkyl, phenyl, naphthyl, benzo[1,3]dioxolyl, benzothiadiazolyl, benzoxadiazolyl, benzothienyl, 2,3-dihydro-benzo[1,4]dioxinyl, benzofuranyl, tetrahydro-quinolinyl, tetrahydro-isoquinolinyl, dihydrobenzofuranyl, thiazolyl, furanyl and thienyl; wherein R$^1$ is optionally substituted with one to five groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$) alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$.

The invention also relates to compounds of Formula I wherein R$^1$ is selected from cyclohexyl, phenyl, naphthyl, benzo[1,3]dioxolyl, 2,1,3-benzothiadiazol-5-yl, 2,1,3-benzoxadiazol-5-yl, benzothien-5-yl, 2,3-dihydro-benzo[1,4]dioxin-6-yl, benzofuranyl, tetrahydro-quinolinyl, tetrahydro-isoquinolinyl, dihydrobenzofuranyl, 1,3-thiazol-2-yl, furanyl, and thienyl; wherein R$^1$ is optionally substituted with one to five groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$) alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$) alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$.

The invention also relates to compounds of Formula I wherein R$^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl;

wherein R$^2$ is optionally substituted with one to five groups independently selected from halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, C(O)NR$^8$R$^{8'}$, and NR$^8$C(O)R$^{8'}$; and preferably with one or two groups independently selected from —Cl, —F or —CF$_3$.

The invention also relates to compounds of Formula I wherein R$^2$ is selected from phenyl-CH=CH—, tetrahydronaphthyl, naphtho[2.3-d]dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, thieno[3,2-c]pyridin-2-yl, naphthyl, phenyl, 3-pyridinyl, tetrahydroisoquinolinyl, quinolinyl and isoquinolinyl;

wherein R$^2$ is optionally substituted with one to five groups independently selected from halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$ and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$; and preferably with one or two groups independently selected from —Cl, —F or —CF$_3$.

The invention also relates to compounds of Formula I wherein R$^a$ is selected from H; C$_{1-2}$-alkyl, such as methyl; or phenyl, optionally substituted with one to three groups selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$.

The invention also relates to compounds of Formula I wherein the one to three basic moieties on R are independently selected from cycloalkylamino(C$_1$-C$_6$)alkyl, cycloalkylalkylamino(C$_1$-C$_6$)alkyl, heteroarylamino(C$_1$-C$_6$)alkyl, heteroaryl(C$_1$-C$_6$)alkylamino(C$_1$-C$_6$)alkyl, arylamino(C$_1$-C$_6$)alkyl, aryl(C$_1$-C$_6$)alkylamino(C$_1$-C$_6$)alkyl, C$_{1-6}$-alkylamino-C$_{1-6}$-alkoxy, C$_{1-6}$-alkylamino-C$_{1-6}$-alkoxy-C$_{1-6}$-alkoxy, aminoalkoxy, amino(C$_1$-C$_6$)alkyl, alkylamino(C$_1$-C$_6$)alkyl; or 5-6 membered heterocyclyloxy, 5-6 membered nitrogen-containing heterocyclyl or 5-7 membered nitrogen-containing heterocyclyl-alkyl, each of which is optionally substituted with one to three groups selected from halo, —NH$_2$, —OH, —CN, —CF$_3$, (C$_1$-C$_6$)alkylamino, haloalkyl, oxo, (C$_1$-C$_6$)alkoxy, (C$_1$-C$_6$)alkoxyalkyl, (C$_1$-C$_6$)alkenyl, (C$_1$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, =NCN; or (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$) alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$.

The invention also relates to compounds of Formula I wherein the one to three basic moieties on R are independently selected from NH$_2$, mono-C$_{1-4}$-alkylamino-C$_{1-4}$-alkyl, di-C$_{1-4}$-alkylamino-C$_{1-4}$-alkyl; or 5-6 membered heterocyclyloxy, 5-6 membered nitrogen-containing heterocyclyl or 5-7 membered nitrogen-containing heterocyclyl-alkyl, each of which is optionally substituted with one to three groups selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$—C(O)NR$^8$R$^{8'}$, —NR$^8$C(O)R$^{8'}$, =NCN; or (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$) alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$.

The invention also relates to compounds of Formula I wherein the one to three basic moieties on R are independently selected from NH$_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II

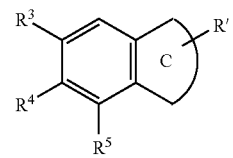

II wherein the C ring is a 4- to 7- membered saturated carbocyclic or heterocyclic moiety;
wherein R' is

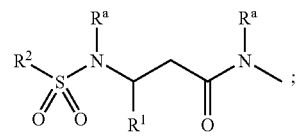

wherein R$^1$ is selected from cycloalkyl, aryl, heteroaryl and heterocyclyl, each of which is optionally substituted with one to five groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$;

wherein R$^2$ is selected from arylalkenyl, aryl, and heterocyclyl, wherein R$^2$ is optionally substituted with one to five groups independently selected from halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, and (C$_1$-C$_6$)alkyl, aryl, heteroaryl, cycloalkyl or heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$;

wherein R$^a$ is independently selected from H and C$_{1-4}$-alkyl, or aryl optionally substituted with one to three groups selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$—C(O)NR$^8$R$^{8'}$, and —NR$^8$C(O)R$^{8'}$;

wherein R$^3$, R$^4$ and R$^5$ are the same or different and represent H, halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, a basic moiety, or (C$_1$-C$_2$)alkyl, aryl, heteroaryl, cycloalkyl or heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$; and wherein R$^8$ and R$^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

provided at least one of R$^3$, R$^4$ and R$^5$ is a basic moiety; and pharmaceutically acceptable derivatives thereof.

The invention also relates to compounds of Formula II wherein R$^3$ and R$^4$ are H; and wherein R$^4$ is selected from NH$_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II wherein R$^4$ and R$^5$ are H; and wherein R$^3$ is selected from NH$_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II wherein R$^3$ and R$^4$ are H; and wherein R$^5$ is selected from NH$_2$, aminomethyl, isopropylaminomethyl, t-butylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula II wherein the C ring is selected from

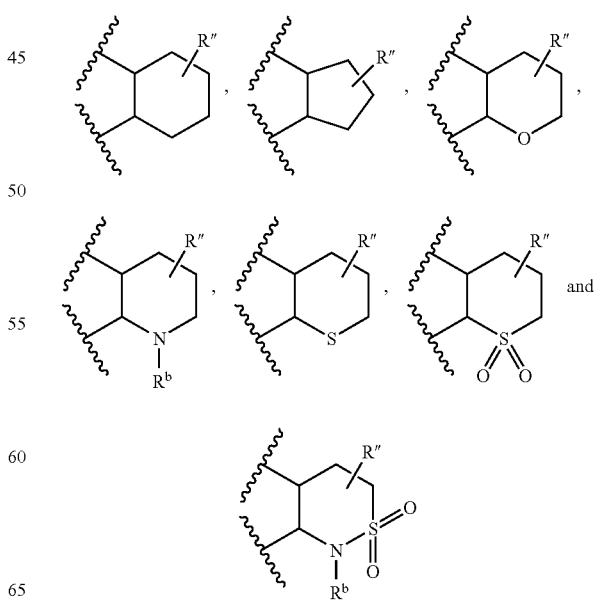

wherein $R^b$ is independently selected from R', H and $C_{1-2}$-alkyl; and wherein R" is R' when $R^b$ is hydrogen or $C_{1-2}$alkyl, or R" is hydrogen when $R^b$ is R'.

The invention also relates to compounds of Formula II wherein $R^1$ is selected from cyclohexyl, phenyl, naphthyl, benzo[1,3]dioxolyl, 2,1,3-benzothiadiazol-5-yl, 2,1,3-benzoxadiazol-5-yl, benzothien-5-yl, 2,3-dihydro-benzo[1,4]dioxin-6-yl, benzofuranyl, tetrahydro-quinolinyl, tetrahydro-isoquinolinyl, dihydrobenzofuranyl, 1,3-thiazol-2-yl, furanyl, and thienyl; wherein $R^1$ is optionally substituted with one to five groups independently selected from halo, —$NH_2$, —OH, —CN, —$CF_3$, ($C_1$-$C_6$)alkylamino, haloalkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$, and ($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$.

The invention also relates to compounds of Formula II wherein $R^2$ is selected from phenyl-CH=CH—, tetrahydronaphthyl, naphtho[2.3-d]dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, thieno[3,2-c]pyridin-2-yl, naphthyl, phenyl, 3-pyridinyl, tetrahydroisoquinolinyl, quinolinyl and isoquinolinyl; wherein $R^2$ is optionally substituted with one or more groups selected from halo, —$NH_2$, —OH, —$CO_2H$, ($C_1$-$C_2$)alkylamino, ($C_1$-$C_2$)alkoxy, ($C_1$-$C_2$)alkoxy-($C_1$-$C_2$)alkyl, ($C_1$-$C_2$)alkyl, halo($C_1$-$C_2$)alkyl, di($C_1$-$C_2$)alkylamino, and phenyl, and preferably with one or two groups independently selected from —Cl, —F or —$CF_3$.

The invention also relates to compounds of Formula II wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 4' chlorophenyl-3-phenyl, 3-methylphenyl, 3-trifluoromethylphenyl, and 3-pyridinyl; wherein $R^2$ is optionally substituted with one or more groups selected from halo, —$NH_2$, —OH, —$CO_2H$, ($C_1$-$C_2$)alkylamino, ($C_1$-$C_2$)alkoxy, ($C_1$-$C_2$)alkoxy-($C_1$-$C_2$)alkyl, ($C_1$-$C_2$)alkyl, halo($C_1$-$C_2$)alkyl, di($C_1$-$C_2$)alkylamino, and phenyl, and preferably with one or two groups independently selected from —Cl, —F or —$CF_3$.

The invention also relates to compounds of Formula II wherein $R^a$ is H.

The invention also relates to compounds of Formula II wherein $R^2$ is 2-naphthyl.

The invention also relates to compounds of Formula II wherein $R^2$ is 3,4-dichlorophenyl.

The invention also relates to compounds of Formula II wherein $R^2$ is 3-trifluoromethylphenyl.

The invention also relates to compounds of Formula II wherein the C ring and the phenyl to which it is attached forms a chroman ring.

The invention also relates to compounds of Formula III

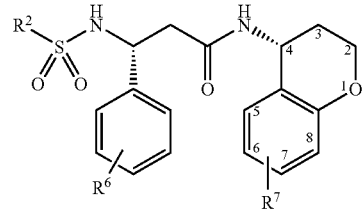

wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from H, halo, phenyl, methyl, methoxy and —$CF_3$;

wherein $R^7$ is selected from amino-$(CH_2)_p$—, mono($C_{1-4}$)alkylamino-$(CH_2)_p$—, di($C_{1-4}$)alkylamino-$(CH_2)_p$—, and a 5-7 membered nitrogen-containing heterocyclyl-$(CH_2)_p$- optionally substituted with one to three groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$—C(O)N$R^8R^{8'}$, —N$R^8$C(O)$R^{8'}$, =NCN;

($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 6, 7 or 8; and pharmaceutically acceptable derivatives thereof.

The invention also relates to compounds of Formula III wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl) piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula III wherein $R^7$ is substituted at position 7.

The invention also relates to compounds of Formula III wherein $R^2$ is 2-naphthyl, 3,4-dichlorophenyl or 3-trifluoromethylphenyl.

The invention also relates to compounds of Formula III wherein $R^6$ is H.

The invention also relates to compounds of Formula IV

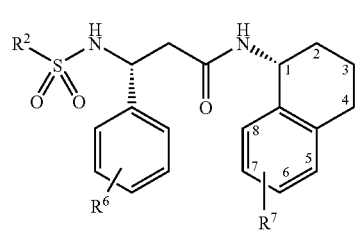

IV wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from H, halo, phenyl, methyl, methoxy and —$CF_3$;

wherein $R^7$ is selected from amino-$(CH_2)_p$—, mono($C_{1-4}$)alkylamino-$(CH_2)_p$—, di($C_{1-4}$)alkylamino-$(CH_2)_p$—, and a 5-7 membered nitrogen-containing heterocyclyl-$(CH_2)_p$—optionally substituted with one to three groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COOR$^8$—C(O)NR$^8$R$^{8'}$, —NR$^8$C(O)R$^{8'}$, =NCN;

($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COOR$^8$, —C(O)NR$^8$R$^{8'}$, and —NR$^8$C(O)R$^{8'}$;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 5, 6 or 7;

and pharmaceutically acceptable derivatives thereof.

The invention also relates to compounds of Formula IV wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylyl-aminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula IV wherein $R^7$ is substituted at position 6.

The invention also relates to compounds of Formula IV wherein $R^2$ is 2-naphthyl, 3,4-dichlorophenyl or 3-trifluoromethylphenyl.

The invention also relates to compounds of Formula IV wherein $R^6$ is H.

The invention also relates to compounds of Formula V

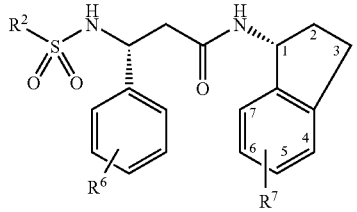

V wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from H, halo, phenyl, methyl, methoxy and —$CF_3$;

wherein $R^7$ is selected from amino-$(CH_2)_p$—, mono($C_{1-4}$)alkylamino-$(CH_2)_p$—, di($C_{1-4}$)alkylamino-$(CH_2)_p$—, and a 5-7 membered nitrogen-containing heterocyclyl-$(CH_2)_p$—optionally substituted with one to three groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COOR$^8$—C(O)NR$^8$R$^{8'}$, —NR$^8$C(O)R$^{8'}$, =NCN;

($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COOR$^8$, —C(O)NR$^8$R$^{8'}$, and —NR$^8$C(O)R$^{8'}$;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 4, 5 or 6;

and pharmaceutically acceptable derivatives thereof.

The invention also relates to compounds of Formula IV wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylyl-aminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl)piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula V wherein $R^7$ is substituted at position 5.

The invention also relates to compounds of Formula V wherein $R^2$ is 2-naphthyl, 3,4-dichlorophenyl or 3-trifluoromethylphenyl.

The invention also relates to compounds of Formula V wherein $R^6$ is H.

The invention also relates to compounds of Formula VI

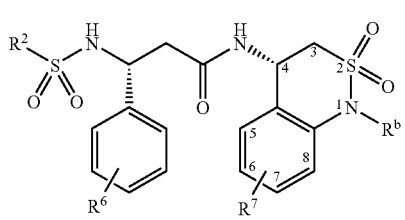

wherein $R^b$ is selected from H and $C_{1-3}$ alkyl;

wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from halo, phenyl, methyl, methoxy and —$CF_3$;

wherein $R^7$ is selected from amino-$(CH_2)_p$—, mono$(C_{1-4})$alkylamino-$(CH_2)_p$—, di$(C_{1-4})$alkylamino-$(CH_2)_p$—, and a 5-7 membered nitrogen-containing heterocyclyl-$(CH_2)_p$—optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —$C(O)R^8$, —$COOR^8$—$C(O)NR^8R^{8'}$, —$NR^8C(O)R^{8'}$, =NCN;

$(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 6, 7 or 8;

and pharmaceutically acceptable derivatives thereof.

The invention also relates to compounds of Formula VI wherein $R^7$ is selected from aminomethyl, isopropylaminomethyl, t-butylaminomethyl, N-isopropyl-N-ethylaminomethyl, N-isopropyl-N-methylaminomethyl, N-t-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl) piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl.

The invention also relates to compounds of Formula VI wherein $R^7$ is substituted at position 7.

The invention also relates to compounds of Formula VI wherein $R^2$ is 2-naphthyl, 3,4-dichlorophenyl or 3-trifluoromethylphenyl.

The invention also relates to compounds of Formula VI wherein $R^6$ is H.

The invention also relates to compounds of Formula I'

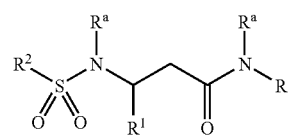

wherein R is a 9-11 membered fused bicyclic carbocyclic or heterocyclic ring substituted with one to three basic moieties, and optionally substituted with one to three groups independently selected from halo, —$NH_2$, —OH, —CN, —$CF_3$, $(C_1-C_6)$alkylamino, oxo, $(C_1-C_6)$alkoxy, $(C_2-C_6)$alkenyl, $(C_2-C_6)$alkynyl, di$(C_1-C_6)$alkylamino, —$C(O)R^8$, —$COOR^8$—$C(O)NR^8R^{8'}$, —$NR^8C(O)R^{8'}$, and $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$;

wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^1$ is selected from cycloalkyl, aryl, aryl-$(CH_2)_{0-2}$—, heteroaryl-$(CH_2)_{0-2}$—, heteroaryl and heterocyclyl, each of which is optionally substituted with one to five groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$—$C(O)NR^8R^{8'}$, and —$NR^8C(O)R^{8'}$, and $(C_2-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, $(C_1-C_6)$alkyl, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, and —$NR^8C(O)R^{8'}$;

wherein $R^2$ is selected from arylalkenyl, aryl, and heterocyclyl selected from thienyl, imidazolyl and benzofused heteroaryl, wherein $R^2$ is optionally substituted with one to five groups independently selected from halo, —$NH_2$, —OH, —CN, —$CF_3$, $(C_1-C_6)$alkylamino, oxo, $(C_1-C_6)$alkoxy, haloalkoxy, $(C_2-C_6)$alkenyl, $(C_2-C_6)$alkynyl, di$(C_1-C_6)$alkylamino, —$C(O)R^8$, —$COOR^8$, —$C(O)NR^8R^{8'}$, —$NR^8C(O)R^{8'}$, and $(C_1-C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1-C_6)$alkylamino, halo$(C_1-C_6)$alkyl, oxo, $(C_1-C_6)$alkoxy, $(C_1-C_6)$alkoxy$(C_1-C_6)$alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; and wherein each $R^a$ is independently selected from H and $C_{1-4}$-alkyl, and aryl optionally substituted with one to three groups selected from halo, —NH$_2$, —OH, —CN, —CF$_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$—C(O)N$R^8R^{8'}$, and —N$R^8$C(O)$R^{8'}$;

and pharmaceutically acceptable derivatives thereof.

The invention also relates to compounds of Formula I' wherein R is a partially unsaturated carbocyclic ring; in conjunction with any of the above or below embodiments.

The invention also relates to compounds of Formula I' wherein R is 1,2,3,4-tetrahydronaphthyl; in conjunction with any of the above or below embodiments.

The invention also relates to compounds of Formula I' wherein R is indanyl; in conjunction with any of the above or below embodiments.

The invention also relates to compounds of Formula I' wherein R is selected from 1,2,3,4-tetrahydronaphth-1-yl, 1,2,3,4-tetrahydronaphth-2-yl, indan-1-yl and indan-2-yl; in conjunction with any of the above or below embodiments.

The invention also relates to compounds of Formula I' wherein R is partially unsaturated heterocyclyl; in conjunction with any of the above or below embodiments.

The invention also relates to compounds of Formula I' wherein R is chroman; in conjunction with any of the above or below embodiments.

The invention also relates to compounds of Formula I' wherein R is 2,2-dioxo-3,4-dihydro-1H-2,1-benzothiazinyl; in conjunction with any of the above or below embodiments.

The invention also relates to compounds of Formula I' wherein R is chroman-4-yl, 5,6,7,8-tetrahydro-quinazolin-5-yl, 5,6,7,8-tetrahydro-[1,6]naphthyridin-4-yl or 2,2-dioxo-3,4-dihydro-1H-2,1-benzothiazin-4-yl; in conjunction with any of the above or below embodiments.

The invention also relates to compounds of Formula I' wherein $R^1$ is selected from $C_{5-6}$ cycloalkyl, phenyl, benzyl, naphthyl, benzo[1,3]dioxolyl, benzothiadiazolyl, thienyl-CH$_2$—, indolyl-CH$_2$—, benzoxadiazolyl, benzothienyl, 2,3-dihydro-benzo[1,4]dioxinyl, benzofuranyl, tetrahydro-quinolinyl, tetrahydro-isoquinolinyl, dihydrobenzofuranyl, thiazolyl, furanyl and thienyl; wherein $R^1$ is optionally substituted with one to five groups independently selected from halo, —NH$_2$, —OH, —CN, —CF$_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$, and ($C_1$-$C_6$)alkyl, aryl, heteroaryl, cycloalkyl and heterocyclyl, each of which is optionally substituted with one to three groups independently selected from halo, —NH$_2$, —OH, —CN, —CF$_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

wherein $R^2$ is selected from phenyl-CH=CH—, tetrahydronaphthyl, naphtho[2.3-d]dioxolyl, benzofuranyl, benzoxadiazolyl, benzothiadiazolyl, benzothiazolyl, 1H-pyrazolyl, thienyl, isoxazolthienyl, benzothienyl, thieno[3,2-c]pyridinyl, naphthyl, phenyl, pyridinyl, tetrahydroisoquinolinyl, quinolinyl and isoquinolinyl; wherein $R^2$ is optionally substituted with one to five groups independently selected from halo, —NH$_2$, —OH, —CN, —CF$_3$, ($C_1$-$C_6$) alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$—C(O)N$R^8R^{8'}$, —N$R^8$C(O)$R^{8'}$, and ($C_1$-$C_6$)alkyl, aryl, heteroaryl, cycloalkyl and heterocyclyl, each of which is optionally substituted with one to three groups independently selected from halo, —NH$_2$, —OH, —CN, —CF$_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; and preferably with one or two groups independently selected from —Cl, —F or —CF$_3$;

wherein $R^a$ is selected from H and $C_{1-2}$-alkyl;

wherein the one to three basic moieties on R are independently selected from cycloalkylamino($C_1$-$C_6$)alkyl, cycloalkyl ($C_1$-$C_6$)alkylamino($C_1$-$C_6$)alkyl,

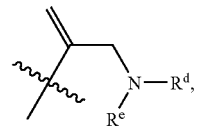

heteroarylamino($C_1$-$C_6$)alkyl, heteroaryl($C_1$-$C_6$)alkylamino($C_1$-$C_6$)alkyl, arylamino($C_1$-$C_6$)alkyl, alkoxyalkylaminoalkyl, hydroxyalkylaminoalkyl, alkenylalkylaminoalkyl, aminocarbonylalkylamino-alkyl, carboxyalkylaminoalkyl, aryl($C_1$-$C_6$)alkylamino($C_1$-$C_6$) alkyl, $C_{1-6}$-alkylamino-$C_{1-6}$-alkoxy, $C_{1-6}$-alkylamino-$C_{1-6}$-alkoxy-$C_{1-6}$-alkoxy, haloalkylaminoalkyl, amino($C_1$-$C_6$)alkoxy, amino($C_1$-$C_6$)alkyl, ($C_1$-$C_6$)alkylamino($C_1$-$C_6$)alkyl, 5-6 membered heterocyclyloxy, 5-8 membered nitrogen-containing heterocyclyl, 5-7 membered nitrogen-containing heterocyclyl-alkylaminoalkyl and 5-7 membered heterocyclyl-alkyl; and wherein each of said basic substituents is optionally substituted with one to three groups independently selected from halo, —NH$_2$, —OH, —CN, —CF$_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$—C(O)N$R^8R^{8'}$, —N$R^8$C(O)$R^{8'}$, and ($C_1$-$C_6$)alkyl, aryl, heteroaryl, cycloalkyl or heterocyclyl, each of which is optionally substituted with one to three groups independently selected from halo, —NH$_2$, —OH, —CN, —CF$_3$, ($C_1$-$C_6$)alkylamino, halo($C_1$-$C_6$) alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; and wherein $R^d$ is selected from alkyl, cycloalkyl, cycloalkylalkyl, hydroxyalkyl, alkoxyalkyl, and H;

wherein $R^e$ is H; or where $R^d$ and $R^e$ together with the nitrogen atom which they are attached form a heterocyclic ring;

and pharmaceutically acceptable derivatives thereof.

The invention also relates to compounds of Formula I' wherein $R^1$ is selected from cyclohexyl, phenyl, benzyl, thienyl-CH$_2$—, indolyl-CH$_2$—, naphthyl, benzo[1,3]dioxolyl, 2,1,3-benzothiadiazol-5-yl, 2,1,3-benzoxadiazol-5-yl, benzothien-5-yl, 2,3-dihydro-benzo[1,4]dioxin-6-yl, benzofuranyl, tetrahydro-quinolinyl, tetrahydro-isoquinolinyl, dihydrobenzofuranyl, 1,3-thiazol-2-yl, furanyl, and thienyl; wherein $R^1$ is optionally substituted with one to five groups independently selected from halo, —NH$_2$, —OH, —CN, —CF$_3$, ($C_1$-$C_6$)alkylamino, halo($C_1$-$C_6$)alkyl, oxo, ($C_1$-$C_6$)

alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$;

wherein R$^2$ is selected from phenyl-CH═CH—, tetrahydronaphthyl, naphtho[2.3-d]dioxol-6-yl, 1-benzofur-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, benzothien-3-yl, thieno[3,2-c]pyridin-2-yl, naphthyl, phenyl, 3-pyridyl, tetrahydroisoquinolyl, quinol-8-yl and isoquinolyl; wherein R$^2$ is optionally substituted with one to five groups independently selected from halo, —NH$_2$, —OH, —CN, —CF$_3$, (C$_1$-C$_6$)alkylamino, oxo, (C$_1$-C$_6$)alkoxy, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, —NR$^8$C(O)R$^{8'}$, and (C$_1$-C$_6$)alkyl, aryl, heteroaryl, cycloalkyl and heterocyclyl, each of which is optionally substituted with one to three groups independently selected from halo, —NH$_2$, —OH, —CN, —CF$_3$, (C$_1$-C$_6$)alkylamino, halo(C$_1$-C$_6$)alkyl, oxo, (C$_1$-C$_6$)alkoxy, (C$_1$-C$_6$)alkoxy(C$_1$-C$_6$)alkyl, (C$_1$-C$_6$)alkyl, (C$_2$-C$_6$)alkenyl, (C$_2$-C$_6$)alkynyl, di(C$_1$-C$_6$)alkylamino, —C(O)R$^8$, —COOR$^8$, —C(O)NR$^8$R$^{8'}$, and —NR$^8$C(O)R$^{8'}$; and preferably with one or two groups independently selected from —Cl, —F or —CF$_3$;

wherein R$^a$ is H or methyl;

wherein the basic substituent on R is selected from —NH$_2$,

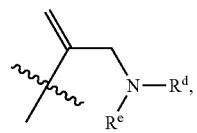

C$_{3-6}$-cycloalkyl (C$_1$-C$_2$)alkylamino(C$_1$-C$_2$)alkyl, C$_{3-6}$-cycloalkylamino(C$_1$-C$_2$)alkyl, (C$_1$-C$_2$)alkoxy(C$_1$-C$_2$)alkylamino(C$_1$-C$_2$)alkyl, mono-C$_{2-4}$-alkenylamino-C$_{1-4}$-alkyl, di-C$_{2-4}$-alkenylamino-C$_{1-4}$-alkyl, hydroxy-C$_{1-4}$-alkylamino-C$_{1-4}$-alkyl, aminocarbonyl-C$_{1-4}$-alkylamino-C$_{1-2}$-alkyl, mono-C$_{1-6}$-alkylamino-C$_{1-4}$-alkyl, di-C$_{1-4}$-alkylamino-C$_{1-4}$-alkyl and 5-8 membered heterocyclyl-C$_{1-4}$-alkyl; and wherein R$^d$ is selected from C$_{1-5}$-alkyl, C$_{3-6}$-cycloalkyl, C$_{3-6}$-cycloalkyl-C$_{1-4}$-alkyl, C$_{1-4}$-hydroxyalkyl, C$_{1-3}$-alkoxy-C$_{1-3}$-alkyl and H; and wherein R$^e$ is H; or where R$^d$ and R$^e$ together with the nitrogen atom form a 4-8 membered nitrogen-containing heterocyclic ring;

and pharmaceutically acceptable derivatives thereof; in conjunction with any of the above or below embodiments.

The invention also relates to compounds of Formula I' wherein R$^2$ is 3-trifluoromethylphenyl; in conjunction with any of the above or below embodiments.

The invention also relates to compounds of Formula I' wherein R$^2$ is 3,4-dichlorophenyl; in conjunction with any of the above or below embodiments.

The invention also relates to compounds of Formula I' wherein R$^2$ is 4-tert-butylphenyl; in conjunction with any of the above or below embodiments.

The invention also relates to compounds of Formula I' wherein R$^2$ is substituted or unsubstituted naphthyl; in conjunction with any of the above or below embodiments.

The invention also relates to compounds of Formula I' wherein R$^2$ is substituted benzothienyl; in conjunction with any of the above or below embodiments.

The invention also relates to compounds of Formula I' wherein R$^2$ is 5-chloro-3-methylbenzothienyl; in conjunction with any of the above or below embodiments.

The invention also relates to compounds of Formula I' wherein R$^2$ is 5-chlorobenzothienyl; in conjunction with any of the above or below embodiments.

The invention also relates to compounds of Formula I' wherein R$^1$ is substituted phenyl; in conjunction with any of the above or below embodiments.

The invention also relates to compounds of Formula I' wherein R$^1$ is 4-fluorophenyl; in conjunction with any of the above or below embodiments.

The invention also relates to compounds of Formula I' wherein R$^1$ is 3-fluorophenyl; in conjunction with any of the above or below embodiments.

The invention also relates to compounds of Formula I' wherein R$^1$ is 2-fluorophenyl; in conjunction with any of the above or below embodiments.

The invention also relates to compounds of Formula I' wherein R$^1$ is 3-chlorophenyl; in conjunction with any of the above or below embodiments.

The invention also relates to compounds of Formula I' wherein R$^1$ is 3,5-dichlorophenyl; in conjunction with any of the above or below embodiments.

The invention also relates to compounds of Formula I' wherein R$^1$ is 3-nitrophenyl; in conjunction with any of the above or below embodiments.

The invention also relates to compounds of Formula I' wherein R$^1$ is 3-cyanophenyl; in conjunction with any of the above or below embodiments.

The invention also relates to compounds of Formula I' wherein R$^1$ is 4-chlorophenyl; in conjunction with any of the above or below embodiments.

The invention also relates to compounds of Formula I' wherein R$^1$ is 4-methoxyphenyl; in conjunction with any of the above or below embodiments.

The invention also relates to compounds of Formula I' wherein R$^1$ is benzyl; in conjunction with any of the above or below embodiments.

The invention also relates to compounds of Formula I' wherein R$^a$ is H; and pharmaceutically acceptable derivatives thereof; in conjunction with any of the above or below embodiments.

The invention also relates to compounds of Formula I' wherein the basic substituent on R is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di (allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; and pharmaceutically acceptable derivatives thereof; in conjunction with any of the above or below embodiments.

The invention also relates to compounds of Formula II'

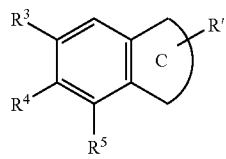

II' wherein the C ring is a 4- to 7- membered saturated carbocyclic or heterocyclic moiety;
wherein R' is

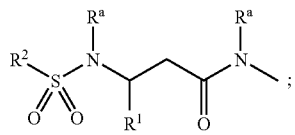

wherein $R^1$ is selected from cycloalkyl, aryl, heteroaryl and heterocyclyl selected from thienyl, imidazolyl and benzo-fused heteroaryl, each of which is optionally substituted with one to five groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, haloalkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$, and ($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

wherein $R^2$ is selected from arylalkenyl, aryl, and heterocyclyl, wherein $R^2$ is optionally substituted with one to five groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, and ($C_1$-$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

wherein $R^a$ is independently selected from H and $C_{1-4}$-alkyl, or aryl optionally substituted with one to three groups selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$—C(O)N$R^8R^{8'}$, and —N$R^8$C(O)$R^{8'}$;

wherein $R^3$, $R^4$ and $R^5$ are the same or different and represent H, halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, a basic moiety, or ($C_1$-$C_2$)alkyl, aryl, heteroaryl, cycloalkyl or heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

provided at least one of $R^3$, $R^4$ and $R^5$ is a basic moiety; and pharmaceutically acceptable derivatives thereof.

The invention also relates to compounds of Formula II' wherein $R^3$ and $R^5$ are H; and wherein $R^4$ is selected from —$NH_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof; in conjunction with any of the above or below embodiments.

The invention also relates to compounds of Formula II' wherein $R^4$ and $R^5$ are H; and wherein $R^3$ is selected from —$NH_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; and pharmaceutically acceptable derivatives thereof; in conjunction with any of the above or below embodiments.

The invention also relates to compounds of Formula II' wherein $R^3$ and $R^4$ are H; and wherein $R^5$ is selected from —$NH_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-tbutyl-N-methylaminomethyl, N-iso-butyl-N-methylaminomethyl, N-t-butyl-N-ethylaminomethyl, N-isobutyl-N-methylaminomethyl, N-t-butyl-N-isopropylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; and pharmaceutically acceptable derivatives thereof; in conjunction with any of the above or below embodiments.

The invention also relates to compounds of Formula II' wherein the C ring is selected from

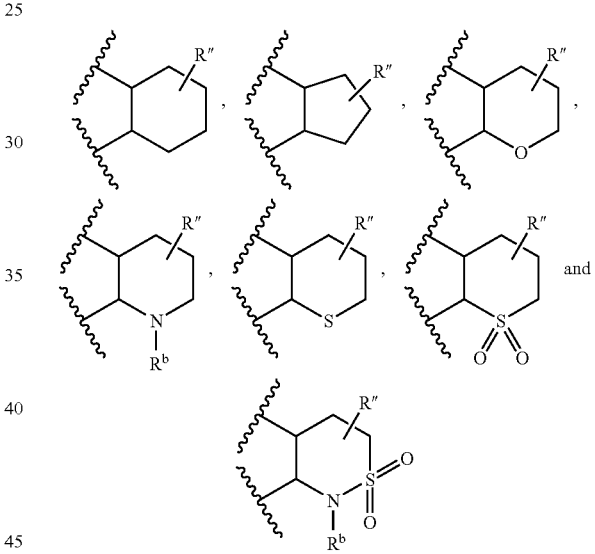

wherein $R^b$ is independently selected from R', H and $C_{1-2}$-alkyl; and wherein R" is R' when $R^b$ is hydrogen or $C_{1-2}$alkyl, or R" is hydrogen when $R^b$ is R'; in conjunction with any of the above or below embodiments.

The invention also relates to compounds of Formula II' wherein the C ring is

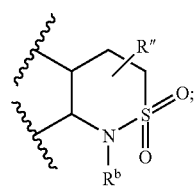

and wherein $R^b$ is R'; in conjunction with any of the above or below embodiments.

The invention also relates to compounds of Formula II' wherein $R^1$ is selected from cyclohexyl, phenyl, naphthyl, benzo[1,3]dioxolyl, 2,1,3-benzothiadiazol-5-yl, 2,1,3-benzoxadiazol-5-yl, benzothien-5-yl, 2,3-dihydro-benzo[1,4]dioxin-6-yl, benzofuranyl, tetrahydro-quinolinyl, tetrahydroisoquinolinyl, dihydrobenzofuranyl, 1,3-thiazol-2-yl, furanyl, and thienyl; wherein $R^1$ is optionally substituted with one to five groups independently selected from halo, —$NH_2$, —OH, —CN, —$CF_3$, $(C_1$-$C_6)$alkylamino, haloalkyl, oxo, $(C_1$-$C_6)$alkoxy, $(C_1$-$C_6)$alkoxy$(C_1$-$C_6)$alkyl, $(C_1$-$C_6)$alkyl, $(C_2$-$C_6)$alkenyl, $(C_2$-$C_6)$alkynyl, di$(C_1$-$C_6)$alkylamino, —$C(O)R^8$, —$COOR^8$, —$C(O)NR^8R^{8'}$, and —$NR^8C(O)R^{8'}$, and $(C_1$-$C_6)$alkyl, aryl, heteroaryl, cycloalkyl and heterocyclyl, each of which is optionally substituted with one to three groups independently selected from halo, —$NH_2$, —OH, —CN, —$CF_3$, $(C_1$-$C_6)$alkylamino, halo$(C_1$-$C_6)$ alkyl, oxo, $(C_1$-$C_6)$alkoxy, $(C_1$-$C_6)$alkoxy$(C_1$-$C_6)$alkyl, $(C_1$-$C_6)$alkyl, $(C_2$-$C_6)$alkenyl, $(C_2$-$C_6)$alkynyl, di$(C_1$-$C_6)$alkylamino, —$C(O)R^8$, —$COOR^8$, —$C(O)NR^8R^{8'}$, and —$NR^8C(O)R^{8'}$; in conjunction with any of the above or below embodiments.

The invention also relates to compounds of Formula II' wherein $R^2$ is selected from phenyl-CH=CH—, tetrahydronaphthyl, naphtho[2.3-d]-dioxol-6-yl, 1-benzofuran-2-yl, 2,1,3-benzoxadiazol-4-yl, 2,1,3-benzothiadiazol-4-yl, 1,3-benzothiazol-2-yl, 1H-pyrazol-4-yl, thien-2-yl, 5-isoxazolthien-2-yl, benzothien-2-yl, benzothien-3-yl, thieno[3,2-c]pyridin-2-yl, naphthyl, phenyl, 3-pyridinyl, tetrahydroisoquinolinyl, quinolinyl and isoquinolinyl; wherein $R^2$ is optionally substituted with one or more groups selected from halo, —$NH_2$, —OH, —$CO_2H$, $(C_1$-$C_2)$alkylamino, $(C_1$-$C_2)$alkoxy, $(C_1$-$C_2)$alkoxy-$(C_1$-$C_2)$alkyl, $(C_1$-$C_2)$alkyl, halo$(C_1$-$C_2)$alkyl, di$(C_1$-$C_2)$alkylamino, and phenyl; in conjunction with any of the above or below embodiments.

The invention also relates to compounds of Formula II' wherein $R^2$ is selected from 2-naphthyl, 1-naphthyl, phenyl, 3-chlorophenyl, 4-chlorophenyl, 3,5-dichlorophenyl, 3,4-dichlorophenyl, 2,4,6-trichlorophenyl, 3-fluorophenyl, 3-methoxyphenyl, 4-methoxyphenyl, 3-biphenyl, 4' chlorophenyl-3-phenyl, 3-methylphenyl, 3-trifluoromethylphenyl, 2-chlorobenzothien-3-yl, and 3-pyridinyl; wherein $R^2$ is optionally substituted with one or more groups selected from halo, —$NH_2$, —OH, —$CO_2H$, $(C_1$-$C_2)$alkylamino, $(C_1$-$C_2)$alkoxy, $(C_1$-$C_2)$alkoxy-$(C_1$-$C_2)$alkyl, $(C_1$-$C_2)$alkyl, halo$(C_1$-$C_2)$alkyl, di$(C_1$-$C_2)$alkylamino, and phenyl; in conjunction with any of the above or below embodiments.

The invention also relates to compounds of Formula II' wherein $R^a$ is H; in conjunction with any of the above or below embodiments.

The invention also relates to compounds of Formula II' wherein $R^2$ is 3-trifluoromethylphenyl; in conjunction with any of the above or below embodiments.

The invention also relates to compounds of Formula II' wherein $R^2$ is 3,4-dichlorophenyl; in conjunction with any of the above or below embodiments.

The invention also relates to compounds of Formula II' wherein $R^2$ is 4-tert-butylphenyl; in conjunction with any of the above or below embodiments.

The invention also relates to compounds of Formula II' wherein $R^2$ is 2-naphthyl; in conjunction with any of the above or below embodiments.

The invention also relates to compounds of Formula II' wherein $R^2$ is substituted benzothienyl; in conjunction with any of the above or below embodiments.

The invention also relates to compounds of Formula II' wherein $R^2$ is 5-chloro-3-methylbenzothienyl; in conjunction with any of the above or below embodiments.

The invention also relates to compounds of Formula II' wherein $R^2$ is 5-chlorobenzothienyl; in conjunction with any of the above or below embodiments.

The invention also relates to compounds of Formula II' wherein $R^1$ is substituted phenyl; in conjunction with any of the above or below embodiments.

The invention also relates to compounds of Formula II' wherein $R^1$ is 4-fluorophenyl; in conjunction with any of the above or below embodiments.

The invention also relates to compounds of Formula II' wherein $R^1$ is 3-fluorophenyl; in conjunction with any of the above or below embodiments.

The invention also relates to compounds of Formula II' wherein $R^1$ is 2-fluorophenyl; in conjunction with any of the above or below embodiments.

The invention also relates to compounds of Formula II' wherein $R^1$ is 3-chlorophenyl; in conjunction with any of the above or below embodiments.

The invention also relates to compounds of Formula II' wherein $R^1$ is 3,5-dichlorophenyl; in conjunction with any of the above or below embodiments.

The invention also relates to compounds of Formula II' wherein $R^1$ is 3-nitrophenyl; in conjunction with any of the above or below embodiments.

The invention also relates to compounds of Formula II' wherein $R^1$ is 3-cyanophenyl; in conjunction with any of the above or below embodiments.

The invention also relates to compounds of Formula II' wherein $R^1$ is 4-chlorophenyl; in conjunction with any of the above or below embodiments.

The invention also relates to compounds of Formula II' wherein $R^1$ is 4-methoxyphenyl; in conjunction with any of the above or below embodiments.

The invention also relates to compounds of Formula II' and/or pharmaceutically acceptable derivatives thereof selected from 3-(naphthalen-2-ylsulfonylamino)-3-phenyl-N-(7-piperidin-1-ylmethyl-chroman-4-yl)-propionamide;

N-[7-(4-methyl-piperazin-1-ylmethyl)-chroman-4-yl]-3-(naphthyl-2-ylsulfonylamino)-3-phenyl-propionamide;

3-(naphthalen-2-ylsulfonylamino)-3-phenyl-N-(7-pyrrolidin-1-ylmethyl-chroman-4-yl)-propionamide;

3-phenyl-N-(7-piperidin-1-ylmethyl-chroman-4-yl)-3-(3-trifluoromethyl-benzenesulfonylamino)-propionamide;

3-(3,4-Dichloro-benzenesulfonylamino)-3-phenyl-N-(7-piperidin-1-ylmethyl-chroman-4-yl)-propionamide;

3-(3,5-dichloro-benzenesulfonylamino)-3-phenyl-N-(7-piperidin-1-ylmethyl-chroman-4-yl)-propionamide;

N-[7-(isopropylamino-methyl)-chroman-4-yl]-3-(naphthalen-2-ylsulfonylamino)-3-phenyl-propionamide;

N-{7-[(isopropyl-methyl-amino)-methyl]-chroman-4-yl}-3-(naphthalen-2-yl-sulfonylamino)-3-phenyl-propionamide;

N-{7-[(ethyl-isopropyl-amino)-methyl]-chroman-4-yl}-3-(naphthalen-2-yl-sulfonylamino)-3-phenyl-propionamide;

N-{7-[(isobutyl-methyl-amino)-methyl]-chroman-4-yl}-3-(naphthalen-2-yl-sulfonylamino)-3-phenyl-propionamide;

N-{7-[(tert-butyl-methyl-amino)-methyl]-chroman-4-yl}-3-(naphthalen-2-yl-sulfonylamino)-3-phenyl-propionamide;

N-{7-[(tert-butyl-ethyl-amino)-methyl]-chroman-4-yl}-3-(naphthalen-2-yl-sulfonylamino)-3-phenyl-propionamide;

N-[7-(2R, 5R-dimethyl-pyrrolidin-1-ylmethyl)-chroman-4-yl]-3-(naphthalen-2-yl-sulfonylamino)-3-phenyl-propionamide;

N-[7-(tert-butylamino-methyl)-chroman-4-yl]-3-(naphthalen-2-yl-sulfonylamino)-3-phenyl-propionamide;

N-(7-morpholin-4-ylmethyl-chroman-4-yl)-3-(naphthalen-2-yl-sulfonylamino)-3-phenyl-propionamide;

N-(7-diethylaminomethyl-chroman-4-yl)-3-(naphthalen-2-yl-sulfonylamino)-3-phenyl-propionamide;

3-(naphthalen-2-yl-sulfonylamino)-3-phenyl-N-(4-piperidin-1-ylmethyl-indan-1-yl)-propionamide;

3-(naphthalen-2-yl-sulfonylamino)-3-phenyl-N-(5-piperidin-1-ylmethyl-indan-1-yl)-propionamide;

3-(naphthalen-2-yl-sulfonylamino)-3-phenyl-N-(6-piperidin-1-ylmethyl-1,2,3,4-tetrahydro-naphthalen-1-yl)-propionamide;

3-(naphthalen-2-yl-sulfonylamino)-N-(1-methyl-2,2-dioxo-7-piperidin-1-ylmethyl-1,2,3,4-tetrahydro-2×6-benzo[c][1,2]thiazin-4-yl)-3-phenyl-propionamide; and 3-(naphthalen-2-yl-sulfonylamino)-3-(R)-phenyl-N—(R)—(7-piperidin-1-ylmethyl-chroman-4-yl)-propionamide.

The invention also relates to compounds of Formula III'

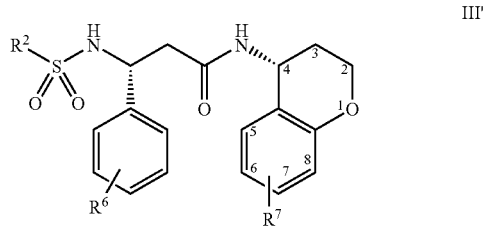

wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from H, halo, phenyl, methyl, methoxy and —$CF_3$;

wherein $R^7$ is selected from

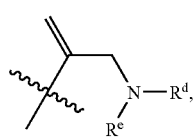

$C_{3-6}$-cycloalkyl($C_1$-$C_2$)alkylamino($C_1$-$C_2$)alkyl, $C_{3-6}$-cycloalkylamino($C_1$-$C_2$)alkyl, ($C_1$-$C_2$)alkoxy($C_1$-$C_2$)alkylamino($C_1$-$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5-8 membered heterocyclyl-$C_{1-4}$-alkyl; wherein the 5-8 membered heterocyclyl-$(CH_2)_p$— optionally substituted with one to three groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$—C(O)N$R^8R^{8'}$, —N$R^8$C(O)$R^{8'}$, =NCN;

wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein $R^e$ is H; or where $R^d$ and $R^e$ together with the nitrogen atom which they are attached form a 4-8 membered nitrogen-containing heterocyclic ring;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 6, 7 or 8;

and pharmaceutically acceptable derivatives thereof.

The invention also relates to compounds of Formula III' wherein $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminoethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,41-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof; in conjunction with any of the above or below embodiments.

The invention also relates to compounds of Formula III' wherein $R^7$ is substituted at position 7; in conjunction with any of the above or below embodiments.

The invention also relates to compounds of Formula III' wherein $R^2$ is 3-trifluoromethylphenyl; in conjunction with any of the above or below embodiments.

The invention also relates to compounds of Formula III' wherein $R^2$ is 3,4-dichlorophenyl; in conjunction with any of the above or below embodiments.

The invention also relates to compounds of Formula III' wherein $R^2$ is 4-tert-butylphenyl; in conjunction with any of the above or below embodiments.

The invention also relates to compounds of Formula III' wherein $R^2$ is 2-naphthyl; in conjunction with any of the above or below embodiments.

The invention also relates to compounds of Formula III' wherein $R^2$ is substituted benzothienyl; in conjunction with any of the above or below embodiments.

The invention also relates to compounds of Formula III' wherein $R^2$ is 5-chloro-3-methylbenzothienyl; in conjunction with any of the above or below embodiments.

The invention also relates to compounds of Formula III' wherein $R^2$ is 5-chlorobenzothienyl; in conjunction with any of the above or below embodiments.

The invention also relates to compounds of Formula III' wherein $R^1$ is substituted phenyl; in conjunction with any of the above or below embodiments.

The invention also relates to compounds of Formula III' wherein $R^1$ is 4-fluorophenyl; in conjunction with any of the above or below embodiments.

The invention also relates to compounds of Formula III' wherein $R^1$ is 3-fluorophenyl; in conjunction with any of the above or below embodiments.

The invention also relates to compounds of Formula III' wherein $R^1$ is 2-fluorophenyl; in conjunction with any of the above or below embodiments.

The invention also relates to compounds of Formula III' wherein $R^1$ is 3-chlorophenyl; in conjunction with any of the above or below embodiments.

The invention also relates to compounds of Formula III' wherein $R^1$ is 3,5-dichlorophenyl; in conjunction with any of the above or below embodiments.

The invention also relates to compounds of Formula III' wherein $R^1$ is 3-nitrophenyl; in conjunction with any of the above or below embodiments.

The invention also relates to compounds of Formula III' wherein $R^1$ is 3-cyanophenyl; in conjunction with any of the above or below embodiments.

The invention also relates to compounds of Formula III' wherein $R^1$ is 4-chlorophenyl; in conjunction with any of the above or below embodiments.

The invention also relates to compounds of Formula III' wherein $R^1$ is 4-methoxyphenyl; in conjunction with any of the above or below embodiments.

The invention also relates to compounds of Formula III' wherein $R^2$ is 2-naphthyl, 3,4-dichlorophenyl or 3-trifluoromethylphenyl; in conjunction with any of the above or below embodiments.

The invention also relates to compounds of Formula III' wherein $R^6$ is H; in conjunction with any of the above or below embodiments.

The invention also relates to compounds of Formula IV'

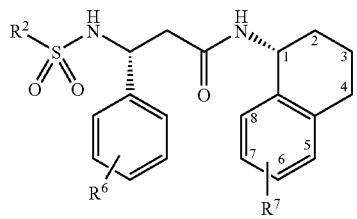

IV' wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from H, halo, phenyl, methyl, methoxy and $-CF_3$;

wherein $R^7$ is selected from

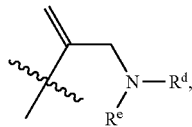

$C_{3-6}$-cycloalkyl($C_1$-$C_2$)alkylamino($C_1$-$C_2$)alkyl, $C_{3-6}$-cycloalkylamino($C_1$-$C_2$)alkyl, ($C_1$-$C_2$)alkoxy($C_1$-$C_2$)alkylamino($C_1$-$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5-8 membered heterocyclyl-$C_{1-4}$-alkyl; wherein the 5-8 membered heterocyclyl-$(CH_2)_p$- optionally substituted with one to three groups independently selected from halo, $-NH_2$, $-OH$, $-CN$, $-CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, $-C(O)R^8$, $-COOR^8$, $-C(O)NR^8R^{8'}$, $-NR^8C(O)R^{8'}$, $=NCN$;

wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein $R^e$ is H; or where $R^d$ and $R^e$ together with the nitrogen atom to which they are attached form a 4-8 membered nitrogen-containing heterocyclic ring;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 5, 6 or 7; and pharmaceutically acceptable derivatives thereof.

The invention also relates to compounds of Formula IV' wherein $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof; in conjunction with any of the above or below embodiments.

The invention also relates to compounds of Formula IV' wherein $R^7$ is substituted at position 6; in conjunction with any of the above or below embodiments.

The invention also relates to compounds of Formula IV' wherein $R^2$ is 3-trifluoromethylphenyl; in conjunction with any of the above or below embodiments.

The invention also relates to compounds of Formula IV' wherein $R^2$ is 3,4-dichlorophenyl; in conjunction with any of the above or below embodiments.

The invention also relates to compounds of Formula IV' wherein $R^2$ is 4-tert-butylphenyl; in conjunction with any of the above or below embodiments.

The invention also relates to compounds of Formula IV' wherein $R^2$ is 2-naphthyl; in conjunction with any of the above or below embodiments.

The invention also relates to compounds of Formula IV' wherein $R^2$ is substituted benzothienyl; in conjunction with any of the above or below embodiments.

The invention also relates to compounds of Formula IV' wherein $R^2$ is 5-chloro-3-methylbenzothienyl; in conjunction with any of the above or below embodiments.

The invention also relates to compounds of Formula IV' wherein $R^2$ is 5-chlorobenzothienyl; in conjunction with any of the above or below embodiments.

The invention also relates to compounds of Formula IV' wherein $R^1$ is substituted phenyl; in conjunction with any of the above or below embodiments.

The invention also relates to compounds of Formula IV' wherein $R^1$ is 4-fluorophenyl; in conjunction with any of the above or below embodiments.

The invention also relates to compounds of Formula IV' wherein $R^1$ is 3-fluorophenyl; in conjunction with any of the above or below embodiments.

The invention also relates to compounds of Formula IV' wherein $R^1$ is 2-fluorophenyl; in conjunction with any of the above or below embodiments.

The invention also relates to compounds of Formula IV' wherein $R^1$ is 3-chlorophenyl; in conjunction with any of the above or below embodiments.

The invention also relates to compounds of Formula IV' wherein $R^1$ is 3,5-dichlorophenyl; in conjunction with any of the above or below embodiments.

The invention also relates to compounds of Formula IV' wherein $R^1$ is 3-nitrophenyl; in conjunction with any of the above or below embodiments.

The invention also relates to compounds of Formula IV' wherein $R^1$ is 3-cyanophenyl; in conjunction with any of the above or below embodiments.

The invention also relates to compounds of Formula IV' wherein $R^1$ is 4-chlorophenyl; in conjunction with any of the above or below embodiments.

The invention also relates to compounds of Formula IV' wherein $R^1$ is 4-methoxyphenyl; in conjunction with any of the above or below embodiments.

The invention also relates to compounds of Formula IV' wherein $R^6$ is H; in conjunction with any of the above or below embodiments.

The invention also relates to compounds of Formula V'

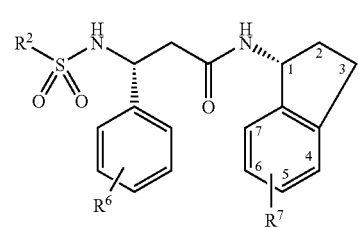

wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from H, halo, phenyl, methyl, methoxy and —$CF_3$;

wherein $R^7$ is selected from

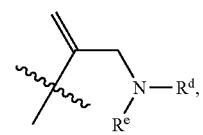

$C_{3-6}$-cycloalkyl($C_1$-$C_2$)alkylamino($C_1$-$C_2$)alkyl, $C_{3-6}$-cycloalkylamino($C_1$-$C_2$)alkyl, ($C_1$-$C_2$)alkoxy($C_1$-$C_2$)alkylamino($C_1$-$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5-8 membered heterocyclyl-$C_{1-4}$-alkyl; wherein the 5-8 membered heterocyclyl-$(CH_2)_p$- optionally substituted with one to three groups independently selected from halo, —$NH_2$, —OH, —CN, —$CF_3$, ($C_1$-$C_6$)alkylamino, oxo, ($C_1$-$C_6$)alkoxy, ($C_2$-$C_6$) alkenyl, ($C_2$-$C_6$)alkynyl, di($C_1$-$C_6$)alkylamino, —C(O)$R^8$, —COO$R^8$—C(O)N$R^8R^{8'}$, —N$R^8$C(O)$R^{8'}$, =NCN;

wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein $R^e$ is H; or where $R^d$ and $R^e$ together with the nitrogen atom which they are attached form a 4-8 membered nitrogen-containing heterocyclic ring;

p is 1 or 2; and wherein $R^8$ and $R^8$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 4, 5 or 6;

and pharmaceutically acceptable derivatives thereof.

The invention also relates to compounds of Formula V' wherein $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof; in conjunction with any of the above or below embodiments.

The invention also relates to compounds of Formula V' wherein $R^7$ is substituted at position 5; in conjunction with any of the above or below embodiments.

The invention also relates to compounds of Formula V' wherein $R^2$ is 3-trifluoromethylphenyl; in conjunction with any of the above or below embodiments.

The invention also relates to compounds of Formula V' wherein $R^2$ is 3,4-dichlorophenyl; in conjunction with any of the above or below embodiments.

The invention also relates to compounds of Formula V' wherein $R^2$ is 4-tert-butylphenyl; in conjunction with any of the above or below embodiments.

The invention also relates to compounds of Formula V' wherein $R^2$ is 2-naphthyl; in conjunction with any of the above or below embodiments.

The invention also relates to compounds of Formula V' wherein $R^2$ is substituted benzothienyl; in conjunction with any of the above or below embodiments.

The invention also relates to compounds of Formula V' wherein $R^2$ is 5-chloro-3-methylbenzothienyl; in conjunction with any of the above or below embodiments.

The invention also relates to compounds of Formula V' wherein $R^2$ is 5-chlorobenzothienyl; in conjunction with any of the above or below embodiments.

The invention also relates to compounds of Formula V' wherein $R^1$ is substituted phenyl; in conjunction with any of the above or below embodiments.

The invention also relates to compounds of Formula V' wherein $R^1$ is 4-fluorophenyl; in conjunction with any of the above or below embodiments.

The invention also relates to compounds of Formula V' wherein $R^1$ is 3-fluorophenyl; in conjunction with any of the above or below embodiments.

The invention also relates to compounds of Formula V' wherein $R^1$ is 2-fluorophenyl; in conjunction with any of the above or below embodiments.

The invention also relates to compounds of Formula V' wherein $R^1$ is 3-chlorophenyl; in conjunction with any of the above or below embodiments.

The invention also relates to compounds of Formula V' wherein $R^1$ is 3,5-dichlorophenyl; in conjunction with any of the above or below embodiments.

The invention also relates to compounds of Formula V' wherein $R^1$ is 3-nitrophenyl; in conjunction with any of the above or below embodiments.

The invention also relates to compounds of Formula V' wherein $R^1$ is 3-cyanophenyl; in conjunction with any of the above or below embodiments.

The invention also relates to compounds of Formula V' wherein $R^1$ is 4-chlorophenyl; in conjunction with any of the above or below embodiments.

The invention also relates to compounds of Formula V' wherein $R^1$ is 4-methoxyphenyl; in conjunction with any of the above or below embodiments.

The invention also relates to compounds of Formula V' wherein $R^6$ is H; in conjunction with any of the above or below embodiments.

The invention also relates to compounds of Formula VI'

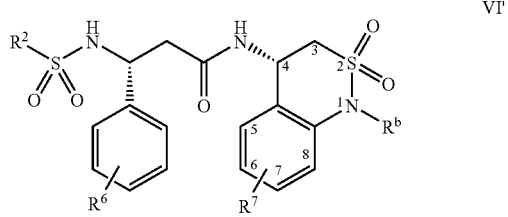

wherein $R^b$ is selected from H and $C_{1-3}$ alkyl;

wherein $R^2$ is selected from naphthyl, phenyl, pyridinyl, quinolinyl and isoquinolinyl, and wherein each is optionally substituted with one to three substituents selected from chloro, fluoro, methoxy, methyl, trifluoromethyl, and phenyl;

wherein $R^6$ is selected from halo, phenyl, methyl, methoxy and —$CF_3$;

wherein $R^7$ is selected from

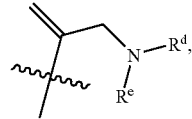

$C_{3-6}$-cycloalkyl($C_1$-$C_2$)alkylamino($C_1$-$C_2$)alkyl, $C_{3-6}$-cycloalkylamino($C_1$-$C_2$)alkyl, ($C_1$-$C_2$)alkoxy($C_1$-$C_2$)alkylamino($C_1$-$C_2$)alkyl, mono-$C_{2-4}$-alkenylamino-$C_{1-4}$-alkyl, di-$C_{2-4}$-alkenylamino-$C_{1-4}$-alkyl, hydroxy-$C_{1-4}$-alkylamino-$C_{1-4}$-alkyl, aminocarbonyl-$C_{1-4}$-alkylamino-$C_{1-2}$-alkyl, mono-$C_{1-6}$-alkylamino-$C_{1-4}$-alkyl, di-$C_{1-4}$-alkylamino-$C_{1-4}$-alkyl and 5-8 membered heterocyclyl-$C_{1-4}$-alkyl; wherein the 5-8 membered heterocyclyl-$(CH_2)_p$- optionally substituted with one to three groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —$C(O)R^8$, —$COOR^8$—$C(O)NR^8R^{8'}$, —$NR^8C(O)R^{8'}$, =NCN;

wherein $R^d$ is selected from $C_{1-5}$-alkyl, $C_{3-6}$-cycloalkyl, $C_{3-6}$-cycloalkyl-$C_{1-4}$-alkyl, $C_{1-4}$-hydroxyalkyl, $C_{1-3}$-alkoxy-$C_{1-3}$-alkyl and H; and wherein $R^e$ is H; or where $R^d$ and $R^e$ together with the nitrogen atom which they are attached form a 4-8 membered nitrogen-containing heterocyclic ring;

p is 1 or 2; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

wherein $R^7$ is at position 6, 7 or 8;

and pharmaceutically acceptable derivatives thereof.

The invention also relates to compounds of Formula VI' wherein $R^7$ is selected from aminomethyl, aminoethyl, aminopropyl, isopropylaminomethyl, t-butylaminomethyl, isobutylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl) ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl;

and pharmaceutically acceptable derivatives thereof; in conjunction with any of the above or below embodiments.

The invention also relates to compounds of Formula VI' wherein $R^7$ is substituted at position 7; in conjunction with any of the above or below embodiments.

The invention also relates to compounds of Formula VI' wherein $R^2$ is 3-trifluoromethylphenyl; in conjunction with any of the above or below embodiments.

The invention also relates to compounds of Formula VI' wherein $R^2$ is 3,4-dichlorophenyl; in conjunction with any of the above or below embodiments.

The invention also relates to compounds of Formula VI' wherein $R^2$ is 4-tert-butylphenyl; in conjunction with any of the above or below embodiments.

The invention also relates to compounds of Formula VI' wherein $R^2$ is 2-naphthyl; in conjunction with any of the above or below embodiments.

The invention also relates to compounds of Formula VI' wherein $R^2$ is substituted benzothienyl; in conjunction with any of the above or below embodiments.

The invention also relates to compounds of Formula VI' wherein $R^2$ is 5-chloro-3-methylbenzothienyl; in conjunction with any of the above or below embodiments.

The invention also relates to compounds of Formula VI' wherein $R^2$ is 5-chlorobenzothienyl; in conjunction with any of the above or below embodiments.

The invention also relates to compounds of Formula VI' wherein $R^1$ is substituted phenyl; in conjunction with any of the above or below embodiments.

The invention also relates to compounds of Formula VI' wherein $R^1$ is 4-fluorophenyl; in conjunction with any of the above or below embodiments.

The invention also relates to compounds of Formula VI' wherein $R^1$ is 3-fluorophenyl; in conjunction with any of the above or below embodiments.

The invention also relates to compounds of Formula VI' wherein $R^1$ is 2-fluorophenyl; in conjunction with any of the above or below embodiments.

The invention also relates to compounds of Formula VI' wherein $R^1$ is 3-chlorophenyl; in conjunction with any of the above or below embodiments.

The invention also relates to compounds of Formula VI' wherein $R^1$ is 3,5-dichlorophenyl; in conjunction with any of the above or below embodiments.

The invention also relates to compounds of Formula VI' wherein $R^1$ is 3-nitrophenyl; in conjunction with any of the above or below embodiments.

The invention also relates to compounds of Formula VI' wherein $R^1$ is 3-cyanophenyl; in conjunction with any of the above or below embodiments.

The invention also relates to compounds of Formula VI' wherein $R^1$ is 4-chlorophenyl; in conjunction with any of the above or below embodiments.

The invention also relates to compounds of Formula VI' wherein $R^1$ is 4-methoxyphenyl; in conjunction with any of the above or below embodiments.

The invention also relates to compounds of Formula VI' wherein $R^6$ is H; in conjunction with any of the above or below embodiments.

A family of specific compounds of particular interest within Formula I consists of compounds and pharmaceutically-acceptable salts thereof as follows:

3-(naphthalen-2-ylsulfonylamino)-3-phenyl-N-(7-piperidin-1-ylmethyl-chroman-4-yl)-propionamide;

N-[7-(4-methyl-piperazin-1-ylmethyl)-chroman-4-yl]-3-(naphthyl-2-ylsulfonylamino)-3-phenyl-propionamide;

3-(naphthalen-2-ylsulfonylamino)-3-phenyl-N-(7-pyrrolidin-1-ylmethyl-chroman-4-yl)-propionamide;

3-phenyl-N-(7-piperidin-1-ylmethyl-chroman-4-yl)-3-(3-trifluoromethyl-benzenesulfonylamino)-propionamide;

3-(3,4-Dichloro-benzenesulfonylamino)-3-phenyl-N-(7-piperidin-1-ylmethyl-chroman-4-yl)-propionamide;

3-(3,5-dichloro-benzenesulfonylamino)-3-phenyl-N-(7-piperidin-1-ylmethyl-chroman-4-yl)-propionamide;

N-[7-(isopropylamino-methyl)-chroman-4-yl]-3-(naphthalen-2-ylsulfonylamino)-3-phenyl-propionamide;

N-{7-[(isopropyl-methyl-amino)-methyl]-chroman-4-yl}-3-(naphthalen-2-yl-sulfonylamino)-3-phenyl-propionamide;

N-{7-[(ethyl-isopropyl-amino)-methyl]-chroman-4-yl}-3-(naphthalen-2-yl-sulfonylamino)-3-phenyl-propionamide;

N-{7-[(isobutyl-methyl-amino)-methyl]-chroman-4-yl}-3-(naphthalen-2-yl-sulfonylamino)-3-phenyl-propionamide;

N-{7-[(tert-butyl-methyl-amino)-methyl]-chroman-4-yl}-3-(naphthalen-2-yl-sulfonylamino)-3-phenyl-propionamide;

N-{7-[(tert-butyl-ethyl-amino)-methyl]-chroman-4-yl}-3-(naphthalen-2-yl-sulfonylamino)-3-phenyl-propionamide;

N-[7-(2R, 5R-dimethyl-pyrrolidin-1-ylmethyl)-chroman-4-yl]-3-(naphthalen-2-yl-sulfonylamino)-3-phenyl-propionamide;

N-[7-(tert-butylamino-methyl)-chroman-4-yl]-3-(naphthalen-2-yl-sulfonylamino)-3-phenyl-propionamide;

N-(7-morpholin-4-ylmethyl-chroman-4-yl)-3-(naphthalen-2-yl-sulfonylamino)-3-phenyl-propionamide;

N-(7-diethylaminomethyl-chroman-4-yl)-3-(naphthalen-2-yl-sulfonylamino)-3-phenyl-propionamide;

3-(naphthalen-2-yl-sulfonylamino)-3-phenyl-N-(4-piperidin-1-ylmethyl-indan-1-yl)-propionamide;

3-(naphthalen-2-yl-sulfonylamino)-3-phenyl-N-(5-piperidin-1-ylmethyl-indan-1-yl)-propionamide;

3-(naphthalen-2-yl-sulfonylamino)-3-phenyl-N-(6-piperidin-1-ylmethyl-1,2,3,4-tetrahydro-naphthalen-1-yl)-propionamide;

3-(naphthalen-2-yl-sulfonylamino)-N-(1-methyl-2,2-dioxo-7-piperidin-1-ylmethyl-1,2,3,4-tetrahydro-2$\lambda^6$-benzo[c][1,2]thiazin-4-yl)-3-phenyl-propionamide; and 3-(naphthalen-2-yl-sulfonylamino)-3-(R)-phenyl-N—(R)—(7-piperidin-1-ylmethyl-chroman-4-yl)-propionamide.

A family of specific compounds of particular interest within Formula I' consists of compounds and pharmaceutically-acceptable salts thereof as follows:

3-(Naphthalen-2-ylsulfonylamino)-3-phenyl-N-(7-piperidin-1-ylmethyl-chroman-4-yl)-propionamide;

3-(3,4-Dichloro-benzenesulfonylamino)-3-phenyl-N-(7-piperidin-1-ylmethyl-chroman-4-yl)-propionamide;

3-(Naphthalen-2-yl-sulfonylamino)-3-phenyl-N-(5-piperidin-1-ylmethyl-indan-1-yl)-propionamide;

3-(Naphthalen-2-yl-sulfonylamino)-3-phenyl-N-(6-piperidin-1-ylmethyl-1,2,3,4-tetrahydro-naphthalen-1-yl)-propionamide;

(3S)-N-((1R)-6-(((1,1-dimethylethyl)amino)-methyl)-1,2,3,4-tetrahydro-1-naphthalenyl)-3-(4-fluorophenyl)-3-(((3-(trifluoromethyl)phenyl)-sulfonyl)amino)propanamide;

(3R)-3-phenyl-N-((1R)-6-(1-piperidinylmethyl)-1,2,3,4-tetrahydro-1-naphthalenyl)-3-(((3-(trifluoromethyl)phenyl)sulfonyl)amino)propanamide;

(3R)-N-((1R)-6-((4-fluoro-1-piperidinyl)methyl)-1,2,3,4-tetrahydro-1-naphthalenyl)-3-phenyl-3-(((3-(trifluoromethyl)phenyl)-sulfonyl)amino)propanamide;

(3R)-N-((1R)-5-((4,4-difluoro-1-piperidinyl)methyl)-2,3-dihydro-1H-inden-1-yl)-3-phenyl-3-(((3-(trifluoromethyl) phenyl)sulfonyl)amino)propanamide;

(3R)-N-((1R)-6-((cyclopentylamino)methyl)-1,2,3,4-tetrahydro-1-naphthalenyl)-3-(4-fluorophenyl)-3-(((3-(trifluoromethyl)phenyl)sulfonyl)-amino)propanamide;

(3R)-3-(4-fluorophenyl)-N-((1R)-6-(1-pyrrolidinylmethyl)-1,2,3,4-tetrahydro-1-naphthalenyl)-3-(((3-(trifluoromethyl)phenyl)sulfonyl)-amino)propanamide;

(3R)-N-((1R)-6-((4,4-difluoro-1-piperidinyl)methyl)-1,2,3,4-tetrahydro-1-naphthalenyl)-3-phenyl-3-(((3-(trifluoromethyl)phenyl)-sulfonyl)amino)propanamide;

(3R)-3-(methyl((3-(trifluoromethyl)phenyl)sulfonyl)amino)-3-phenyl-N-((1R)-6-(1-piperidinylmethyl)-1,2,3,4-tetrahydro-1-naphthalenyl)propanamide;

(3R)-3-(((5-chloro-3-methyl-1-benzothien-2-yl)sulfonyl)amino)-N-(6-(((1,1-dimethylethyl)amino)methyl)-1,2,3,4-tetrahydro-1-naphthalenyl)-3-phenylpropanamide;

(3R)-3-(((5-chloro-3-methyl-1-benzothien-2-yl)sulfonyl)amino)-3-phenyl-N-(6-(1-piperidinylmethyl)-1,2,3,4-tetrahydro-1-naphthalenyl)propanamide;

(3R)-N-((1R)-6-(3,6-dihydro-1(2H)-pyridinylmethyl)-1,2,3,4-tetrahydro-1-naphthalenyl)-3-phenyl-3-(((3-(trifluoromethyl)phenyl)sulfonyl)amino)propanamide;

(3R)-3-(((5-chloro-1-benzothien-2-yl)sulfonyl)amino)-3-(6-(methyloxy)-3-pyridinyl)-N-((1R)-6-(1-piperidinylmethyl)-1,2,3,4-tetrahydro-1-naphthalenyl)propanamide;

(3R)-3-(6-(methyloxy)-3-pyridinyl)-N-((1R)-6-(1-piperidinylmethyl)-1,2,3,4-tetrahydro-1-naphthalenyl)-3-(((3-(trifluoromethyl)phenyl)sulfonyl)amino)propanamide;

(3S)-3-(4-fluorophenyl)-N-((1R)-6-(1-piperidinylmethyl)-1,2,3,4-tetrahydro-1-naphthalenyl)-3-(((3-(trifluoromethyl)phenyl)sulfonyl)amino)propanamide;

(3R)-3-(((3,4-dichlorophenyl)sulfonyl)amino)-N-((1R)-6-(((1,1-dimethylethyl)amino)methyl)-1,2,3,4-tetrahydro-1-naphthalenyl)-3-phenylpropanamide;

(3R)-N-((1R)-6-((cyclopentylamino)methyl)-1,2,3,4-tetrahydro-1-naphthalenyl)-3-(((3,4-dichlorophenyl)sulfonyl)amino)-3-phenylpropanamide;

(3R)-3-(((3,4-dichlorophenyl)sulfonyl)amino)-N-((1R)-6-(((2-methylpropyl)amino)methyl)-1,2,3,4-tetrahydro-1-naphthalenyl)-3-phenylpropanamide;

(3R)-3-(((3,4-dichlorophenyl)sulfonyl)amino)-N-((1R)-6-(((1, 1-dimethylethyl)amino)methyl)-1,2,3,4-tetrahydro-1-naphthalenyl)-3-phenylpropanamide;

3-(3,4-Dichloro-benzenesulfonylamino)-3-(4-fluoro-phenyl)-N-(7-piperidin-1-ylmethyl-chroman-4-yl)-propionamide;

3-(4-Fluoro-phenyl)-N-(7-piperidin-1-ylmethyl-chroman-4-yl)-3-(3-trifluoromethyl-benzenesulfonylamino)-propionamide;

3-(3,4-Dichloro-benzenesulfonylamino)-3-(4-fluoro-phenyl)-N-{7-[(2-methoxy-ethylamino)-methyl]-chroman-4-yl}-propionamide;

3-(3,4-Dichloro-benzenesulfonylamino)-3-(4-fluoro-phenyl)-N-[6-(isobutylamino-methyl)-1,2,3,4-tetrahydro-naphthalen-1-yl]-propionamide;

3-(3,4-Dichloro-benzenesulfonylamino)-3-(4-fluoro-phenyl)-N-[6-(isopropylamino-methyl)-1,2,3,4-tetrahydro-naphthalen-1-yl]-propionamide;

3-(3,4-Dichloro-benzenesulfonylamino)-3-(4-fluoro-phenyl)-N-{6-[(2-methoxy-ethylamino)-methyl]-1,2,3,4-tetrahydro-naphthalen-1-yl}-propionamide;

N-[7-(tert-Butylamino-methyl)-chroman-4-yl]-3-(3,4-dichloro-benzenesulfonylamino)-3-(4-fluoro-phenyl)-propionamide;

N-[6-(tert-Butylamino-methyl)-1,2,3,4-tetrahydro-naphthalen-1-yl]-3-(3,4-dichloro-benzenesulfonylamino)-3-(4-fluoro-phenyl)-propionamide;

3-(4-Fluoro-phenyl)-N-[7-(isobutylamino-methyl)-chroman-4-yl]-3-(3-trifluoromethyl-benzenesulfonylamino)-propionamide;

N-[7-(tert-Butylamino-methyl)-chroman-4-yl]-3-(4-fluoro-phenyl)-3-(3-trifluoromethyl-benzenesulfonylamino)-propionamide;

N-(6-Cyclobutylaminomethyl-1,2,3,4-tetrahydro-naphthalen-1-yl)-3-(4-fluoro-phenyl)-3-(3-trifluoromethyl-benzenesulfonylamino)-propionamide;

3-(4-Fluoro-phenyl)-N-[6-(isobutylamino-methyl)-1,2,3,4-tetrahydro-naphthalen-1-yl]-3-(3-trifluoromethyl-benzenesulfonylamino)-propionamide;

3-(4-Fluoro-phenyl)-N-[6-(isopropylamino-methyl)-1,2,3,4-tetrahydro-naphthalen-1-yl]-3-(3-trifluoromethyl-benzenesulfonylamino)-propionamide;

3-(4-Fluoro-phenyl)-N-{6-[(2-methoxy-ethylamino)-methyl]-1,2,3,4-tetrahydro-naphthalen-1-yl}-3-(3-trifluoromethyl-benzenesulfonylamino)-propionamide;

3-(4-Fluoro-phenyl)-N-(7-pyrrolidin-1-ylmethyl-chroman-4-yl)-3-(3-trifluoromethyl-benzenesulfonylamino)-propionamide;

N-[6-(tert-Butylamino-methyl)-1,2,3,4-tetrahydro-naphthalen-1-yl]-3-(3-nitro-phenyl)-3-(3-trifluoromethyl-benzenesulfonylamino)-propionamide;

N-[6-(tert-Butylamino-methyl)-1,2,3,4-tetrahydro-naphthalen-1-yl]-3-(3-cyano-phenyl)-3-(3-trifluoromethyl-benzenesulfonylamino)-propionamide;

3-(4-tert-Butyl-benzenesulfonylamino)-N-(6-cyclobutylaminomethyl-1,2,3,4-tetrahydro-naphthalen-1-yl)-3-(4-fluoro-phenyl)-propionamide;

3-(4-tert-Butyl-benzenesulfonylamino)-3-(4-fluoro-phenyl)-N-(6-piperidin-1-ylmethyl-1,2,3,4-tetrahydro-naphthalen-1-yl)-propionamide;

3-(4-tert-Butyl-benzenesulfonylamino)-3-(4-fluoro-phenyl)-N-[6-(isobutylamino-methyl)-1,2,3,4-tetrahydro-naphthalen-1-yl]-propionamide;

N-[6-(tert-Butylamino-methyl)-1,2,3,4-tetrahydro-naphthalen-1-yl]-3-(4-tert-butyl-benzenesulfonylamino)-3-(4-fluoro-phenyl)-propionamide;

3-(3-Fluoro-phenyl)-N-(6-piperidin-1-ylmethyl-1,2,3,4-tetrahydro-naphthalen-1-yl)-3-(3-trifluoromethyl-benzenesulfonylamino)-propionamide;

N-(6-Cyclopentylaminomethyl-1,2,3,4-tetrahydro-naphthalen-1-yl)-3-(3,4-dichloro-benzenesulfonylamino)-3-(3-fluoro-phenyl)-propionamide;

N-[7-(tert-Butylamino-methyl)-6-chloro-chroman-4-yl]-3-(4-fluoro-phenyl)-3-(3-trifluoromethyl-benzenesulfonylamino)-propionamide;

3-(4-Fluoro-phenyl)-N-[6-(4-fluoro-piperidin-1-ylmethyl)-1,2,3,4-tetrahydro-naphthalen-1-yl]-3-(3-trifluoromethyl-benzenesulfonylamino)-propionamide;

3-(3-Chloro-phenyl)-3-(3,4-dichloro-benzenesulfonylamino)-N-(6-piperidin-1-ylmethyl-1,2,3,4-tetrahydro-naphthalen-1-yl)-propionamide;

3-(3,4-Dichloro-benzenesulfonylamino)-3-(3-fluoro-phenyl)-N-(6-piperidin-1-ylmethyl-1,2,3,4-tetrahydro-naphthalen-1-yl)-propionamide;

N-[6-(tert-Butylamino-methyl)-1,2,3,4-tetrahydro-naphthalen-1-yl]-3-(3,4-dichloro-benzenesulfonylamino)-3-(3-fluoro-phenyl)-propionamide;

N-[6-(tert-Butylamino-methyl)-1,2,3,4-tetrahydro-naphthalen-1-yl]-3-(3,4-dichloro-benzenesulfonylamino)-3-(3-fluoro-phenyl)-propionamide;

N-{7-[(Cyclopropylmethyl-amino)-methyl]-chroman-4-yl}-3-(4-fluoro-phenyl)-3-(3-trifluoromethyl-benzenesulfonylamino)-propionamide;

N-{6-[(Cyclopropylmethyl-amino)-methyl]-1,2,3,4-tetrahydro-naphthalen-1-yl}-3-(4-fluoro-phenyl)-3-(3-trifluoromethyl-benzenesulfonylamino)-propionamide;

N-[7-(tert-Butylamino-methyl)-chroman-4-yl]-3-(2-chloro-5-trifluoromethyl-benzenesulfonylamino)-3-(4-fluoro-phenyl)-propionamide;

N-[6-(tert-Butylamino-methyl)-1,2,3,4-tetrahydro-naphthalen-1-yl]-3-(4-nitro-phenyl)-3-(3-trifluoromethyl-benzenesulfonylamino)-propionamide;

3-(4-Chloro-phenyl)-N-(6-piperidin-1-ylmethyl-1,2,3,4-tetrahydro-naphthalen-1-yl)-3-(3-trifluoromethyl-benzenesulfonylamino)-propionamide;

3-(3,5-Dichloro-phenyl)-N-(6-piperidin-1-ylmethyl-1,2,3,4-tetrahydro-naphthalen-1-yl)-3-(3-trifluoromethyl-benzenesulfonylamino)-propionamide;

3-(2-Fluoro-phenyl)-N-(6-piperidin-1-ylmethyl-1,2,3,4-tetrahydro-naphthalen-1-yl)-3-(3-trifluoromethyl-benzenesulfonylamino)-propionamide;

3-(4-Fluoro-phenyl)-N-(6-piperidin-1-ylmethyl-1,2,3,4-tetrahydro-naphthalen-1-yl)-3-(3-trifluoromethyl-benzenesulfonylamino)-propionamide;

(3R)-3-Phenyl-N-((4R)-7-(1-piperidinylmethyl)-3,4-dihydro-2H-chromen-4-yl)-3-(((3-(trifluoromethyl)phenyl)sulfonyl)amino)propanamide;

(3R)-3-(((3,4-Dichlorophenyl)sulfonyl)amino)-3-phenyl-N-((4R)-7-(1-piperidinylmethyl)-3,4-dihydro-2H-chromen-4-yl)propanamide;

(3R)-3-(((3,4-Dichlorophenyl)sulfonyl)amino)-N-((4R)-7-(4-morpholinylmethyl)-3,4-dihydro-2H-chromen-4-yl)-3-phenylpropanamide;

(3R)-N-((4R)-7-(((1,1-Dimethylethyl)amino)methyl)-3,4-dihydro-2H-chromen-4-yl)-3-phenyl-3-(((3-(trifluoromethyl)phenyl)sulfonyl)amino)propanamide;

(3R)-3-((2-Naphthalenylsulfonyl)amino)-3-phenyl-N-((1S)-6-(1-piperidinylmethyl)-1,2,3,4-tetrahydro-1-naphthalenyl)propanamide;

(3R)-N-((4R)-1-Methyl-2,2-dioxido-7-(1-piperidinylmethyl)-3,4-dihydro-1H-2,1-benzothiazin-4-yl)-3-((2-naphthalenylsulfonyl)amino)-3-phenylpropanamide;

(3R)-3-((2-Naphthalenylsulfonyl)amino)-3-phenyl-N-((1S)-5-(1-piperidinylmethyl)-2,3-dihydro-1H-inden-1-yl)propanamide;

(3R)-N-((4R)-7-((4-Fluoro-1-piperidinyl)methyl)-3,4-dihydro-2H-chromen-4-yl)-3-phenyl-3-(((3-(trifluoromethyl)phenyl)sulfonyl)amino)propanamide;

(3R)-N-((4R)-7-((4,4-Difluoro-1-piperidinyl)methyl)-3,4-dihydro-2H-chromen-4-yl)-3-phenyl-3-(((3-(trifluoromethyl)phenyl)sulfonyl)amino)propanamide;

(3R)-3-(((3,4-dichlorophenyl)sulfonyl)amino)-3-phenyl-N-((1R)-6-(1-(1-piperidinylmethyl)ethenyl)-1,2,3,4-tetrahydro-1-naphthalenyl)propanamide;

(3R)-N-((1R)-6-(1-(((3S)-3-hydroxy-1-pyrrolidinyl)methyl)ethenyl)-1,2,3,4-tetrahydro-1-naphthalenyl)-3-phenyl-3-(((3-(trifluoromethyl)phenyl)sulfonyl)amino)propanamide;

(3R)-3-phenyl-N-((1R)-6-(1-(1-pyrrolidinylmethyl)ethenyl)-1,2,3,4-tetrahydro-1-naphthalenyl)-3-(((3-(trifluoromethyl)phenyl)sulfonyl)amino)propanamide;

(3R)-3-phenyl-N-((1R)-6-(1-(1-piperidinylmethyl)ethenyl)-1,2,3,4-tetrahydro-1-naphthalenyl)-3-(((3-(trifluoromethyl)phenyl)sulfonyl)amino)propanamide;

(3R)-3-((hydroxy(oxido)(3-(trifluoromethyl)phenyl)-lambda-4—sulfanyl)amino)-N-((1R)-6-((1R)-1-((2-methylpropyl)amino)ethyl)-1,2,3,4-tetrahydro-1-naphthalenyl)-3-phenylpropanamide;

(3R)-N-((1R)-6-((1R)-1-((2-methylpropyl)amino)ethyl)-1,2,3,4-tetrahydro-1-naphthalenyl)-3-((2-naphthalenylsulfonyl)amino)-3-phenylpropanamide.

Indications

The present invention also provides methods of using the compounds in for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The invention also provides for the use of the compounds of the present invention for the prevention or for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

Accordingly, the present invention also relates to the use of one or more of the compounds of the present invention in the manufacture of a medicament for the treatment of a disorder such as acute pain, dental pain, back pain, lower back pain, pain from trauma, surgical pain, pain resulting from amputation or abscess, causalgia, fibromyalgia, demyelinating diseases, trigeminal neuralgia, cancer, chronic alcoholism, stroke, thalamic pain syndrome, diabetes, acquired immune deficiency syndrome ("AIDS"), toxins and chemotherapy, general headache, migraine, cluster headache, mixed-vascular and non-vascular syndromes, tension headache, general inflammation, arthritis, rheumatic diseases, lupus, osteoarthritis, inflammatory bowel disorders, inflammatory eye disorders, inflammatory or unstable bladder disorders, psoriasis, skin complaints with inflammatory components, sunburn, carditis, dermatitis, myositis, neuritis, collagen vascular diseases, chronic inflammatory conditions, inflammatory pain and associated hyperalgesia and allodynia, neuropathic pain and associated hyperalgesia and allodynia, diabetic neuropathy pain, sympathetically maintained pain, deafferentation syndromes, asthma, vasomotor or allergic rhinitis, epithelial tissue damage or dysfunction, herpes simplex, post-herpetic neuralgia, disturbances of visceral motility at respiratory, genitourinary, gastrointestinal or vascular regions, wounds, burns, allergic skin reactions, pruritis, vitiligo, general gastrointestinal disorders, colitis, inflammatory bowel disease, gastric ulceration, duodenal ulcers, thalamic pain syndrome, diabetes, toxins and chemotherapy, septic shock, and bronchial disorders.

The compounds of this invention may also act as inhibitors of other receptors or kinases, and thus be effective in the treatment of diseases associated with other protein kinases.

Besides being useful for human treatment, these compounds are also useful for veterinary treatment of companion animals, exotic animals and farm animals, including mammals, rodents, and the like. More preferred animals include horses, dogs, and cats.

Definitions

The phrase "therapeutically-effective" is intended to qualify the amount of each agent, which will achieve the goal of improvement in disorder severity and the frequency of incidence over treatment of each agent by itself, while avoiding adverse side effects typically associated with alternative therapies. For example, effective pain therapeutic agents relieve the pain sensation of the patient. Alternatively, effective therapeutic agents for the treatment of inflammation minimize the damage from the inflammation, and the like.

The term "treatment" includes therapeutic treatment as well as prophylactic treatment (either preventing the onset of disorders altogether or delaying the onset of a preclinically evident stage of disorders in individuals).

The term "H" denotes a single hydrogen atom. This radical may be attached, for example, to an oxygen atom to form a hydroxyl radical.

Where the term "alkyl" is used, either alone or within other terms such as "haloalkyl", "cyanoalkyl" and "alkylamino", it embraces linear or branched radicals having one to about twenty carbon atoms or, preferably, one to about twelve carbon atoms, or as otherwise indicated. More preferred alkyl radicals are "lower alkyl" radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. Even more preferred are lower alkyl radicals having one to four carbon atoms. The term "alkylenyl" embraces bridging divalent alkyl radicals such as methylenyl and ethyleneyl.

The term "alkenyl" embraces linear or branched radicals having at least one carbon-carbon double bond of two to about twenty carbon atoms or, preferably, two to about twelve carbon atoms, or as otherwise indicated. More preferred alkenyl radicals are "lower alkenyl" radicals having two to about four carbon atoms. Examples of alkenyl radicals include ethenyl, 2-propenyl, allyl, butenyl and 4-methylbutenyl. The terms "alkenyl" and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms, or as otherwise indicated. More preferred alkynyl radicals are "lower alkynyl" radicals having two to about four carbon atoms. Examples of alkynyl radicals include ethynyl, 2-propynyl, and 4-methylbutynyl.

The term "halo" means halogens such as fluorine, chlorine, bromine or iodine atoms.

The term "haloalkyl" embraces radicals wherein any one or more of the alkyl carbon atoms is substituted with halo as defined above. Specifically embraced are monohaloalkyl, dihaloalkyl and polyhaloalkyl radicals including perhaloalkyl. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1-6 carbon atoms. Even more preferred are lower haloalkyl radicals having one to three carbon atoms. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl" means alkyl radicals having all hydrogen atoms replaced with fluoro atoms. Examples include trifluoromethyl and pentafluoroethyl.

The term "hydroxyalkyl", embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. Even more preferred are lower hydroxyalkyl radicals having one to three carbon atoms.

The term "alkoxy" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. Even more preferred are lower alkoxy radicals having one to three carbon atoms. The "alkoxy" radicals may be further substituted with one or more halo atoms, such as fluoro, chloro or bromo, to provide "haloalkoxy" radicals. Even more preferred are lower haloalkoxy radicals having one to three carbon atoms. Examples of such radicals include fluoromethoxy, chloromethoxy, trifluoromethoxy, trifluoroethoxy, fluoroethoxy, and fluoropropoxy.

The term "alkoxyalkyl" embraces linear or branched alkyl radicals having one to about ten carbon atoms any one of which may be substituted with one or more alkoxyl radicals. More preferred alkoxyalkyl radicals are "lower alkoxyalkyl" radicals repectively having one to six carbon atoms. Examples of such radicals include methoxymethyl, methoxyethyl, and the like. Even more preferred are lower alkoxyalkyl radicals respectivly having one to three carbon atoms alkyl radicals.

The term "aryl", alone or in combination, means a carbocyclic aromatic system containing one or two rings wherein such rings may be attached together in a pendent manner or may be fused. The term "aryl", embraces aromatic radicals such as phenyl, naphthyl, tetrahydronaphthyl, indane and biphenyl. More preferred aryl is phenyl. Said "aryl" group may have 1 to 3 substituents such as lower alkyl, hydroxyl, halo, haloalkyl, nitro, cyano, alkoxy, and lower alkylamino. Benzodioxolyl is considered aryl.

The term "heterocyclyl" embraces saturated, partially saturated and unsaturated heteroatom-containing ring radicals, where the heteroatoms may be selected from nitrogen, sulfur and oxygen. It does not include rings containing —O—O— or —S—S— portions. Said "heterocyclyl" group may have 1 to 3 substituents such as hydroxyl, halo, haloalkyl, cyano, lower alkyl, lower aralkyl, oxo, lower alkoxy, amino, and lower alkylamino.

Examples of saturated heterocyclic radicals include saturated 3 to 8-membered heteromonocyclic group containing 1 to 4 nitrogen atoms [e.g. pyrrolidinyl, imidazolidinyl, piperidino, piperazinyl]; saturated 3 to 8-membered heteromonocyclic group containing 1 to 2 oxygen atoms and 1 to 3 nitrogen atoms [e.g. morpholinyl]; saturated 3 to 8-membered heteromonocyclic group containing 1 to 2 sulfur atoms and 1 to 3 nitrogen atoms [e.g., thiazolidinyl]. Examples of partially saturated heterocyclyl radicals include dihydrothiophene, dihydropyran, dihydrofuran and dihydrothiazole.

Examples of unsaturated heterocyclic radicals, also termed "heteroaryl" radicals, include unsaturated 5 to 6 membered heteromonocyclyl groups containing 1 to 4 nitrogen atoms, for example, pyrrolyl, pyrrolinyl, imidazolyl, pyrazolyl, 2-pyridinyl, 3-pyridinyl, 4-pyridinyl, pyrimidinyl, pyrazinyl, pyridazinyl, triazolyl [e.g., 4H-1,2,4-triazolyl, 1H-1,2,3-triazolyl, 2H-1,2,3-triazolyl]; unsaturated 3 to 6-membered heteromonocyclic group containing an oxygen atom, for example, pyranyl, 2-furyanl, 3-furyanl, etc.; unsaturated 5 to 6-membered heteromonocyclic group containing a sulfur atom, for example, 2-thienyl, 3-thienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term also embraces radicals where heterocyclic radicals are fused/condensed with aryl radicals: unsaturated condensed heterocyclic group containing 1 to 5 nitrogen atoms, for example, indolinyl, isoindolinyl, indolizinyl, benzimidazolyl, quinolinyl, isoquinolinyl, indazolyl, benzotriazolyl, tetrazolopyridazinyl [e.g., tetrazolo [1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl].

The term also includes bridged, spiro and oxo-containing heterocyclic rings, such as 1,4-dioxa-8-aza-spiro[4.5]decyl, phthalimidyl, 1,4-dioxa-8-aza-spiro[4.5]decyl, and (1-azabicyclo[2.2.2]oct-3-yl).

Preferred heterocyclic radicals include five to ten membered fused or unfused radicals. More preferred examples of heteroaryl radicals include quinolinyl, isoquinolinyl, imidazolyl, pyridinyl, thienyl, thiazolyl, oxazolyl, furanyl, and pyrazinyl. Even more preferred heteroaryl radicals are 5- or 6-membered heteroaryl, containing one or two heteroatoms selected from sulfur, nitrogen and oxygen, selected from thienyl, furanyl, pyrrolyl, thiazolyl, oxazolyl, imidazolyl, pyrazolyl, isoxazolyl, isothiazolyl, pyridinyl, piperidinyl and pyrazinyl.

The term "sulfonyl", whether used alone or linked to other terms such as alkylsulfonyl, denotes respectively divalent radicals —$SO_2$—.

The terms "sulfamyl," "aminosulfonyl" and "sulfonamidyl," whether alone or used with terms such as "N-alkylaminosulfonyl", "N-arylaminosulfonyl", "N,N-dialkylaminosulfonyl" and "N-alkyl-N-arylaminosulfonyl", denotes a sulfonyl radical substituted with an amine radical, forming a sulfonamide (—$SO_2NH_2$).

The term "cycloalkylaminoalkyl" includes "N-cycloalkylaminoalkyl" and "N,N-dicycloalkylaminoalkyl" where alkyl radicals are independently substituted, respectively, with one cycloalkyl radical, or two cycloalkyl radicals. More preferred cycloalkylaminoalkyl radicals are "lower cycloalkylaminoalkyl", radicals having alkyl radicals with one to six carbon atoms. Even more preferred are lower cycloalkylaminoalkyl radicals having alkyl radicals with one to three carbon atoms. Examples of such lower alkylaminosulfonyl radicals include N-cyclohexylaminomethyl, and N-cyclopentylaminoethyl.

The term "cycloalkyl-alkylaminoalkyl" embraces cycloalkyl radicals as described above, attached to an alkylaminoalkyl radical. More preferred are lower cycloalkyl-alkylaminoalkyl radicals independently having alkyl radicals of one to three carbon atoms.

The term "N-arylaminoalkyl" denotes alkyl radicals substituted with an aryl radical. More preferred arylaminoalkyl radicals are "lower N-arylaminoalkyl" radicals having alkyl radicals of one to six carbon atoms. Even more preferred are phenylaminoalkyl radicals having one to three carbon atoms. Examples of such radicals include N-phenylaminomethyl and N-phenylaminoethyl.

The term "aralkylaminoalkyl" embraces aralkyl radicals as described above, attached to an aminoalkyl radical. More preferred are lower arylalkylaminoalkyl radicals independently having alkyl radicals of one to three carbon atoms.

The term "heterocyclylaminoalkyl" embraces heterocyclyl radicals as described above, attached to an aminoalkyl radical.

The term "heteroarylalkylaminoalkyl" embraces heteroarylalkyl radicals as described above, attached to an aminoalkyl radical. More preferred are lower heteroarylalkylaminoalkyl radicals having, independently, alkyl radicals of one to three carbon atoms.

The terms "carboxy" or "carboxyl", whether used alone or with other terms, such as "carboxyalkyl", denotes —$CO_2H$.

The term "carbonyl", whether used alone or with other terms, such as "aminocarbonyl", denotes —(C═O)—.

The terms "alkylcarbonyl" denotes carbonyl radicals which have been substituted with an alkyl radical. More preferred are "lower alkylcarbonyl" having lower alkyl radicals as described above attached to a carbonyl radical.

The terms "arylcarbonyl" denotes carbonyl radicals substituted with an aryl radical. More preferred are "optionally substituted phenylcarbonyl" radicals.

The terms "cycloalkylcarbonyl" denotes carbonyl radicals substituted with an cycloalkyl radical. More preferred are "optionally substituted cycloalkylcarbonyl" radicals, even more preferably containing $C_{3-6}$ cycloalkyl.

The terms "heterocyclylcarbonyl" denotes carbonyl radicals substituted with an heterocyclyl radical. More preferred are "optionally substituted 5-6 membered heterocyclylcarbonyl" radicals.

The term "aminocarbonyl" when used by itself or with other terms such as "aminocarbonylalkyl", "N-alkylaminocarbonyl", "N-arylaminocarbonyl", "N,N-dialkylaminocarbonyl", "N-alkyl-N-arylaminocarbonyl", "N-alkyl-N-hydroxyaminocarbonyl" and "N-alkyl-N-hydroxyaminocarbonylalkyl", denotes an amide group of the formula $H_2NC$(═O)—.

The terms "N-alkylaminocarbonyl" and "N,N-dialkylaminocarbonyl" denote aminocarbonyl radicals which have been substituted with one alkyl radical and independently with two alkyl radicals, respectively. More preferred are "lower alkylaminocarbonyl" having lower alkyl radicals as described above attached to an aminocarbonyl radical.

The terms "N-arylaminocarbonyl" and "N-alkyl-N-arylaminocarbonyl" denote aminocarbonyl radicals substituted, respectively, with one aryl radical, or one alkyl and one aryl radical.

The term "aminoalkyl" embraces linear or branched alkyl radicals having one to about ten carbon atoms any one of which may be substituted with one or more amino radicals. More preferred aminoalkyl radicals are "lower aminoalkyl" radicals having one to six carbon atoms and one or more amino radicals. Examples of such radicals include aminomethyl, aminoethyl, aminopropyl, aminobutyl and aminohexyl. Even more preferred are lower aminoalkyl radicals having one to three carbon atoms.

The term "alkylaminoalkyl" embraces aminoalkyl radicals having the nitrogen atom independently substituted with an alkyl radical. More preferred alkylaminoalkyl radicals are "lower alkylaminoalkyl" radicals having alkyl radicals of one to six carbon atoms. Even more preferred are lower alkylaminoalkyl radicals having alkyl radicals of one to three carbon atoms. Suitable alkylaminoalkyl radicals may be mono or dialkyl substituted, such as N-methylaminomethyl, N,N-dimethyl-aminoethyl, N,N-diethylaminomethyl and the like.

The term "heterocyclylalkyl" embraces heterocyclic-substituted alkyl radicals. More preferred heterocyclylalkyl radicals are "5- or 6-membered heteroarylalkyl" radicals having alkyl portions of one to six carbon atoms and a 5- or 6-membered heteroaryl radical. Even more preferred are lower heteroarylalkyl radicals having alkyl portions of one to three carbon atoms. Examples include such radicals as pyridinylmethyl and thienylmethyl.

The term "aralkyl" embraces aryl-substituted alkyl radicals. Preferable aralkyl radicals are "lower aralkyl", radicals having aryl radicals attached to alkyl radicals having one to six carbon atoms. Even more preferred are lower aralkyl radicals phenyl attached to alkyl portions having one to three carbon atoms. Examples of such radicals include benzyl, diphenylmethyl and phenylethyl. The aryl in said aralkyl may be additionally substituted with halo, alkyl, alkoxy, haloalkyl and haloalkoxy.

The term "arylalkenyl" embraces aryl-substituted alkenyl radicals. Preferable arylalkenyl radicals are "lower arylalkenyl" radicals having aryl radicals attached to alkenyl radicals having two to six carbon atoms. Examples of such radicals include phenylethenyl. The aryl in said arylalkenyl may be additionally substituted with halo, alkyl, alkoxy, haloalkyl and haloalkoxy.

The term "alkylthio" embraces radicals containing a linear or branched alkyl radical, of one to ten carbon atoms, attached to a divalent sulfur atom. Even more preferred are lower alkylthio radicals having one to three carbon atoms. An example of "alkylthio" is methylthio, ($CH_3S$—).

The term "haloalkylthio" embraces radicals containing a haloalkyl radical, of one to ten carbon atoms, attached to a divalent sulfur atom. Even more preferred are lower haloalkylthio radicals having one to three carbon atoms. An example of "haloalkylthio" is trifluoromethylthio.

The term "alkylsulfinyl" embraces radicals containing a linear or branched alkyl radical, of one to ten carbon atoms, attached to a divalent —S(═O)— atom. More preferred are lower alkylsulfinyl radicals having one to three carbon atoms.

The term "arylsulfinyl", embraces radicals containing an aryl radical, attached to a divalent —S(═O)— atom. Even more preferred are optionally substituted phenylsulfinyl radicals.

The term "haloalkylsulfinyl" embraces radicals containing a haloalkyl radical, of one to ten carbon atoms, attached to a divalent —S(═O)— atom. Even more preferred are lower haloalkylsulfinyl radicals having one to three carbon atoms.

The term "alkylamino" denotes amino groups which have been substituted with one alkyl radical and with two alkyl radicals, including terms "N-alkylamino" and "N,N-dialkylamino". More preferred alkylamino radicals are "lower alkylamino" radicals having one or two alkyl radicals of one to six carbon atoms, attached to a nitrogen atom. Even more preferred are lower alkylamino radicals having one to three carbon atoms. Suitable "alkylamino" may be mono or dialkylamino such as N-methylamino, N-ethylamino, N,N-dimethylamino, N,N-diethylamino and the like.

The term "arylamino" denotes amino groups which have been substituted with one or two aryl radicals, such as N-phenylamino. The "arylamino" radicals may be further substituted on the aryl ring portion of the radical.

The term "heteroarylamino" denotes amino groups which have been substituted with one or two heteroaryl radicals, such as N-thienylamino. The "heteroarylamino" radicals may be further substituted on the heteroaryl ring portion of the radical.

The term "aralkylamino" denotes amino groups which have been substituted with one or two aralkyl radicals. More preferred are phenyl-$C_1$-$C_3$-alkylamino radicals, such as N-benzylamino. The "aralkylamino" radicals may be further substituted on the aryl ring portion of the radical.

The term "alkylaminoalkylamino" denotes alkylamino groups which have been substituted with one or two alkylamino radicals. More preferred are $C_1$-$C_3$-alkylamino-$C_1$-$C_3$-alkylamino radicals.

The term "alkylaminoalkoxyalkoxy" embraces alkoxy radicals substituted with alkylaminoalkoxy radicals. More preferred alkylaminoalkoxyalkoxy radicals are "lower alkylaminoalkoxyalkoxy" radicals independently having alkoxy radicals of one to six carbon atoms. Even more preferred are lower alkylaminoalkoxyalkoxy radicals having alkyl radicals of one to three carbon atoms. Suitable alkylaminoalkoxyalkoxy radicals may be mono or dialkyl substituted, such as N-methylaminoethoxymethoxy, N,N-dimethylaminoethoxymethoxy, N,N-diethylaminomethoxymethoxy, and the like.

The term "alkylaminoalkoxy" embraces alkoxy radicals substituted with alkylamino radicals. More preferred alkylaminoalkoxy radicals are "lower alkylaminoalkoxy" radicals having alkoxy radicals of one to six carbon atoms. Even more preferred are lower alkylaminoalkoxy radicals having alkyl radicals of one to three carbon atoms. Suitable alkylaminoalkoxy radicals may be mono or dialkyl substituted, such as N-methylaminoethoxy, N,N-dimethylaminoethoxy, N,N-diethylaminoethoxy and the like.

The term "aminoalkoxy" embraces alkoxy radicals substituted with an amino radical. More preferred aminoalkoxy radicals are "lower aminoalkoxy" radicals having alkoxy radicals of one to six carbon atoms. Suitable aminoalkoxy radicals may be aminoethoxy, aminomethoxy, aminopropoxy and the like.

The terms "N-aralkyl-N-alkylamino" and "N-alkyl-N-arylamino" denote amino groups which have been substituted with one aralkyl and one alkyl radical, or one aryl and one alkyl radical, respectively, to an amino group.

The term "arylthio" embraces aryl radicals of six to ten carbon atoms, attached to a divalent sulfur atom. An example of "arylthio" is phenylthio.

The term "aralkylthio" embraces aralkyl radicals as described above, attached to a divalent sulfur atom. More preferred are phenyl-$C_1$-$C_3$-alkylthio radicals. An example of "aralkylthio" is benzylthio.

The term "aryloxy" embraces optionally substituted aryl radicals, as defined above, attached to an oxygen atom. Examples of such radicals include phenoxy.

The term "aralkoxy" embraces oxy-containing aralkyl radicals attached through an oxygen atom to other radicals. More preferred aralkoxy radicals are "lower aralkoxy" radicals having optionally substituted phenyl radicals attached to lower alkoxy radical as described above.

The term "heterocyclyloxy" embraces optionally substituted heterocyclyl radicals, as described above, attached to an oxygen atom. Examples of such radicals include piperidyloxy.

The term "heterocyclylalkoxy" embraces oxy-containing heterocyclylalkyl radicals attached through an oxygen atom to other radicals. More preferred heterocyclylalkoxy radicals are "lower heteroarylalkoxy" radicals having optionally substituted heteroaryl radicals attached to lower alkoxy radical as described above.

The term "heterocyclyloxyalkyl", embraces heteroaryl radicals attached through an ether oxygen atom to an alkyl radical. More preferred heterocyclyloxyalkyl radicals are "lower heteroaryloxyalkyl" radicals having optionally substituted heteroaryl radicals attached to an —O—$C_{1-6}$ alkyl radical.

The term "cycloalkyl", includes saturated carbocyclic groups. Preferred cycloalkyl groups include $C_3$-$C_6$ rings. More preferred compounds include cyclopentyl, cyclopropyl, and cyclohexyl.

The term "cycloalkenyl" includes carbocyclic groups have one or more carbon-carbon double bonds. "Cycloalkenyl" and "cycloalkyldienyl" compounds are included. Preferred cycloalkenyl groups include $C_3$-$C_6$ rings. More preferred compounds include, for example, cyclopentenyl, cyclopentadienyl, cyclohexenyl and cycloheptadienyl.

The term "basic moiety" or "basic moieties" means a chemical moiety that has a measured or calculated $pK_a$ of from about 7 to about 13. The term also can include a chemical moiety that is protonable, to some extent, between a pH range of from about 7 to about 10. Examples of basic moieties include, but are not limited to, cycloalkylaminoalkyl, cycloalkylalkylaminoalkyl, heteroarylaminoalkyl, heteroarylalkylaminoalkyl, arylaminoalkyl, arylalkylaminoalkyl, $C_{1-6}$-alkylamino-$C_{1-6}$-alkoxy, $C_{1-6}$-alkylamino-$C_{1-6}$-alkoxy-$C_{1-6}$-alkoxy, aminoalkoxy, aminoalkyl, alkylaminoalkyl, 5-6 membered heterocyclyloxy, 5-6 membered nitrogen-containing heterocyclyl, 5-7 membered nitrogen-containing heterocyclyl-alkyl, $NH_2$; and more preferably aminomethyl, isopropylaminomethyl, t-butylaminomethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, 1-piperidinylmethyl, 4-(piperidin-1-yl) piperidinylmethyl, 4-(dimethylamino)piperidin-1-ylmethyl, 2,6-dimethylpiperidin-1-ylmethyl, 4-morpholinylmethyl, 1-pyrrolidinylmethyl, 2-methylpyrrolidin-1-ylmethyl, 2,5-dimethylpyrrolidin-1-ylmethyl, piperazin-1-ylmethyl and 4-methylpiperazin-1-ylmethyl. Each basic moiety can be optionally substituted with one to three groups independently selected from halo, —$NH_2$, —OH, —CN, —$CF_3$, ($C_1$-$C_6$) alkylamino, halo($C_1$-$C_6$)alkyl, oxo, ($C_1$-$C_6$)alkoxy, ($C_1$-$C_6$) alkoxy($C_1$-$C_6$)alkyl, ($C_1$-$C_6$)alkenyl, ($C_1$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, =NCN; and ($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, haloalkyl, oxo, ($C_1$-$C_6$)alkoxy, ($C_1$-$C_6$)alkoxyalkyl, ($C_1$-$C_6$) alkyl, ($C_1$-$C_6$)alkenyl, ($C_1$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$.

The term "comprising" is meant to be open ended, including the indicated component but not excluding other elements.

The present invention preferably includes compounds that antagonize bradykinin 1.

The present invention also comprises the use of a compound of the invention, or pharmaceutically acceptable salt thereof, in the manufacture of a medicament for the treatment either acutely or chronically of pain or an inflammation mediated disease state, including those described previously. The compounds of the present invention are also useful in the manufacture of an anti-inflmmatory medicament. The compounds of the present invention are also useful in the manufacture of a medicament to attenuate or prevent disorders through inhibition of bradykinin 1. The compounds of the present invention are also useful in the manufacture of a medicament to treat pain.

The present invention comprises a pharmaceutical composition comprising a therapeutically-effective amount of a compound of Formulas I-VI in association with at least one pharmaceutically-acceptable carrier, adjuvant or diluent.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

The present compounds may also be used in combination therapies with opioids and other anti-pain analgesics, including narcotic analgesics, Mu receptor antagonists, Kappa receptor antagonists, non-narcotic (i.e. non-addictive) analgesics, monoamine uptake inhibitors, adenosine regulating agents, cannabinoid derivatives, Substance P antagonists, neurokinin-1 receptor antagonists, COX-2 inhibitors such as celecoxib, rofecoxib, valdecoxib, parecoxib, and darecoxib, NSAID's, and sodium channel blockers, among others. More preferred would be combinations with compounds selected from morphine, meperidine, codeine, pentazocine, buprenorphine, butorphanol, dezocine, meptazinol, hydrocodone, oxycodone, methadone, tetrahydrocannibinol, pregabalin, Tramadol [(+) enantiomer], DuP 747, Dynorphine A, Enadoline, RP-60180, HN-11608, E-2078, ICI-204448, acetominophen (paracetamol), propoxyphene, nalbuphine, E-4018, filenadol, mirtentanil, amitriptyline, DuP631, Tramadol [(−) enantiomer], GP-531, acadesine, AKI-1, AKI-2, GP-1683, GP-3269, 4030W92, tramadol racemate, Dynorphine A, E-2078, AXC3742, SNX-111, ADL2-1294, ICI-204448, CT-3, CP-99,994, and CP-99,994.

Alternatively, the present compounds may also be used in co-therapies with other treatments for inflammation, e.g. steroids, NSAIDs, iNOS inhibitors, p38 inhibitors, TNF inhibitors, 5-lipoxygenase inhibitors, $LTB_4$ receptor antagonists and $LTA_4$, hydrolase inhibitors.

The present invention comprises a process for the preparation of a compound of Formula I-VI.

Compounds of the present invention can possess, in general, one or more asymmetric carbon atoms and are thus capable of existing in the form of optical isomers as well as in the form of racemic or non-racemic mixtures thereof. Unless otherwise indicated, the compounds of the present invention, as depicted or named, may exist as the racemate, a single enantiomer, or any uneven (i.e. non 50/50) mixture of enantiomers. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column, such as, for example, a CHIRAL-AGP column, optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

Compounds of the present invention can possess, in general, tautomeric forms, which are included in the family of compounds in Formula I-VI.

Also included in the family of compounds of Formula I-VI are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I-VI may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, arylaliphatic, heterocyclic carboxylic and sulfonic classes of organic acids, example of which are formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, tartaric, thiocyanic, mesylic, undecanoic, stearic, algenic, β-hydroxybutyric, salicylic, galactaric and galacturonic acid. Suitable pharmaceutically-acceptable base addition salts of compounds of Formula I-VI include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethylmorpholine, piperazine, piperidine, triethylamine, trimethylamine. All of these salts may be prepared by conventional means from the corresponding compound of the invention by reacting, for example, the appropriate acid or base with the compound of Formula I-VI.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as HCl, $H_2SO_4$ and $H_3PO_4$ and such organic acids as oxalic acid, maleic acid, succinic acid and citric acid. Other examples include salts with alkali metals or alkaline earth metals, such as sodium, potassium, calcium or magnesium or with organic bases.

General Synthetic Procedures

The compounds of the invention can be synthesized according to the following procedures of Schemes 1-20, wherein the substituents are as defined for Formulas I-VI, above, except where further noted.

The following abbreviations are used:

| | |
|---|---|
| AcOH, HOAc | acetic acid |
| $CH_3CN$ | acetonitrile |
| $NH_3$ | ammonia |
| $NH_4Cl$ | ammonium chloride |
| $NH_4OH$ | ammonium hydroxide |
| $(PPh_3)_2NiBr_2$ | bis(triphenylphosphine)nickel(II) bromide |
| $BH_3$ | borane |
| $Br_2$ | bromine |
| BMS | borane dimethylsulfide complex |
| $BH_3$—$SMe_2$ | borane dimethylsulfide complex |
| Boc | butyloxycarbonyl |
| $Boc_2O$ | Boc anhydride |
| $CHCl_3$ | chloroform |
| CBS | (R)-2-methyl-CBS-oxazaborolidine |
| DBU | 1,8-diazabicyclo[5.4.0]undec-7-ene |
| DEAD | diethyl azodicarboxylate |
| DIAD | diisopropyl azodicarboxylate |
| $CH_2Cl_2$ | dichloromethane |
| $Et_2O$ | diethyl ether |
| DMAP | 4-(dimethylamino)pyridine |
| DIPEA, DIEA | diisopropylethylamine |
| DIBALH | diisobutylaluminum hydride |
| $Me_2NH$ | dimethylamine |
| DPPA, dppa | diphenylphosphoryl azide |
| DMF | dimethylformamide |
| DMSO | dimethyl sulfoxide (also known as methyl sulfoxide) |
| EtOAc | ethyl acetate |
| EDC, EDCI | (3-dimethylamino-propyl)-ethyl-carbodiimide-HCl salt |
| EtOH | ethanol |
| HCOOH | formic acid |
| g | gram |
| h | hour |
| HATU | O-(7-azabenzotriazol-1-yl)-N,N,N',N'-tetramethyluronium hexafluorophoshate |
| HCl | hydrochloric acid |
| $H_2$ | hydrogen |
| HOBt | 1-hydroxybenzotriazole |
| $NH_2OH$ | hydroxylamine |
| $H_3PO_4$ | phosphoric acid |
| $H_2SO_4$ | sulfuric acid |
| IPA | isopropanol |
| iPrOH | isopropanol |
| $K_2CO_3$ | potassium carbonate |
| LAH | lithium aluminum hydride |
| $LiBH_4$ | lithium borohydride |
| LDA | lithium diisopropylamide |
| MnO2 | manganese oxide |
| MeOH | methanol |
| MsCl | mesyl chloride |
| $Ms_2O$ | methanesulfonic anhydride |
| MeMgBr | methylmagnesium bromide |
| $MeAlClNH_2$ | methylchloroaluminum amide |
| mL | milliliter |
| min | minutes |
| $MgSO_4$ | magnesium sulfate |
| MeI | methyliodide |
| Ni—Al | Raney nickel |
| $N_2$ | nitrogen |
| NMM | N-methylmorpholine |
| NMO | 4-methylmorpholine N-oxide |
| $OsO_4$ | osmium tetroxide |
| Pd/C | palladium on carbon |
| $Pd(OH)_2$ | paladdium hydroxide |
| $Pd_2(dba)_3$ | tris(dibenzylideneacetone)dipalladium |
| $(PPh_3)_2NiBr_2$ | bis(triphenylphosphinyl)nickel(II)bromide |
| KCN | potassium cyanide |
| KOH | potassium hydroxide |
| RT | room temperature |
| $SiO_2$ | silica |
| NaOAc | sodium acetate |
| $NaN_3$ | sodium azide |
| $NaHCO_3$ | sodium bicarbonate |
| $NaBH_4$ | soduim borohydride |
| $NaIO_4$ | sodium periodate |
| NaH | sodium hydride |
| $Na_2CO_3$ | sodium carbonate |
| $NaBH(OAc)_3$ | sodium triacetoxyborohydride |
| NaOH | sodium hydroxide |
| $SOCl_2$ | thionyl chloride |
| TBDPSCl | tert-butyldiphenylchlorosilane |
| TBAF | tetrabutylammonium fluoride |
| $Tf_2O$ | triflic anhydride |
| TFA | trifluoroacetic acid |
| THF | tetrahydrofuran |
| TEA, $Et_3N$ | triethylamine |
| $Me_3Al$ | trimethylaluminum |
| $PPh_3$ | triphenylphosphine |
| TBu3P | tri (tert-butyl)phosphine |
| $H_2O$ | water |

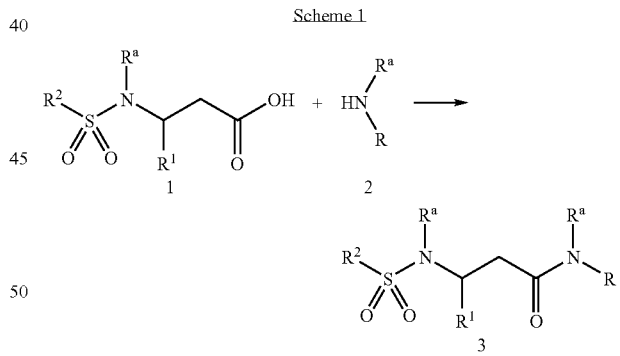

Scheme 1

Compounds of Formula I may be prepared in a convergent manner as described in Scheme 1. β-Amino acids 1 are coupled with the substituted amine 2 using standard peptide coupling conditions, such as with HOBT, EDC, and DIEA in a solvent, such as $CH_2Cl_2$, and reacted at RT, to afford the substituted amide 3. The β-amino acids 1 are commercially available or may be prepared by literature methods. Similarly, substituted amine 2 are either commercially available, can be prepared via literature methods, or may be prepared following literature methods described for analogous compounds. Some of these methods are illustrated in the subsequent schemes. Alternatively, substituted amide 3 is an intermediate to the compounds of Formula I. Protective groups employed in compounds 3 can be removed to provide deprotected compounds of formula I.

Scheme 2

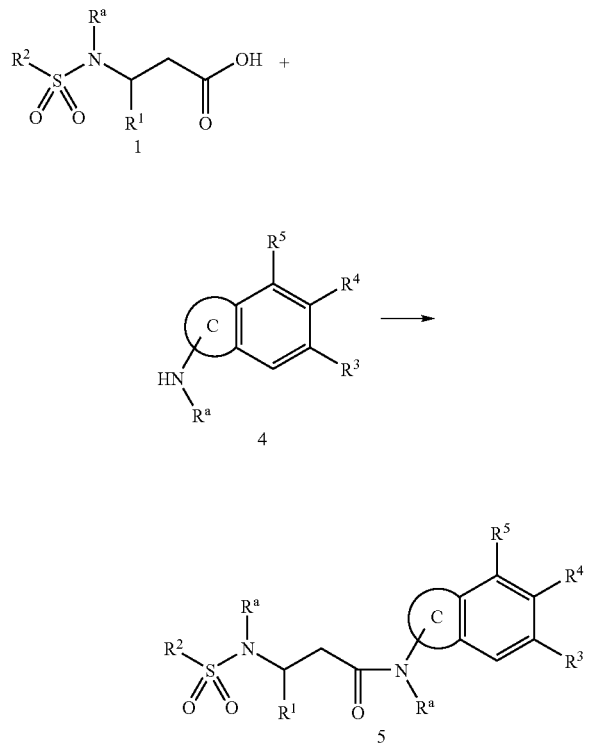

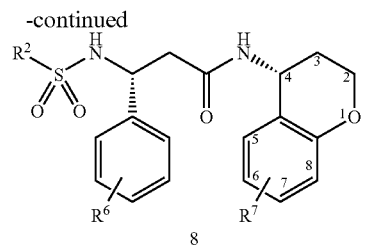

Compounds of Formula II may be prepared in a convergent manner as described in Scheme 2. β-Amino acids 1 are coupled with the bicyclic-ring-substituted amine 4 using standard peptide coupling conditions, such as with HOBT EDC, and DIEA in a solvent, such as $CH_2Cl_2$, and reacted at RT, to afford the bicyclic-ring-substituted amide 5. The β-amino acids 1 are commercially available or may be prepared by literature methods. Similarly, substituted amine 3 are either commercially available, can be prepared via literature methods, or may be prepared following literature methods described for analogous compounds. Some of these methods are illustrated in the subsequent schemes. Alternatively, bicyclic-ring-substituted amide 5 is an intermediate to the compounds of Formula II. Protective groups employed in compounds 5 can be removed to provide deprotected compounds of Formula II.

Scheme 3

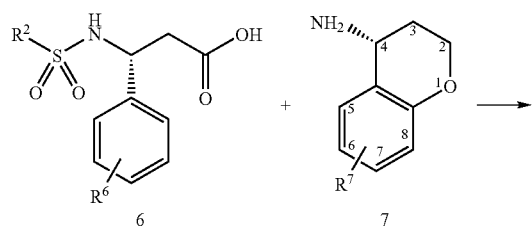

Compounds of Formula III may be prepared in a convergent manner as described in Scheme 3. β-phenylalanine derivatives 6 are coupled with the substituted chroman 7 using standard peptide coupling conditions, such as with HOBT EDC, and DIEA in a solvent, such as $CH_2Cl_2$, and reacted at RT, to afford the chroman-substituted amide 8. The β-amino Amino acids 6 are commercially available or may be prepared by literature methods. Similarly, substituted amine 7 are either commercially available, can be prepared via literature methods, or may be prepared following literature methods described for analogous compounds. Some of these methods are illustrated in the subsequent schemes. Alternatively, bicyclic-ring-substituted amide 8 is an intermediate to the compounds of Formula II. Protective groups employed in compounds 8 can be removed to provide deprotected compounds of Formula III.

Scheme 4

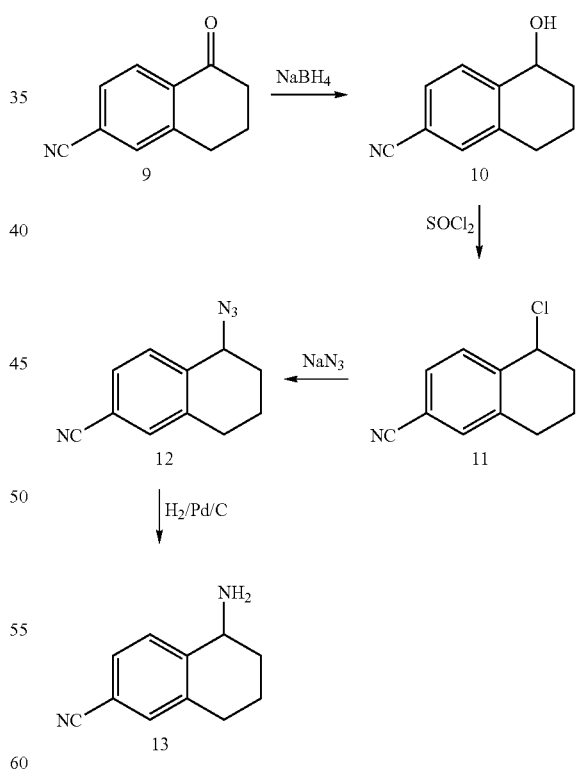

Cyano substituted bicylic amines 13 may be prepared in a convergent manner as described in Scheme 4. 5-Oxo-5,6,7,8-tetrahydro-naphth-2-yl carbonitrile 9 is reduced, such as with $NaBH_4$, in a solvent such as THF and MeOH at a temperature between about 0° C. and about 30° C., preferably about RT, to form the 5-hydroxy-5,6,7,8-tetrahydro-naphth- 2-yl carbonitrile 10. The alcohol 10 is converted to the halide 11, such as the chloride, such as by treatment with SOCl$_2$ in a solvent such as CH$_2$Cl$_2$, at a temperature between about 0° C. and about 30° C., preferably about RT. The 5-chloro-5,6,7,8-tetrahydro-naphth-2-yl carbonitrile 11 is treated with NaN$_3$ in a solvent such as dry DMF, at a temperature above RT, preferably above about 50° C., even more preferably at about 75° C., to form the 5-azido-5,6,7,8-tetrahydro-naphth-2-yl carbonitrile 12. The azide is hydrogenated, such as with H$_2$ in the presence of a catalyst, such as Pd/C, in the presence of solvent, such as in EtOAc, to form the amine 13. These steps can be used to form analogous cyano substituted bicyclic amines.

Scheme 5

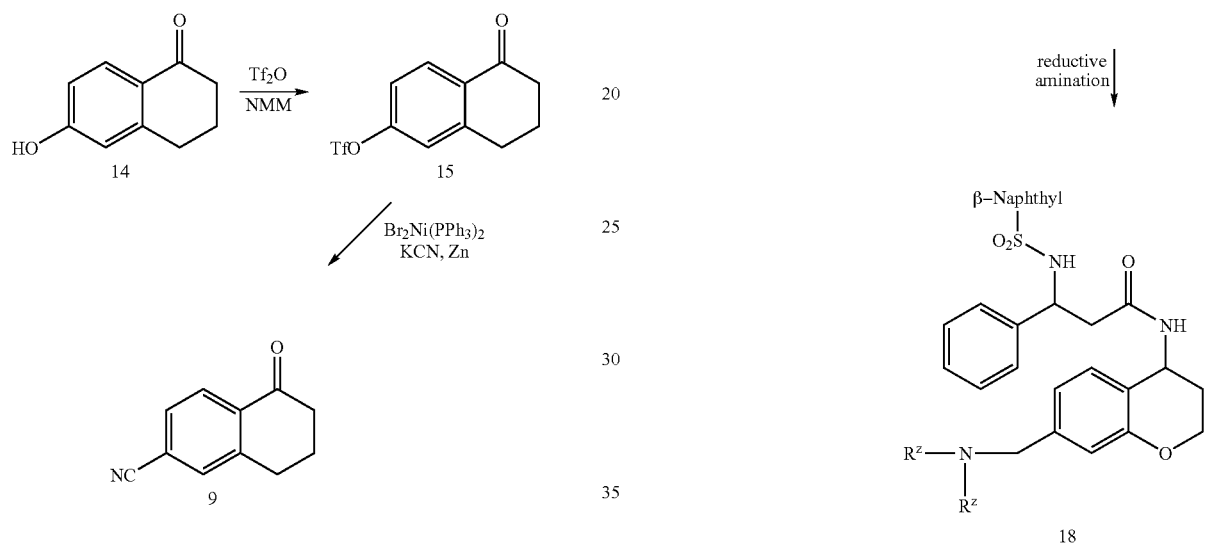

5-Oxo-5,6,7,8-tetrahydro-naphth-2-yl carbonitrile 9 can be prepared from corresponding alcohols by the methods described in Scheme 5. 6-Hydroxy-3,4-dihydro-2H-naphthalen-1-one 14 is converted to the triflate 15 by treatment with trifluoro-methanesulfonic anhydride in a solvent such as CH$_2$Cl$_2$, in the presence of base, such as NMM, and DMAP, and at a temperature below RT, preferably at a temperature at about 0° C. The triflate 15 is reacted with KCN in the presence of PPh$_3$ and (PPh$_3$)$_2$NiBr$_2$ in a solvent such as 5 degassed CH$_3$CN, a temperature above RT, preferably above about 50° C., even more preferably at about 60° C., to form the cyano compound 9. These steps can be used to form analogous oxo substituted bicyclic carbonitriles.

Compounds of Formula I may be prepared in a convergent manner as described in Scheme 6. Cyano chromans 16 are reduced, such as with Raney nickel in the presence of formic acid, a temperature above RT, preferably above about 75° C., even more preferably at about 100° C., to form the formyl compounds 17. Reductive amination of the formyl compounds 17, such as with NaBH(OAc)$_3$ and an amine, provides the aminomethyl compounds 18 (where R$^Z$ is H or alkyl or together with the amine forms a cyclic compound). The compounds can be isolated as a salt or as the free base. These steps can be used to form analogous compounds.

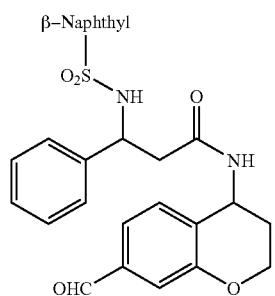

17 reductive amination

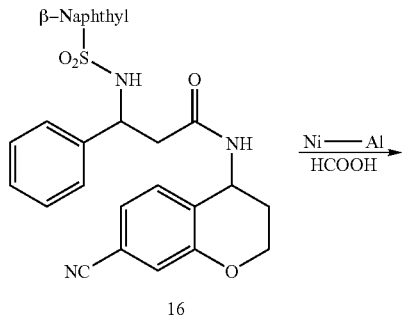

Scheme 6

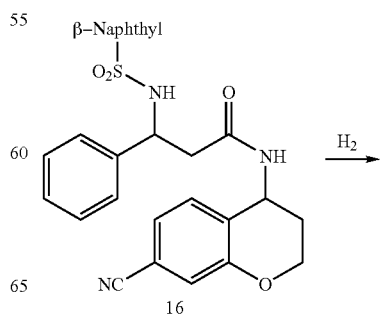

Scheme 7

-continued

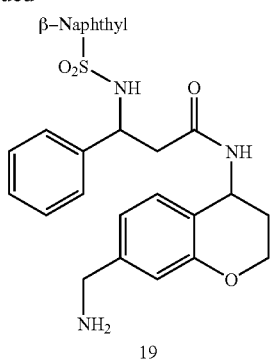
19

Compounds of Formula I may be prepared in a convergent manner as described in Scheme 7. Cyano chromans 16 are reduced, such as with hydrogen in the presence of a catalyst such as Pd(OH)$_2$, in a solvent, such as MeOH, to form the corresponding aminomethyl compounds 19.

Amino compounds 22 are prepared from the corresponding ketones 20 by the method described in Scheme 8. Treatment of the ketones 20 with hydroxylamine in a solvent such as NaOAc, at a temperature above RT, preferably above about 75° C., even more preferably at reflux, provides the oxime 21. Hydrogenation of the oxime 21, such as in the presence of a catalyst such as Pd/C, provides the amine 22.

Scheme 9

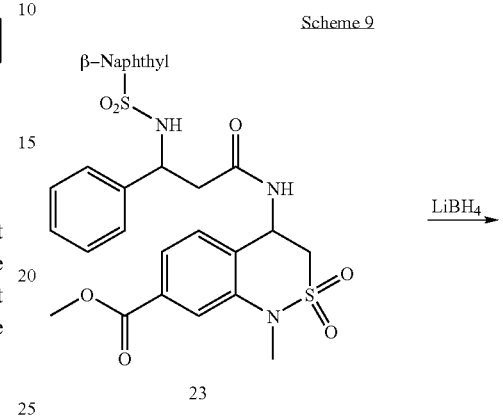

Scheme 8

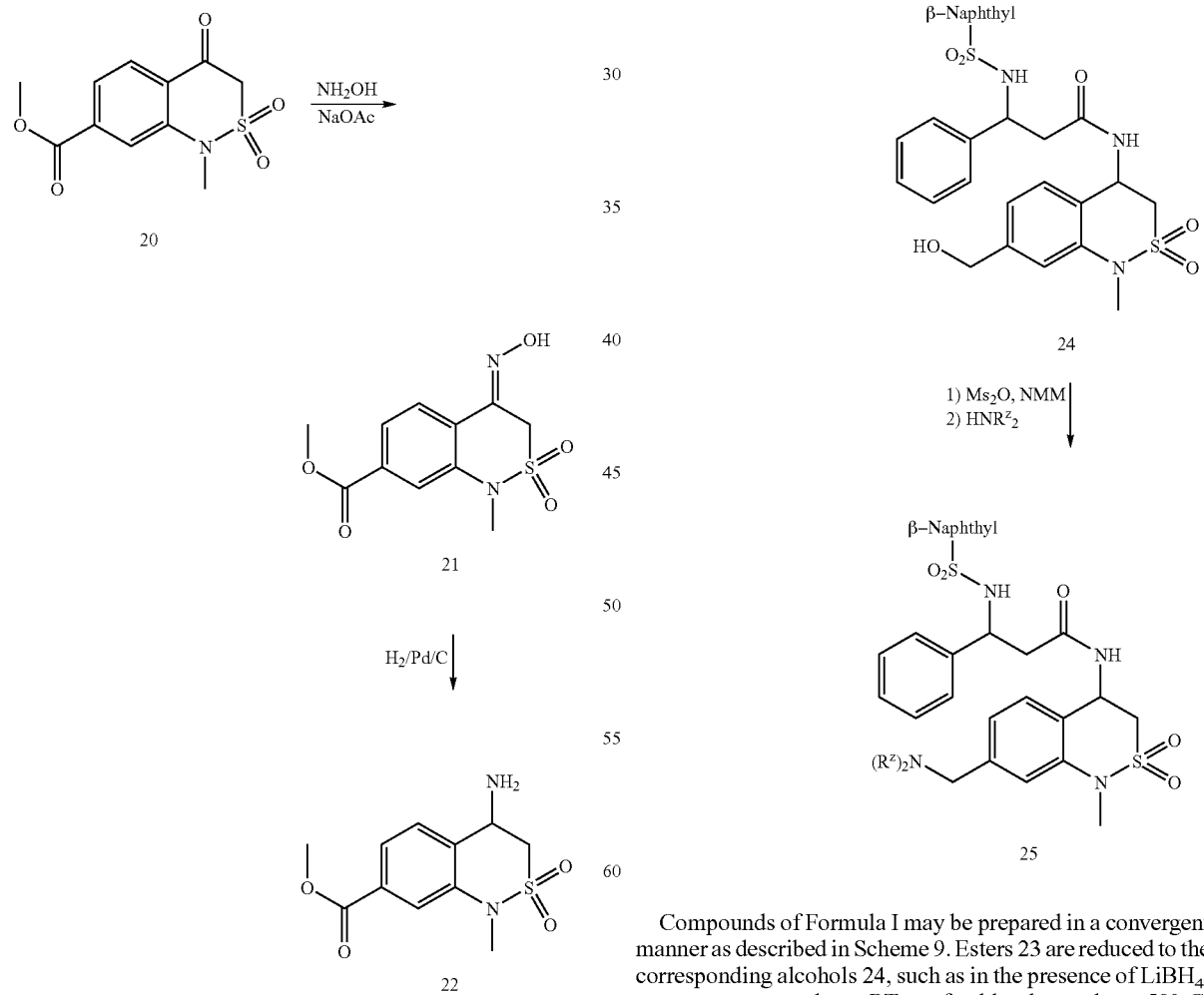

Compounds of Formula I may be prepared in a convergent manner as described in Scheme 9. Esters 23 are reduced to the corresponding alcohols 24, such as in the presence of LiBH$_4$, at a temperature above RT, preferably above about 50° C. Derivatization to the mesylate and treatment with an amine provides compounds 25.

Scheme 10

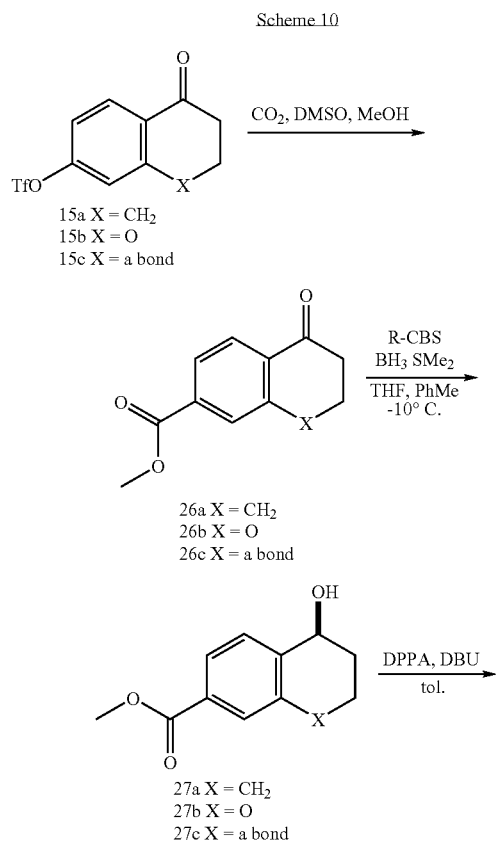
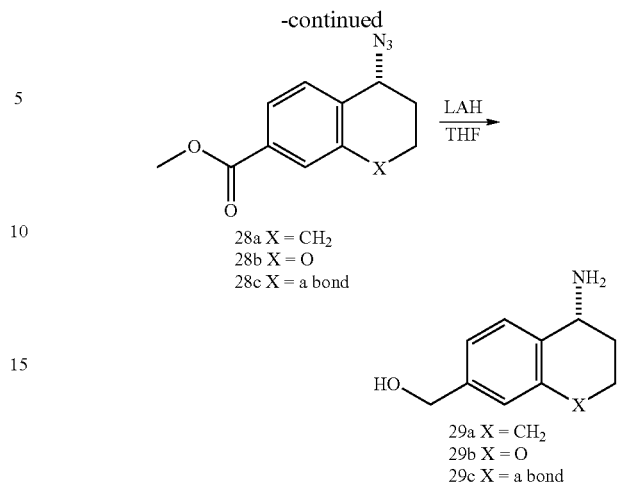

In addition compounds of Formula I can be prepared in diasteromerically pure forms using the method described in Scheme 10. Keto-trifalates 15a-c are subjected to Pd mediated carbonylation in a mixture of DMSO and MeOH to afford the ketoesters 26a-c. Enantioselective reduction of the ketone moieties, e.g. using either the CBS (E. J. Corey et al., J. Am. Chem. Soc. 109, 5551 (1987)) or Noyori. (T. Noyori, et al., *J. Am. Chem. Soc.*, 1995, 117, 2675-2676) protocols affords either enantiomer of the alcohols with an enantiomeric excess of >99%. Either the R or S enantiomer of the amine may be prepared by using either of the enantioselective reduction protocols. Azidation of the resulting secondary alcohol using a method described by Thompson et al. (Journal of Org. Chem. (1993), 58(22), 5886-8.) and LAH reduction affords the enantiopure amino alcohols 29a-c in high yield.

Scheme 11

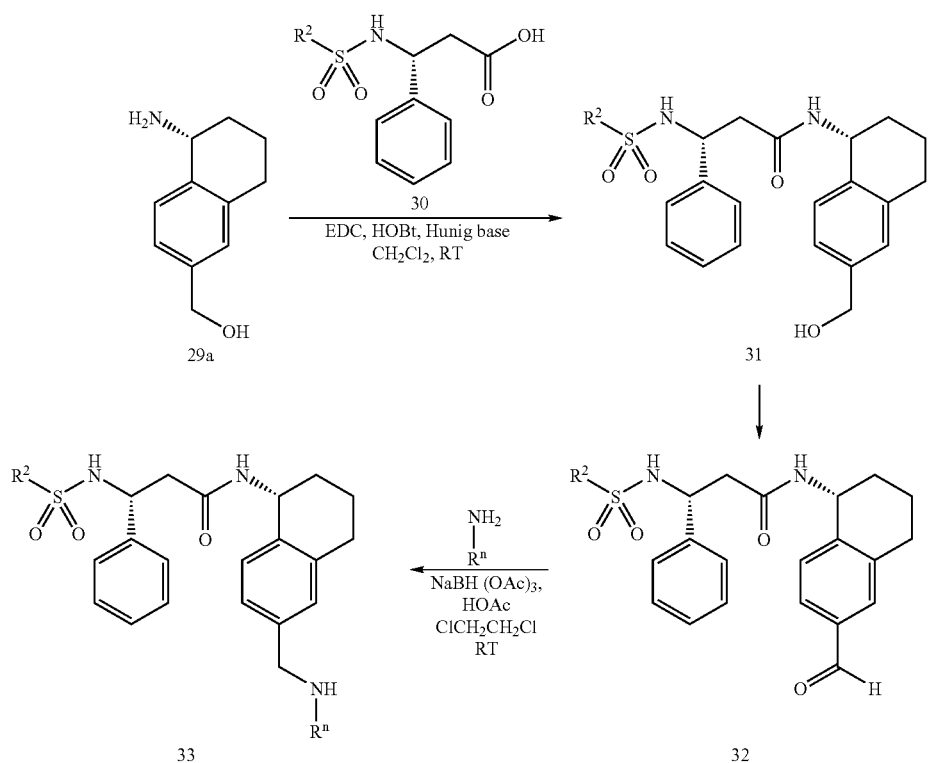

The resulting amino alcohols further elaborated into compounds of Formula I as depicted in Scheme 11, similar to that described in Scheme 6.

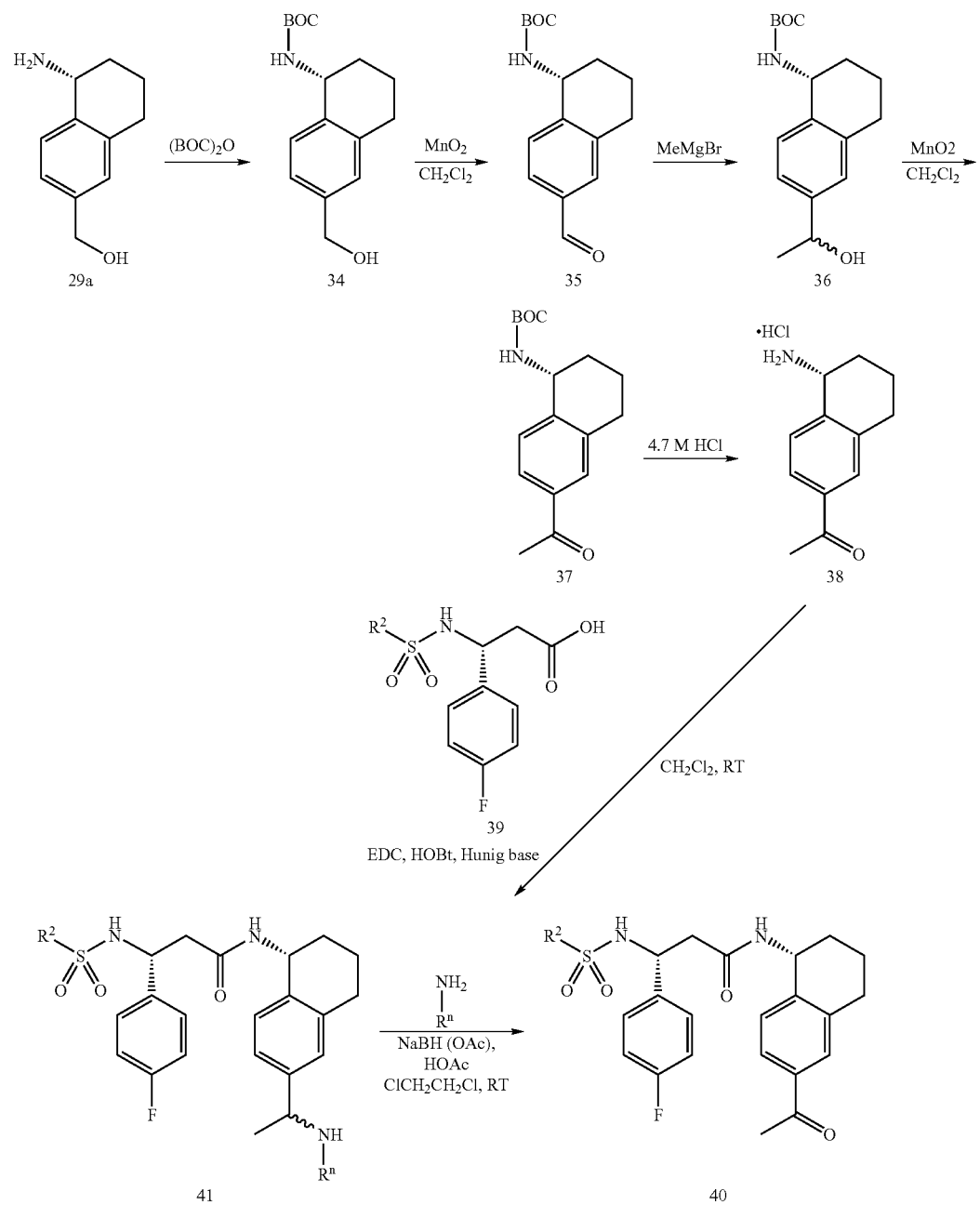

Scheme 12

Analogs of compounds of Formula II may be prepared as illustrated in Schemes 12-14. Following Boc protection, amino alcohol 29a is converted to its methyl ketone 37 by the three step procedure depicted in scheme 12. Protected 1-amino-6-hydroxymethyl-1,2,3,4-tetrahydro-naphthalene 34 is oxidized, such as with $MnO_2$ in an organic solvent, such as $CH_2Cl_2$, preferably at a temperature of about RT, to form the aldehyde 35. The aldehyde is alkylated, such as with a Grignard reagent in a solvent such as THF, at a temperature initially below RT, preferably about −30° C. and more preferably at about −78° C., then at about RT, to form the alcohol 36. The alcohol 36 is oxidized, such as with $MnO_2$ as previously described, to form the protected ketone 37. The resulting ketone 37 is deprotected such as with HCl, and converted to compound 41 similar to the method described in Scheme 11.

Scheme 13

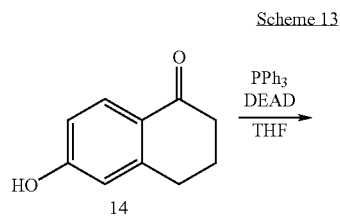

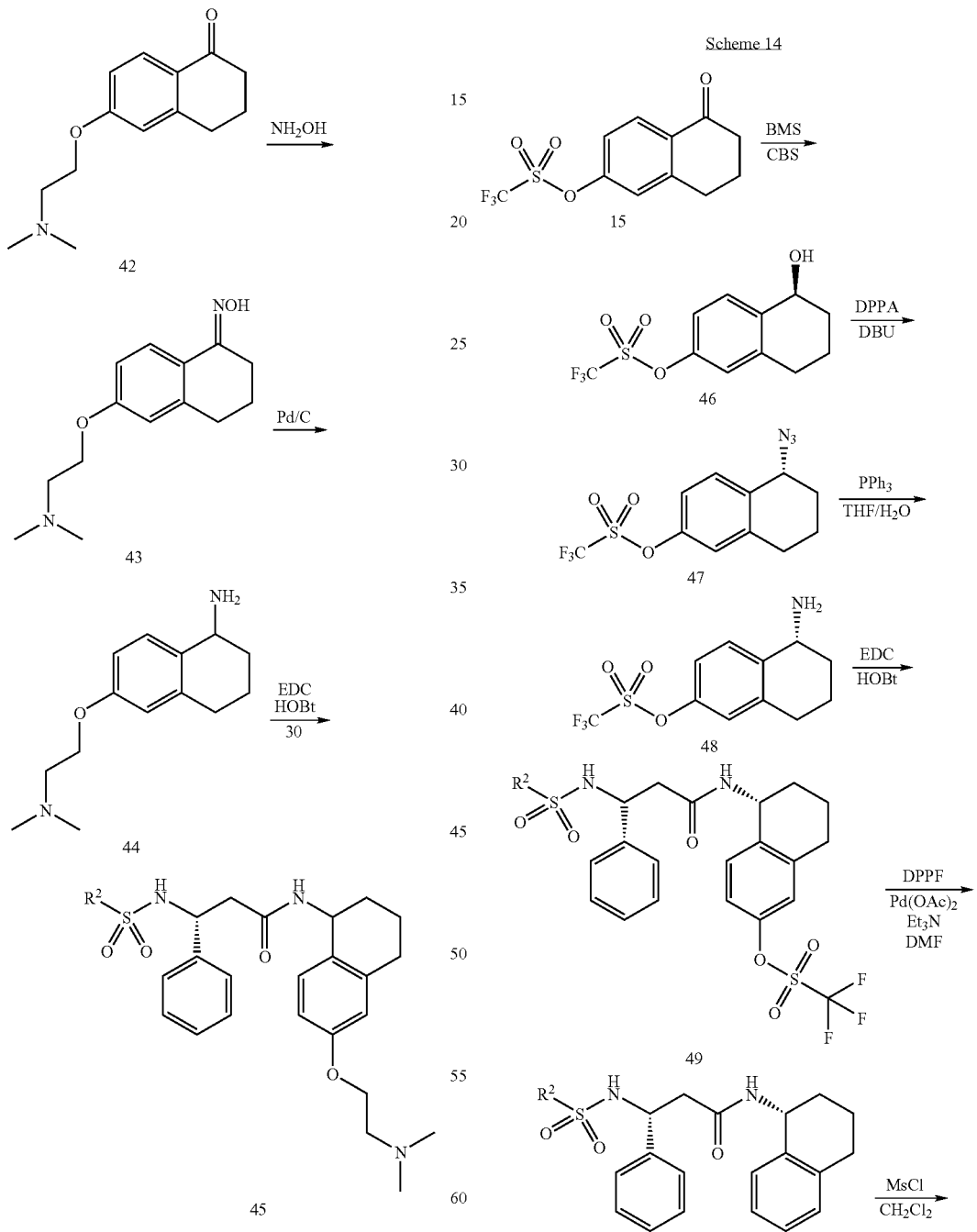

Ether linked analogs such as 45, are prepared by the convergent synthesis depicted in scheme 13. The 6-hydroxy-1-tetralone 14 is reacted with an amine, such as N,N-dimethyl-ethanolamine, preferably in the presence of PPh$_3$ and DEAD at a temperature preferably between about 0° C. and about RT to form the 6-(2-dimethylamino-ethoxy)-3,4-dihydro-2H-naphthalen-1-one 42. the 6-(2-dimethylamino-ethoxy)-3,4-dihydro-2H-naphthalen-1-one 42 is reacted with hydroxylamine hydrochloride and base, such as Et$_3$N. The reaction is heated above RT, preferably at reflux to form the oxime 43. Hydrogenation of the oxime 43, such as with Pd/C and H$_2$ provides the amine 44 which can be coupled with the appropriate acid to form the desired compound 45.

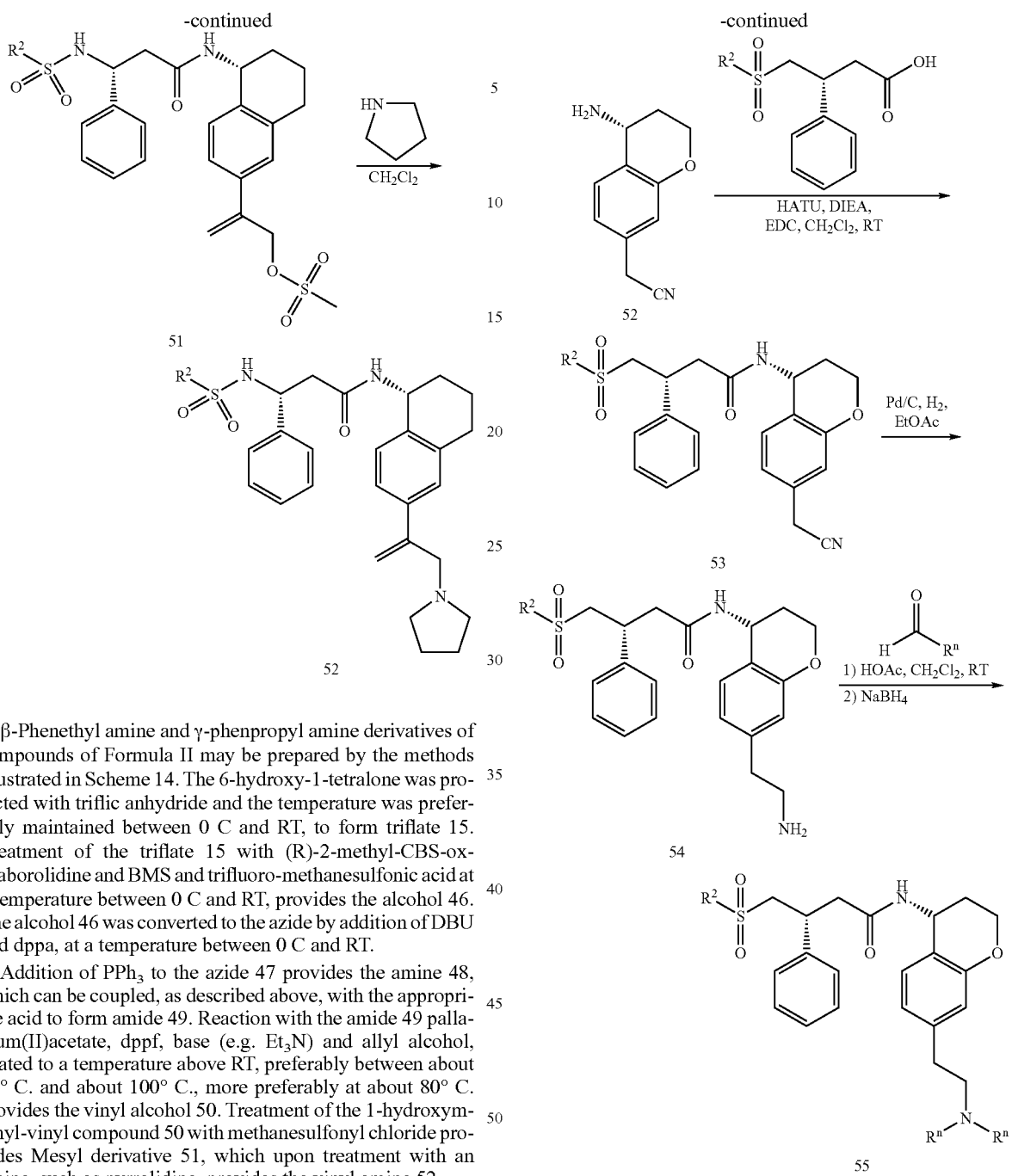

β-Phenethyl amine and γ-phenpropyl amine derivatives of compounds of Formula II may be prepared by the methods illustrated in Scheme 14. The 6-hydroxy-1-tetralone was protected with triflic anhydride and the temperature was preferably maintained between 0 C and RT, to form triflate 15. Treatment of the triflate 15 with (R)-2-methyl-CBS-oxazaborolidine and BMS and trifluoro-methanesulfonic acid at a temperature between 0 C and RT, provides the alcohol 46. The alcohol 46 was converted to the azide by addition of DBU and dppa, at a temperature between 0 C and RT.

Addition of $PPh_3$ to the azide 47 provides the amine 48, which can be coupled, as described above, with the appropriate acid to form amide 49. Reaction with the amide 49 palladium(II)acetate, dppf, base (e.g. $Et_3N$) and allyl alcohol, heated to a temperature above RT, preferably between about 50° C. and about 100° C., more preferably at about 80° C. provides the vinyl alcohol 50. Treatment of the 1-hydroxymethyl-vinyl compound 50 with methanesulfonyl chloride provides Mesyl derivative 51, which upon treatment with an amine, such as pyrrolidine, provides the vinyl amine 52.

Scheme 15

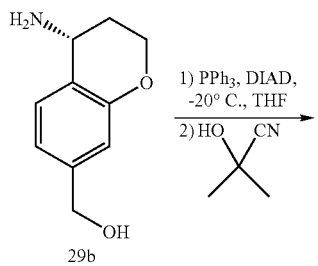

Following the protocols described above the tether length for all of the amino compounds of Formulas I and II may be varied from 1-4 carbons. The alcohol 29b can be converted to the carbonitrile 52 such as with treatment with $P(Ph)_3$, DEAD and acetone cyanohydrin. The nitrile 52 can be coupled with the acid, such as with HATU, EDC and DIEA. The (7-cyanomethyl-4-chroman 53 is hydrogenated, such as with palladium catalyst in an alcohol, e.g. MeOH, to form the alkyl amine 54 of the present invention. The alkyl amine can be substituted using standard methods to make the substituted amines 55 (where $R''$ is alkyl, substituted alkyl, and the like).

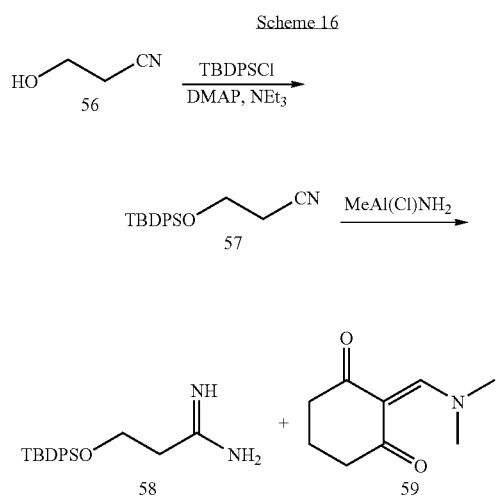

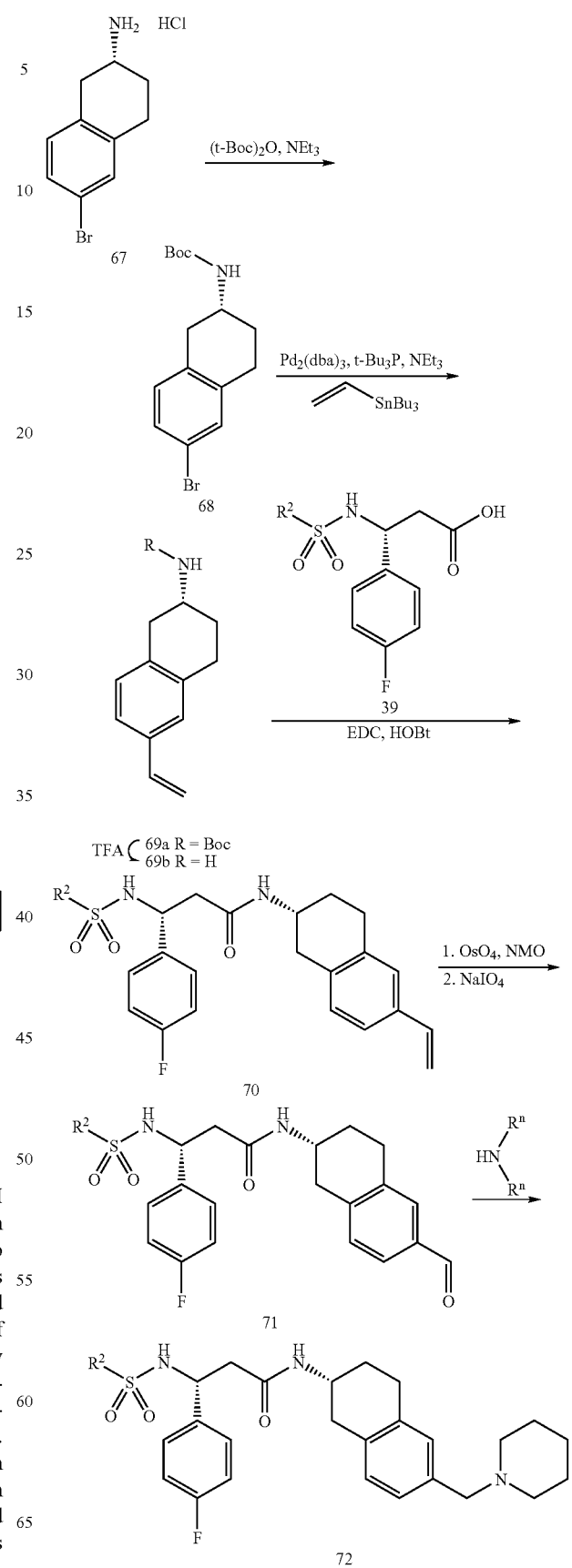

Methods for preparing additional compounds of formulas I and II are illustrated in scheme 16. The cyano alcohol 56 can be treated with DMAP, base (e.g. NEt₃), and PBDPSCl to form the protected alcohol 57. The protected alcohol 56 is aminated, such as with Me₃Al, at a temperature below RT and preferably at about 0 C, to yield the amidine 58. Formation of the 5,6,7,8-tetrahydro-quinazolone 60 is achieved such as by reaction of amidine 58 and 2-dimethylaminomethylene-cyclohexane-1,3-dione 59 at a temperature above RT, preferably above about 50 C and more preferably at about 80 C. 5,6,7,8-tetrahydro-quinazolone 60 is reduced such as with NaBH₄ to give the alcohol 61. The alcohol 61 is treated with DPPA and DBU to form the azide derivative which is reduced to form the amine 62. The amine 62 is deprotected, such as with TBAF to form the desired intermediate 63.

Compounds of the invention 72 can be prepared as described in Scheme 18. The protected amino bicyclic compound 68 was treated with is alkylated, such as with vinyltributyltin in the presence of $PPh_3$, a base such as $Et_3N$ and a palladium catalyst, e.g. $Pd_2(dba)_3$. The reaction is maintained at a temperature above RT, preferably in a range between about 50 C and about 100 C, more preferably at about 80 C, more preferably in a microwave. After deprotection, such as with TFA in the case the amine is BOC protected, the free amine 69b can be coupled as described above. Oxidation of the vinyl compound 70, such as with $OsO4$ produces aldehyde 71. Reductive amination, such as with $NaHB(OAc)_3$ in the presence of an amine provides compounds 72.

Compounds with alkylated sulfonamides 74 can be prepared as described in Scheme 19 Treatment of the free sulfonamide 32 with iodoalkyl compounds, e.g. MeI, in the presence of base such as $Na_2CO_3$ provides the alkylated intermediate 73 which can be further treated as described above to provide compounds 74.

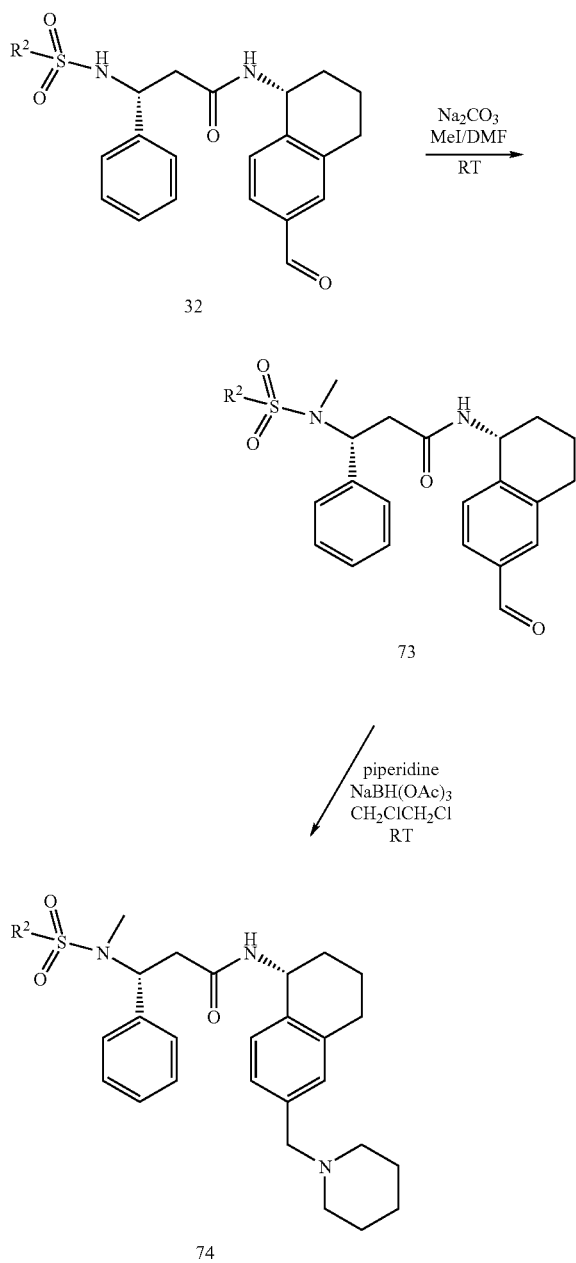

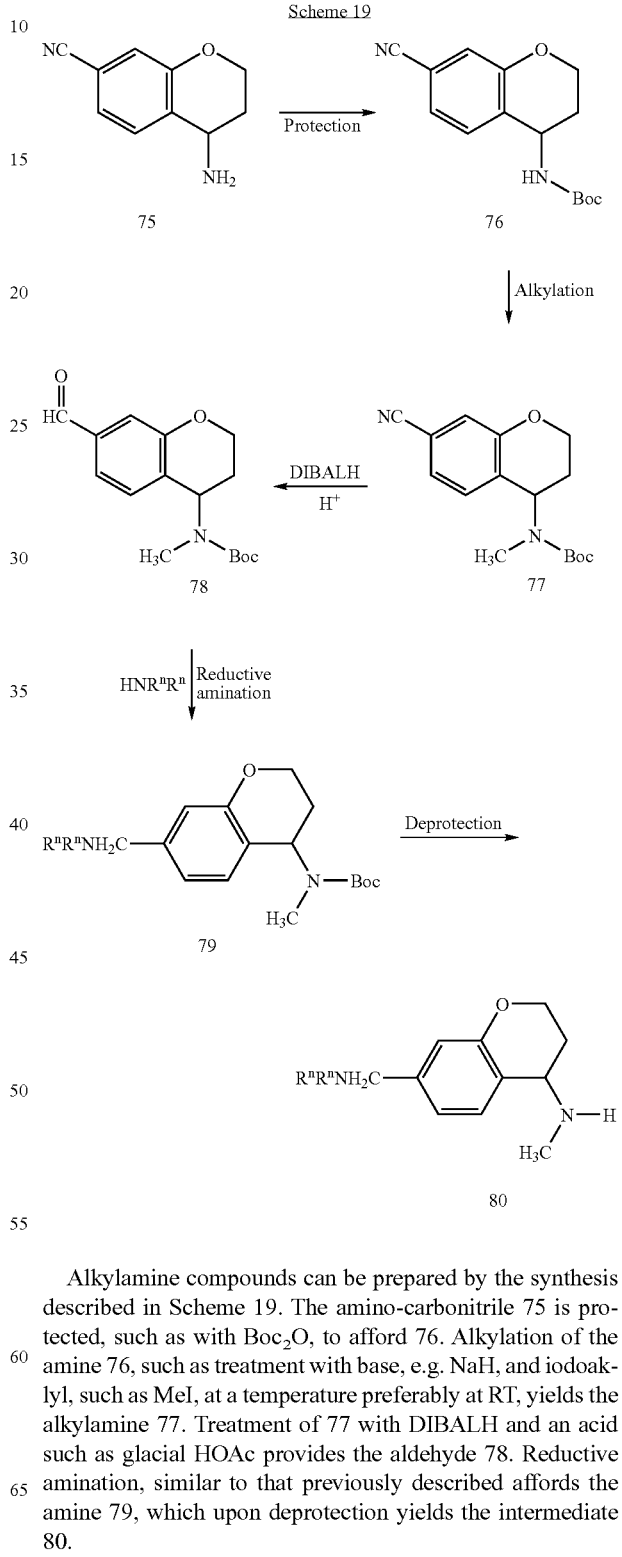

Alkylamine compounds can be prepared by the synthesis described in Scheme 19. The amino-carbonitrile 75 is protected, such as with $Boc_2O$, to afford 76. Alkylation of the amine 76, such as treatment with base, e.g. NaH, and iodoakly, such as MeI, at a temperature preferably at RT, yields the alkylamine 77. Treatment of 77 with DIBALH and an acid such as glacial HOAc provides the aldehyde 78. Reductive amination, similar to that previously described affords the amine 79, which upon deprotection yields the intermediate 80.

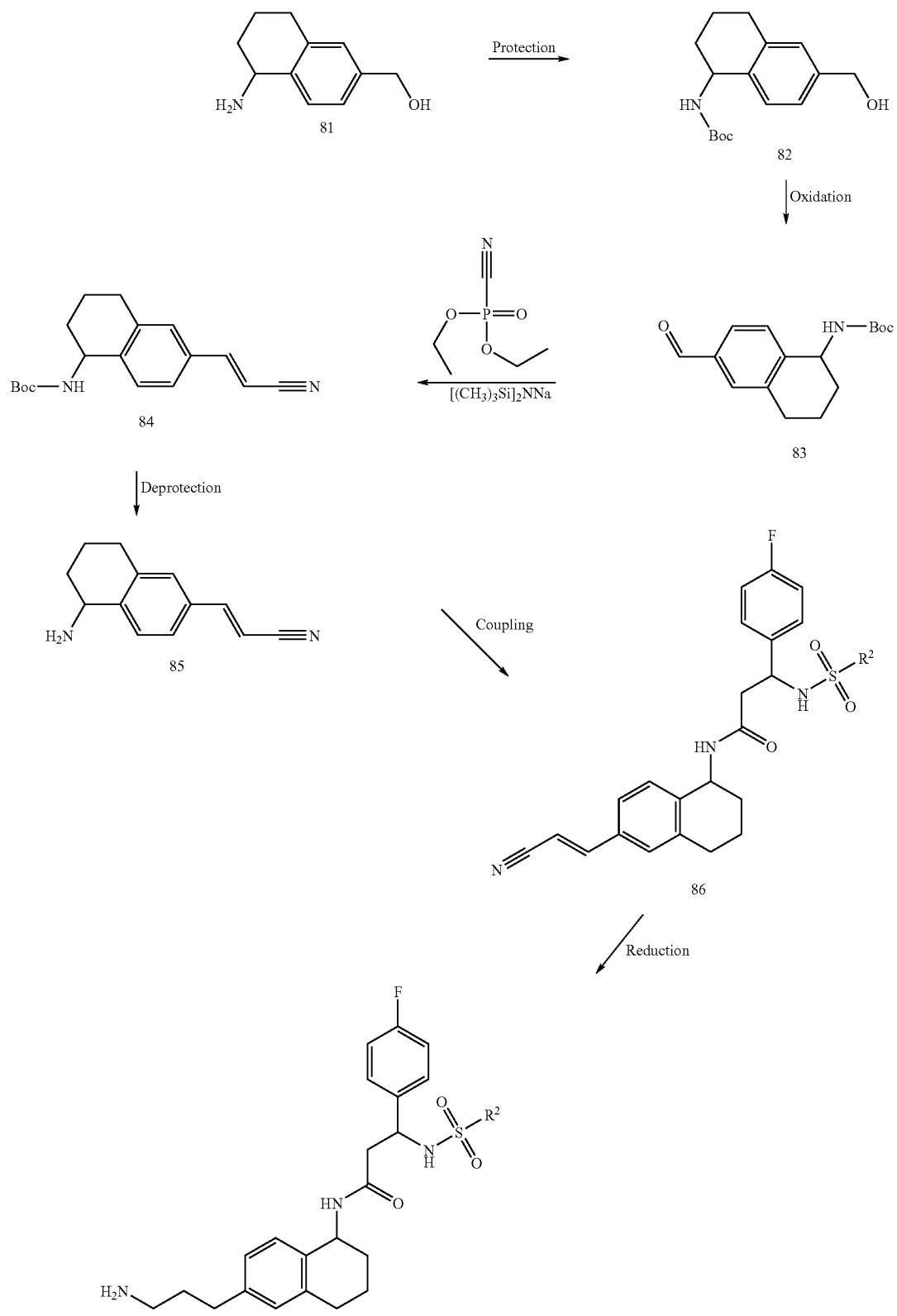

Alternatively, compounds with longer tethers are prepared by the method described in Scheme 20. (5-Amino-5,6,7,8-tetrahydro-naphthalen-2-yl)-methanol 81 is protected, such as with $(Boc)_2O$ to provide 82. The protected amine 82 is oxidized, using methods described in other schemes above, to form the aldehyde 83. The cyano-vinyl compound 84 is prepared via treatment with diethyl cyanophosphate and sodium bis(trimethylsilyl)amide at a temperature between about −78° C. and RT. Deprotection yields the free amine 85 which can be coupled as described above, to provide the intermediate 86. Reduction, such as with Pt catalyzed treatment with $H_2$ yields the aminopropyl compound 87 of the present invention.

Additional analogs of any of the templates in described in Schemes 1-20 may be prepared using the procedures analogous to those described for above and illustrated in the examples below. In addition elaboration of all intermediates in the above schemes to compounds of Formula I may be accomplished using known by those skilled in the arts of organic and medicinal chemistry.

If one or more other functional groups, for example carboxy, hydroxy, amino, or mercapto, are or need to be protected in a compound of Formulas I-VI and I'-VI', because they should not take part in the reaction, these are such groups as are usually used in the synthesis of peptide compounds, and also of cephalosporins and penicillins, as well as nucleic acid derivatives and sugars.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by solvolysis, reduction, photolysis or also by enzyme activity, for example under conditions analogous to physiological conditions, and that they are not present in the end-products. The specialist knows, or can easily establish, which protecting groups are suitable with the reactions mentioned above and hereinafter.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Wiley, New York 1981, in "The Peptides"; Volume 3 (editors: E. Gross and J. Meienhofer), Academic Press, London and New York 1981, in "Methoden der organischen Chemie" (Methods of organic chemistry), Houben Weyl, 4th edition, Volume 15/1, Georg Thieme Verlag, Stuttgart 1974, in H.-D. Jakubke and H. Jescheit, "Aminosäuren, Peptide, Proteine" (Amino acids, peptides, proteins), Verlag Chemie, Weinheim, Deerfield Beach, and Basel 1982, and in Jochen Lehmann, "Chemie der Kohlenhydrate: Monosaccharide und Derivate" (Chemistry of carbohydrates: monosaccharides and derivatives), Georg Thieme Verlag, Stuttgart 1974.

In the additional process steps, carried out as desired, functional groups of the starting compounds which should not take part in the reaction may be present in unprotected form or may be protected for example by one or more of the protecting groups mentioned above under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130-170° C., one molecule of the acid being expelled per molecule of a compound of formula I.

Salts can usually be converted to free compounds, e.g. by treating with suitable basic agents, for example with alkali metal carbonates, alkali metal hydrogen carbonates, or alkali metal hydroxides, typically potassium carbonate or sodium hydroxide.

All process steps described here can be carried out under known reaction conditions, preferably under those specifically mentioned, in the absence of or usually in the presence of solvents or diluents, preferably such as are inert to the reagents used and able to dissolve these, in the absence or presence of catalysts, condensing agents or neutralizing agents, for example ion exchangers, typically cation exchangers, for example in the He form, depending on the type of reaction and/or reactants at reduced, normal, or elevated temperature, for example in the range from about −100° C. to about 190° C., preferably from about −80° C. to about 150° C., for example at about −80 to about 60° C., at RT, at about −20 to about 40° C. or at the boiling point of the solvent used, under atmospheric pressure or in a closed vessel, where appropriate under pressure, and/or in an inert atmosphere, for example, under argon or nitrogen.

Salts may be present in all starting compounds and transients, if these contain salt-forming groups. Salts may also be present during the reaction of such compounds, provided the reaction is not thereby disturbed.

In certain cases, typically in hydrogenation processes, it is possible to achieve stereoselective reactions, allowing for example easier recovery of individual isomers.

The solvents from which those can be selected which are suitable for the reaction in question include, for example, $H_2O$, esters, typically lower alkyl-lower alkanoates, e.g. EtOAc, ethers, typically aliphatic ethers, e.g. $Et_2O$, or cyclic ethers, e.g. THF, liquid aromatic hydrocarbons, typically benzene or toluene, alcohols, typically MeOH, EtOH or 1-propanol, IPA, nitriles, typically $CH_3CN$, halogenated hydrocarbons, typically $CH_2Cl_2$, acid amides, typically DMF, bases, typically heterocyclic nitrogen bases, e.g. pyridine, carboxylic acids, typically lower alkanecarboxylic acids, e.g. HOAc, carboxylic acid anhydrides, typically lower alkane acid anhydrides, e.g. acetic anhydride, cyclic, linear, or branched hydrocarbons, typically cyclohexane, hexane, or isopentane, or mixtures of these solvents, e.g. aqueous solutions, unless otherwise stated in the description of the process.

The invention relates also to those forms of the process in which one starts from a compound obtainable at any stage as a transient and carries out the missing steps, or breaks off the process at any stage, or forms a starting material under the reaction conditions, or uses said starting material in the form of a reactive derivative or salt, or produces a compound obtainable by means of the process according to the invention and processes the said compound in situ. In the preferred embodiment, one starts from those starting materials which lead to the compounds described above as preferred.

The compounds of Formula I-VI and I'-VI', including their salts, are also obtainable in the form of hydrates, or their crystals can include for example the solvent used for crystallization (present as solvates).

New starting materials and/or intermediates, as well as processes for the preparation thereof, are likewise the subject of this invention. In the preferred embodiment, such starting materials are used and reaction conditions so selected as to enable the preferred compounds to be obtained.

Starting materials of the invention, are known, are commercially available, or can be synthesized in analogy to or according to methods that are known in the art.

In the preparation of starting materials, existing functional groups which do not participate in the reaction should, if necessary, be protected. Preferred protecting groups, their introduction and their removal are described above or in the examples.

All remaining starting materials are known, capable of being prepared according to known processes, or commercially obtainable; in particular, they can be prepared using processes as described in the examples.

The following examples contain detailed descriptions of the methods of preparation of compounds of Formulas I-VI and I'-VI'. These detailed descriptions fall within the scope, and serve to exemplify, the above described General Synthetic Procedures which form part of the invention. These detailed descriptions are presented for illustrative purposes only and are not intended as a restriction on the scope of the invention.

The compounds of this invention may contain one or more asymmetric centers and thus occur as racemates and racemic mixtures, scalemic mixtures, single enantiomers, individual diastereomers and diastereomeric mixtures. All such isomeric forms of these compounds are expressly included in the present invention. The compounds of this invention may also be represented in multiple tautomeric forms, for example, as illustrated below:

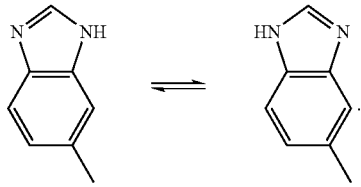

The invention expressly includes all tautomeric forms of the compounds described herein. The compounds may also occur in cis- or trans- or E- or Z- double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

Alternatively, a compound of any of the formulas delineated herein may be synthesized according to any of the processes delineated herein. In the processes delineated herein, the steps may be performed in an alternate order and may be preceded, or followed, by additional protection/deprotection steps as necessary. The processes may further comprise use of appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase), extraction, distillation, trituration, reverse phase HPLC and the like. Reactions conditions such as temperature, duration, pressure, and atmosphere (inert gas, ambient) are known in the art and may be adjusted as appropriate for the reaction.

As can be appreciated by the skilled artisan, the above synthetic schemes are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the inhibitor compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 3rd. Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Unless otherwise noted, all materials were obtained from commercial suppliers and used without further purification. All parts are by weight and temperatures are in Degrees centigrade unless otherwise indicated. All compounds showed NMR spectra consistent with their assigned structures.

In order that the invention described herein may be more readily understood, the following examples are set forth. It should be understood that these examples are for illustrative purposes only and are not to be construed as limiting this invention in any manner.

The following examples contain detailed descriptions of the methods of preparation of compounds of Formulas I-VI. These detailed descriptions fall within the scope, and serve to exemplify, the above-described General Synthetic Procedures which form part of the invention. These detailed descriptions are presented for illustrative purposes only and are not intended as a restriction on the scope of the invention.

Unless otherwise noted, all materials were obtained from commercial suppliers and used without further purification. All parts are by weight unless otherwise indicated. All compounds showed NMR spectra consistent with their assigned structures. Melting points were determined on a Buchi apparatus and are uncorrected. Mass spectral data was determined by electrospray ionization technique. All examples were purified to >95% purity as determined by high-performance liquid chromatography. Unless otherwise stated, reactions were run at RT.

Preparation I —(R)-3-(Naphthalene-2-sulfonylamino)-3-phenyl-propionic Acid

Naphthalene-2-sulfonyl chloride (18.18 g, 80.2 mmol) and NaOH (60 mL, 2 N) were added portion-wise over 1 h to a mixture of (R)-3-amino-3-phenyl-propionic acid HCl salt (14.70 g, 72.9 mmol) and N-methylmorpholine (4.0 mL, 36.5 mmol) in dioxane (250 mL). The pH was maintained at pH 11 with the 2N NaOH solution during the addition. After stirring for an additional 3 h, the mixture was diluted with $CH_2Cl_2$ (1 L), acidified, washed with water, dried over $MgSO_4$, filtered, and concentrated in vacuo. Crystallization from $CH_2Cl_2$/hexane furnished the title compound. MS (-ESI, m/z) 354 $(M-H)^-$.

EXAMPLE 1

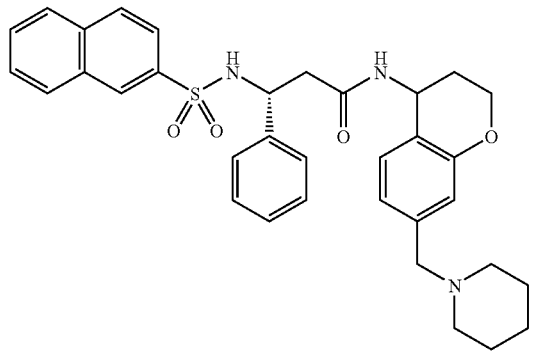

3-(Naphthalen-2-ylsulfonylamino)-3-phenyl-N-(7-piperidin-1-ylmethyl-chroman-4-yl)-propionamide

Step A—Preparation of 7-cyano-4-chromanone

7-[[(Trifluoromethyl)sulfonyl]oxy]-4-chromanone (27.8 g, 94 mmol) and $PPh_3$ (2.5 g, 9.6 mmol) were dissolved in degassed $CH_3CN$ (350 mL). KCN (6.8 g, 105 mmol), $(PPh_3)_2NiBr_2$ (3.5 g, 4.7 mmol) and acid washed (stirred in 0.5 N HCl 1 min, washed successively with $H_2O$, acetone, and $Et_2O$) zinc dust (2.0 g, 31 mmol) were added and the reaction was purged with $N_2$. The reaction was heated in a 60° C. bath for 6 h. The reaction was cooled, poured into $H_2O$ (400 mL) and extracted with EtOAc (3×300 mL). The organic layers were combined and washed with $H_2O$ (200 mL) and brine (150 mL). The solution was dried over $MgSO_4$, filtered and concentrated in vacuo to provide a residue which was purified on a plug of silica ($CH_2Cl_2$ eluant) to provide the title compound.

Step B—Preparation of 7-cyano-4-chromanol

7-Cyano-4-chromanone (Step A) (7.7 g, 44 mmol) was dissolved in THF (75 mL) and MeOH (150 mL), and cooled to 10° C. $NaBH_4$ (1.9 g, 49 mmol) was added and the reaction was warmed to RT and stirred overnight (14 h). The reaction was quenched with acetone (5 mL) and 2 N HCl (100 mL) was added. The reaction was concentrated in vacuo to approximately 75 mL in volume and the reaction was partitioned between 2N HCl (200 mL) and EtOAc (400 mL). The layers were separated and the aqueous layer was back extracted with EtOAc (200 mL). The organic layers were combined, washed successively with $H_2O$ (200 mL) and brine (200 mL). The solution was dried over $MgSO_4$, filtered and concentrated in vacuo to provide the title compound which was used without further purification.

Step C—Preparation of 4-chloro-7-cyanochroman

7-Cyano-4-chromanol (Step B) (8.0 g, 46 mmol) was dissolved in $CH_2Cl_2$ (120 mL) and cooled to 10° C. $SOCl_2$ (5.0 mL, 70 mmol) was added, the reaction was warmed to RT and stirred overnight. The reaction was concentrated in vacuo and azeotroped with $CH_2Cl_2$ (2×50 mL). The residue was dissolved in EtOAc (500 mL), washed with saturated $NaHCO_3$ (250 mL), and with brine (150 mL), dried over $MgSO_4$, filtered and concentrated in vacuo to provide the title compound which was used without further purification.

Step D—Preparation of 4-azido-7-cyanochroman

4-Chloro-7-cyanochroman (Step C) (8.1 g, 42 mmol) was dissolved in dry DMF (90 mL) and $NaN_3$ (4.0 g, 62 mmol) was added and the reaction was heated to 80° C. under $N_2$. After 5 h TLC ($SiO_2$, toluene) showed that no starting chloride was present. The reaction was cooled and partitioned between EtOAc (200 mL) and $H_2O$ (150 mL). The organic phase was washed with $H_2O$ (2×100 mL) and brine (100 mL). The solution was dried over $MgSO_4$, filtered and concentrated in vacuo to provide a residue which was purified by column chromatography ($SiO_2$, 15% EtOAc in hexane) to provide the title compound.

Step E—Preparation of 4-amino-7-cyanochroman

4-Azido-7-cyanochroman (Step D) (4.3 g, 21 mmol) was dissolved in EtOAc (200 mL) and purged with $N_2$. Pd/C (10%, 0.6 g) was added and the reaction was purged with $N_2$. The reaction was purged with $H_2$ and rapidly stirred under a $H_2$ atmosphere until consumption of starting material was complete by TLC analysis (approximately 1 h). The reaction was purged with $N_2$, and filtered through Celite®. The Celite® was washed with MeOH. The solution was concentrated in vacuo to provide a residue which was purified by column chromatography (silica, 3% MeOH in $CH_2Cl_2$ plus 0.5% $NH_4OH$) to provide the title compound. TLC $R_f$=0.3 (5% MeOH in $CH_2Cl_2$ plus 0.5% $Et_3N$.

Step F—Preparation of N-(7-cyano-chroman-4-yl)-3-(naphthalen-2-ylsulfonylamino)-3-phenyl-propionamide 4-Amino-chroman-7-carbonitrile (Step E) (50 mg, 0.28 mmol), 3-(naphthalen-2-ylsulfonylamino)-3-phenyl-propionic acid (100 mg, 0.28 mmol), HOBt (42 mg, 0.31 mmol), and DIEA (72 mg, 0.56 mmol) were dissolved in $CH_2Cl_2$ (10 mL). EDC (52 mg, 0.34 mmol) was added and the reaction was stirred at 22-25° C. overnight until completed. The reaction solution was washed with dilute (~5%) $NaHCO_3$—$H_2O$ and $H_2O$, and solution was dried over $MgSO_4$, filtered and concentrated in vacuo to provide a residue which was purified by column chromatography (silica gel, 25% hexane in EtOAc) to provide the title compound as a white solid mixture of diastereomers (ca. 3:2 by $^1$H NMR after flash column chromotography).

Step G—Preparation of N-(7-formyl-chroman-4-yl)-3-(naphthalen-2-ylsulfonylamino)-3-phenyl-propionamide N-(7-Cyano-chroman-4-yl)-3-(naphthyl-2-ylsulfonylamino)-3-phenyl-propionamide (Step F) (100 mg, 0.2 mmol) and 100 mg Raney-Nickel were added into 3.0 mL of 78% formic acid-H$_2$O solution, and the reaction solution was heated at 102° C. overnight until the reaction was complete. The reaction solution was filtered and poured into 40 mL ice-water. The compound was extracted with CH$_2$Cl$_2$ (2×30 mL), and the CH$_2$Cl$_2$ solution was washed with dilute NaHCO$_3$—H$_2$O and H$_2$O, and dried over MgSO$_4$. The solution was filtered and concentrated in vacuo, and the crude compound was purified by column chromatography (silica gel, EtOAc:Et$_2$O:Hexane=2:3:1, v/v) to provide the title compound as a white solid.

Step H—Preparation of 3-(naphthalen-2-ylsulfonylamino)-3-phenyl-N-(7-piperidin-1-ylmethyl-chroman-4-yl)-propionamide N-(7-Formyl-chroman-4-yl)-3-(naphthyl-2-ylsulfonylamino)-3-phenyl-propionamide (Step G) (15 mg, 0.03 mmol) and piperidine (3.0 mg, 0.036 mmol) were added into N,N-dimethyl-acetamide (1.5 mL) solution, followed by adding NaBH(OAc)$_3$ (14 mg, 0.06 mmol). The reaction was stirred at 22-25° C. overnight until complete. The reaction was quenched with dilute NaHCO$_3$—H$_2$O (10 mL), and the compound was extracted with CH$_2$Cl$_2$ (2×10 mL), and the CH$_2$Cl$_2$ solution was washed with dilute NaHCO$_3$—H$_2$O and H$_2$O, and dried over MgSO$_4$. The solution was filtered and concentrated in vacuo. The compound was purified by precipitation as HCl salt in Et$_2$O to provide the title compound as a white solid mixture of diastereomers as the HCl salt (ca. 1:1 by $^1$H NMR). HCl Salt, MS (ESI) 584 (M+H)$^+$.

The following compounds were prepared using essentially the same procedure used in Example 1, Step H except using the cited amine in place of piperidine.

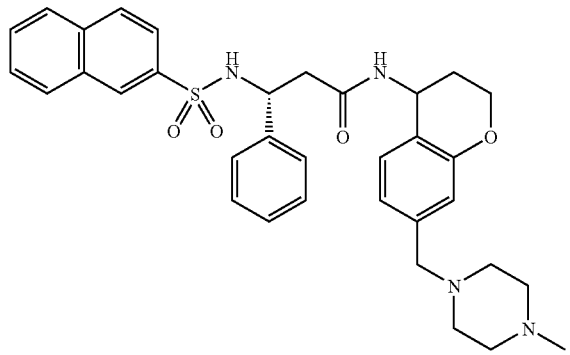

EXAMPLE 1a

N-[7-(4-Methyl-piperazin-1-ylmethyl)-chroman-4-yl]-3-(naphthyl-2-ylsulfonylamino)-3-phenyl-propionamide was prepared from N-methylpiperazine. MS (ESI) 599 (M+H)$^+$.

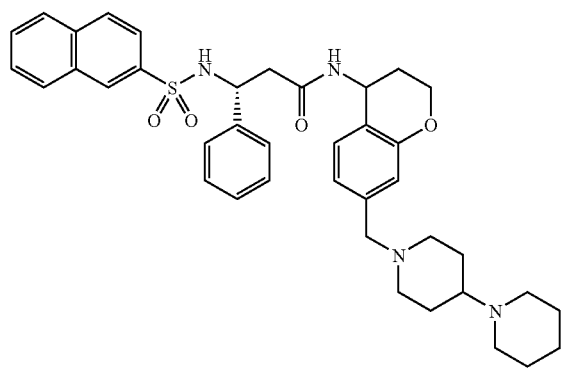

EXAMPLE 1b

N-(7-[1,411]Bipiperidinyl-1'-ylmethyl-chroman-4-yl)-3-(naphthalen-2-ylsulfonylamino)-3-phenyl-propionamide was prepared from 4-piperidinopiperidine. MS (ESI) 667 (M+H)$^+$.

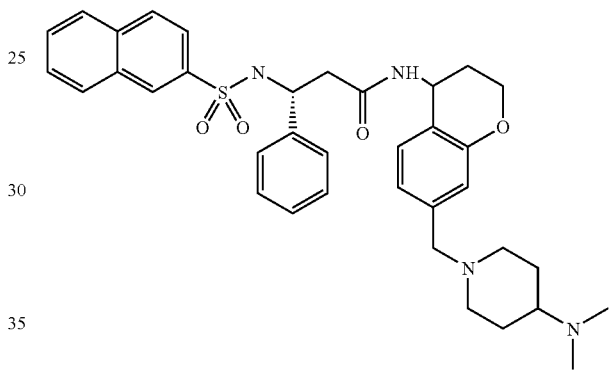

EXAMPLE 1c

N-[7-(4-Dimethylamino-piperidin-1-ylmethyl)-chroman-4-yl]-3-(naphthalen-2-ylsulfonylamino)-3-phenyl-propionamide was prepared from dimethylamine. MS (ESI) 627 (M+H)$^+$.

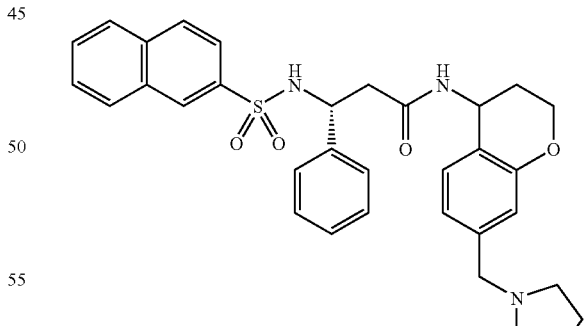

EXAMPLE 1d 3-(Naphthalen-2-ylsulfonylamino)-3-phenyl-N-(7pyrrolidin-2-ylmethyl-chroman-4-yl)-propionamide was prepared from pyrrolidine. MS (ESI) 570 (M+H)$^+$.

The following compounds were prepared using essentially the same procedures used in Example 1 above except using the required acid in Step F and amine in Step H.

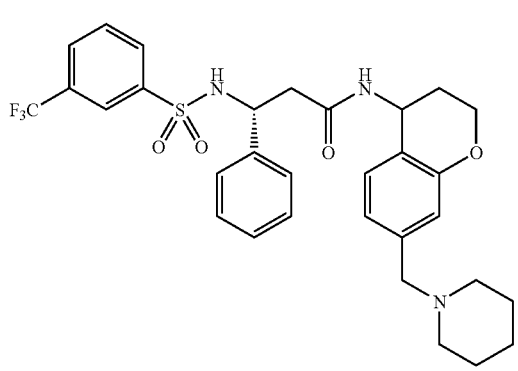

EXAMPLE 1e

3-Phenyl-N-(7-piperidin-1-ylmethyl-chroman-4-yl)-3-(3-trifluoromethyl-benzenesulfonylamino)-propionamide. MS (ESI) 602 (M+H)+

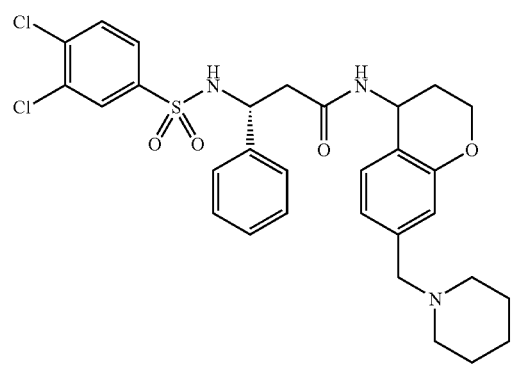

EXAMPLE 1f 3-(3,4-Dichloro-benzenesulfonylamino)-3-phenyl-N-(7-piperidin-1-ylmethyl-chroman-4-yl)-propionamide. MS (ESI) 602 (M+H)+

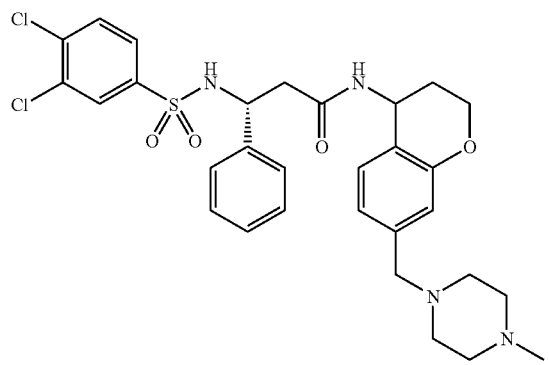

EXAMPLE 1g 3-(3,4-Dichloro-benzenesulfonylamino)-N-[7-(4-methyl-piperazin-1-ylmethyl)-chroman-4-yl]-3-phenyl-propionamide. MS (ESI) 617 (M+H)+

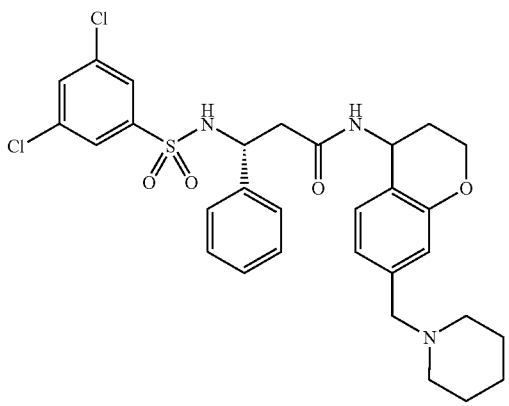

EXAMPLE 1h 3-(3,5-Dichloro-benzenesulfonylamino)-3-phenyl-N-(7-piperidin-1-ylmethyl-chroman-4-yl)-propionamide. MS (ESI) 602 (M+H)+.

EXAMPLE 2

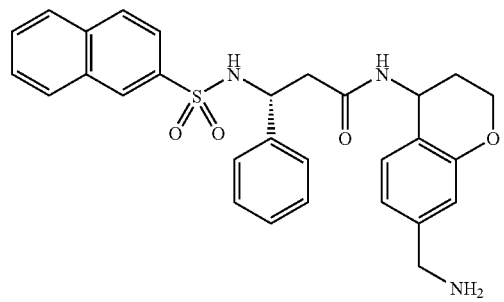

N-(7-Aminomethyl-chroman-4-yl)-3-(naphthalen-2-ylsulfonylamino)-3-phenyl-propionamide N-(7-Cyano-chroman-4-yl)-3-(naphthalen-2-ylsulfonylamino)-3-phenyl-propionamide (Example 1, Step F) (30 mg, 0.06 mmol) and Pd(OH)$_2$ (6 mg) was added in MeOH (10 mL), followed by adding 1.0 mL of 3.0 M HCl-MeOH. The solution was purged with N$_2$, then sealed with H$_2$ (50 psi) and shaken overnight until the reduction was completed. The solution was filtered, and concentrated to near dryness in vacuo. The crude compound was purified by precipitation in EtOAc-Et$_2$O to provide the HCl salt as a white solid mixture of diastereomer. MS (ESI) 516 (M+H)+.

EXAMPLE 3

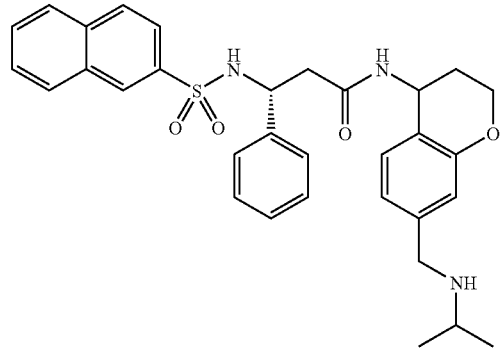

N-[7-(Isopropylamino-methyl)-chroman-4-yl]-3-(naphthalen-2-ylsulfonylamino)-3-phenyl-propionamide

Step A—Preparation of N-(7-hydroxymethyl-chroman-4-yl)-3-(naphthalen-2-yl-sulfonylamino)-3-phenyl-propionamide N-(7-Formyl-chroman-4-yl)-3-(naphthalen-2-yl-sulfonylamino)-3-phenyl-propionamide (Example 1, Step G) (1.83 g, 3.56 mmol) was dissolved in a 1:1 solution of THF and MeOH (100 mL). The solution was cooled to 0° C. and NaBH$_4$ (0.135 g, 3.56 mmol) was added. The reaction was stirred for 30 min. The volatiles were removed in vacuo and the resulting residue was dissolved in EtOAc and washed sequentially with a saturated NaHCO$_3$ solution and brine. The aqueous phases were extracted once with EtOAc. The organic phases were combined, dried over MgSO$_4$, filtered, and concentrated in vacuo to provide the title compound. MS (ESI) m/z 517 (M+H)$^+$.

Step B—Preparation of N-[7-(isopropylamino-methyl)-chroman-4-yl]-3-(naphthalen-2-yl-sulfonylamino)-3-phenyl-propionamide N-(7-Hydroxymethyl-chroman-4-yl)-3-(naphthalen-2-yl-sulfonylamino)-3-phenyl-propionamide (Step A) (0.050 g, 0.010 mmol) and DIEA (0.038 g, 0.030 mmol) were dissolved in THF (1.5 mL). The solution was cooled to 0° C. and methanesulfonic anhydride (0.023 g, 0.014 mmol) was added. After the reaction was stirred for 3.5 h, isopropylamine (0.14 g, 2.3 mmol) was added and the solution was stirred at RT overnight. The reaction was diluted with CHCl$_3$ and washed with brine. The aqueous phase was extracted once with CHCl$_3$. The organic phases were combined, dried over MgSO$_4$, filtered, and concentrated in vacuo to provide a residue which was purified by column chromatography (silica, 0.2% TEA in acetone) to provide the title compound. MS (ESI) m/z 558 (M+H)$^+$.

The following compounds were prepared from N-(7-hydroxymethyl-chroman-4-yl)-3-(naphthalen-2-yl-sulfonylamino)-3-phenyl-propionamide (Example 3 Step A) using essentially the same procedure used in Example 3, Step B except using the cited amine in place of DIEA.

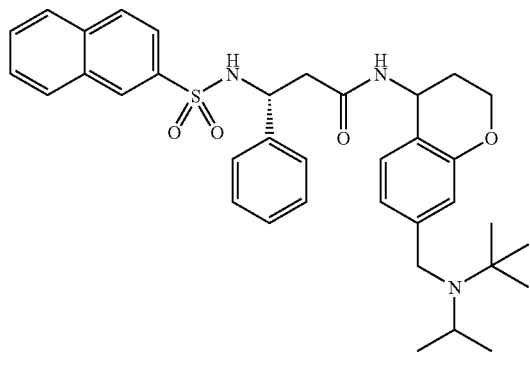

EXAMPLE 3a

N-{7-[(tert-Butyl-isopropyl-amino)-methyl)]-chroman-4-yl}-3-(naphthalen-2-yl-sulfonylamino)-3-phenyl-propionamide was prepared with tert-butylisopropylamine as a colorless oil. MS (ESI) m/z 614 (M+H)$^+$.

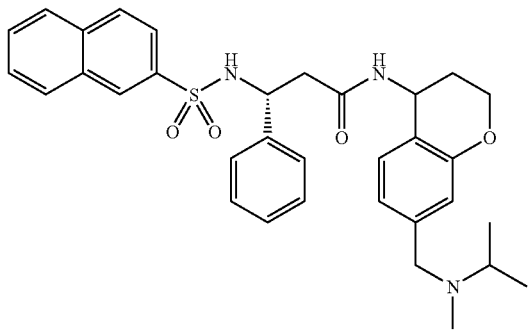

EXAMPLE 3b

N-{7-[(Isopropyl-methyl-amino)-methyl)]-chroman-4-yl}-3-(naphthalen-2-yl-sulfonylamino)-3-phenyl-propionamide was prepared with isopropylmethylamine as a white solid. (ESI) m/z 572 (M+H)$^+$.

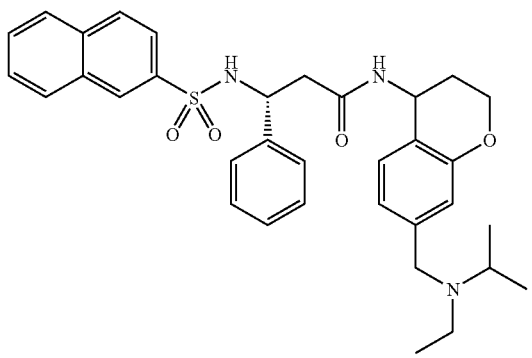

EXAMPLE 3c

N-{7-[(Ethyl-isopropyl-amino)-methyl]-chroman-4-yl}-3-(naphthalen-2-yl-sulfonylamino)-3-phenyl-propionamide was prepared with isopropylethylamine as a white solid. MS (ESI) m/z 586 (M+H)$^+$.

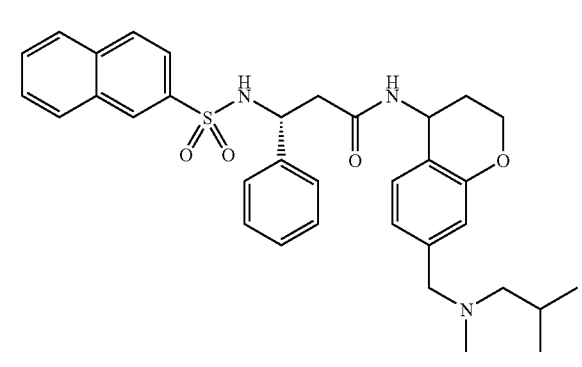

EXAMPLE 3d

N-{7-[(Isobutyl-methyl-amino)-methyl]-chroman-4-yl}-3-(naphthalen-2-yl-sulfonylamino)-3-phenyl-propionamide was prepared with isobutylmethylamine as a white solid. MS (ESI) m/z 586 (M+H)$^+$.

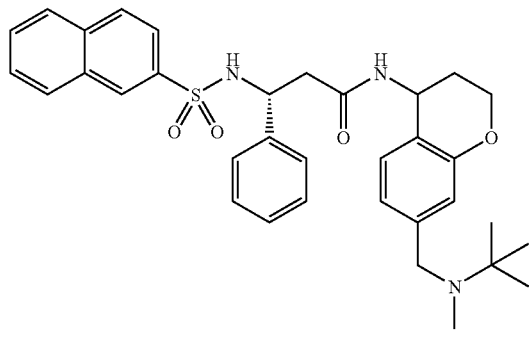

EXAMPLE 3e

N-{7-[(tert-Butyl-methyl-amino)-methyl]-chroman-4-yl}-3-(naphthalen-2-yl-sulfonylamino)-3-phenyl-propionamide was prepared with tert-butylmethylamine as a white solid. MS (ESI) m/z 586 (M+H)$^+$.

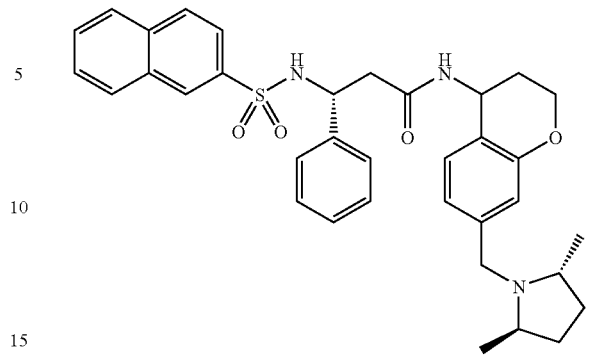

EXAMPLE 3h

N-[7-(2R, 5R-Dimethyl-pyrrolidin-1-ylmethyl)-chroman-4-yl]-3-(naphthalen-2-yl-sulfonylamino)-3-phenyl-propionamide was prepared with (2R, 5R)-(trans)-dimethylpyrrolidine as a white solid. MS (ESI) m/z 598 (M+H)$^+$.

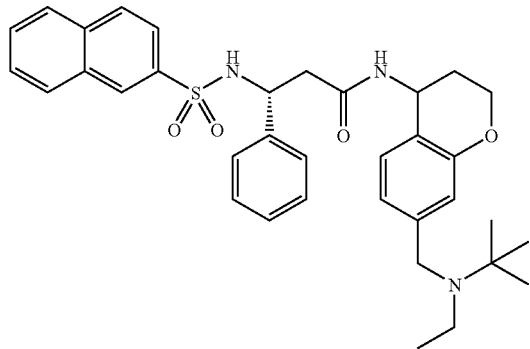

EXAMPLE 3f

N-{7-[(tert-Butyl-ethyl-amino)-methyl]-chroman-4-yl}-3-(naphthalen-2-yl-sulfonylamino)-3-phenyl-propionamide was prepared with tert-butylethylamine as a white solid. MS (ESI) m/z 600 (M+H)$^+$.

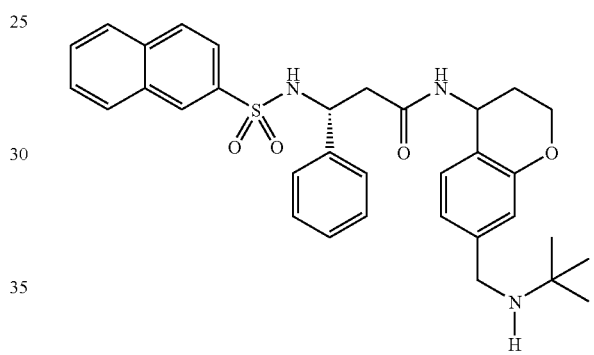

EXAMPLE 3i

N-[7-(tert-Butylamino-methyl)-chroman-4-yl]-3-(naphthalen-2-yl-sulfonylamino)-3-phenyl-propionamide was prepared with tert-butylamine as a white solid. MS (ESI) m/z 572 (M+H)$^+$.

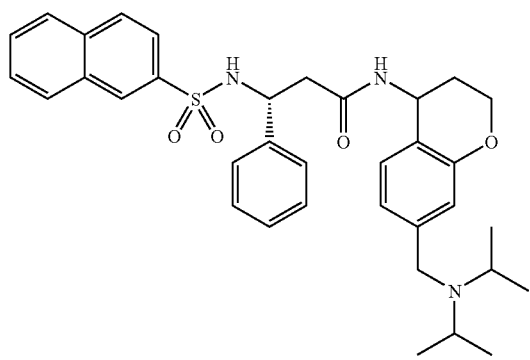

EXAMPLE 3g

N-{7-[(Diisopropylamino)-methyl]-chroman-4-yl}-3-(naphthalen-2-yl-sulfonylamino)-3-phenyl-propionamide was prepared with diisopropylamine as a white solid. MS (ESI) m/z 600 (M+H)$^+$.

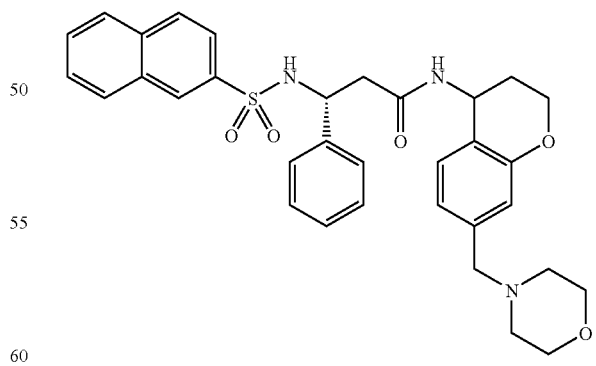

EXAMPLE 3j

N-(7-Morpholin-4-ylmethyl-chroman-4-yl)-3-(naphthalen-2-yl-sulfonylamino)-3-phenyl-propionamide was prepared with morpholine as a white solid. MS (ESI) m/z 586 (M+H)$^+$.

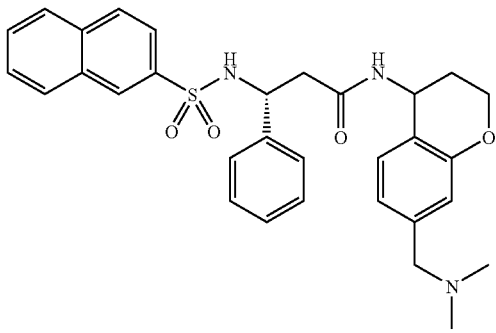

EXAMPLE 3k

N-(7-Dimethylaminomethyl-chroman-4-yl)-3-(naphthalen-2-yl-sulfonylamino)-3-phenyl-propionamide was prepared with dimethylamine as a white solid. MS (ESI) m/z 544 (M+H)+.

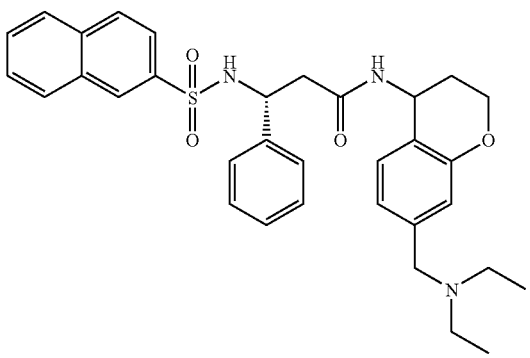

EXAMPLE 3l

N-(7-Diethylaminomethyl-chroman-4-yl)-3-(naphthalen-2-yl-sulfonylamino)-3-phenyl-propionamide was prepared with diethylamine as a white solid. MS (ESI) m/z 572 (M+H)+.

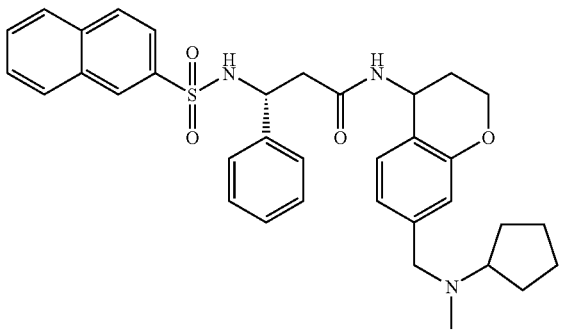

EXAMPLE 3m

N-{7-[(Cyclopentyl-methyl-amino)-methyl]-chroman-4-yl}-3-(naphthalen-2-yl-sulfonylamino)-3-phenyl-propionamide was prepared with N-methylcyclopentylamine as a white solid. MS (ESI) m/z 598 (M+H)+.

The following Examples below use essentially the same procedures described in Examples 1 and 2 using the alternative starting materials described in each step.

EXAMPLE 4

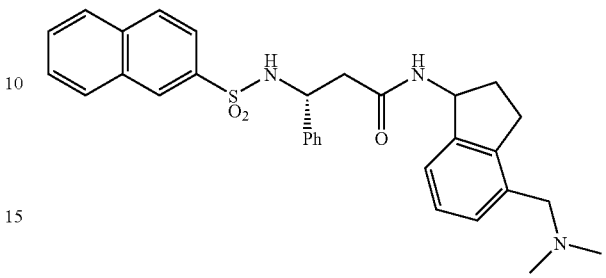

N-(4-Dimethylaminomethyl-indan-1-yl)-3-(naphthalen-2-yl-sulfonylamino)-3-phenyl-propionamide Step A—Preparation of trifluoro-methanesulfonic acid 1-oxo-indan-4-yl Ester Trifluoro-methanesulfonic acid 1-oxo-indan-4-yl ester was prepared from 4-hydroxy-indan-1-one using essentially the same procedure described in Example 6, Step A, yielding a brown oil.

Step B—Preparation of 1-oxo-indan-4-carbonitrile

1-Oxo-indan-4-carbonitrile was prepared from trifluoromethanesulfonic acid 1-oxo-indan-4-yl ester (Step A) using essentially the same procedure described in Example 1, Step A, yielding a yellow solid.

Step C—Preparation of 1-hydroxy-indan-4-carbonitrile

1-Hydroxy-indan-4-carbonitrile was prepared from 1-oxo-indan-4-carbonitrile (Step B) using essentially the same procedure described in Example 1, Step B.

Step D—Preparation of 1-azido-indan-4-carbonitrile

1-Azido-indan-4-carbonitrile was prepared in several steps from 1-hydroxy-indan-4-carbonitrile (Step C), using essentially the same procedure described in Example 1, Steps C-D, yielding a colorless oil.

Step E—Preparation of 1-amino-indan-4-carbonitrile

1-Amino-indan-4-carbonitrile was prepared from 1-azido-indan-4-carbonitrile (Step D), using essentially the same procedure described in Example 1, Step E, yielding a yellow-green solid.

Step F—Preparation of N-(4-cyano-indan-1-yl)-3-(naphthalen-2-yl-sulfonylamino)-3-phenyl-propionamide N-(4-Cyano-indan-1-yl)-3-(naphthalen-2-yl-sulfonylamino)-3-phenyl-propionamide was prepared from 3-(naphthalen-2-yl-sulfonylamino)-3-phenyl-propionic acid ( ) and 1-amino-indan-4-carbonitrile (Step E), using essentially the same procedure described in Example 1, Step F, yielding a white solid. MS (ESI) m/z 496 (M+H)+.

Step G—Preparation of N-(4-formyl-indan-1-yl)-3-(naphthalen-2-yl-sulfonylamino)-3-phenyl-propionamide N-(4-Formyl-indan-1-yl)-3-(naphthalen-2-yl-sulfonylamino)-3-phenyl-propionamide was prepared from N-(4-cyano-indan-1-yl)-3-(naphthalen-2-yl-sulfonylamino)-3-phenyl-propionamide (Step F), using essentially the same procedure described in Example 1, Step G, yielding an off-white solid. MS (ESI) m/z 499 (M+H)+.

Step H—Preparation of N-(4-dimethylaminomethyl-indan-1-yl)-3-(naphthalen-2-yl-sulfonylamino)-3-phenyl-propionamide N-(4-Dimethylaminomethyl-indan-1-yl)-3-(naphthalen-2-yl-sulfonylamino)-3-phenyl-propionamide was prepared from N-(4-formyl-indan-1-yl)-3-(naphthalen-2-yl-sulfonylamino)-3-phenyl-propionamide (Step G) and Me₂NH, using essentially the same procedure described in Example 1, Step H, yielding a White solid. MS (ESI) m/z 528 (M+H)+.

EXAMPLE 4a 3-(Naphthalen-2-yl-sulfonylamino)-3-phenyl-N-(4-piperidin-1-ylmethyl-indan-1-yl)-propionamide was prepared from N-(4-formyl-indan-1-yl)-3-(naphthalen-2-yl-sulfonylamino)-3-phenyl-propionamide Example 4, Step G and piperidine, using essentially the same procedure described in Example 1, Step H, yielding a white solid. MS (ESI) m/z 568 (M+H)+.

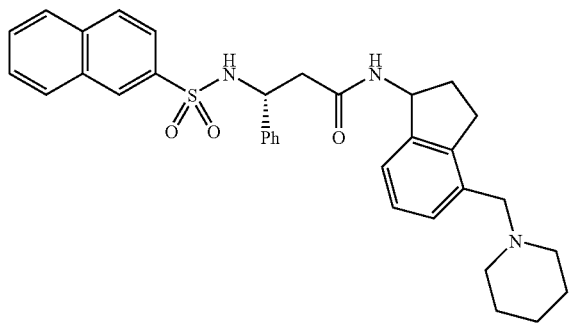

EXAMPLE 4b

N-(4-Aminomethyl-indan-1-yl)-3-(naphthalen-2-yl-sulfonylamino)-3-phenyl-propionamide hydrochloride was prepared from N-(4-cyano-indan-1-yl)-3-(naphthalen-2-yl-sulfonylamino)-3-phenyl-propionamide (Step F), using

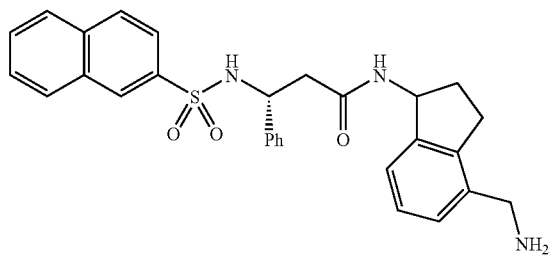

essentially the same procedure described in Example 2, yielding the HCl salt as a white solid. MS (ESI) m/z 500 (M+H)+.

EXAMPLE 5

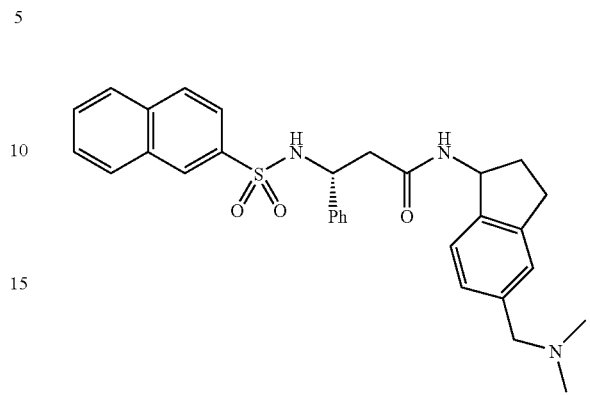

N-(5-Dimethylaminomethyl-indan-1-yl)-3-(naphthalen-2-yl-sulfonylamino)-3-phenyl-propionamide

Step A—Preparation of trifluoro-methanesulfonic acid 1-oxo-indan-5-yl ester

The title compound was prepared from 5-hydroxy-indan-1-one, using essentially the same procedure described in Example 6, Step A, yielding a brown oil.

Step B—Preparation of 1-oxo-indan-5-carbonitrile

The title compound was prepared from trifluoro-methanesulfonic acid 1-oxo-indan-5-yl ester (Step A), using essentially the same procedure described in Example 1, Step A.

Step C—Preparation of 1-hydroxy-indan-5-carbonitrile

The title compound was prepared from 1-oxo-indan-5-carbonitrile (Step B), using essentially the same procedure described in Example 1, Step B, yielding a yellow solid.

Step D—Preparation of 1-azido-indan-5-carbonitrile

The title compound was prepared in several steps from i-hydroxy-indan-5-carbonitrile (Step C), using essentially the same procedure described in Example 1, Steps C-D.

Step E—Preparation of 1-amino-indan-5-carbonitrile

The title compound was prepared from 1-azido-indan-5-carbonitrile (Step D), using essentially the same procedure described in Example 1, Step E. MS (APCI) m/z 142 (M+H)+.

Step F—Preparation of N-(5-cyano-indan-1-yl)-3-(naphthalen-2-yl-sulfonylamino)-3-phenyl-propionamide The title compound was prepared from 3-(naphthalen-2-yl-sulfonylamino)-3-phenyl-propionic acid [Example 1, Step F] and 1-amino-indan-5-carbonitrile (Step E), using essentially the same procedure described in Example 1, Step F, yielding a white solid. MS (ESI) m/z 496 (M+H)+.

Step G—Preparation of N-(5-formyl-indan-1-yl)-3-(naphthalen-2-yl-sulfonylamino)-3-phenyl-propionamide The title compound was prepared from N-(5-cyano-indan-1-yl)-3-(naphthalen-2-yl-sulfonylamino)-3-phenyl-propionamide (Step F), using essentially the same procedure described in Example 1, Step G, yielding an off-white solid. MS (ESI) m/z 499 (M+H)+.

Step H—Preparation of N-(5-dimethylaminomethyl-indan-1-yl)-3-(naphthalen-2-yl-sulfonylamino)-3-phenyl-propionamide The title compound was prepared from N-(5-formyl-indan-1-yl)-3-(naphthalen-2-yl-sulfonylamino)-3-phenyl-propionamide (Step G) and Me₂NH, using essentially the same procedure described in Example 1, Step H, yielding a white solid. MS (ESI) m/z 528 (M+H)+.

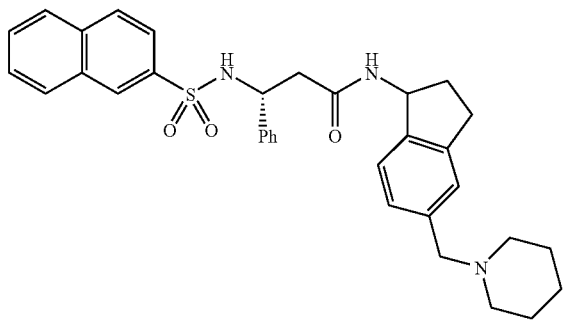

EXAMPLE 5a 3-(Naphthalen-2-yl-sulfonylamino)-3-phenyl-N-(5-piperidin-1-ylmethyl-indan-1-yl)-propionamide The title compound was prepared from N-(5-formyl-indan-1-yl)-3-(naphthalen-2-yl-sulfonylamino)-3-phenyl-propionamide (Example 5, Step F) and piperidine yielding a white solid. MS (ESI) m/z 568 (M+H)+.

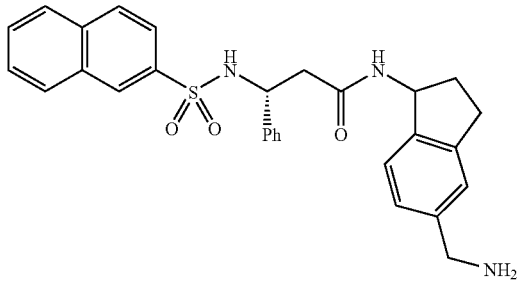

EXAMPLE 5b

N-(5-Aminomethyl-indan-1-yl)-3-(naphthalen-2-yl-sulfonylamino)-3-phenyl-propionamide Hydrochloride The title compound was prepared from N-(5-cyano-indan-1-yl)-3-(naphthalen-2-yl-sulfonylamino)-3-phenyl-propionamide yielding the HCl salt as a white solid. MS (ESI) m/z 500 (M+H)+.

EXAMPLE 6

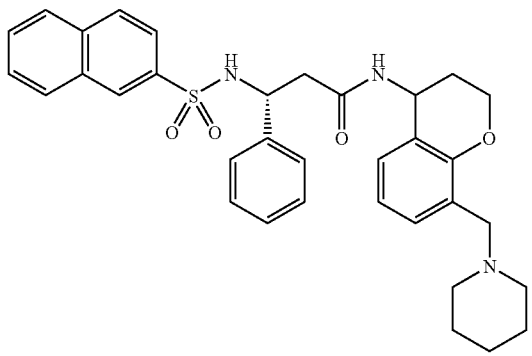

3-(Naphthalen-2-yl-sulfonylamino)-3-phenyl-N-(8-piperidin-1-ylmethyl-chroman-4-yl)-propionamide Hydrochloride Step A—Preparation of tert-butyl-(chroman-4-yloxy)-dimethyl-silane tert-Butyl-chloro-dimethyl-silane (10.54 g, 70 mmol) was added to a CH₂Cl₂ (200 mL) solution of 4-chromanol (10.00 g, 66.6 mmol), N-methylmorpholine (10.98 mL, 100 mmol) and imidazole (0.20 g, 3 mmol) at 0° C. The mixture was stirred for 3 days at RT. The reaction was diluted with CH₂Cl₂ (200 mL), washed with dilute HCl and H₂O, dried over MgSO₄, filtered, and concentrated in vacuo to provide the title compound.

Step B—Preparation of 4-(tert-butyl-dimethyl-silanyloxy)-chroman-8-carbaldehyde

Butyllithium was added to an Et₂O (80 mL) solution of tert-butyl-(chroman-4-yloxy)-dimethyl-silane (Step A) (6.21 g, 23.5 mmol) at −80° C. After stirring the mixture at 3° C. for 15 h, DMF (10 mL) was added at 0° C. Following a 30 min stirring at RT, the reaction was quenched with saturated NH₄Cl solution. The reaction was diluted with Et₂O (200 mL) and washed with brine. The organic phase was dried over MgSO₄, filtered, and concentrated in vacuo to provide the crude compound (40% conversion by ¹H NMR) which was purified by column chromatography (silica, 0 to 10% ether in hexane) to provide the title compound.

Step C—Preparation of 1-[4-(tert-butyl-dimethyl-silanyloxy)-chroman-8-ylmethyl]-piperidine NaBH(OAc)₃ (3.86 g, 18.21 mmol) was added to a dichloroethane (30 mL) solution of 4-(tert-butyl-dimethyl-silanyloxy)-chroman-8-carbaldehyde (Step B) (2.66 g, 9.10 mmol) and piperidine (2.70 mL, 27.31 mmol) at RT. After stirring for 1 h, the reaction was quenched with MeOH (10 mL) while the stirring was continued for 20 more min. The reaction was diluted with CH₂Cl₂ (200 mL) and washed with saturated NaHCO₃ solution and brine. The organic phase was dried over MgSO₄, filtered, and concentrated in vacuo from heptane to provide the title compound.

Step D—Preparation of 1-(4-azido-chroman-8-ylmethyl)-piperidine

HCl (1.2 mL, 37%) was added to a MeOH (60 mL) solution of 1-[4-(tert-butyl-dimethyl-silanyloxy)-chroman-8-ylmethyl]-piperidine (Step C) (3.00 g, 8.30 mmol). After stirring for 1 h, the mixture was evaporated to dryness from benzene. The resulting crude alcohol was dissolved in $SOCl_2$ (5 mL) and stirred for 3 days at RT. Following the removal of the excess $SOCl_2$ in vacuo from hexane, the crude chloride was dissolved in DMF (20 mL) and $NaN_3$ (1.618 g, 24.9 mmol) was added. The mixture was stirred at 80° C. for 1 h and, upon cooling, it was diluted with $Et_2O$ (100 mL), hexane (100 mL) and $H_2O$ (100 mL). After separation, the organic phase was washed with brine, dried over $MgSO_4$, filtered, and concentrated in vacuo to provide the title compound. MS (APCI+, m/z): 273 $(M+1)^+$.

Step E—Preparation of 8-piperidin-1-ylmethyl-chroman-4-ylamine bis-hydrochloride 1-(4-Azido-chroman-8-ylmethyl)-piperidine (Step D) (1.862 g, 6.84 mmol) was hydrogenated over $Pd(OH)_2$ (200 mg, 20% on carbon, Pearlman type) in EtOAc (100 mL) at atmospheric pressure for two days. After filtration of the catalyst and evaporation of the solution, HCl (20 mL, 1M in THF) was added while stirring vigorously. The precipitated, hygroscopic solid was filtered, washed with $Et_2O$ and dried to furnish the title compound. MS (APCI+, m/z): 247 $(M+1)^+$.

Step F—Preparation of 3-(naphthalen-2-yl-sulfonylamino)-3-phenyl-N-(8-piperidin-1-ylmethyl-chroman-4-yl)-propionamide 8-Piperidin-1-ylmethylchroman-4-ylamine dihydrochloride (Step E) (28 mg, 0.11 mmol), 3-(naphthalen-2-yl-sulfonylamino)-3-phenylpropionic acid (40 mg, 0.11 mmol), HOBt (17 mg, 0.12 mmol), and DIEA (21 mg, 0.16 mmol) were dissolved in $CH_2Cl_2$ (5 mL). EDC (25 mg, 0.13 mmol) was added and the reaction was kept at 22-25° C. overnight until completed. The reaction solution was washed with dilute (~5%) $NaHCO_3$—$H_2O$ and $H_2O$, then dried over $MgSO_4$, filtered and concentrated in vacuo to provide a residue which was purified by column chromatography (silica gel, 0.5% $Et_3N$ in EtOAc). The compound was converted to the HCl salt in $Et_2O$ to provide the title compound as a mixture of diastereomers, as a white solid (ca. 1:1 by $^1H$ NMR). MS (ESI) 584 $(M+H)^+$.

The following Examples below use essentially the same procedures described in Example 1 using the alternative starting materials described in each step.

EXAMPLE 7

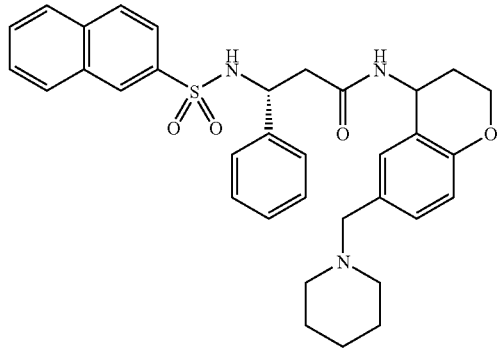

3-(Naphthalen-2-yl-sulfonylamino)-3-phenyl-N-(6-piperidin-1-ylmethyl-chroman-4-yl)-propionamide Hydrochloride

Step A—Preparation of chroman-4-one Oxime

To a mixture of 4-chromanone (10.00 g, 67.50 mmol) and hydroxylamine hydrochloride (7.04 g, 101 mmol) in EtOH (100 mL) was added a solution of NaOAc (16.61 g, 202.5 mmol) in $H_2O$ (30 mL). The reaction was heated to reflux for 2 h. The mixture was cooled to RT and concentrated in vacuo. The residue was diluted with $H_2O$ and acidified with 1 N HCl. The aqueous was extracted with EtOAc until tlc analysis showed no evidence of title compound in the aqueous layer. The combined organics were dried with $MgSO_4$ and concentrated in vacuo to furnish the crude title compound which was used without further purification. MS (APCI pos) 164 (M+H).

Step B—Preparation of chroman-4-ylamine

LAH (6.35 g, 167 mmol) was suspended in THF (100 mL) at 0° C. A solution of chroman-4-one oxime (Step A) (10.92 g, 66.92 mmol) in THF (100 mL) was added drop-wise. The mixture was heated slowly to reflux for 4 h. The reaction was cooled to RT and added drop-wise to a stirred saturated solution of Rochelle's salt in $H_2O$. The bi-phasic mixture was stirred rapidly at RT for 1 h. The layers were separated and the aqueous layer was extracted with EtOAc until tlc analysis of the aqueous layer showed no evidence of the title compound. The combined organics were dried over $MgSO_4$ and concentrated in vacuo to furnish the crude material, which was purified by flash column chromatography to afford the title compound. MS (APCI pos) 150 (M+H).

Step C—Preparation of 6-bromo-chroman-4-ylamine

A solution of chroman-4-ylamine (Step B) (2.550 g, 17.09 mmol) in AcOH (50 mL) at RT was treated with $Br_2$ (3.01 g, 0.96 mL, 18.8 mmol) drop-wise. The reaction was stirred at RT until HPLC analysis showed complete consumption of starting material. The mixture was diluted with $H_2O$ (100 mL) and NaOH was added until the solution became basic. The aqueous layer was extracted with EtOAc until tlc analysis of the aqueous layer showed no evidence of the title compound. The combined organics were dried over $MgSO_4$ and concentrated in vacuo to yield the crude compound, which was purified by flash column chromatography to afford the pure title compound. MS (APCI pos) 229 (M+H).

Step D—Preparation of (6-bromo-chroman-4-yl)-carbamic acid tert-butyl ester To a RT solution of 6-bromo-chroman-4-ylamine (Step C) (2.270 g, 9.952 mmol) and di-tert-butyl dicarbonate (2.606 g, 11.94 mmol) in $CH_2Cl_2$ (50 mL) was added a solution of $NaHCO_3$ (1.672 g, 19.90 mmol) in $H_2O$ (50 mL). The bi-phasic mixture was rapidly stirred until complete consumption of starting material was observed by HPLC analysis (over night). The reaction was diluted with EtOAc and $H_2O$ and the layers were separated. The organics were dried with $MgSO_4$ and concentrated in vacuo to afford the crude title compound, which was used without further purification.

Step E—Preparation of (6-formyl-chroman-4-yl)-carbamic acid tert-butyl ester (6-Bromo-chroman-4-yl)-carbamic acid tert-butyl ester (Step D) (3.859 g, 11.76 mmol) was dissolved in THF (50 mL) and cooled to −78° C. n-Butyllithium (2.5 M) (11.76 mL, 29.40 mmol) was added drop-wise to the stirred solution. The reaction mixture was stirred at −78° C. for 30 min and DMF (4.55 mL, 58.8 mmol) was added drop-wise and the system was slowly warmed to RT overnight. The reaction was quenched with saturated aqueous $NH_4Cl$ solution and extracted with EtOAc. The combined organics were dried with $MgSO_4$ and concentrated in vacuo to afford the crude compound, which was purified by flash column chromatography to furnish the pure title compound.

Step F—Perparation of 3-(naphthalen-2-yl-sulfonylamino)-3-phenyl-N-(6-piperidin-1-ylmethyl-chroman-4-yl)-propionamide hydrochloride The reductive amination procedure in Example 1, Step H was used to react (6-formyl-chroman-4-yl)-carbamic acid tert-butyl ester (Step E) with piperidine to provide (6-piperidin-1-ylmethyl-chroman-4-yl)-carbamic acid tert-butyl ester. The Boc group was deprotected with TFA in $CH_2Cl_2$ to provide the amine salt. The coupling procedure described in the preparation of Example 1, Step F with 3-(naphthalen-2-yl-sulfonylamino)-3-phenylpropionic acid was used to provide the title compound as a mixture of diastereomers (ca. 1:1 by $^1$H NMR) isolated as the HCl salt. MS (ESI) 584 $(M+H)^+$.

EXAMPLE 8

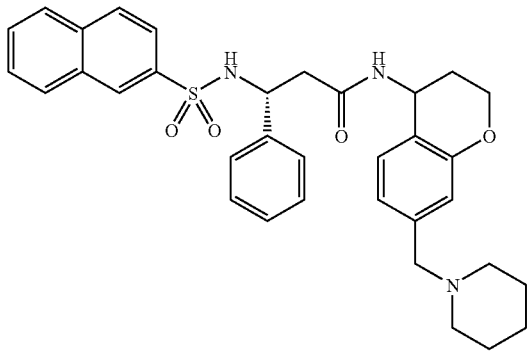

3-(Naphthalen-2-yl-sulfonylamino)-3-phenyl-N-(6-piperidin-1-ylmethyl-1,2,3,4-tetrahydro-naphthalen-1-yl)-propionamide

Step A—Preparetion of trifluoro-methanesulfonic acid 5-oxo-5,6,7,8-tetrahydro-naphthalen-2-yl ester Trifluoro-methanesulfonic anhydride (14.35 mL, 77.3 mmol) was added to a $CH_2Cl_2$ (150 mL) solution of 6-hydroxy-3,4-dihydro-2H-naphthalen-1-one (11.40 g, 70.3 mmol), N-methylmorpholine (8.5 mL, 77.3 mmol) and DMAP (130 mg, 1 mmol) in 5 min at −80° C. The mixture was warmed to 0° C. in 1 h then poured into a cold solution of saturated $NH_4Cl$. The mixture was diluted with $CH_2Cl_2$ (400 mL), washed with $H_2O$, dried over $MgSO_4$, filtered, and concentrated in vacuo to provide the crude compound which was purified by column chromatography (silica, 0 to 60% $CH_2Cl_2$ in hexane) to provide the title compound.

Step B—Preparation of 5-oxo-5,6,7,8-tetrahydro-naphthalen-2-carbonitrile

The title compound was prepared from trifluoro-methanesulfonic acid 5-oxo-5,6,7,8-tetrahydro-naphthalen-2-yl ester (Step A) by a method similar to that described in Example 1, Step A.

Step C—Preparaion of 5-hydroxy-5,6,7,8-tetrahydro-naphthalen-2-carbonitrile

The title compound was prepared from 5-oxo-5,6,7,8-tetrahydro-naphthalen-2-carbonitrile (Step B) by a method similar to that described in Example 1, Step B.

Step D—Preparation of 5-azido-5,6,7,8-tetrahydro-naphthalen-2-carbonitrile

The title compound was prepared from 5-hydroxy-5,6,7,8-tetrahydro-naphthalen-2-carbonitrile (Step C) via 5-chloro-5,6,7,8-tetrahydro-naphthalen-2-carbonitrile by a method similar to that described in Example 1, Steps C-D. MS (+APCI m/z): 171 $(M-N_2+H)^+$.

Step E—Preparation of 5-amino-5,6,7,8-tetrahydro-naphthalen-2-carbonitrile

The title compound was prepared from 5-azido-5,6,7,8-tetrahydro-naphthalen-2-carbonitrile (Step D) by catalytic hydrogenation similar to that described in Example 1, Step E.

Step F—Preparation of N-(6-cyano-1,2,3,4-tetrahydro-naphthalen-1-yl)-3-(naphthalen-2-yl-sulfonylamino)-3-phenyl-propionamide The title compound was prepared from 3-(naphthalen-2-yl-sulfonylamino)-3-phenyl-propionic acid and 5-amino-5,6,7,8-tetrahydro-naphthalen-2-carbonitrile (Step E) by a method similar to that described in Example 1, Step F. MS (−APCI m/z): 508 $(M-H)^-$.

Step G—Preparation of N-(6-formyl-1,2,3,4-tetrahydro-naphthalen-1-yl)-3-(naphthalen-2-yl-sulfonylamino)-3-phenyl-propionamide The title compound was prepared from N-(6-cyano-1,2,3,4-tetrahydro-naphthalen-1-yl)-3-(naphthalen-2-yl-sulfonylamino)-3-phenyl-propionamide (Step F) by a method similar to that described in Example 1, Step G. MS (+APCI m/z): 513 $(M+H)^+$. MS (−APCI m/z): 511 $(M-H)^-$.

Step H—Preparation of 3-(naphthalen-2-yl-sulfonylamino)-3-phenyl-N-(6-piperidin-1-ylmethyl-1,2,3,4-tetrahydro-naphthalen-1-yl)-propionamide The title compound was prepared from N-(6-formyl-1,2,3,4-tetrahydro-naphthalen-1-yl)-3-(naphthalen-2-yl-sulfonylamino)-3-phenyl-propionamide (Step G) by reductive amination with piperidine similar to that described in Example 1, Step H. MS (+ESI m/z): 582 $(M+H)^+$.

EXAMPLE 9

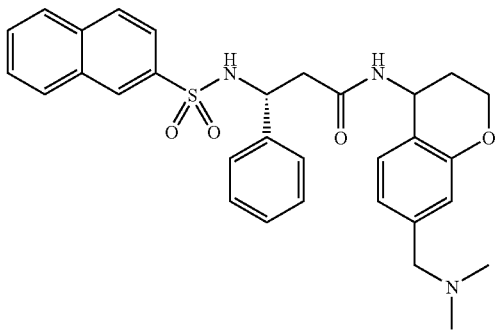

N-(6-Dimethylaminomethyl-1,2,3,4-tetrahydro-naphthalen-1-yl)-3-(naphthalen-2-yl-sulfonylamino)-3-phenyl-propionamide The title compound was prepared from N-(6-formyl-1,2,3,4-tetrahydro-naphthalen-1-yl)-3-(naphthalen-2-yl-sulfonylamino)-3-phenyl-propionamide (Example 8, Step G) using essentially the same procedure used in Example 8, Step H except using dimethylamine. MS (+ESI m/z): 542 (M+H)$^+$.

EXAMPLE 10

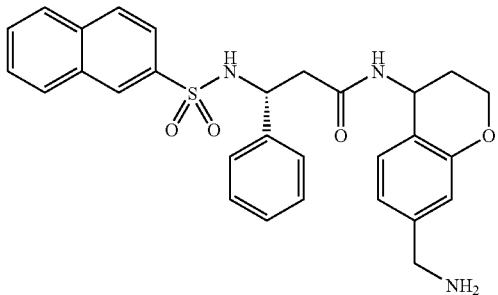

N-(6-Aminomethyl-1,2,3,4-tetrahydro-naphthalen-1-yl)-3-(naphthalen-2-yl-sulfonylamino)-3-phenyl-propionamide The title compound was prepared from N-(6-cyano-1,2,3,4-tetrahydro-naphthalen-1-yl)-3-(naphthalen-2-yl-sulfonylamino)-3-phenyl-propionamide (Example 8, Step F) by catalytic hydrogenation and HCl salt formation as described in Example 2. MS (+ESI m/z): 514 (M+H)$^+$.

EXAMPLE 11

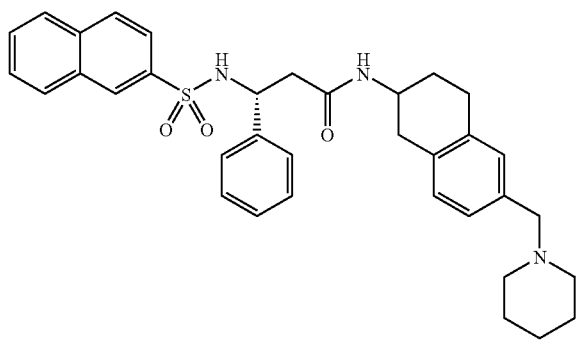

3-(Naphthalen-2-yl-sulfonylamino)-3-phenyl-N-(6-piperidin-1-ylmethyl-1,2,3,4-tetrahydro-naphthalen-2-yl)-propionamide

Step A—Preparation of 6-bromo-3,4-dihydro-1H-naphthalen-2-one oxime

To a mixture of 6-bromo-3,4-dihydro-1H-naphthalen-2-one (5.370 g, 23.86 mmol) and hydroxylamine hydrochloride (2.487 g, 35.79 mmol) in EtOH (80 mL) was added a solution of NaOAc (5.871 g, 71.57 mmol) in H$_2$O (20 mL). The mixture was heated to reflux for 2 h. The reaction was cooled to RT and concentrated in vacuo. The residue was suspended in H$_2$O and filtered. The pad was washed with H$_2$O (2×50 mL) and Et$_2$O (2×50 mL) and the solids were dried in vacuo to furnish the title compound, which was used without further purification. MS (APCI pos) 242 (M+H).

Step B—Preparation of 6-bromo-1,2,3,4-tetrahydro-naphthalen-2-ylamine

A solution of BH$_3$-THF complex (1M) (35.9 mL, 35.9 mmol) was added drop-wise to a stirred solution of 6-bromo-3,4-dihydro-1H-naphthalen-2-one oxime (Step A) (3.450 g, 14.37 mmol) in THF (125 ml) at 0° C. The mixture was warmed to RT and to reflux for 24 h. The reaction was cooled to RT and 1 N aqueous HCl was added carefully until the mixture was acidic and the system was stirred until no further gas was evolved. The solution was made basic by the addition of NaOH and the aqueous layer was extracted with EtOAc. The combined organics were dried over MgSO$_4$ and concentrated in vacuo to afford the crude title compound, which was purified by flash column chromatography to yield the title compound. MS (APCI pos) 228 (M+H).

Step C—Preparation of (6-bromo-1,2,3,4-tetrahydro-naphthalen-2-yl)-carbamic acid tert-butyl ester Di-tert-butyl dicarbonate (1.030 g, 4.719 mmol) was added to a stirred RT solution of 6-bromo-1,2,3,4-tetrahydro-naphthalen-2-ylamine (Step B) (0.970 g, 4.290 mmol) in CH$_2$Cl$_2$ (100 mL). TEA (0.897 mL, 6.435 mmol) was added to the reaction and the mixture was stirred at RT until HPLC analysis showed complete consumption of starting material. The reaction was diluted with CH$_2$Cl$_2$, washed with saturated aqueous NaHCO$_3$, dried over MgSO$_4$ and concentrated in vacuo to afford the crude material. The crude was purified by flash column chromatography to yield the title compound. MS (APCI pos) 269 (M-t-Bu).

Step D—Preparationo of (6-formyl-1,2,3,4-tetrahydro-naphthalen-2-yl)-carbamic acid tert-butyl ester (6-Bromo-1,2,3,4-tetrahydro-naphthalen-2-yl)-carbamic acid tert-butyl ester (Step C) (1.080 g, 3.311 mmol) was dissolved in THF (30 mL) and cooled to −78° C. n-Butyl-lithium (2.5 M) (3.311 mL, 8.276 mmol) was added drop-wise to the stirred solution. The reaction was stirred at −78° C. for 30 min and DMF (1.282 mL, 16.55 mmol) was added drop-wise and the mixture was slowly warmed to RT overnight. The reaction was quenched with saturated aqueous NH$_4$Cl solution and extracted with EtOAc. The combined organics were dried over MgSO$_4$ and concentrated in vacuo to afford the crude material, which was purified by flash column chromatography to furnish the pure title compound. MS (APCI pos) 217 (M-t-Bu).

Step E—Preparation of (6-piperidin-1-ylmethyl-1,2,3,4-tetrahydro-naphthalen-2-yl)-carbamic acid tert-butyl ester (6-Formyl-1,2,3,4-tetrahydro-naphthalen-2-yl)-carbamic acid tert-butyl ester (Step D) (0.090 g, 0.33 mmol) was dissolved in N,N-dimethylacetamide (10 mL). Piperdine (0.162 mL, 1.63 mmol) was added and the mixture was stirred at RT for 30 min. NaBH(OAc)$_3$ (0.173 g, 0.817 mmol) was added in one portion and the reaction was stirred at RT until complete consumption of starting material was observed by HPLC analysis. The reaction was in concentrated in vacuo and the residue was diluted with CH$_2$Cl$_2$ and H$_2$O and the aqueous layer was made basic with NaOH. The layers were separated and the organics were dried over MgSO$_4$ and concentrated in vacuo to afford the crude title compound, which was used without further purification. MS (APCI pos) 345 (M+H).

Step F—Preparation of 6-piperidin-1-ylmethyl-1,2,3,4-tetrahydro-naphthalen-2-ylamine (6-Piperidin-1-ylmethyl-1,2,3,4-tetrahydro-naphthalen-2-yl)-carbamic acid tert-butyl ester (Step E) (0.113 g, 0.327 mmol) was suspended in CH$_2$Cl$_2$ (2.5 mL) then TFA was added (2.5 mL). The reaction was stirred at RT until complete consumption of starting material was observed by HPLC analysis (2 h). The reaction mixture was concentrated in vacuo to afford the crude title compound as the bis-TFA salt, which was used without further purification. MS (APCI pos) 245 (M+H).

Step G—Preparation of 3-(naphthalen-2-yl-sulfonylamino)-3-phenyl-N-(6-piperidin-1-ylmethyl-1,2,3,4-tetrahydro-naphthalen-2-yl)-propionamide 6-Piperidin-1-ylmethyl-1,2,3,4-tetrahydro-naphthalen-2-ylamine bis-TFA salt (Step F) (0.143 g, 0.327 mmol), 3-(naphthalen-2-yl-sulfonylamino)-3-phenyl-propionic acid (0.128 g, 0.360 mmol), HOBt (0.057 g, 0.425 mmol) and EDC (0.081 g, 0.425 mmol) were dissolved in CH$_2$Cl$_2$ (25 mL) and stirred at RT. TEA (0.228 mL, 1.64 mmol) was added drop-wise to the mixture and the reaction was stirred at RT until HPLC analysis showed complete consumption of starting material. The reaction mixture was diluted with CH$_2$Cl$_2$ and washed with saturated aqueous NaHCO$_3$. The organic layer was dried over MgSO$_4$ and concentrated in vacuo to afford the crude material. The crude was purified by flash column chromatography to furnish the title compound. MS (APCI pos) 582 (M+H).

EXAMPLE 12

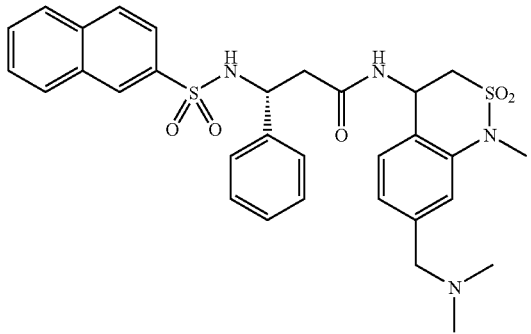

N-(7-Dimethylaminomethyl-1-methyl-2,2-dioxo-1,2,3,4-tetrahydro-2$\lambda^6$-benzo[c][1,2]thiazin-4-yl)-3-(naphthalen-2-yl-sulfonylamino)-3-phenyl-propionamide

Step A—Preparation of 4-hydroxyimino-1-methyl-2,2-dioxo-1,2,3,4-tetrahydro-2$\lambda^6$-benzo[c][1,2]thiazine-7-carboxylic acid methyl ester NaOAc (3.66 g, 44.5 mmol) was added to an EtOH (100 mL) solution of 1-methyl-2,2,4-trioxo-1,2,3,4-tetrahydro-2$\lambda^6$-benzo[c][1,2]thiazine-7-carboxylic acid methyl ester (4.00 g, 14.8 mmol) and hydroxylamine hydrochloride (1.55 g, 22.3 mmol). After heating at reflux for 4 days, it was evaporated, diluted with CH$_2$Cl$_2$ (400 mL), washed with H$_2$O, dried over MgSO$_4$, filtered, and concentrated in vacuo. Crystallization from MeOH provided the title compound. MS (−APCI, m/z): 283 (M−H)$^-$.

Step B—Preparation of 4-Amino-1-methyl-2,2-dioxo-1,2,3,4-tetrahydro-2$\lambda^6$-benzo[c][1,2]thiazine-7-carboxylic acid methyl ester 4-Hydroxyimino-1-methyl-2,2-dioxo-1,2,3,4-tetrahydro-2$\lambda^6$-benzo[c)][1,2]thiazine-7-carboxylic acid methyl ester (Step A) (1.50 g, 5.28 mmol) was hydrogenated over Pd(OH)$_2$ (1.30 g, 20% on carbon, wet) in MeOH (100 mL) for 60 h. After filtration and evaporation, chromatography (silica, 0-3% MeOH in CH$_2$CL$_2$) furnished the title compound. MS (+APCI, m/z): 271 (M+H)$^+$, 254 (M−NH$_2$)$^+$, MS (−APCI, m/z): 252 (M−NH$_4$)$^-$.

Step C—Preparation of 4-(3-(naphthalen-2-yl-sulfonylamino)-3-phenyl-propionylamino)-1-methyl-2,2-dioxo-1,2,3,4-tetrahydro-2$\lambda^6$-benzo[c][1,2]thiazine-7-carboxylic acid methyl ester The title compound was prepared from 3-(naphthalen-2-yl-sulfonylamino)-3-phenyl-propionic acid Example 1, Step H and 4-amino-1-methyl-2,2-dioxo-1,2,3,4-tetrahydro-2$\lambda^6$-benzo[c][1,2]thiazine-7-carboxylic acid methyl ester (Step B) similar to that described in Example 1, Step F. MS (+APCI, m/z): 608 (M+H)$^+$.

Step D—Preparation of N-(7-hydroxymethyl-1-methyl-2,2-dioxo-1,2,3,4-tetrahydro-2$\lambda^6$-benzo[c][1,2]thiazin-4-yl)-3-(naphthalen-2-yl-sulfonylamino)-3-phenyl-propionamide Lithium borohydride (10.0 mL, 20 mmol, 2.0 M in THF) was added to a THF (50 mL) solution of 4-(3-(naphthalen-2-yl-sulfonylamino)-3-phenyl-propionylamino)-1-methyl-2,2-dioxo-1,2,3,4-tetrahydro-2$\lambda^6$-benzo[c][1,2]thiazine-7-carboxylic acid methyl ester (Step C) (1.76 g, 2.9 mmol). Following addition of MeOH (0.3 mL, 8 mmol), the mixture was stirred for 20 h at 50° C. The reaction was quenched with acetone, MeOH and dilute HCl at 0° C. The mixture was diluted with CH$_2$Cl$_2$ (400 mL), washed with H$_2$O, dried over MgSO$_4$, filtered, and concentrated in vacuo. Chromatography on silica (0-5% MeOH in CH$_2$Cl$_2$) provided the title compound. MS (−APCI, m/z): 578 (M−H)$^-$.

Step E—Preparation of N-(7-dimethylaminomethyl-1-methyl-2,2-dioxo-1,2,3,4-tetrahydro-2λ⁶-benzo[c][1,2]thiazin-4-yl)-3-(naphthalen-2-yl-sulfonylamino)-3-phenyl-propionamide Methanesulfonic anhydride (100 mg, 0.55 mmol) was added to a THF (5 mL) solution of N-(7-hydroxymethyl-1-methyl-2,2-dioxo-1,2,3,4-tetrahydro-2λ⁶-benzo[c][1,2]thiazin-4-yl)-3-(naphthalen-2-yl-sulfonylamino)-3-phenyl-propionamide (Step D) (200 mg, 0.345 mmol) and N-methylmorpholine (0.11 mL, 0.55 mmol). After 30 min stirring, Me₂NH (1.73 mL, 3.45 mmol, 2.0 M in THF) was added to this freshly prepared mesylate solution. After stirring overnight, the mixture was diluted with CH₂Cl₂ (30 mL), washed with H₂O, dried over MgSO₄, filtered, and concentrated in vacuo. Chromatography on silica (0-5% MeOH in CH₂Cl₂) provided the title compound. MS (+ESI, m/z): 607 (M+H)⁺.

EXAMPLE 13

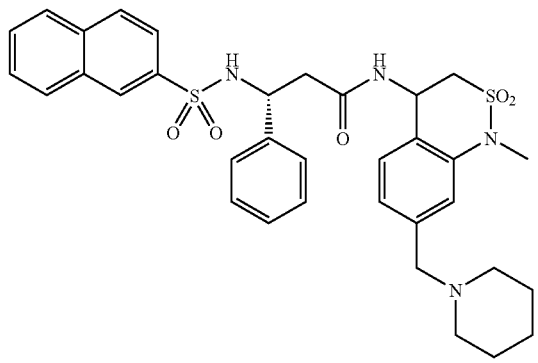

3-(Naphthalen-2-yl-sulfonylamino)-N-(1-methyl-2,2-dioxo-7-piperidin-1-ylmethyl-1,2,3,4-tetrahydro-2λ⁶-benzo[c][1,2]thiazin-4-yl)-3-phenyl-propionamide The title compound was prepared from N-(7-hydroxymethyl-1-methyl-2,2-dioxo-1,2,3,4-tetrahydro-2λ⁶-benzo[c][1,2]thiazin-4-yl)-3-(naphthalen-2-yl-sulfonylamino)-3-phenyl-propionamide (Example 12, Step D) via its mesylate and addition of piperidine by a method similar to that described in Example 12, Step E. MS (+ESI, m/z): 647 (M+H)⁺.

EXAMPLE 14

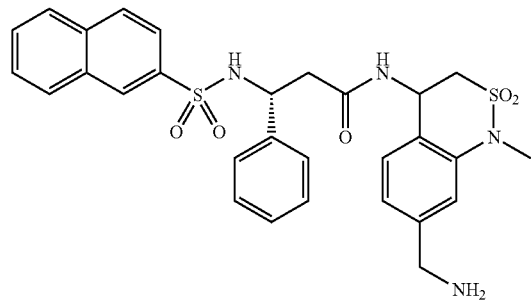

N-(7-Aminomethyl-1-methyl-2,2-dioxo-1,2,3,4-tetrahydro-2λ⁶-benzo[c][1,2]thiazin-4-yl)-3-(naphthalen-2-yl-sulfonylamino)-3-phenyl-propionamide The title compound was prepared from N-(7-hydroxymethyl-1-methyl-2,2-dioxo-1,2,3,4-tetrahydro-2λ⁶-benzo[c][1,2]thiazin-4-yl)-3-(naphthalen-2-yl-sulfonylamino)-3-phenyl-propionamide (Example 12, Step E) via its mesylate and addition of NH₃ by a method similar to that described in Example 12, Step E. MS (+ESI, m/z): 579 (M+H)⁺.

EXAMPLE 15

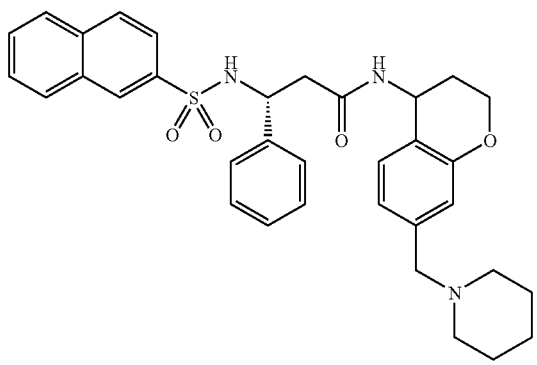

3-(Naphthalen-2-yl-sulfonylamino)-3-(R)-phenyl-N—(R)-(7-piperidin-1-ylmethyl-chroman-4-yl)-propionamide Step A—Preparation of (S)-4-hydroxy-chroman-7-carbonitrile A ruthenium chiral complex was prepared as follows: (1S,2S)-(+)—N-p-Tosyl-1,2-diphenylethylenediamine (1.10 g, 3.0 mmol, Aldrich) and [RuCl₂(η⁶-para-cymene)]₂ (0.92 g, 1.5 mmol, STREM) were dissolved in 35 ml of i-PrOH and stirred at 80° C. for 1 h. The reaction was concentrated under reduced pressure to ~5 ml. The mixture was cooled to −20° C., and 10 mL of H₂O was added with shaking. The solution was scratched with a spatula until it all solidifies. The solid was filtered and washed with H₂O to provide the desired chiral complex. The complex was dried in vacuo. A 5/2 mixture of formic acid and Et₃N was prepared as follows: A mixture of formic acid (190 ml, 232 g, 5.03 mmol) and Et₃N (280 mL, 203 g, 2.01 mmol) were heated to 100° C. under reduced pressure (~100 mm Hg) to remove volatile chemicals. The residue was used without further purification. 7-Cyanochroman-4-one (10.2 g, 58.9 mmol) and a 5/2 mixture of formic acid and Et₃N (50 mL) were dissolved in CH₃CN (120 ml). The ruthenium chiral complex (S, S—, 0.380 g, 0.589 mmol) was added. The reaction was stirred at RT for 14 h. After the addition of H₂O (100 mL), the mixture was extracted with EtOAc (300 ml, 3×). The organic phases were combined and washed sequentially with a saturated NaHCO₃ solution and brine. The organic solution was dried over MgSO₄, filtered and concentrated in vacuo to provide a crude brown solid which was purified by flash column chromatography (silica, 50% EtOAc in hexane) to provide the title compound.

Step B—Preparation of (R)-4-azido-chroman-7-carbonitrile

Azeotropically dried (S)-4-hydroxy-chroman-7-carbonitrile (Step A) (2.0 g, 11 mmol) was dissolved in dry THF (55 ml). DPPA (3.0 mL, 3.8 g, 14 mmol) was added to the solution at RT and the mixture was stirred for 5 min. The solution was cooled to 0° C. and DBU (2.0 mL, 2.1 g, 14 mmol) was added. After stirring for 10 min at 0° C., the reaction was warmed to RT, at which time a white precipitate formed, and was stirred for 14 h. The resulting solution was poured into $H_2O$ (100 mL) and extracted with $Et_2O$ (300 mL, 3×). The organic phases were combined, washed with brine, dried over $MgSO_4$, filtered and concentrated in vacuo to provide a residue which was purified by flash column chromatography (silica, 33% hexane in $CH_2Cl_2$) to provide the title compound. Using the chiral azide, (R)-4-azido-chroman-7-carbonitrile, and the procedures from Example 1 the following diastereomerically pure compounds were prepared.

Step C—Preparation of N—(R)-(7-cyano-chroman-4-yl)-3-(naphthalen-2-yl-sulfonylamino)-3-(R)-phenylpropionamide The title compound was prepared from (R)-4-azido-chroman-7-carbonitrile by the methods described in Example 1, Step F.

Step D—Preparation of N—(R)-(7-formyl-chroman-4-yl)-3-(naphthalen-2-yl-sulfonylamino)-3-(R)-phenyl-propionamide The title compound was prepared from N—(R)-(7-cyano-chroman-4-yl)-3-(naphthalen-2-yl-sulfonylamino)-3-(R)-phenylpropionamide by the methods described in Example 1, Step G.

The following compounds can be prepared by methods similar to that described above:

| Example | Structure | Name | Formula | MW | M + H |
|---|---|---|---|---|---|
| a | 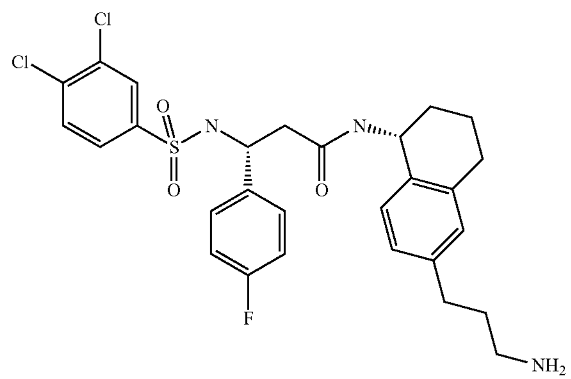 | (3S)-N-((1R)-6-(((1,1-dimethylethyl)amino)methyl)-1,2,3,4-tetrahydro-1-naphthalenyl)-3-(4-fluorophenyl)-3-(((3-(trifluoromethyl)phenyl)sulfonyl)amino)propanamide | $C_{31}H_{35}F_4N_3O_3S$ | 605.693 | 606 |
| b | 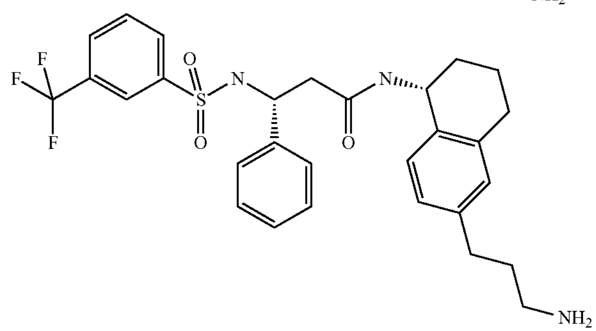 | (3R)-3-(((3,4-dichlorophenyl)sulfonyl)amino)-N-((4R)-7-(((1,1-dimethylethyl)amino)methyl)-3,4-dihydro-2H-chromen-4-yl)-3-phenylpropanamide | $C_{29}H_{33}Cl_2N_3O_4S$ | 590.569 | 591 |
| c | 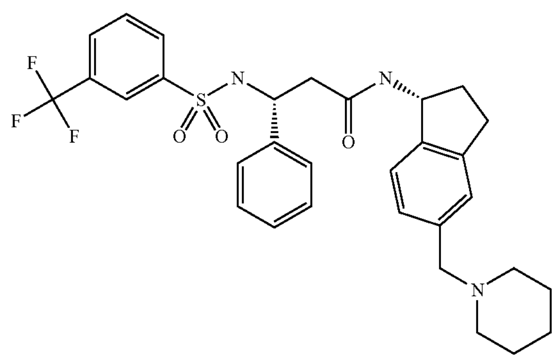 | (3R)-3-phenyl-N-((1R)-5-(1-piperidinylmethyl)-2,3-dihydro-1H-inden-1-yl)-3-(((3-(trifluoromethyl)phenyl)sulfonyl)amino)propanamide | $C_{31}H_{34}F_3N_3O_3S$ | 585.688 | 586 |

| Example | Structure | Name | Formula | MW | M + H |
|---|---|---|---|---|---|
| d | 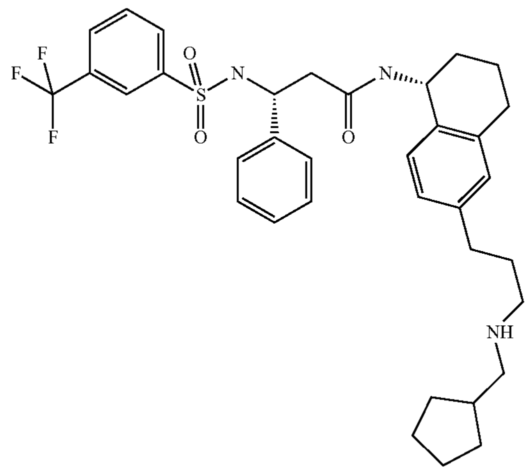 | (3R)-N-((4R)-7-(((cyclopropylmethyl)amino)methyl)-3,4-dihydro-2H-chromen-4-yl)-3-phenyl-3-(((3-(trifluoromethyl)phenyl)sulfonyl)amino)propanamide | $C_{30}H_{32}F_3N_3O_4S$ | 587.66 | 588 |
| e | 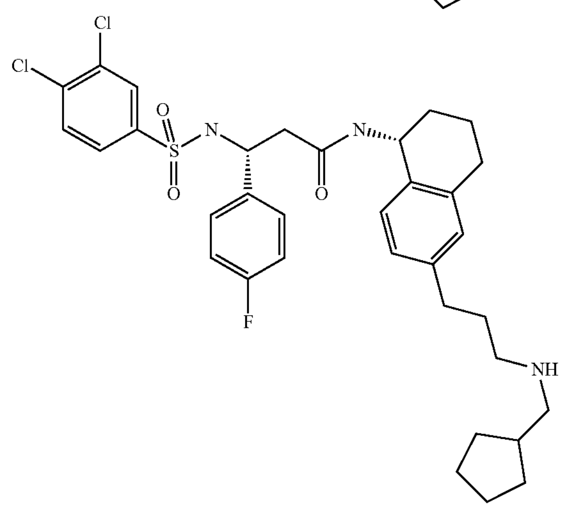 | (3R)-N-((1R)-6-(((cyclopropylamino)methyl)-1,2,3,4-tetrahydro-1-naphthalenyl)-3-phenyl-3-(((3-(trifluoromethyl)phenyl)sulfonyl)amino)propanamide | $C_{30}H_{32}F_3N_3O_3S$ | 571.661 | 572 |

-continued
| Example | Structure | Name | Formula | MW | M + H |
|---|---|---|---|---|---|
| f | 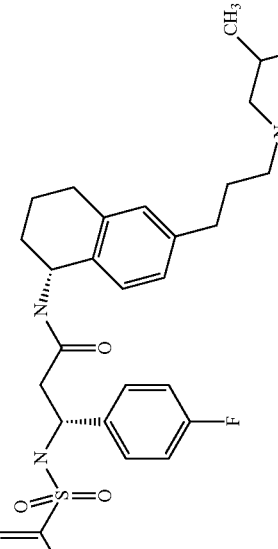 | (3R)-N-((4R)-7-(((3R)-3-hydroxy-1-piperidinyl)methyl)-3,4-dihydro-2H-chromen-4-yl)-3-phenyl-3-(((3-(trifluoromethyl)phenyl)sulfonyl)amino)-propanamide | C₃₁H₃₄F₃N₃O₃S | 617.68 | 617 |
| g | 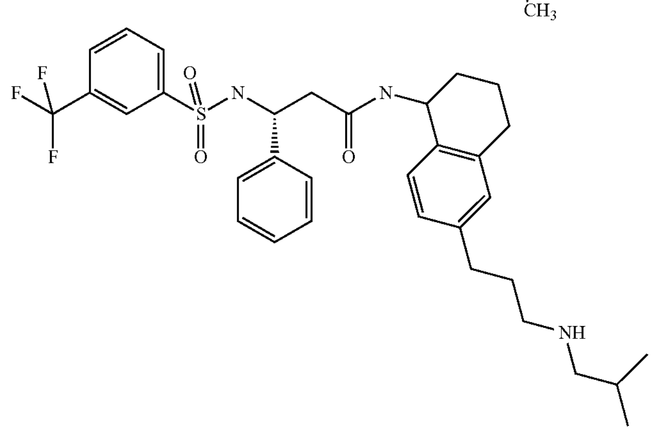 | (3R)-3-phenyl-N-((1R)-6-(1-piperidinylmethyl)-1,2,3,4-tetrahydro-1-naphthalenyl)-3-(((3-(trifluoromethyl)phenyl)sulfonyl)amino)propanamide | C₃₂H₃₆F₃N₃O₃S | 599.714 | |

-continued

| Example | Structure | Name | Formula | MW | M + H |
|---|---|---|---|---|---|
| h | 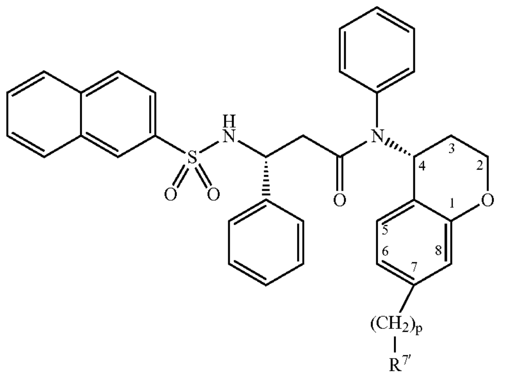 | (3R)-N-((1R)-6-((4-fluoro-1-piperidinyl)methyl)-1,2,3,4-tetrahydro-1-naphthalenyl)-3-phenyl-3-(((3-trifluoromethyl)phenyl)sulfonyl)amino)propanamide | $C_{32}H_{35}F_4N_3O_3S$ | 617.705 | 618 |
| i | 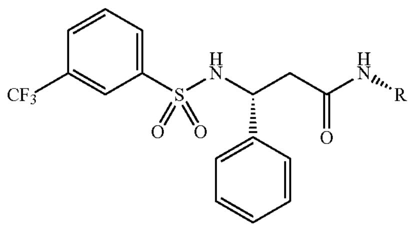 | (3R)-N-((4R)-7-(((cyclobutyl)amino)methyl)-3,4-dihydro-2H-chromen-4-yl)-3-phenyl-3-(((3-(trifluoromethyl)phenyl)sulfonyl)amino)propanamide | $C_{30}H_{32}F_3N_3O_4S$ | 587.66 | 588 |
| j | 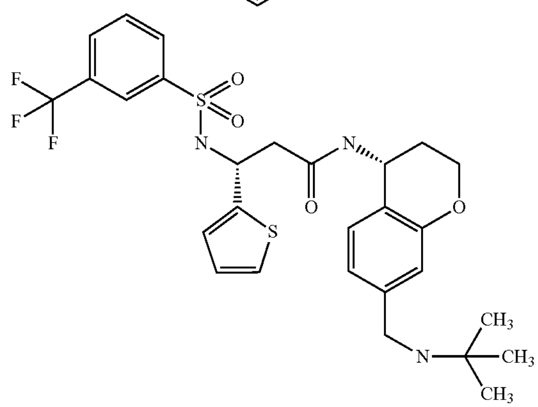 | (3R)-N-((4R)-7-(((1,1-dimethylethyl)amino)methyl)-3,4-dihydro-2H-chromen-4-yl)-3-(2-thienyl)-3-(((3-(trifluoromethyl)phenyl)sulfonyl)amino)propanamide | $C_{28}H_{32}F_3N_3O_4S_2$ | 595.704 | 596 |

-continued

| Example | Structure | Name | Formula | MW | M + H |
|---|---|---|---|---|---|
| k | 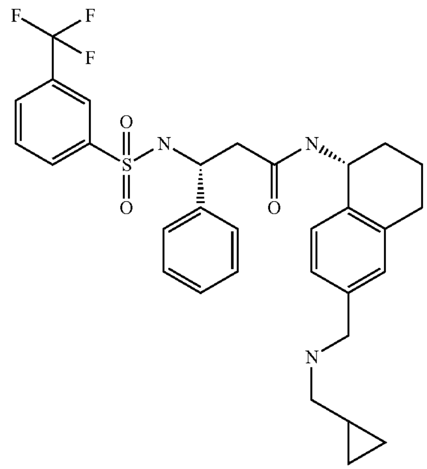 | (3R)-N-((1R)-6-(((cyclopropylmethyl)amino)methyl)-1,2,3,4-tetrahydro-1-naphthalenyl)-3-phenyl)-3-(((3-(trifluoromethyl)phenyl)sulfonyl)amino)propanamide | C₃₁H₃₄F₃N₃O₃S | 585.688 | 586 |
| l | 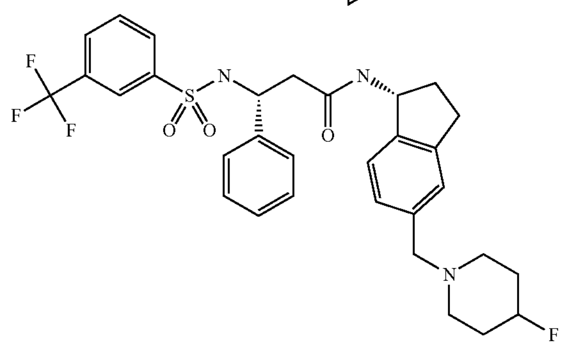 | (3R)-N-((1R)-5-((4,4-difluoro-1-piperidinyl)methyl)-2,3-dihydro-1H-inden-1-yl)-3-phenyl-3-(((3-(trifluoromethyl)phenyl)sulfonyl)amino)propanamide | C₃₁H₃₃F₄N₃O₃S | 603.678 | 604 |

| Example | Structure | Name | Formula | MW | M + H |
|---|---|---|---|---|---|
| m | 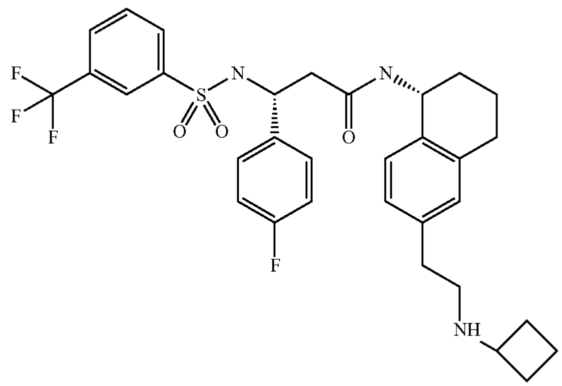 | (3S)-3-(4-cyanophenyl)-N-((1R)-6-(((1,1-dimethylethyl)amino)methyl)-1,2,3,4-tetrahydro-1-naphthalenyl)-3-(((3-trifluoromethyl)phenyl)sulfonyl)amino)propanamide | $C_{32}H_{35}F_3N_4O_3S$ | 612.714 | 613 |
| n | 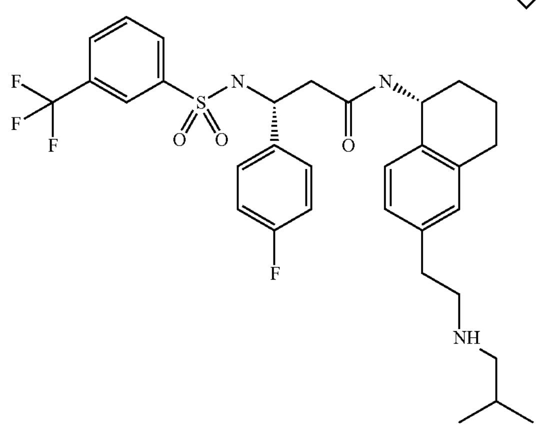 | (3R)-N-((1R)-6-((cyclopentylamino)methyl)-1,2,3,4-tetrahydro-1-naphthalenyl)-3-(((3-(trifluoromethyl)phenyl)sulfonyl)amino)propanamide | $C_{32}H_{35}F_4N_3O_3S$ | 617.705 | 618 |

| Example | Structure | Name | Formula | MW | M + H |
|---|---|---|---|---|---|
| o | 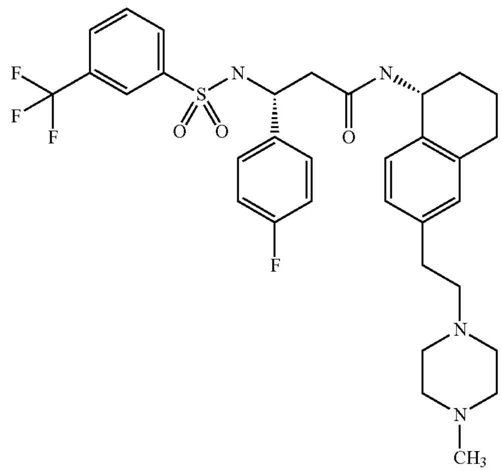 | (3R)-3-(4-fluorophenyl)-N-((1R)-6-(1-pyrrolidinylmethyl)-1,2,3,4-tetrahydro-1-naphthalenyl)-3-(((3-(trifluoromethyl)phenyl)sulfonyl)-amino)propanamide | $C_{31}H_{33}F_4N_3O_3S$ | 603.78 | 604 |
| p | 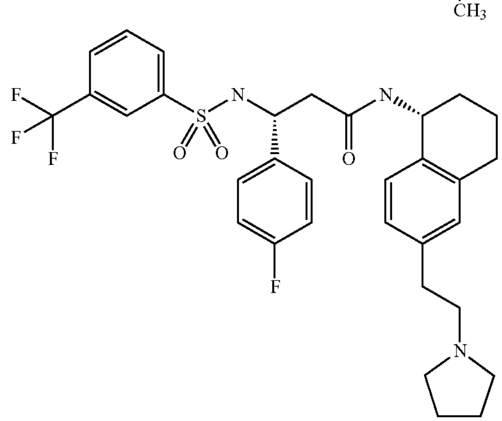 | 3-(3,4-Dichloro-benzenesulfonylamino)-N-{7-[(2-methoxy-ethylamino)-methyl]-chroman-4-yl}-3-phenyl-propionamide | $C_{28}H_{31}Cl_2N_3O_5S$ | 592.541 | 593 |

| Example | Structure | Name | Formula | MW | M + H |
|---|---|---|---|---|---|
| q | 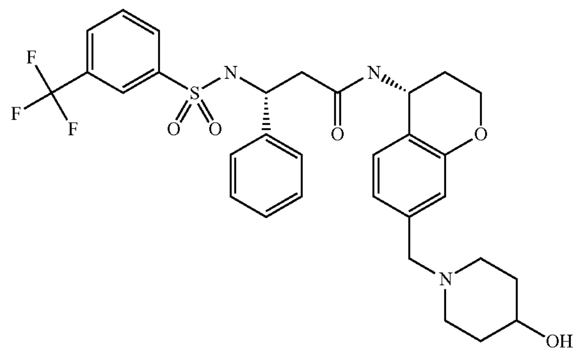 | (3R)-N-((4R)-7-((4-hydroxy-1-piperidinyl)methyl)-3,4-dihydro-2H-chromen-4-yl)-3-phenyl-3-(((3-(trifluoromethyl)phenyl)sulfonyl)amino)propanamide | C₃₁H₃₄F₃N₃O₅S | 617.67 | 618 |
| r | 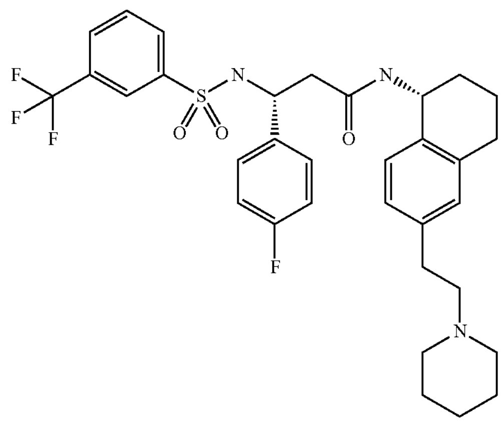 | (3R)-3-phenyl-N-((4R)-7-((((2S)-tetrahydro-2-furanyl)methyl)amino)methyl)-3,4-dihydro-2H-chromen-4-yl)-3-(((3-(trifluoromethyl)phenyl)sulfonyl)amino)propanamide | C₃₁H₃₄F₃N₃O₅S | 617.686 | 617 |

| Example | Structure | Name | Formula | MW | M + H |
|---|---|---|---|---|---|
| s | 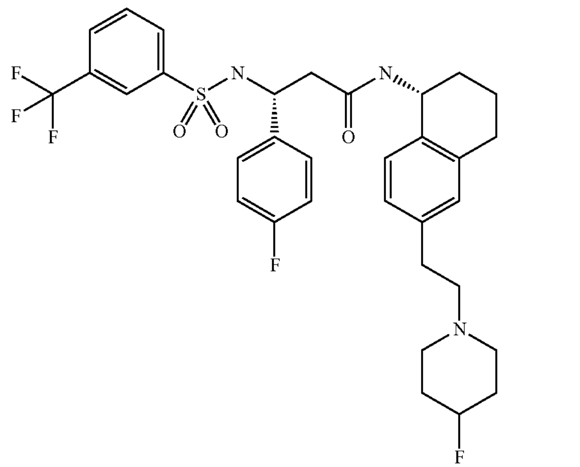 | (3R)-N-((4R)-7-(((3-hydroxy-2,2-dimethyl)propyl)amino)methyl)-3,4-dihydro-2H-chromen-4-yl)-3-phenyl-3-(((3-(trifluoromethyl)phenyl)sulfonyl)amino)propanamide | $C_{31}H_{36}F_3N_3O_5S$ | 619.701 | 620 |
| t | 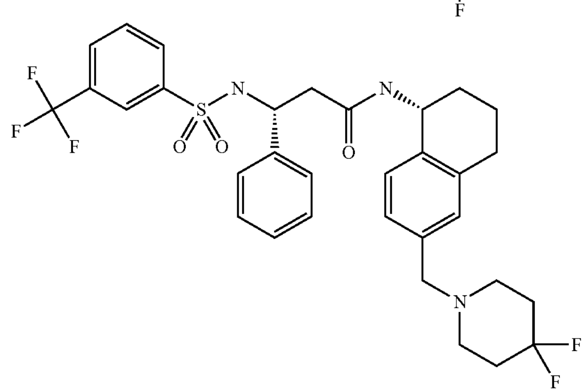 | (3R)-N-((1R)-6-((4,4-difluoro-1-piperidinyl)methyl)-1,2,3,4-tetrahydro-1-naphthalenyl)-3-phenyl-3-(((3-(trifluoromethyl)phenyl)sulfonyl)amino)propanamide | $C_{32}H_{34}F_5N_3O_3S$ | 635.695 | 635 |

-continued
| Example | Structure | Name | Formula | MW | M + H |
|---|---|---|---|---|---|
| u | 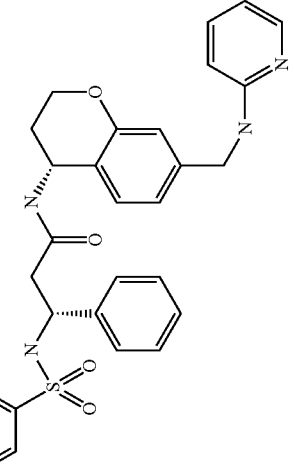 | (3R)-3-phenyl-N-((4R)-7-((2-pyridinylamino)methyl)-3,4-dihydro-2H-chromen-4-yl)-3-(((3-(trifluoromethyl)phenyl)-sulfonyl)amino)propanamide | $C_{31}H_{29}F_3N_4O_4S$ | 610.654 | 611 |
| v | 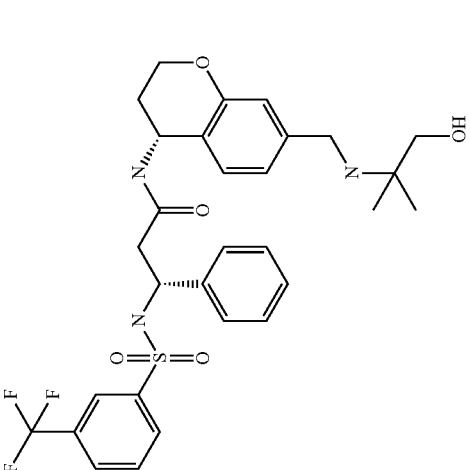 | (3R)-N-((4R)-7-(((2-hydroxy-1,1-dimethylethyl)amino)methyl)-3,4-dihydro-2H-chromen-4-yl)-3-phenyl-3-(((3-(trifluoromethyl)phenyl)-sulfonyl)amino)propanamide | $C_{30}H_{34}F_3N_3O_5S$ | 605.675 | 606 |

| Example | Structure | Name | Formula | MW | M + H |
|---|---|---|---|---|---|
| w | 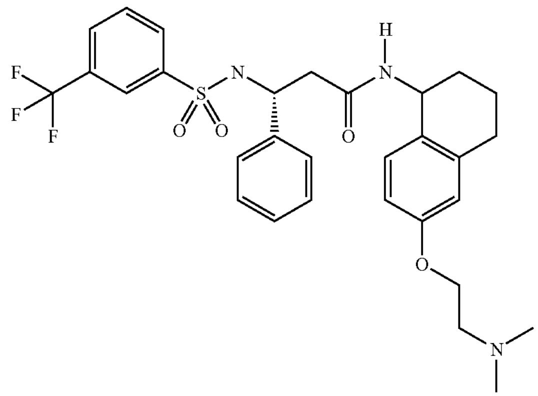 | (3R)-N-((1S)-6-((2-(dimethylamino)ethyl)oxy)-1,2,3,4-tetrahydro-1-naphthalenyl)-3-phenyl-3-(((3-(trifluoromethyl)phenyl)-sulfonyl)amino)propanamide | $C_{30}H_{34}F_3N_3O_4S$ | 589.67 | 590 |
| x | 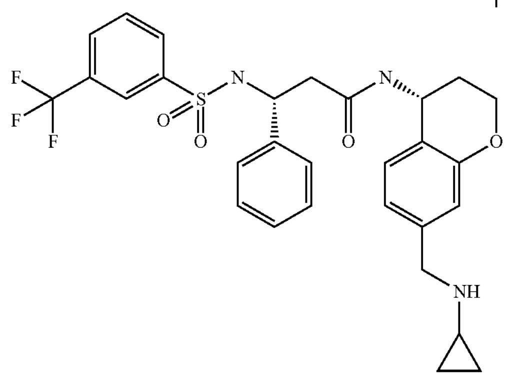 | (3R)-N-((4R)-7-((cyclopropylamino)methyl)-3,4-dihydro-2H-chromen-4-yl)-3-phenyl-3-(((3-(trifluoromethyl)phenyl)-sulfonyl)amino)propanamide | $C_{29}H_{30}F_3N_3O_4S$ | 573.633 | 574 |

-continued

| Example | Structure | Name | Formula | MW | M + H |
|---|---|---|---|---|---|
| y | 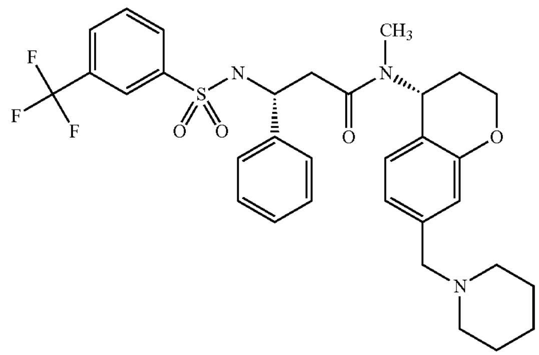 | (3R)-N-methyl-3-phenyl-N-((4R)-7-(1-piperidinylmethyl)-3,4-dihydro-2H-chromen-4-yl)-3-(((3-(trifluoromethyl)phenyl)sulfonyl)amino)propanamide | $C_{32}H_{36}F_3N_3O_4S$ | 615.71 | 616 |
| z | 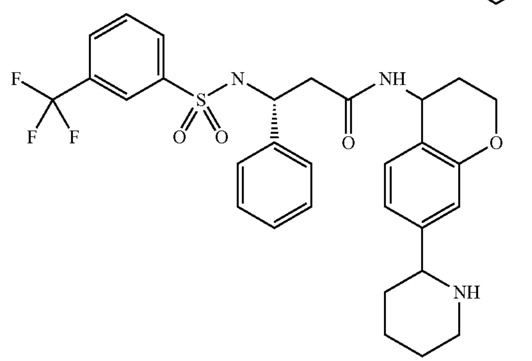 | (3R)-3-phenyl-N-((4S)-7-((2R)-2-piperidinyl)-3,4-dihydro-2H-chromen-4-yl)-3-(((3-(trifluoromethyl)phenyl)sulfonyl)amino)propanamide | $C_{30}H_{32}F_3N_3O_4S$ | 647.66 | 648 |
| aa | 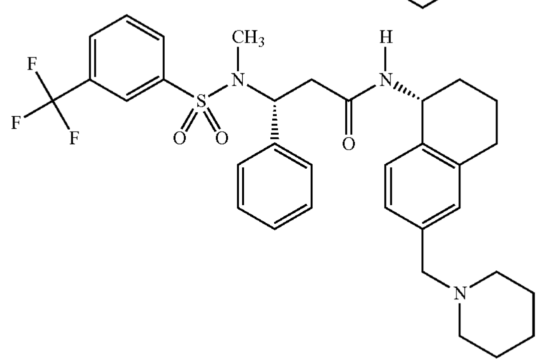 | (3R)-3-(methyl((3-(trifluoromethyl)phenyl)sulfonyl)amino)-3-phenyl-N-((1R)-6-(1-piperidinylmethyl)-1,2,3,4-tetrahydro-1-naphthalenyl)propanamide | $C_{33}H_{38}F_3N_3O_3S$ | 613.74 | 614 |

| Example | Structure | Name | Formula | MW | M + H |
|---|---|---|---|---|---|
| ab | 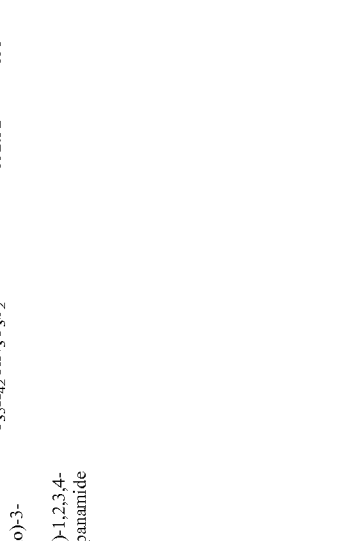 | (3R)-3-(((5-chloro-3-methyl-1-benzothien-2-yl)sulfonyl)amino)-3-phenyl-N-(6-((((1R)-1,2,2-trimethylpropyl)amino)methyl)-1,2,3,4-tetrahydro-1-naphthalenyl)propanamide | $C_{35}H_{42}ClN_3O_3S_2$ | 652.32 | 653 |
| ac | 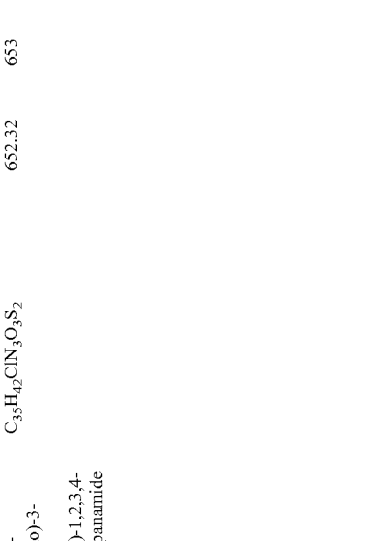 | (3R)-3-(((5-chloro-3-methyl-1-benzothien-2-yl)sulfonyl)amino)-3-phenyl-N-(6-((((1S)-1,2,2-trimethylpropyl)amino)methyl)-1,2,3,4-tetrahydro-1-naphthalenyl)propanamide | $C_{35}H_{42}ClN_3O_3S_2$ | 652.32 | 653 |

-continued

| Example | Structure | Name | Formula | MW | M + H |
|---|---|---|---|---|---|
| ad | 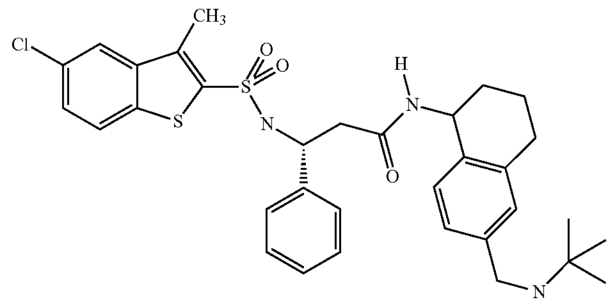 | (3R)-3-(((5-chloro-3-methyl-1-benzothien-2-yl)sulfonyl)amino)-N-(6-(((1,1-dimethylethyl)amino)methyl)-1,2,3,4-tetrahydro-1-naphthalenyl)-3-phenylpropanamide | $C_{33}H_{38}ClN_3O_3S_2$ | 624.23 | 625 |
| ae | 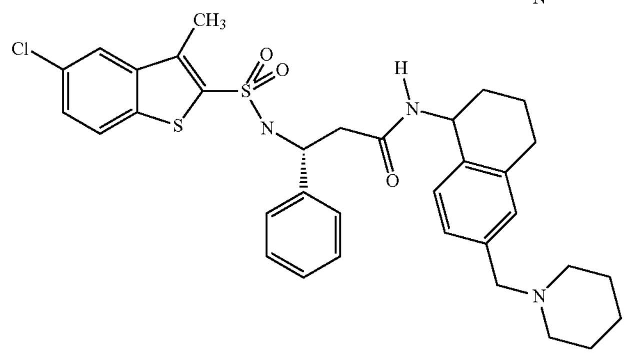 | (3R)-3-(((5-chloro-3-methyl-1-benzothien-2-yl)sulfonyl)amino)-3-phenyl-N-(6-(1-piperidinylmethyl)-1,2,3,4-tetrahydro-1-naphthalenyl)propanamide | $C_{34}H_{38}ClN_3O_3S_2$ | 636.277 | 637 |
| af | 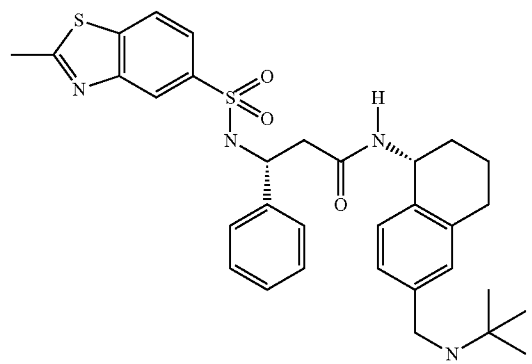 | (3R)-N-((1R)-6-(((1,1-dimethylethyl)amino)methyl)-1,2,3,4-tetrahydro-1-naphthalenyl)-3-(((2-methyl-1,3-benzothiazol-5-yl)sulfonyl)amino)-3-phenylpropanamide | $C_{32}H_{38}N_4O_3S_2$ | 590.81 | 591 |

| Example | Structure | Name | Formula | MW | M + H |
|---|---|---|---|---|---|
| ag | 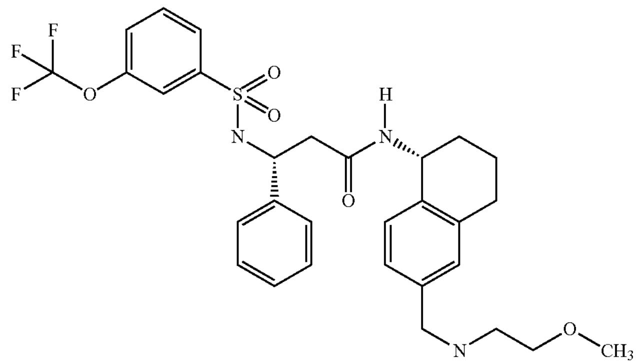 | (3R)-N-((1R)-6-(((2-(methyloxy)ethyl)amino)methyl)-1,2,3,4-tetrahydro-1-naphthalenyl)-3-phenyl-3-(((3-((trifluoromethyl)oxy)phenyl)sulfonyl)amino)propanamide | $C_{30}H_{34}F_3N_3O_5S$ | 605.67 | 606 |
| ah | 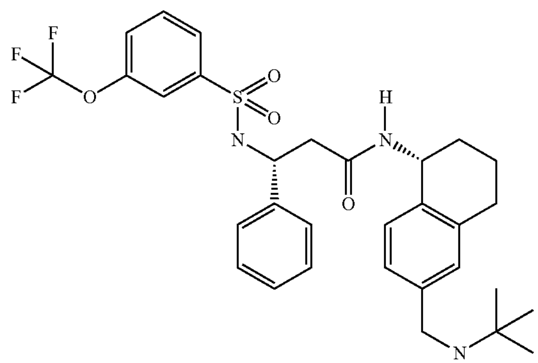 | (3R)-N-((1R)-6-((((1,1-dimethylethyl)amino)methyl)-1,2,3,4-tetrahydro-1-naphthalenyl)-3-phenyl-3-(((3-((trifluoromethyl)oxy)phenyl)sulfonyl)amino)propanamide | $C_{31}H_{36}F_3N_3O_4S$ | 603.70 | 603 |

| Example | Structure | Name | Formula | MW | M + H |
|---|---|---|---|---|---|
| ai | 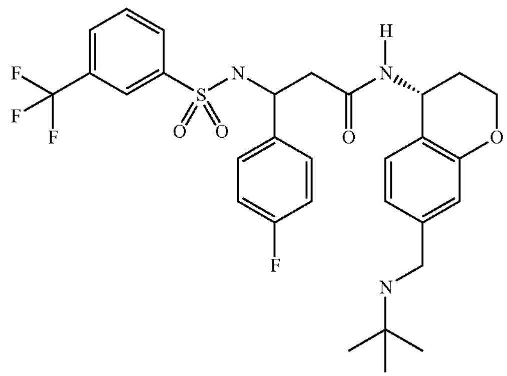 | (3S)-N-((4R)-7-(((1,1-dimethylethyl)amino)methyl)-3,4-dihydro-2H-chromen-4-yl)-3-(4-fluorophenyl)-3-(((3-(trifluoromethyl)phenyl)sulfonyl)amino)propanamide | $C_{30}H_{33}F_4N_3O_4S$ | 607.6 | 608 |
| aj | 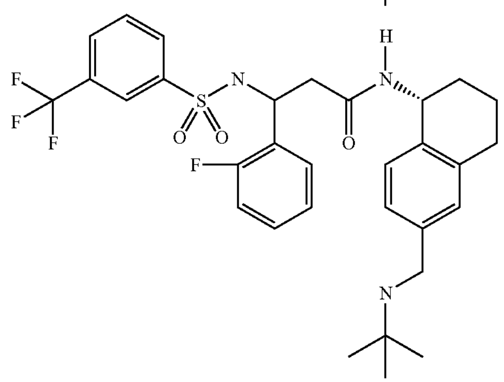 | (3S)-N-((1R)-6-(((1,1-dimethylethyl)amino)methyl)-1,2,3,4-tetrahydro-1-naphthalenyl)-3-(2-fluorophenyl)-3-(((3-(trifluoromethyl)phenyl)sulfonyl)amino)propanamide | $C_{31}H_{35}F_4N_3O_3S$ | 605.7 | 606 |

| Example | Structure | Name | Formula | MW | M + H |
|---|---|---|---|---|---|
| ak | 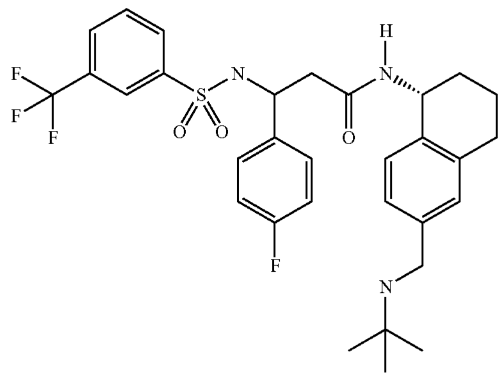 | (3S)-N-((1R)-6-(((1,1-dimethylethyl)amino)methyl)-1,2,3,4-tetrahydro-1-naphthalenyl)-3-(4-fluorophenyl)-3-(((3-(trifluoromethyl)phenyl)sulfonyl)amino)propanamide | C₃₁H₃₅F₄N₃O₃S | 605.7 | 606 |
| al | 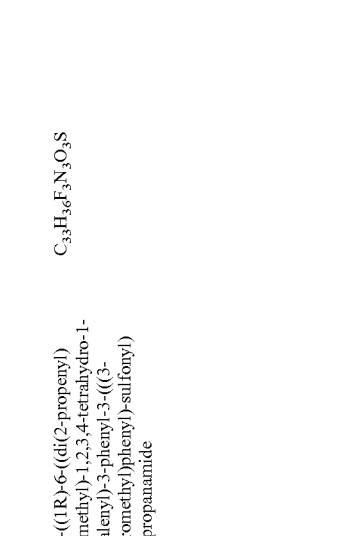 | (3R)-N-((1R)-6-((di(2-propenyl)amino)methyl)-1,2,3,4-tetrahydro-1-naphthalenyl)-3-phenyl-3-(((3-(trifluoromethyl)phenyl)sulfonyl)amino)propanamide | C₃₃H₃₆F₃N₃O₃S | 611.725 | 612 |

-continued

| Example | Structure | Name | Formula | MW | M + H |
|---|---|---|---|---|---|
| am | 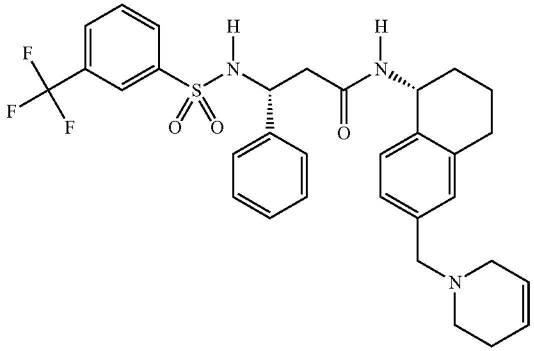 | (3R)-N-((1R)-6-(3,6-dihydro-1(2H)-pyridinylmethyl)-1,2,3,4-tetrahydro-1-naphthalenyl)-3-phenyl-3-(((3-(trifluoromethyl)phenyl)sulfonyl)amino)propanamide | $C_{32}H_{34}F_3N_3O_3S$ | 597.70 | 598 |
| an | 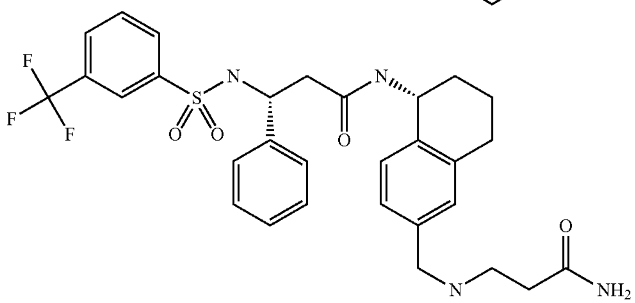 | N-3-(((5R)-5-(((3R)-3-phenyl-3-(((3-(trifluoromethyl)phenyl)sulfonyl)amino)propanoyl)amino)-5,6,7,8-tetrahydro-2-naphthalenyl)methyl)-beta-alaninamide | $C_{30}H_{33}F_3N_4O_4S$ | 602.68 | 603 |
| ao | 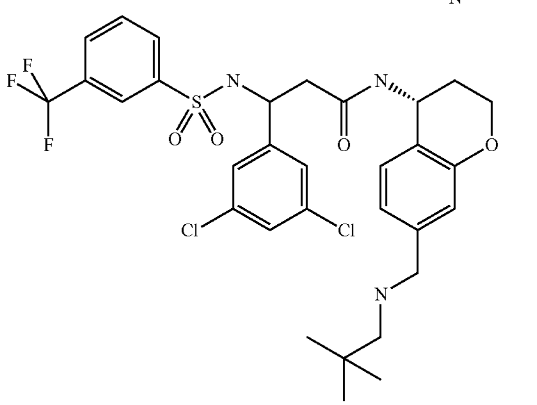 | (3S)-3-(3,5-dichlorophenyl)-N-((4R)-7-(((2,2-dimethylpropyl)amino)methyl)-3,4-dihydro-2H-chromen-4-yl)-3-(((3-(trifluoromethyl)phenyl)sulfonyl)amino)propanamide | $C_{31}H_{34}Cl_2F_3N_3O_4S$ | 672.5 | 673 |

-continued

| Example | Structure | Name | Formula | MW | M + H |
|---|---|---|---|---|---|
| ap | 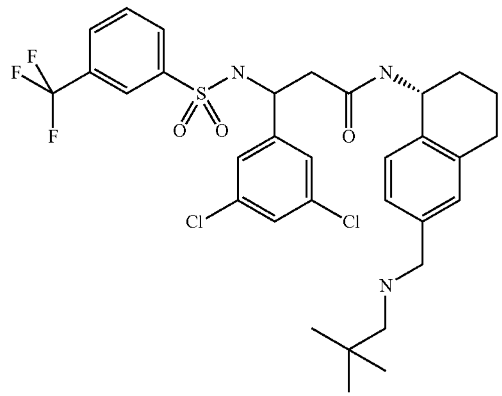 | (3S)-3-(3,5-ddichlorophenyl)-N-((1R)-6-(((2,2-dimethylpropyl)amino)methyl)-1,2,3,4-tetrahydro-1-naphthalenyl)-3-(((3-(trifluoromethyl)phenyl)sulfonyl)amino)propanamide | $C_{32}H_{36}Cl_2F_3N_3O_3S$ | 670.62 | 671 |
| aq | 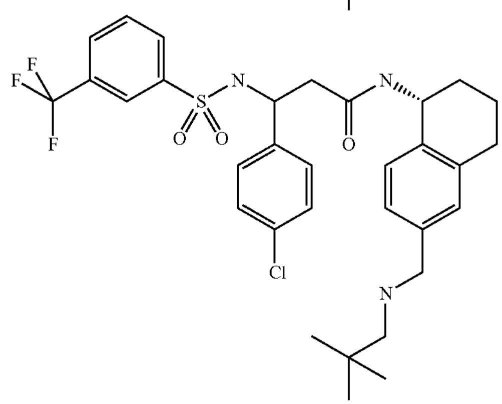 | (3S)-3-(4-chlorophenyl)-N-((1R)-6-(((2,2-dimethylpropyl)amino)methyl)-1,2,3,4-tetrahydro-1-naphthalenyl)-3-(((3-(trifluoromethyl)phenyl)sulfonyl)amino)propanamide | $C_{32}H_{37}ClF_3N_3O_3S$ | 636.18 | 637 |

| Example | Structure | Name | Formula | MW | M + H |
|---|---|---|---|---|---|
| as | 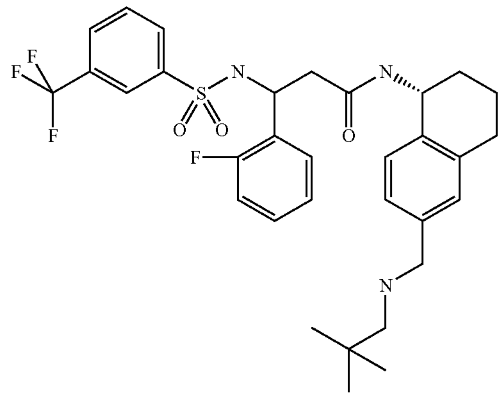 | (3S)-N-((1R)-6-(((2,2-dimethylpropyl)amino)methyl)-1,2,3,4-tetrahydro-1-naphthalenyl)-3-(2-fluorophenyl)-3-(((3-(trifluoromethyl)phenyl)sulfonyl)amino)propanamide | $C_{32}H_{37}F_4N_3O_3S$ | 619.72 | 619 |
| at | 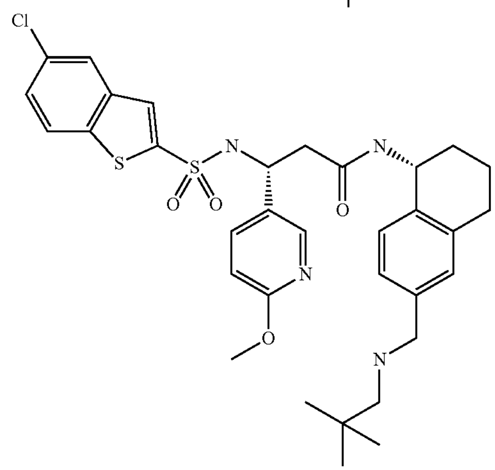 | (3R)-3-(((5-chloro-1-benzothien-2-yl)sulfonyl)amino)-N-((1R)-6-(((2,2-dimethylpropyl)amino)methyl)-1,2,3,4-tetrahydro-1-naphthalenyl)-3-(6-(methyloxy)-3-pyridinyl)propanamide | $C_{33}H_{39}ClN_4O_4S_2$ | 655.28 | 656 |

| Example | Structure | Name | Formula | MW | M + H |
|---|---|---|---|---|---|
| au | 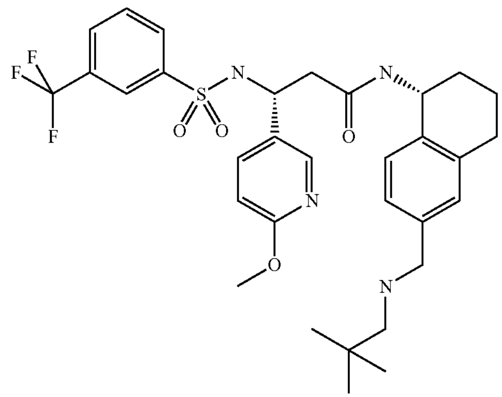 | (3R)-N-((1R)-6-(((2,2-dimethylpropyl)amino)methyl)-1,2,3,4-tetrahydro-1-naphthalenyl)-3-(6-(methyloxy)-3-pyridinyl)-3-(((3-(trifluoromethyl)phenyl)sulfonyl)amino)propanamide | $C_{32}H_{39}F_3N_4O_4S$ | 632.744 | 633 |
| av | 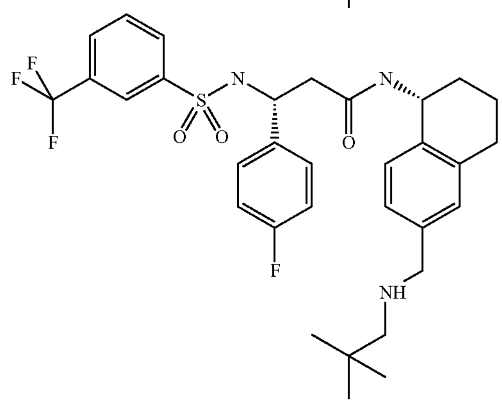 | (3S)-N-((1R)-6-(((2,2-dimethylpropyl)amino)methyl)-1,2,3,4-tetrahydro-1-naphthalenyl)-3-(4-fluorophenyl)-3-(((3-(trifluoromethyl)phenyl)sulfonyl)amino)propanamide | $C_{32}H_{37}F_4N_3O_3S$ | 619.72 | 620 |

-continued
| Example | Structure | Name | Formula | MW | M + H |
|---|---|---|---|---|---|
| aw | 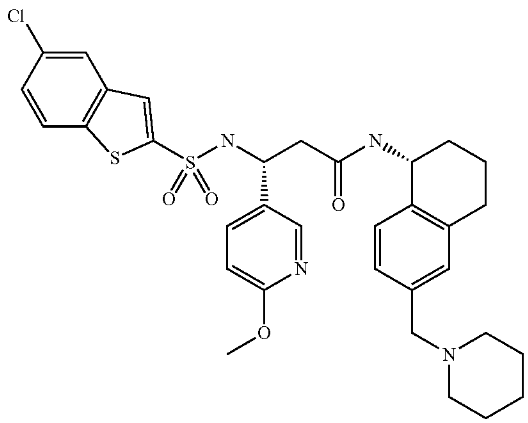 | (3R)-3-(((5-chloro-1-benzothien-2-yl)sulfonyl)amino)-3-(6-(methyloxy)-3-pyridinyl)-N-((1R)-6-(1-piperidinylmethyl)-1,2,3,4-tetrahydro-1-naphthalenyl)propanamide | $C_{33}H_{37}ClN_4O_4S_2$ | 653.264 | 654 |
| ax | 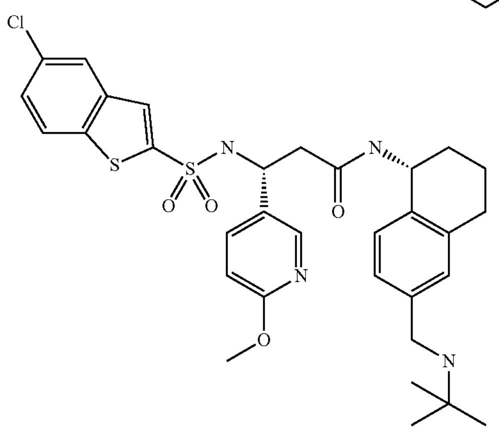 | (3R)-3-(((5-chloro-1-benzothien-2-yl)sulfonyl)amino)-N-(((1R)-6-(((1,1-dimethyl)amino)methyl)-1,2,3,4-tetrahydro-1-naphthalenyl)-3-(6-(methyloxy)-3-pyridinyl)propanamide | $C_{32}H_{37}ClN_4O_4S_2$ | 641.253 | 641 |

-continued

| Example | Structure | Name | Formula | MW | M + H |
|---|---|---|---|---|---|
| ay | 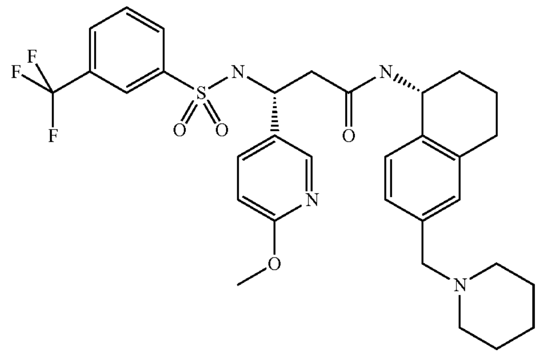 | (3R)-3-(6-(methyloxy)-3-pyridinyl)-N-((1R)-6-(1-piperidinylmethyl)-1,2,3,4-tetrahydro-1-naphthalenyl)-3-(((3-(trifluoromethyl)phenyl)sulfonyl)amino)propanamide | $C_{32}H_{37}F_3N_4O_4S$ | 630.728 | 631 |
| az | 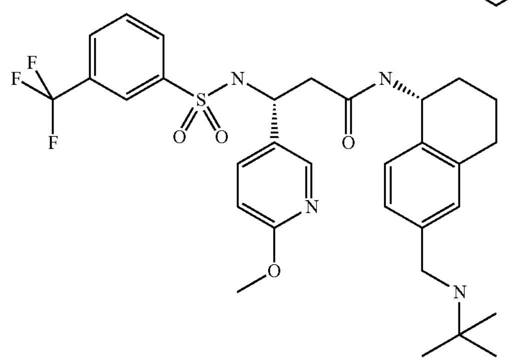 | (3R)-N-((1R)-6-(((1,1-dimethylethyl)amino)methyl)-1,2,3,4-tetrahydro-1-naphthalenyl)-3-(6-(methyloxy)-3-pyridinyl)-3-(((3-(trifluoromethyl)phenyl)sulfonyl)amino)propanamide | $C_{31}H_{37}F_3N_4O_4S$ | 618.717 | 619 |
| ba | 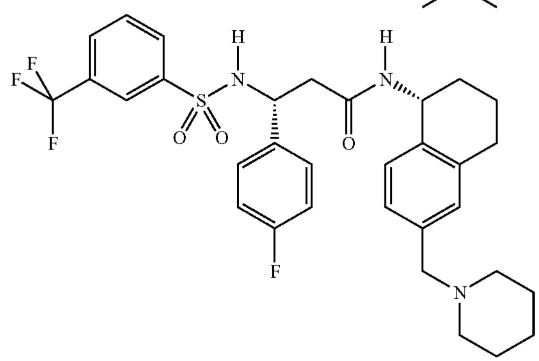 | (3S)-3-(4-fluorophenyl)-N-((1R)-6-(1-piperidinylmethyl)-1,2,3,4-tetrahydro-1-naphthalenyl)-3-(((3-(trifluoromethyl)phenyl)sulfonyl)amino)propanamide | $C_{32}H_{35}F_4N_3O_3S$ | 617.705 | 618 |

-continued

| Example | Structure | Name | Formula | MW | M + H |
|---|---|---|---|---|---|
| bb | 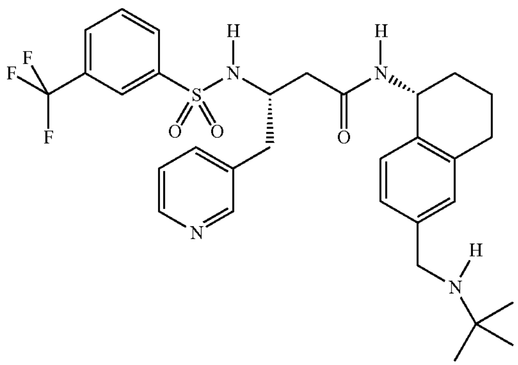 | (3S)-N-((1R)-6-(((1,1-dimethylethyl)amino)methyl)-1,2,3,4-tetrahydro-1-naphthalenyl)-4-(3-pyridinyl)-3-(((3-(trifluoromethyl)phenyl)sulfonyl)amino)butanamide | $C_{31}H_{37}F_3N_4O_3S$ | 602.718 | 603 |
| bc | 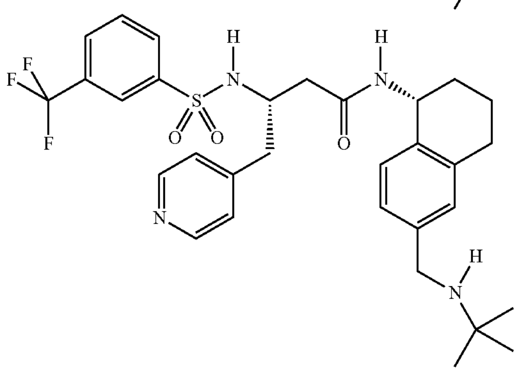 | (3S)-N-((1R)-6-(((1,1-dimethylethyl)amino)methyl)-1,2,3,4-tetrahydro-1-naphthalenyl)-4-(4-pyridinyl)-3-(((3-(trifluoromethyl)phenyl)sulfonyl)amino)butanamide | $C_{31}H_{37}F_3N_4O_3S$ | 602.718 | 603 |
| bd | 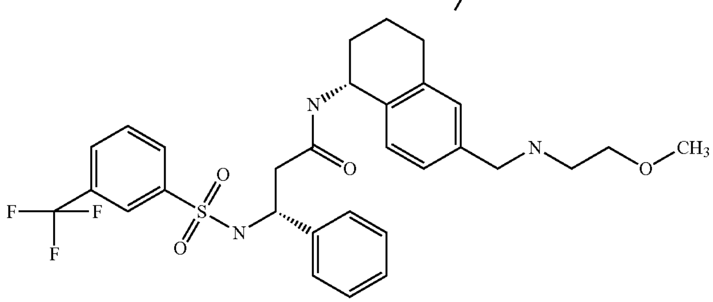 | (3R)-N-((1R)-6-(((2-(methyloxy)ethyl)amino)methyl)-1,2,3,4-tetrahydro-1-naphthalenyl)-3-phenyl-3-(((3-(trifluoromethyl)phenyl)sulfonyl)amino)propanamide | $C_{30}H_{34}F_3N_3O_4S$ | 589.676 | 590 |

-continued

| Example | Structure | Name | Formula | MW | M + H |
|---|---|---|---|---|---|
| be | 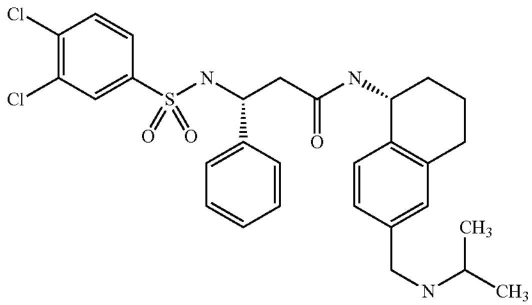 | (3R)-3-(((3,4-dichlorophenyl)sulfonyl)amino)-N-((1R)-6-(((1,1-dimethylethyl)amino)methyl)-1,2,3,4-tetrahydro-1-naphthalenyl)-3-phenylpropanamide | C₂₉H₃₃Cl₂N₃O₃S | 574.57 | 575 |
| bf | 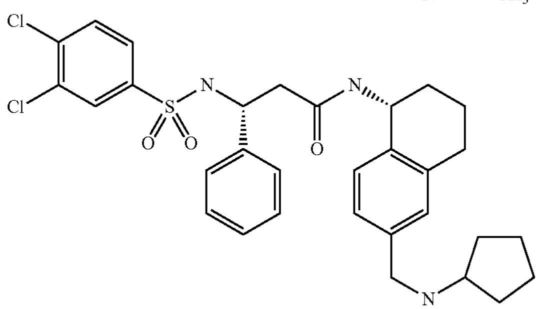 | (3R)-N-((1R)-6-((cyclopentylamino)methyl)-1,2,3,4-tetrahydro-1-naphthalenyl)-3-(((3,4-dichlorophenyl)sulfonyl)amino)-3-phenylpropanamide | C₃₁H₃₅Cl₂N₃O₃S | 600.607 | 601 |
| bg | 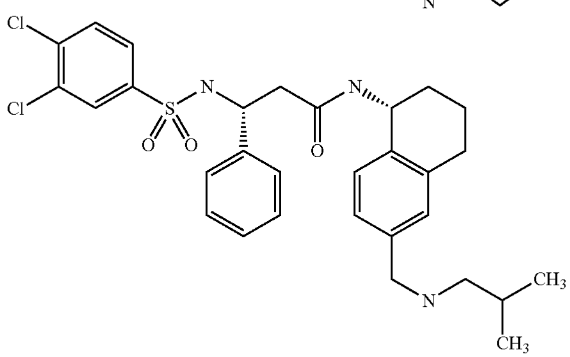 | (3R)-3-(((3,4-dichlorophenyl)sulfonyl)amino)-N-((1R)-6-(((2-methylpropyl)amino)methyl)-1,2,3,4-tetrahydro-1-naphthalenyl)-3-phenylpropanamide | C₃₀H₃₅Cl₂N₃O₃S | 588.596 | 589 |

-continued

| Example | Structure | Name | Formula | MW | M + H |
|---|---|---|---|---|---|
| bh | 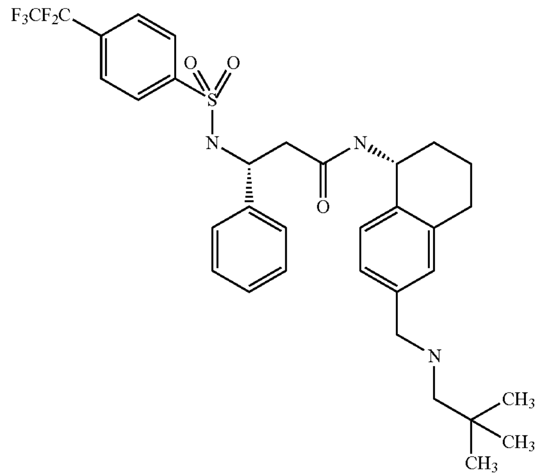 | (3R)-N-((1R)-6-(((2,2-dimethylpropyl)amino)methyl)-1,2,3,4-tetrahydro-1-naphthalenyl)-3-(((4-(pentafluoroethyl)phenyl)sulfonyl)amino)-3-phenylpropanamide | $C_{33}H_{38}F_5N_3O_3S$ | 651.737 | 652 |
| bi | 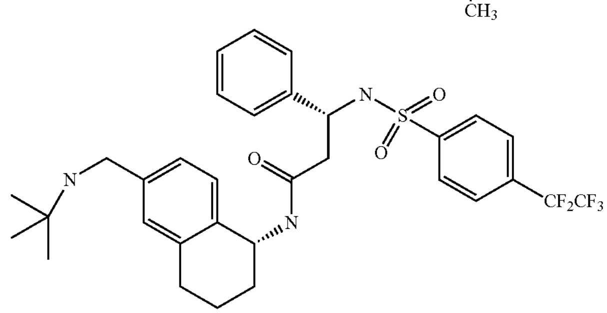 | (3R)-N-((1R)-6-(((1,1-dimethylethyl)amino)methyl)-1,2,3,4-tetrahydro-1-naphthalenyl)-3-(((4-(pentafluoroethyl)phenyl)sulfonyl)amino)-3-phenylpropanamide | $C_{32}H_{36}F_5N_3O_3S$ | 637.71 | 638 |

| Example | Structure | Name | Formula | MW | M + H |
|---|---|---|---|---|---|
| bj | 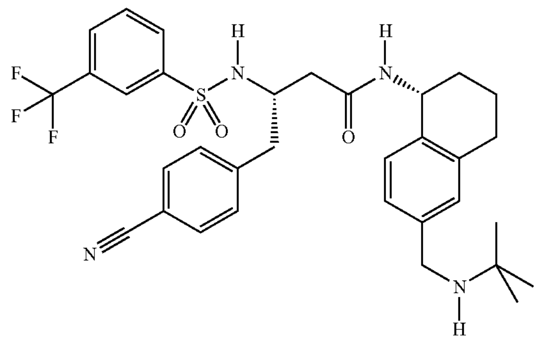 | (3S)-4-(4-cyanophenyl)-N-((1R)-6-(((1,1-dimethylethyl)amino)methyl)-1,2,3,4-tetrahydro-1-naphthalenyl)-3-(((3-(trifluoromethyl)phenyl)sulfonyl)amino)butanamide | $C_{33}H_{37}F_3N_4O_3S$ | 626.74 | 627 |
| bk | 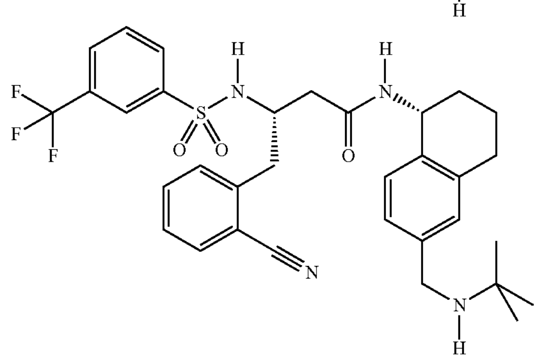 | (3S)-4-(2-cyanophenyl)-N-((1R)-6-(((1,1-dimethylethyl)amino)methyl)-1,2,3,4-tetrahydro-1-naphthalenyl)-3-(((3-(trifluoromethyl)phenyl)sulfonyl)amino)butanamide | $C_{33}H_{37}F_3N_4O_3S$ | 626.74 | 627 |
| bl | 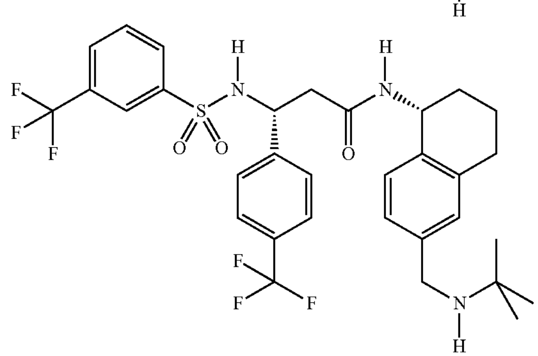 | (3R)-N-((1R)-6-(((1,1-dimethylethyl)amino)methyl)-1,2,3,4-tetrahydro-1-naphthalenyl)-3-(4-(trifluoromethyl)phenyl)-3-(((3-(trifluoromethyl)phenyl)sulfonyl)amino)propanamide | $C_{32}H_{35}F_6N_3O_3S$ | 655.701 | 656 |

-continued

| Example | Structure | Name | Formula | MW | M + H |
|---|---|---|---|---|---|
| bm | 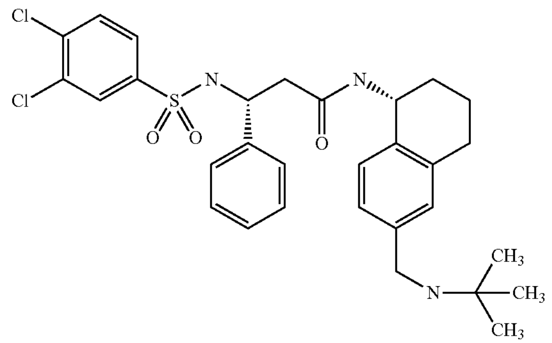 | (3R)-3-(((3,4-dichlorophenyl)sulfonyl)amino)-N-((1R)-6-(((1,1-dimethylethyl)amino)methyl)-1,2,3,4-tetrahydro-1-naphthalenyl)-3-phenyl)propanamide | $C_{30}H_{35}Cl_2N_3O_3S$ | 588.596 | 589 |
| bn | 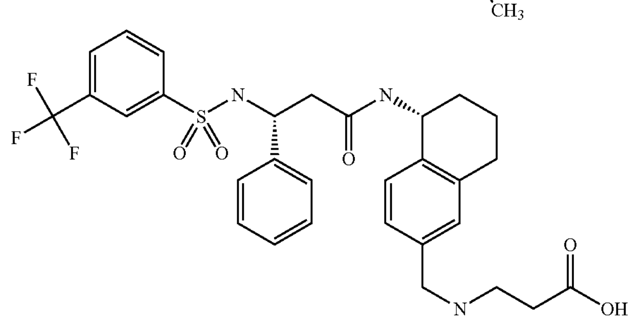 | N-(((5R)-5-(((3R)-3-phenyl-3-(((3-(trifluoromethyl)phenyl)sulfonyl)amino)propanoyl)amino)-5,6,7,8-tetrahydro-2-naphthalenyl)methyl)-beta-alanine | $C_{30}H_{32}F_3N_3O_5S$ | 603.659 | 604 |
| bo | 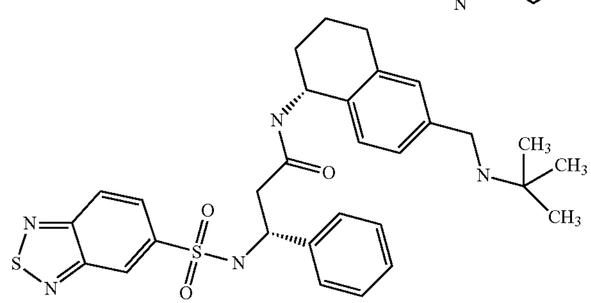 | (3R)-3-((2,1,3-benzothiadiazol-5-ylsulfonyl)amino)-N-((1R)-6-(((1,1-dimethylethyl)amino)methyl)-1,2,3,4-tetrahydro-1-naphthalenyl)-3-phenylpropanamide | $C_{30}H_{35}N_5O_3S_2$ | 577.771 | 578 |

-continued

| Example | Structure | Name | Formula | MW | M + H |
|---|---|---|---|---|---|
| bp | 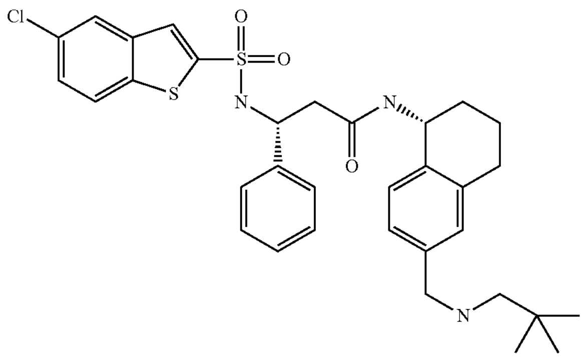 | (3R)-3-(((5-chloro-1-benzothien-2-yl)sulfonyl)amino)-N-((1R)-6-(((2,2-dimethylpropyl)amino)methyl)-1,2,3,4-tetrahydro-1-naphthalenyl)-3-phenylpropanamide | $C_{33}H_{38}ClN_3O_3S_2$ | 624.266 | 625 |
| bq | 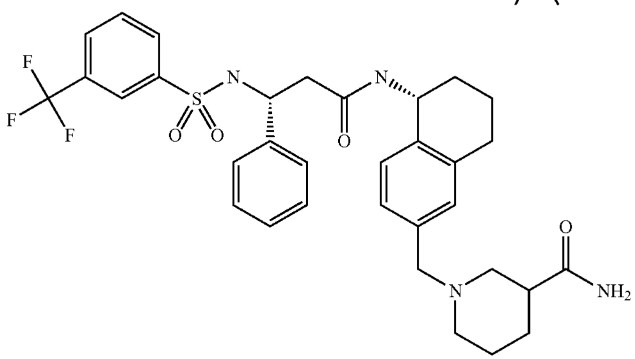 | (3S)-1-(((5R)-5-(((3R)-3-phenyl-3-(((3-(trifluoromethyl)phenyl)sulfonyl)amino)propanoyl)amino)-5,6,7,8-tetrahydro-2-naphthalenyl)methyl)-3-piperidinecarboxamide | $C_{33}H_{37}F_3N_4O_4S$ | 642.74 | 643 |
| br | 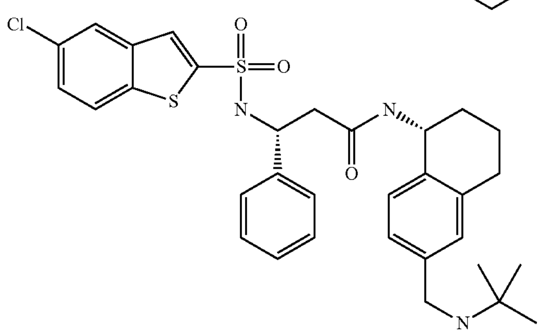 | (3R)-3-(((5-chloro-1-benzothien-2-yl)sulfonyl)amino)-N-((1R)-6-(((1,1-dimethylethyl)amino)methyl)-1,2,3,4-tetrahydro-1-naphthalenyl)-3-phenylpropanamide | $C_{32}H_{36}ClN_3O_3S_2$ | 610.239 | 611 |

-continued

| Example | Structure | Name | Formula | MW | M + H |
|---|---|---|---|---|---|
| bs | 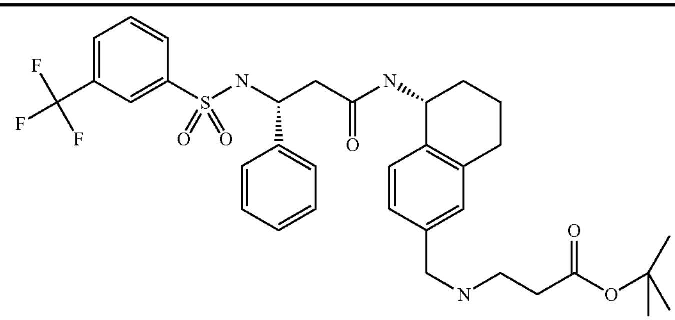 | 1,1-dimethylethyl N-(((5R)-5-(((3R)-3-phenyl-3-(((3-(trifluoromethyl)phenyl)sulfonyl)amino)propanoyl)amino)-5,6,7,8-tetrahydro-2-naphthalenyl)methyl)-beta-alaninate | C₃₄H₄₀F₃N₃O₅S | 659.766 | 660 |
| bt | 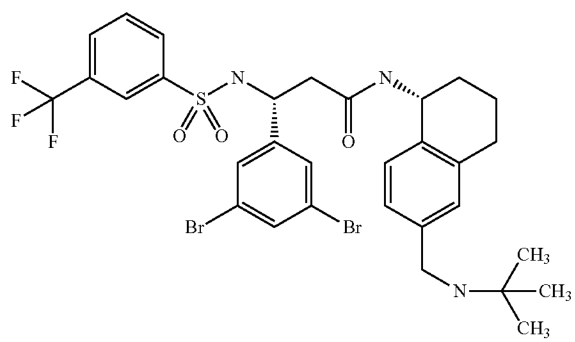 | N-[6-((tert-Butyl)amino-methyl)-1,2,3,4-tetrahydro-naphthalen-1-yl]-3-(3,5-dibromo-phenyl)-3-(3-trifluoromethyl-benzenesulfonylamino)-propionamide | C₃₁H₃₄Br₂F₃N₃O₃S | 745.496 | 746 |
| bu | 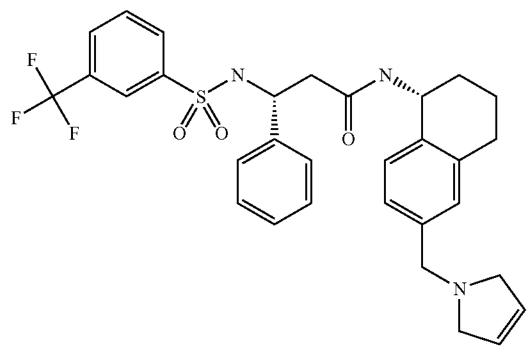 | N-[6-(2,5-Dihydro-pyrrol-1-ylmethyl)-1,2,3,4-tetrahydro-naphthalen-1-yl]-3-phenyl-3-(3-trifluoromethyl-benzenesulfonylamino)-propionamide | C₃₁H₃₂F₃N₃O₃S | 583.672 | 584 |

| Example | Structure | Name | Formula | MW | M + H |
|---|---|---|---|---|---|
| bv | 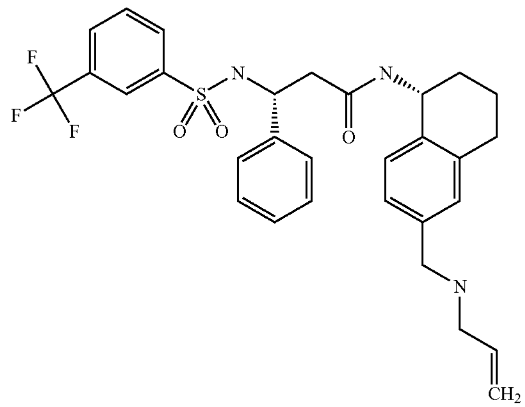 | N-(6-Allylaminomethyl-1,2,3,4-tetrahydro-naphthalen-1-yl)-3-phenyl-3-(3-trifluoromethyl-benzenesulfonylamino)-propionamide | $C_{30}H_{32}F_3N_3O_3S$ | 571.661 | 572 |
| bw | 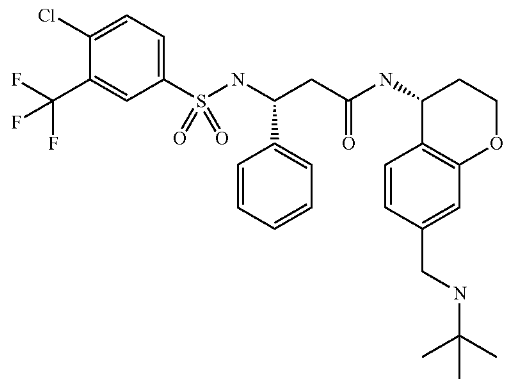 | N-[7-(tert-Butylamino-methyl)-chroman-4-yl]-3-(4-chloro-3-trifluoromethyl-benzenesulfonylamino)-3-phenyl-propionamide | $C_{30}H_{33}ClF_3N_3O_4S$ | 624.121 | 625 |

-continued
| Example | Structure | Name | Formula | MW | M + H |
|---|---|---|---|---|---|
| bx | 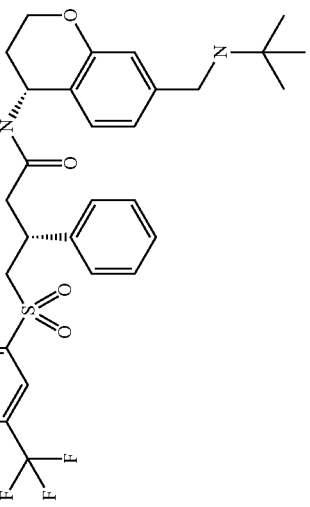 | N-[7-((tert-Butylamino-methyl)-chroman-4-yl]-3-(4-methyl-3-trifluoromethyl-benzenesulfonylamino)-3-phenyl-propionamide | $C_{31}H_{36}F_3N_3O_4S$ | 603.702 | 604 |
| by | 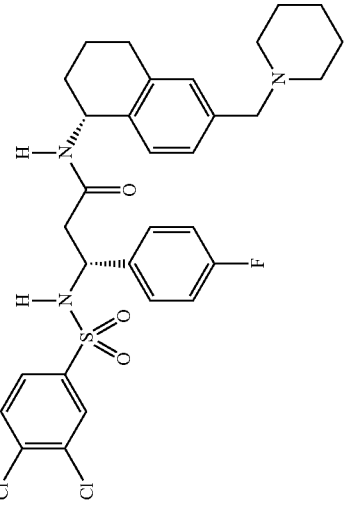 | 3-(3,4-Dichloro-benzenesulfonylamino)-3-(4-fluoro-phenyl)-N-(7-piperidin-1-ylmethyl-chroman-4-yl)-propionamide | $C_{30}H_{32}Cl_2FN_3O_4S$ | 620.57 | 621 |

-continued

| Example | Structure | Name | Formula | MW | M + H |
|---|---|---|---|---|---|
| bz | 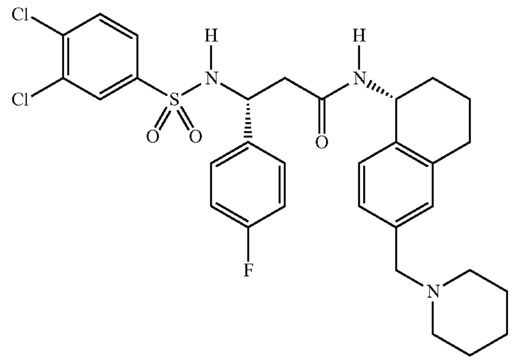 | 3-(3,4-Dichloro-benzenesulfonylamino)-3-(4-fluoro-phenyl)-N-(6-piperidin-1-ylmethyl-1,2,3,4-tetrahydro-naphthalen-1-yl)-propionamide | $C_{31}H_{34}Cl_2FN_3O_3S$ | 618.598 | 619 |
| cb | 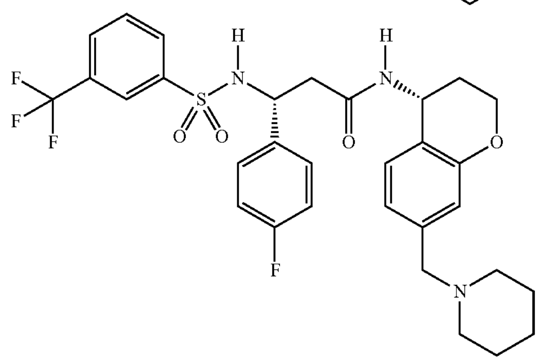 | 3-(4-Fluoro-phenyl)-N-(7-piperidin-1-ylmethyl-chroman-4-yl)-3-(3-trifluoromethyl-benzenesulfonylamino)-propionamide | $C_{31}H_{33}F_4N_3O_4S$ | 619.677 | 620 |
| cc | 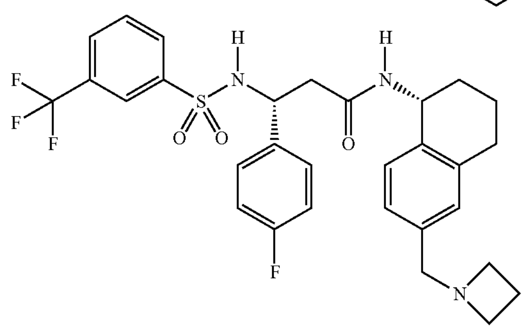 | N-(6-Azetidin-1-ylmethyl-1,2,3,4-tetrahydro-naphthalen-1-yl)-3-(4-fluoro-phenyl)-3-(3-trifluoromethyl-benzenesulfonylamino)-propionamide | $C_{30}H_{31}F_4N_3O_3S$ | 589.651 | 590 |

| Example | Structure | Name | Formula | MW | M + H |
|---|---|---|---|---|---|
| cd | 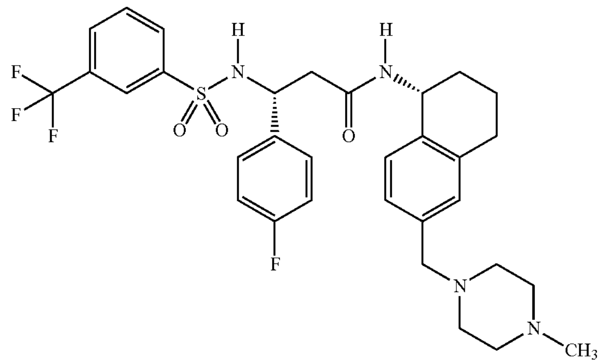 | 3-(4-Fluoro-phenyl)-N-[6-(4-methyl-piperazin-1-ylmethyl)-1,2,3,4-tetrahydro-naphthalen-1-yl]-3-(3-trifluoromethyl-benzenesulfonylamino)-propionamide | $C_{32}H_{36}F_4N_4O_3S$ | 632.719 | 633 |
| ce | 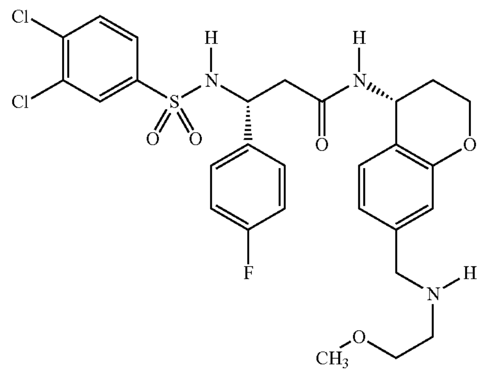 | 3-(3,4-Dichloro-benzenesulfonylamino)-3-(4-fluoro-phenyl)-N-{7-[(2-methoxy-ethylamino)-methyl]-chroman-4-yl}-propionamide | $C_{28}H_{30}Cl_2FN_3O_5S$ | 610.531 | 610 |

-continued

| Example | Structure | Name | Formula | MW | M + H |
|---|---|---|---|---|---|
| cf | 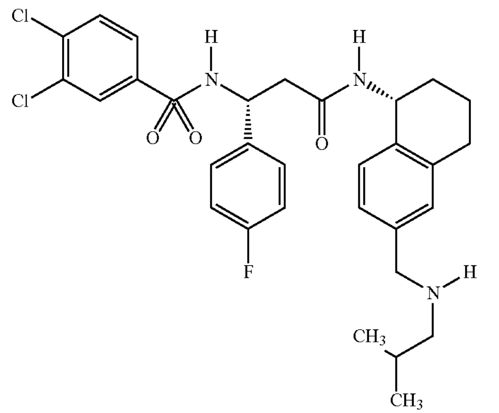 | 3-(3,4-Dichloro-benzenesulfonylamino)-3-(4-fluoro-phenyl)-N-[6-(isobutylamino-methyl)-1,2,3,4-tetrahydro-naphthalen-1-yl]-propionamide | $C_{30}H_{34}Cl_2FN_3O_3S$ | 606.587 | 606 |
| cg | 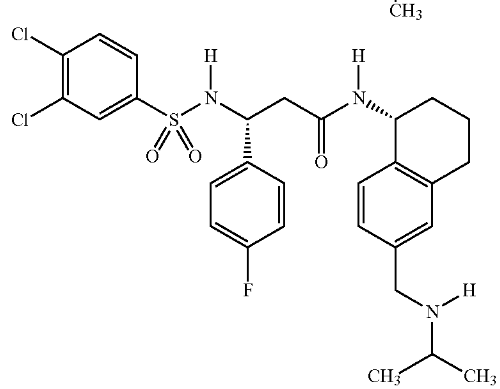 | 3-(3,4-Dichloro-benzenesulfonylamino)-3-(4-fluoro-phenyl)-N-[6-(isopropylamino-methyl)-1,2,3,4-tetrahydro-naphthalen-1-yl]-propionamide | $C_{29}H_{32}Cl_2FN_3O_3S$ | 592.56 | 592 |

| Example | Structure | Name | Formula | MW | M + H |
|---|---|---|---|---|---|
| ch | 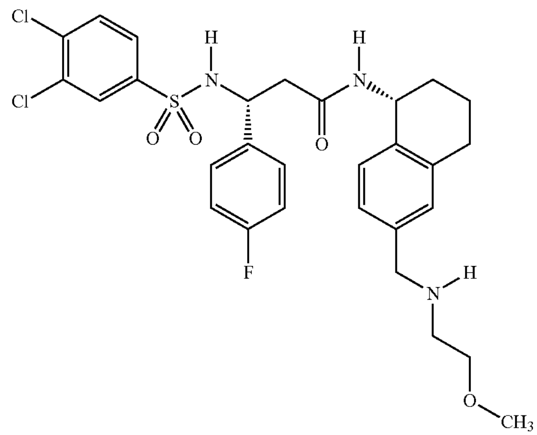 | 3-(3,4-Dichloro-benzenesulfonylamino)-3-(4-fluoro-phenyl)-N-{6-[(2-methoxy-ethylamino)-methyl]-1,2,3,4-tetrahydro-naphthalen-1-yl}-propionamide | $C_{29}H_{32}Cl_2FN_3O_4S$ | 608.559 | 609 |
| ci | 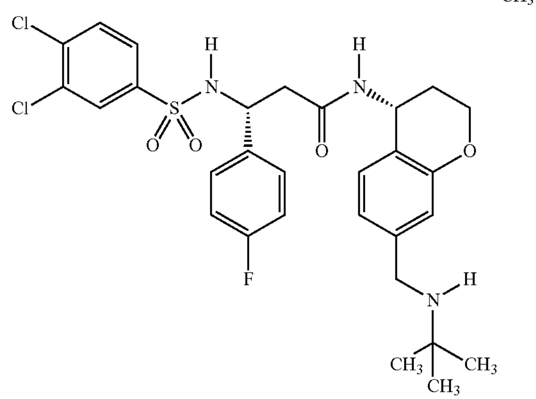 | N-[7-(tert-Butylamino-methyl)-chroman-4-yl]-3-(3,4-dichloro-benzenesulfonylamino)-3-(4-fluoro-phenyl)-propionamide | $C_{29}H_{32}Cl_2FN_3O_4S$ | 608.559 | 609 |

-continued

| Example | Structure | Name | Formula | MW | M + H |
|---|---|---|---|---|---|
| cj | 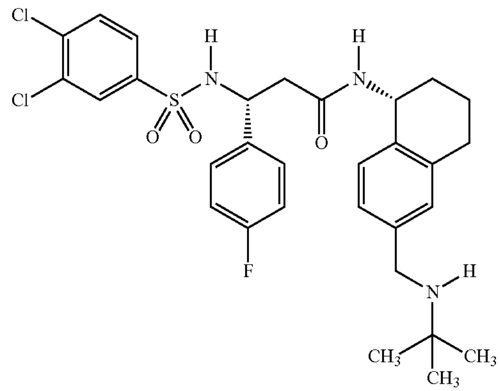 | N-[6-((tert-Butylamino-methyl)-1,2,3,4-tetrahydro-naphthalen-1-yl]-3-(3,4-dichloro-benzenesulfonylamino)-3-(4-fluoro-phenyl)-propionamide | $C_{30}H_{34}Cl_2FN_3O_3S$ | 606.587 | 607 |
| ck | 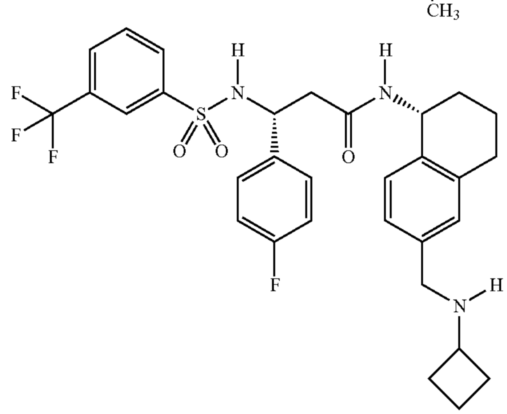 | N-(7-Cyclobutylaminomethyl-chroman-4-yl)-3-(4-fluoro-phenyl)-3-(3-trifluoromethyl-benzenesulfonylamino)-propionamide | $C_{30}H_{31}F_4N_3O_4S$ | 605.65 | 606 |

| Example | Structure | Name | Formula | MW | M + H |
|---|---|---|---|---|---|
| cl | 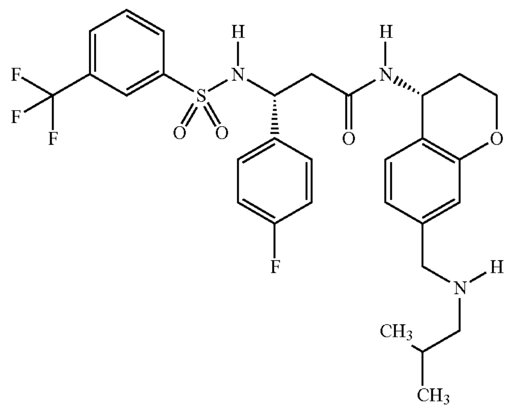 | 3-(4-Fluoro-phenyl)-N-[7-(isobutylamino-methyl)-chroman-4-yl]-3-(3-trifluoromethyl-benzenesulfonylamino)-propionamide | C30 H33 F4 N3 O4 S | 607.66 | 608 |
| cm | 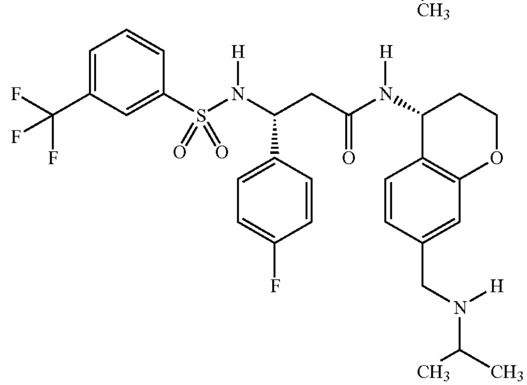 | 3-(4-Fluoro-phenyl)-N-[7-(isopropylamino-methyl)-chroman-4-yl]-3-(3-trifluoromethyl-benzenesulfonylamino)-propionamide | C29 H31 F4 N3 O4 S | 593.639 | 594 |

| Example | Structure | Name | Formula | MW | M+H |
|---|---|---|---|---|---|
| cn | 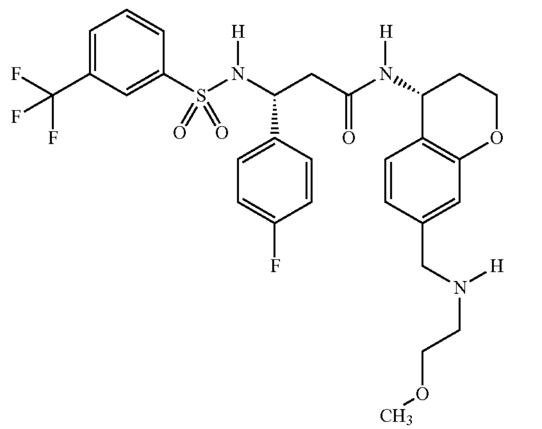 | 3-(4-Fluoro-phenyl)-N-{7-[(2-methoxy-ethylamino)-methyl]-chroman-4-yl]-3-(3-trifluoromethyl-benzenesulfonylamino)-propionamide | C29 H31 F4 N3 O5 S | 609.638 | 610 |
| co | 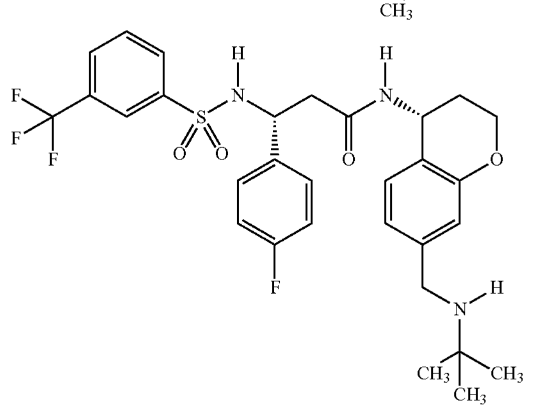 | N-[7-(tert-Butylamino-methyl)-chroman-4-yl]-3-(4-fluoro-phenyl)-3-(3-trifluoromethyl-benzenesulfonylamino)-propionamide | C30 H33 F4 N3 O4 S | 607.666 | 608 |

| Example | Structure | Name | Formula | MW | M + H |
|---|---|---|---|---|---|
| cp | 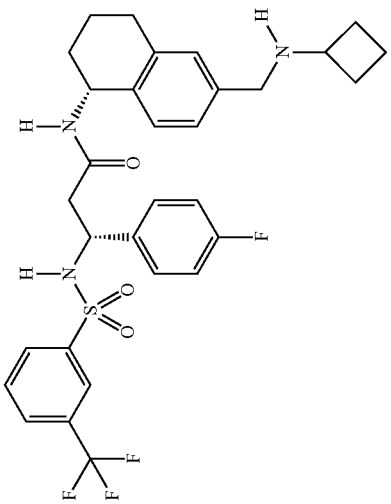 | N-(6-Cyclobutylaminomethyl-1,2,3,4-tetrahydro-naphthalen-1-yl)-3-(4-fluoro-phenyl)-3-(3-trifluoromethyl-benzenesulfonylamino)-propionamide | C31 H33 F4 N3 O3 S | 603.678 | 604 |
| cq | 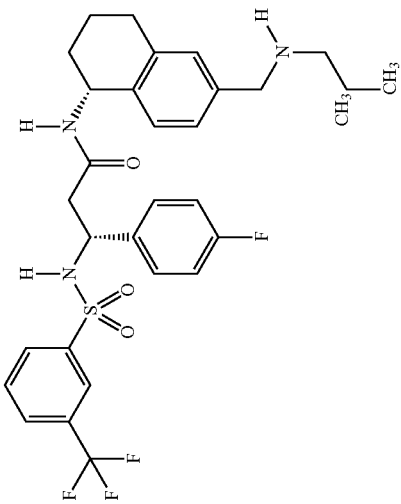 | 3-(4-Fluoro-phenyl)-N-[6-(isobutylamino-methyl)-1,2,3,4-tetrahydro-naphthalen-1-yl]-3-(3-trifluoromethyl-benzenesulfonylamino)-propionamide | C31 H35 F4 N3 O3 S | 605.693 | 606 |

| Example | Structure | Name | Formula | MW | M + H |
|---|---|---|---|---|---|
| cr | 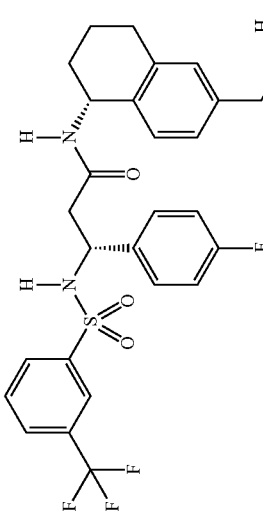 | 3-(4-Fluoro-phenyl)-N-[6-(isopropylamino-methyl)-1,2,3,4-tetrahydro-naphthalen-1-yl]-3-(3-trifluoromethyl-benzenesulfonylamino)-propionamide | C30 H33 F4 N3 O3 S | 591.667 | 592 |
| cs | 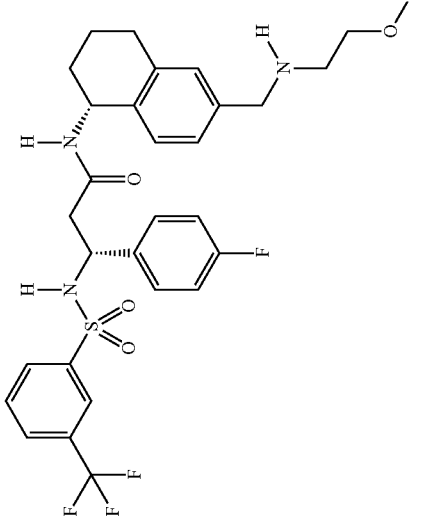 | 3-(4-Fluoro-phenyl)-N-{6-[(2-methoxy-ethylamino)-methyl]-1,2,3,4-tetrahydro-naphthalen-1-yl}-3-(3-trifluoromethyl-benzenesulfonylamino)-propionamide | C30 H33 F4 N3 O4 S | 607.666 | 608 |

| Example | Structure | Name | Formula | MW | M + H |
|---|---|---|---|---|---|
| ct | 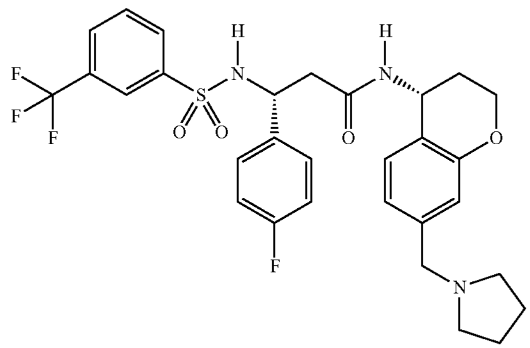 | 3-(4-Fluoro-phenyl)-N-(7-pyrrolidin-1-ylmethyl-chroman-4-yl)-3-(3-trifluoromethyl-benzenesulfonylamino)-propionamide | C30 H31 F4 N3 O4 S | 605.65 | 606 |
| cu | 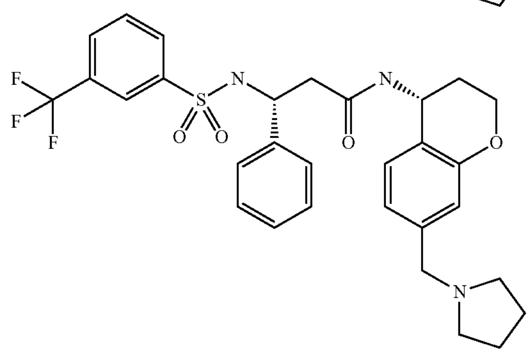 | 3-Phenyl-N-(7-pyrrolidin-1-ylmethyl-chroman-4-yl)-3-(3-trifluoromethyl-benzenesulfonylamino)-propionamide | C30 H32 F3 N3 O4 S | 587.66 | 588 |
| cv | 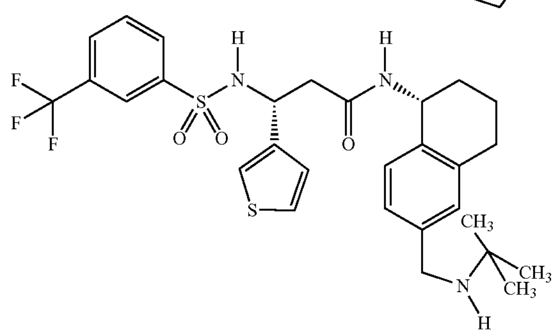 | N-[6-(tert-Butylamino-methyl)-1,2,3,4-tetrahydro-naphthalen-1-yl]-3-thiophen-3-yl-3-(3-trifluoromethyl-benzenesulfonylamino)-propionamide | C29 H34 F3 N3 O3 S2 | 593.732 | 594 |

| Example | Structure | Name | Formula | MW | M + H |
|---|---|---|---|---|---|
| cw | 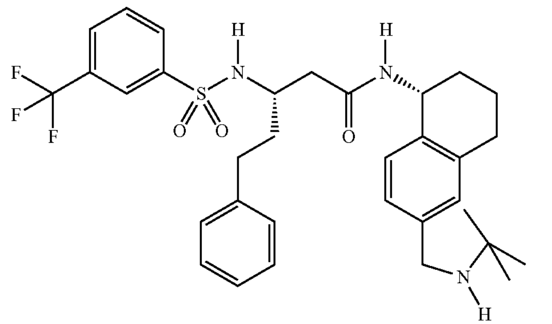 | 5-Phenyl-3-(3-trifluoromethyl-benzenesulfonylamino)-pentanoic acid [6-(tert-butylamino-methyl)-1,2,3,4-tetrahydro-naphthalen-1-yl]-amide | C33 H40 F3 N3 O3 S | 615.757 | 616 |
| cx | 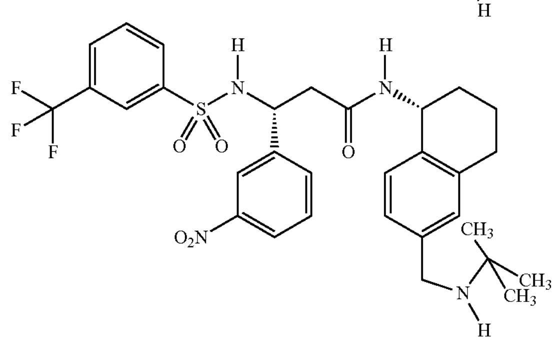 | N-[6-(tert-Butylamino-methyl)-1,2,3,4-tetrahydro-naphthalen-1-yl]-3-(3-nitro-phenyl)-3-(3-trifluoromethyl-benzenesulfonylamino)-propionamide | C31 H35 F3 N4 O5 S | 632.701 | 633 |
| cy | 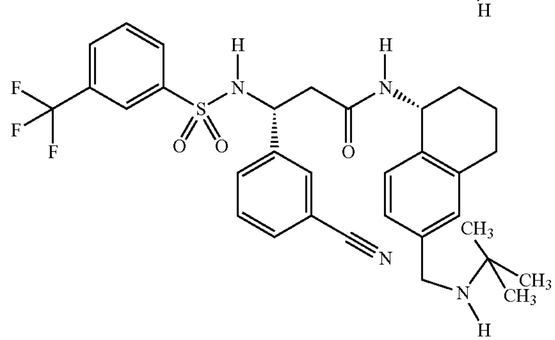 | N-[6-(tert-Butylamino-methyl)-1,2,3,4-tetrahydro-naphthalen-1-yl]-3-(3-cyano-phenyl)-3-(3-trifluoromethyl-benzenesulfonylamino)-propionamide | C32 H35 F3 N4 O3 S | 612.714 | 613 |

-continued

| Example | Structure | Name | Formula | MW | M + H |
|---|---|---|---|---|---|
| cz | 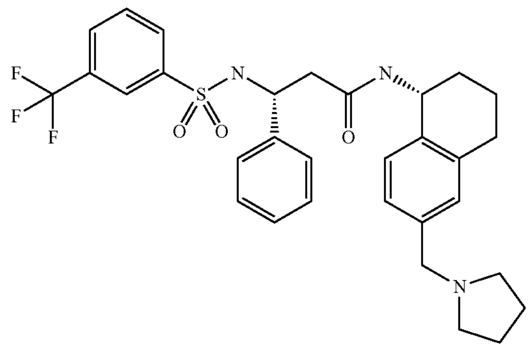 | 3-Phenyl-N-(6-pyrrolidin-1-ylmethyl-1,2,3,4-tetrahydro-naphthalen-1-yl)-3-(3-trifluoromethyl-benzenesulfonylamino)-propionamide | C31 H34 F3 N3 O3 S | 585.688 | 586 |
| da | 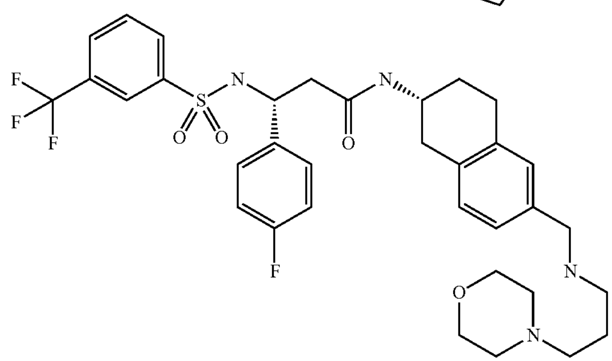 | 3-(4-Fluoro-phenyl)-N-{6-[(3-morpholin-4-yl-propylamino)-methyl]-1,2,3,4-tetrahydro-naphthalen-2-yl}-3-(3-trifluoromethyl-benzenesulfonylamino)-propionamide | C34 H40 F4 N4 O4 S | 676.772 | 677 |

| Example | Structure | Name | Formula | MW | M + H |
|---|---|---|---|---|---|
| db | 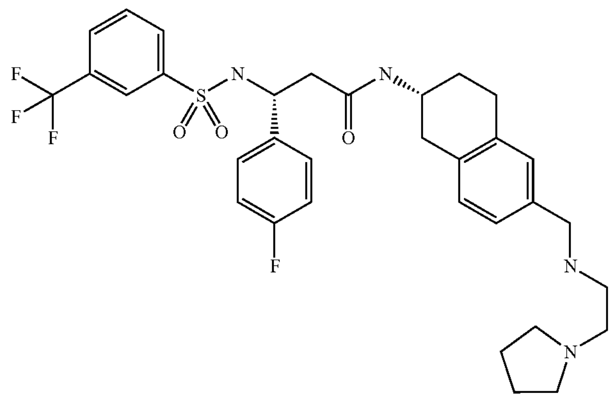 | 3-(4-Fluoro-phenyl)-N-{6-[(2-pyrrolidin-1-yl-ethylamino)methyl]-1,2,3,4-tetrahydro-naphthalen-2-yl}-3-(3-trifluoromethyl-benzenesulfonylamino)-propionamide | C33 H38 F4 N4 O3 S | 646.746 | 645 |
| dc | 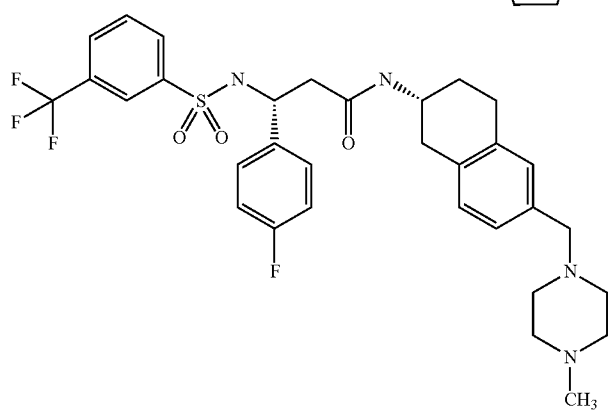 | 3-(4-Fluoro-phenyl)-N-[6-(4-methyl-piperazin-1-ylmethyl)-1,2,3,4-tetrahydro-naphthalen-2-yl]-3-(3-trifluoromethyl-benzenesulfonylamino)-propionamide | C32 H36 F4 N4 O3 S | 632.719 | 633 |

-continued

| Example | Structure | Name | Formula | MW | M + H |
|---|---|---|---|---|---|
| dd | 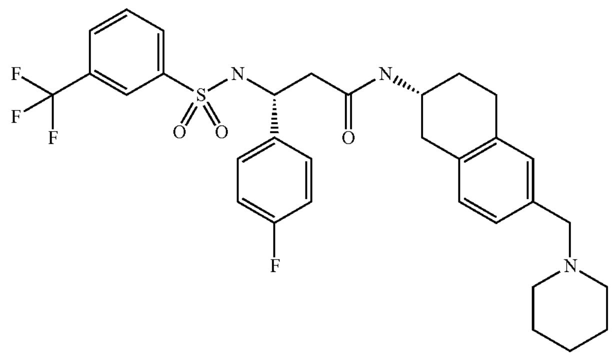 | 3-(4-Fluoro-phenyl)-N-(6-piperidin-1-ylmethyl-1,2,3,4-tetrahydro-naphthalen-2-yl)-3-(3-trifluoromethyl-benzenesulfonylamino)-propionamide | C32 H35 F4 N3 O3 S | 617.705 | 618 |
| de | 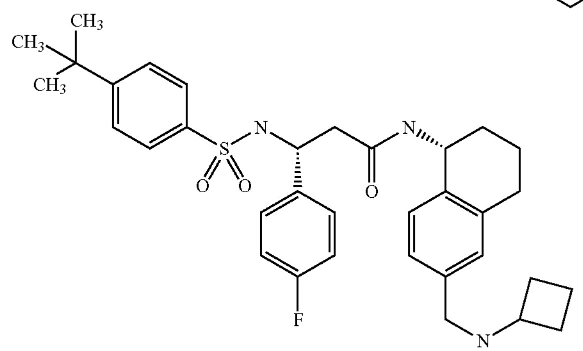 | 3-(4-tert-Butyl-benzenesulfonylamino)-N-(6-cyclobutylaminomethyl-1,2,3,4-tetrahydro-naphthalen-1-yl)-3-(4-fluoro-phenyl)-propionamide | C34 H42 F N3 O3 S | 591.788 | 592 |
| df | 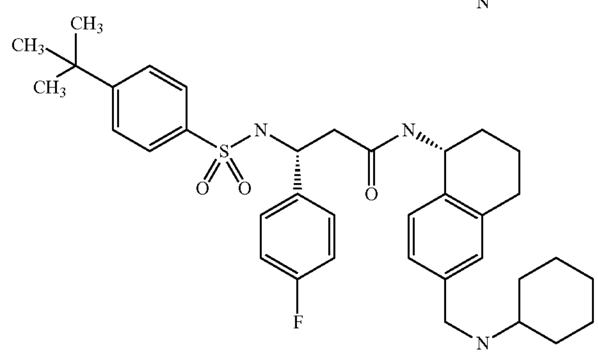 | 3-(4-tert-Butyl-benzenesulfonylamino)-N-(6-cyclohexylaminomethyl-1,2,3,4-tetrahydro-naphthalen-1-yl)-3-(4-fluoro-phenyl)-propionamide | C36 H46 F N3 O3 S | 619.841 | 620 |

| Example | Structure | Name | Formula | MW | M + H |
|---|---|---|---|---|---|
| dg | 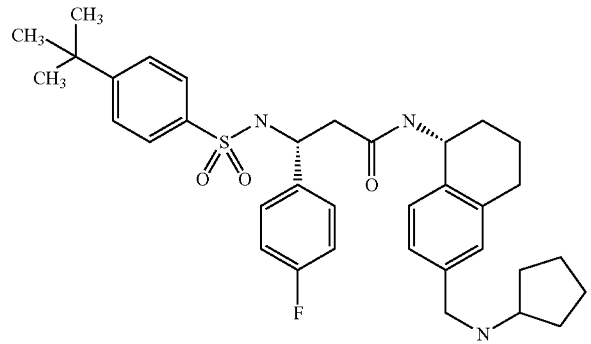 | 3-(4-tert-Butyl-benzenesulfonylamino)-N-(6-cyclopentylaminomethyl-1,2,3,4-tetrahydro-naphthalen-1-yl)-3-(4-fluoro-phenyl)-propionamide | C35 H44 F N3 O3 S | 605.815 | 606 |
| dh | 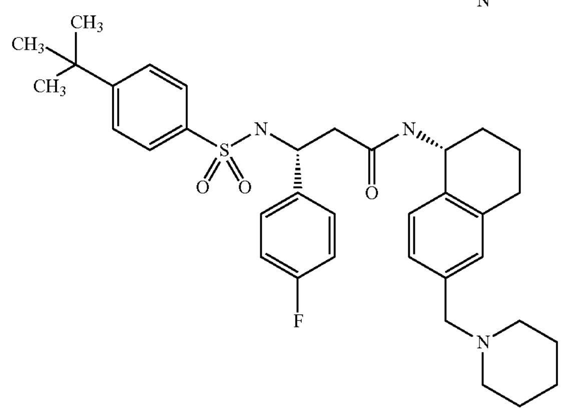 | 3-(4-tert-Butyl-benzenesulfonylamino)-3-(4-fluoro-phenyl)-N-(6-piperidin-1-ylmethyl-1,2,3,4-tetrahydro-naphthalen-1-yl)-propionamide | C35 H44 F N3 O3 S | 605.815 | 606 |

-continued

| Example | Structure | Name | Formula | MW | M + H |
|---|---|---|---|---|---|
| di | 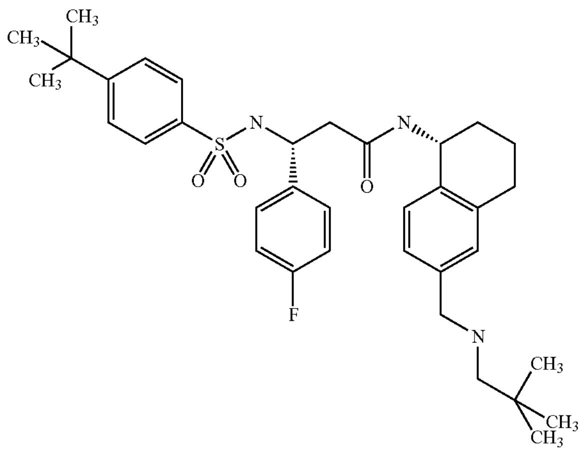 | 3-(4-tert-Butyl-benzenesulfonylamino)-N-{6-[(2,2-dimethyl-propylamino)-methyl]-1,2,3,4-tetrahydro-naphthalen-1-yl}-3-(4-fluoro-phenyl)-propionamide | C35 H46 F N3 O3 S | 607.83 | 608 |
| dj | 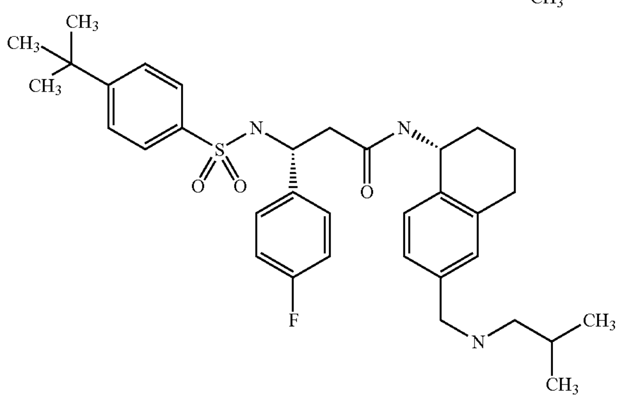 | 3-(4-tert-Butyl-benzenesulfonylamino)-3-(4-fluoro-phenyl)-N-[6-(isobutylamino-methyl)-1,2,3,4-tetrahydro-naphthalen-1-yl]-propionamide | C34 H44 F N3 O3 S | 593.804 | 594 |

-continued

| Example | Structure | Name | Formula | MW | M + H |
|---|---|---|---|---|---|
| dk | 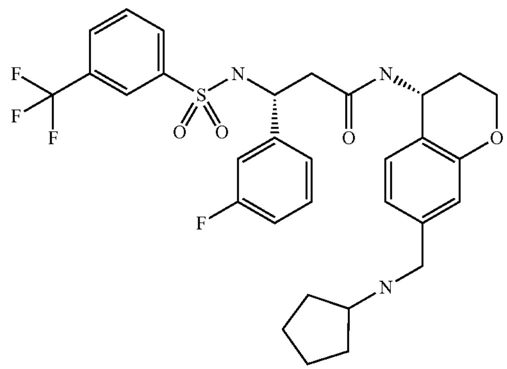 | N-(7-Cyclopentylaminomethyl-chroman-4-yl)-3-(3-fluoro-phenyl)-3-(3-trifluoromethyl-benzenesulfonylamino)-propionamide | C31 H33 F4 N3 O4 S | 619.677 | 620 |
| dl | 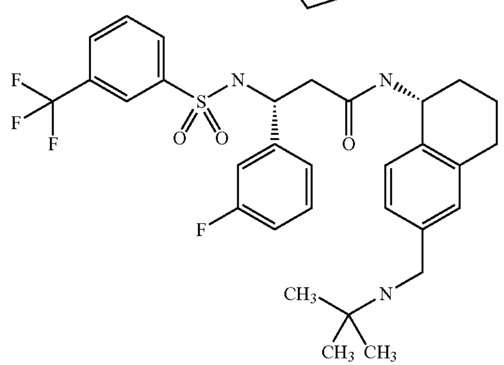 | N-[6-(tert-Butylamino-methyl)-1,2,3,4-tetrahydro-naphthalen-1-yl]-3-(3-fluoro-phenyl)-3-(3-trifluoromethyl-benzenesulfonylamino)-propionamide | C31 H35 F4 N3 O3 S | 605.693 | 606 |
| dm | 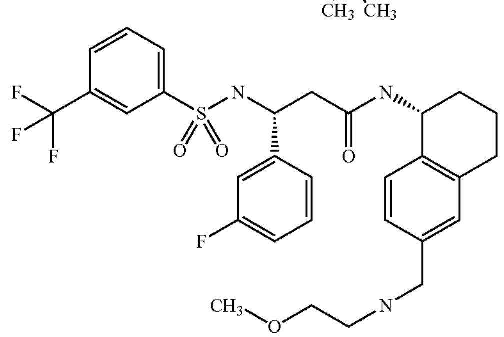 | 3-(3-Fluoro-phenyl)-N-{6-[(2-methoxy-ethylamino)-methyl]-1,2,3,4-tetrahydro-naphthalen-1-yl}-3-(3-trifluoromethyl-benzenesulfonylamino)-propionamide | C30 H33 F4 N3 O4 S | 607.666 | 608 |

| Example | Structure | Name | Formula | MW | M + H |
|---|---|---|---|---|---|
| dn | 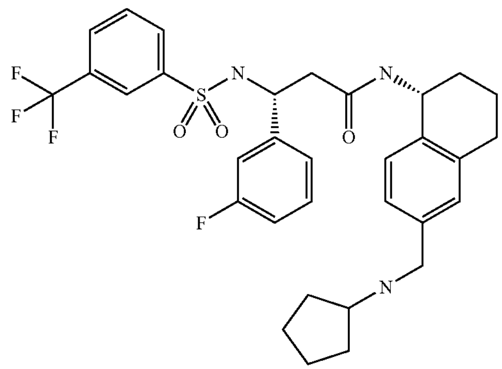 | N-(6-Cyclopentylaminomethyl-1,2,3,4-tetrahydro-naphthalen-1-yl)-3-(3-fluoro-phenyl)-3-(3-trifluoromethyl-benzenesulfonylamino)-propionamide | C32 H35 F4 N3 O3 S | 617.705 | 617 |
| do | 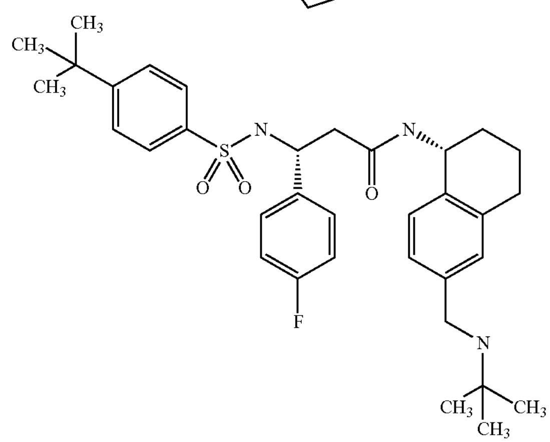 | N-[6-(tert-Butylamino-methyl)-1,2,3,4-tetrahydro-naphthalen-1-yl]-3-(4-tert-butyl-benzenesulfonylamino)-3-(4-fluoro-phenyl)-propionamide | C34 H44 F N3 O3 S | 593.804 | 594 |

-continued

| Example | Structure | Name | Formula | MW | M + H |
|---|---|---|---|---|---|
| dp | 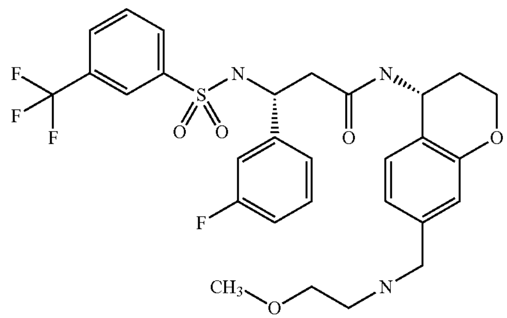 | 3-(3-Fluoro-phenyl)-N-{7-[(2-methoxy-ethyl)amino)-methyl]-chroman-4-yl}-3-(3-trifluoromethyl-benzenesulfonylamino)-propionamide | C29 H31 F4 N3 O5 S | 609.638 | 610 |
| dq | 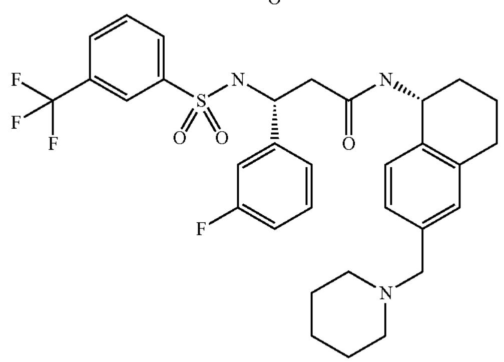 | 3-(3-Fluoro-phenyl)-N-(6-piperidin-1-ylmethyl-1,2,3,4-tetrahydro-naphthalen-1-yl)-3-(3-trifluoromethyl-benzenesulfonylamino)-propionamide | C32 H35 F4 N3 O3 S | 617.705 | 618 |
| dr | 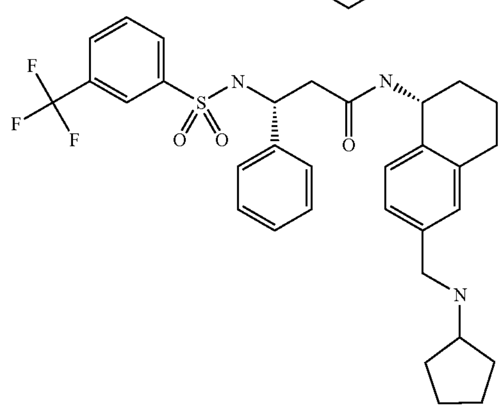 | N-(6-Cyclopentylaminomethyl-1,2,3,4-tetrahydro-naphthalen-1-yl)-3-phenyl-3-(3-trifluoromethyl-benzenesulfonylamino)-propionamide | C32 H36 F3 N3 O3 S | 599.714 | 600 |

| Example | Structure | Name | Formula | MW | M + H |
|---|---|---|---|---|---|
| ds | 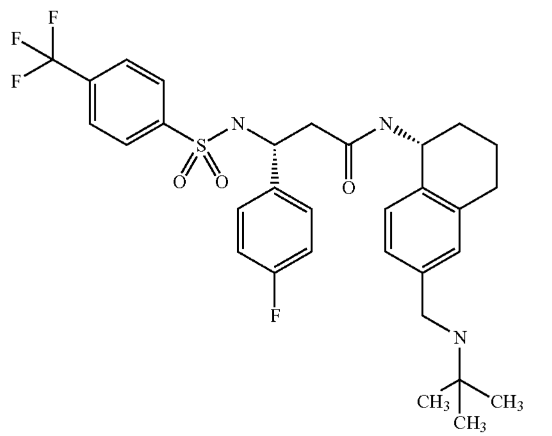 | N-[6-(tert-Butylamino-methyl)-1,2,3,4-tetrahydro-naphthalen-1-yl]-3-(4-fluoro-phenyl)-3-(3-trifluoromethyl-phenylmethanesulfonylamino)-propionamide | C32 H37 F4 N3 O3 S | 619.72 | 620 |
| dt | 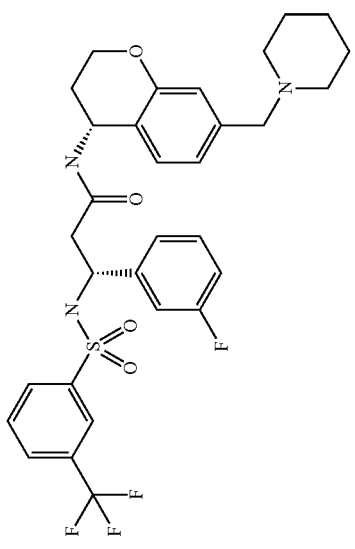 | 3-(Fluoro-phenyl)-N-(7-piperidin-1-ylmethyl-chroman-4-yl)-3-(3-trifluoromethyl-benzenesulfonylamino)-propionamide | C31 H33 F4 N3 O4 S | 619.677 | 620 |

-continued

| Example | Structure | Name | Formula | MW | M + H |
|---|---|---|---|---|---|
| du | 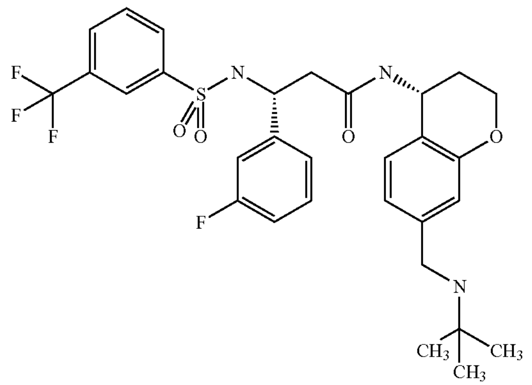 | N-[7-(tert-Butylamino-methyl)-chroman-4-yl]-3-(3-fluoro-phenyl)-3-(3-trifluoromethyl-benzenesulfonylamino)-propionamide | C30 H33 F4 N3 O4 S | 607.666 | 608 |
| dv | 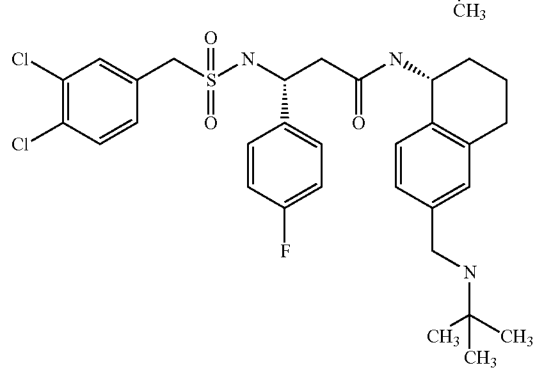 | N-[6-(tert-Butylamino-methyl)-1,2,3,4-tetrahydro-naphthalen-1-yl]-3-(3,4-dichloro-phenylmethanesulfonylamino)-3-(4-fluoro-phenyl)-propionamide | C31 H36 Cl2 F N3 O3 S | 620.613 | 621 |

| Example | Structure | Name | Formula | MW | M + H |
|---|---|---|---|---|---|
| dw | 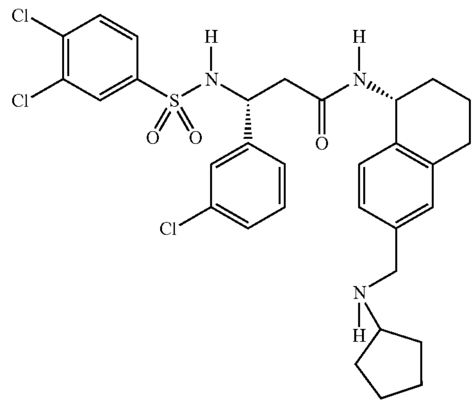 | 3-(3-Chloro-phenyl)-N-(6-cyclopentylaminomethyl-1,2,3,4-tetrahydro-naphthalen-1-yl)-3-(3,4-dichloro-benzenesulfonylamino)-propionamide | C31 H34 Cl3 N3 O3 S | 635.053 | 636 |
| dx | 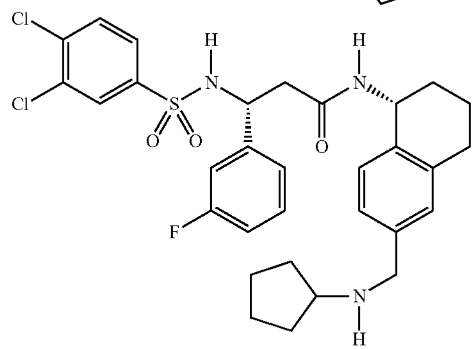 | N-(6-Cyclopentylaminomethyl-1,2,3,4-tetrahydro-naphthalen-1-yl)-3-(3,4-dichloro-benzenesulfonylamino)-3-(3-fluoro-phenyl)-propionamide | C31 H34 Cl2 F N3 O3 S | 618.598 | 619 |
| dy | 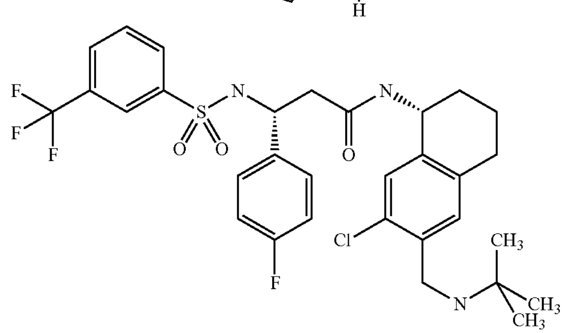 | N-[7-(tert-Butylamino-methyl)-6-chloro-chroman-4-yl]-3-(4-fluoro-phenyl)-3-(3-trifluoromethyl-benzenesulfonylamino)-propionamide | C30 H32 Cl F4 N3 O4 S | 642.111 | 643 |

| Example | Structure | Name | Formula | MW | M + H |
|---|---|---|---|---|---|
| dz | 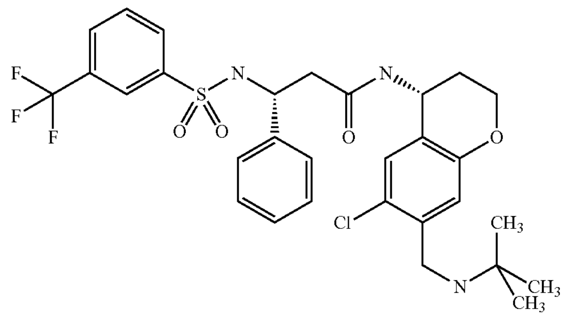 | N-[7-(tert-Butylamino-methyl)-6-chloro-chroman-4-yl]-3-phenyl-3-(3-trifluoromethyl-benzenesulfonylamino)-propionamide | C30 H33 Cl F3 N3 O4 S | 624.121 | 625 |
| ea | 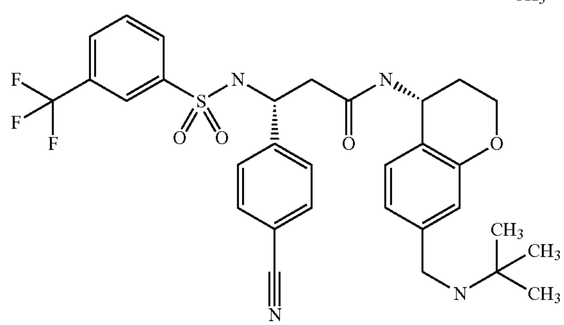 | N-[7-(tert-Butylamino-methyl)-chroman-4-yl]-3-(4-cyano-phenyl)-3-(3-trifluoromethyl-benzenesulfonylamino)-propionamide | C31 H33 F3 N4 O4 S | 614.686 | 615 |
| eb | 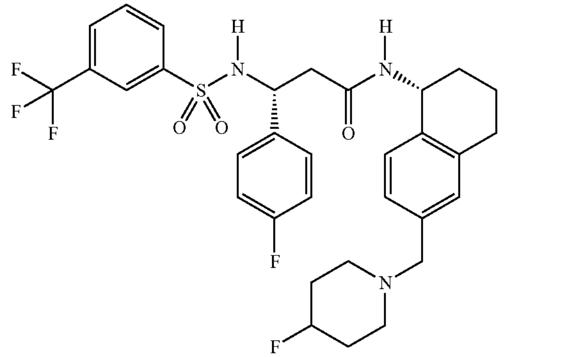 | 3-(4-Fluoro-phenyl)-N-[6-(4-fluoro-piperidin-1-ylmethyl)-1,2,3,4-tetrahydro-naphthalen-1-yl]-3-(3-trifluoromethyl-benzenesulfonylamino)-propionamide | C32 H34 F5 N3 O3 S | 635.695 | 636 |

| Example | Structure | Name | Formula | MW | M + H |
|---|---|---|---|---|---|
| ec | 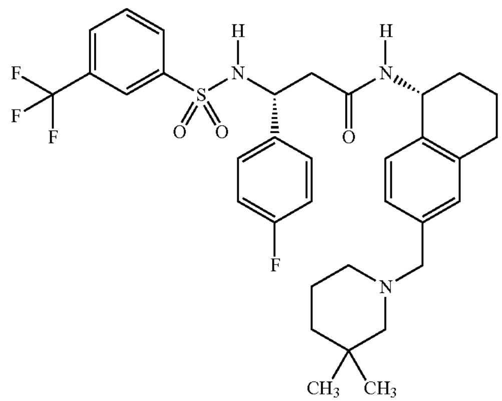 | N-[6-(3,3-Dimethyl-piperidin-1-ylmethyl)-1,2,3,4-tetrahydro-naphthalen-1-yl]-3-(4-fluoro-phenyl)-3-(3-trifluoromethyl-benzenesulfonylamino)-propionamide | C34 H39 F4 N3 O3 S | 645.758 | 646 |
| ed | 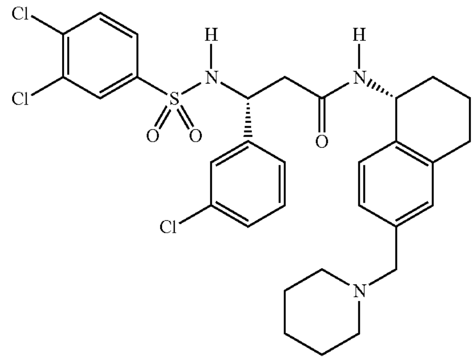 | 3-(3-Chloro-phenyl)-3-(3,4-dichloro-benzenesulfonylamino)-N-(6-piperidin-1-ylmethyl-1,2,3,4-tetrahydro-naphthalen-1-yl)-propionamide | C31 H34 Cl3 N3 O3 S | 635.053 | 631 |

-continued

| Example | Structure | Name | Formula | MW | M + H |
|---|---|---|---|---|---|
| ee | 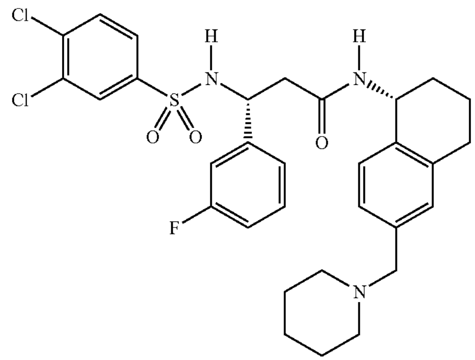 | 3-(3,4-Dichloro-benzenesulfonylamino)-3-(3-fluoro-phenyl)-N-(6-piperidin-1-ylmethyl-1,2,3,4-tetrahydro-naphthalen-1-yl)-propionamide | C31 H34 Cl2 F N3 O3 S | 618.598 | 619 |
| ef | 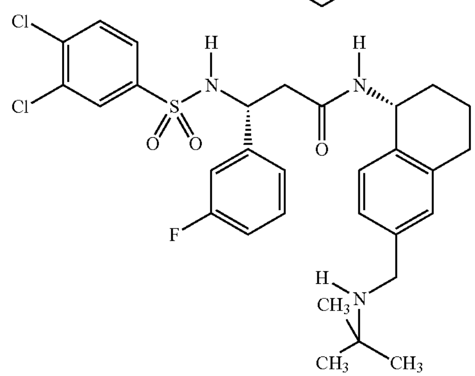 | N-[6-(tert-Butylamino-methyl)-1,2,3,4-tetrahydro-naphthalen-1-yl]-3-(3,4-dichloro-benzenesulfonylamino)-3-(3-fluoro-phenyl)-propionamide | C30 H34 Cl2 F N3 O3 S | 606.587 | 607 |

-continued

| Example | Structure | Name | Formula | MW | M + H |
|---|---|---|---|---|---|
| eg | 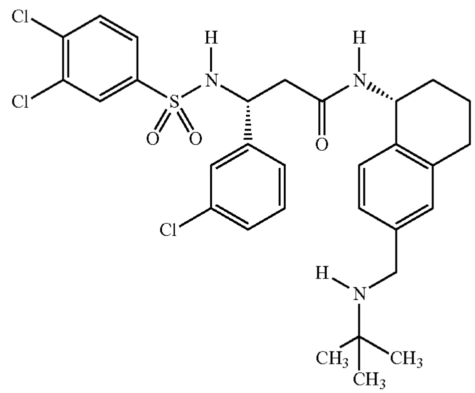 | N-[6-(tert-Butylamino-methyl)-1,2,3,4-tetrahydro-naphthalen-1-yl]-3-(3-chloro-phenyl)-3-(3,4-dichloro-benzenesulfonylamino)-propionamide | C30 H34 Cl3 N3 O3 S | 623.042 | 624 |
| eh | 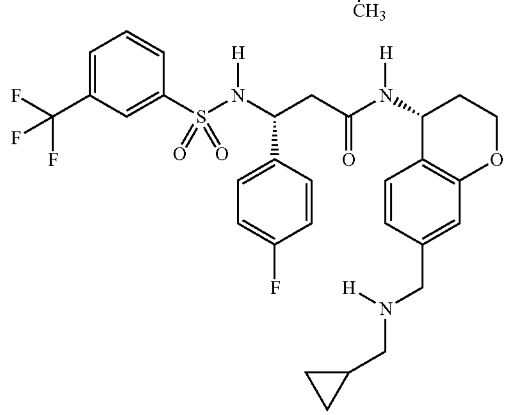 | N-{7-[(Cyclopropylmethyl-amino)-methyl]-chroman-4-yl}-3-(4-fluoro-phenyl)-3-(3-trifluoromethyl-benzenesulfonylamino)-propionamide | C30 H31 F4 N3 O4 S | 605.65 | 606 |

-continued

| Example | Structure | Name | Formula | MW | M + H |
|---|---|---|---|---|---|
| ei | 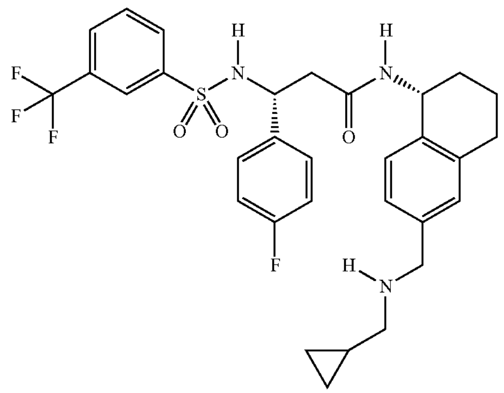 | N-{6-[(Cyclopropylmethyl-amino)-methyl]-1,2,3,4-tetrahydro-naphthalen-1-yl}-3-(4-fluoro-phenyl)-3-(3-trifluoromethyl-benzenesulfonylamino)-propionamide | C31 H33 F4 N3 O3 S | 603.678 | 604 |
| ej | 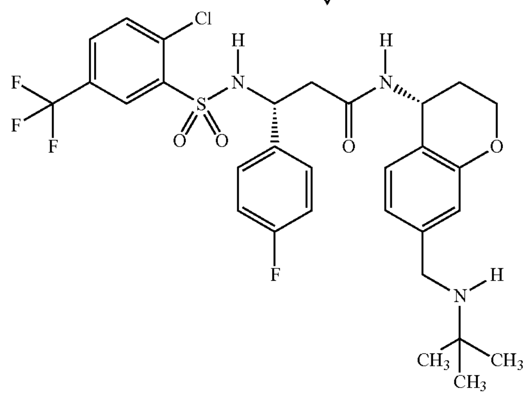 | N-[7-(tert-Butylamino-methyl)-chroman-4-yl]-3-(2-chloro-5-trifluoromethyl-benzenesulfonylamino)-3-(4-fluoro-phenyl)-propionamide | C30 H32 Cl F4 N3 O4 S | 642.111 | 643 |
| ek | 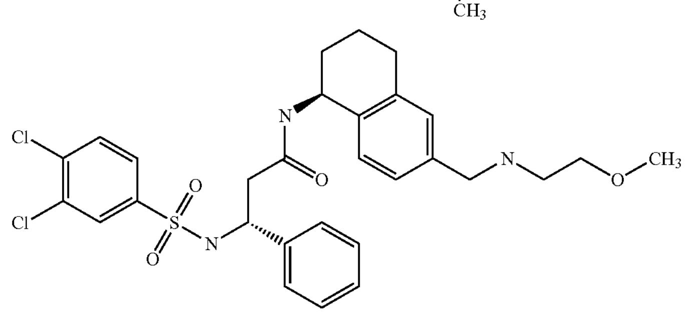 | 3-(3,4-Dichloro-benzenesulfonylamino)-N-{6-[((2-methoxy-ethyl)amino)-methyl]-1,2,3,4-tetrahydro-naphthalen-1-yl}-3-phenyl-propanamide | C29 H33 Cl2 N3 O4 S | 590.569 | 591 |

| Example | Structure | Name | Formula | MW | M + H |
|---|---|---|---|---|---|
| el | 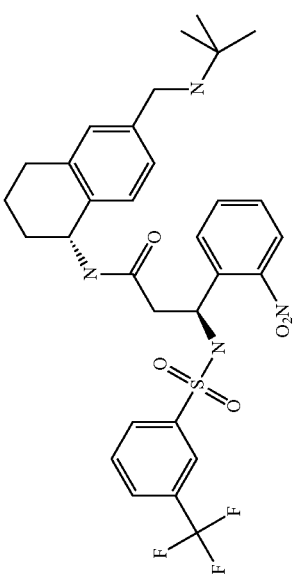 | N-[6-((tert-Butylamino-methyl)-1,2,3,4-tetrahydro-naphthalen-1-yl]-3-(2-nitro-phenyl)-3-(3-trifluoromethyl-benzenesulfonylamino)-propionamide | C31 H35 F3 N4 O5 S | 632.701 | 633 |
| em | 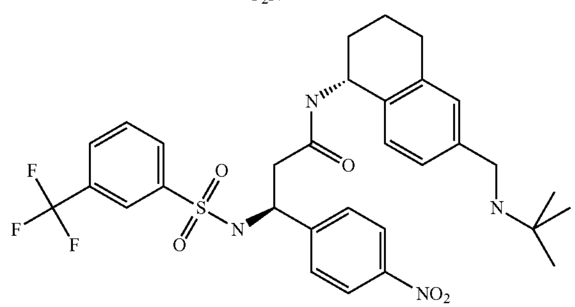 | N-[6-((tert-Butylamino-methyl)-1,2,3,4-tetrahydro-naphthalen-1-yl]-3-(4-nitro-phenyl)-3-(3-trifluoromethyl-benzenesulfonylamino)-propionamide | C31 H35 F3 N4 O5 S | 632.701 | 633 |

| Example | Structure | Name | Formula | MW | M + H |
|---|---|---|---|---|---|
| en | 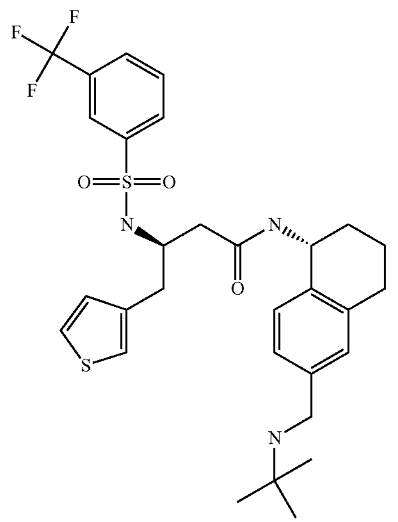 | (3R)-N-((1R)-6-(((1,1-dimethylethyl)amino)methyl)-1,2,3,4-tetrahydro-1-naphthalenyl)-4-(3-thienyl)-3-(((3-(trifluoromethyl)phenyl)sulfonyl)amino)butanamide | C30 H36 F3 N3 O3 S2 | 607.758 | 608 |
| eo | 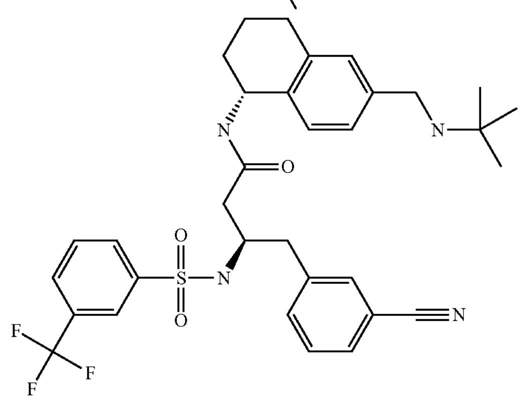 | (3R)-4-(3-cyanophenyl)-N-((1R)-6-(((1,1-dimethylethyl)amino)methyl)-1,2,3,4-tetrahydro-1-naphthalenyl)-3-(((3-(trifluoromethyl)phenyl)sulfonyl)amino)butanamide | C33 H37 F3 N4 O3 S | 626.74 | 627 |

| Example | Structure | Name | Formula | MW | M + H |
|---|---|---|---|---|---|
| ep | 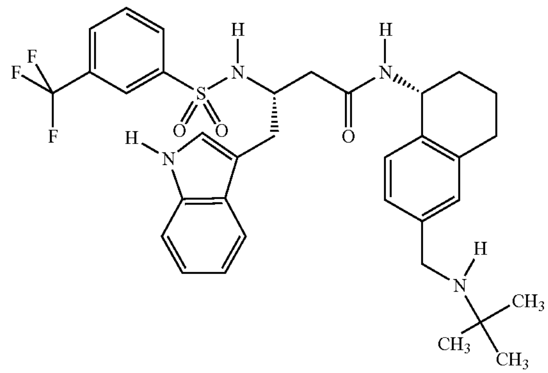 | (3S)-N-((1R)-6-(((1,1-dimethylethyl)amino)methyl)-1,2,3,4-tetrahydro-1-naphthalenyl)-4-((1H-indol-3-yl)-3-(((3-(trifluoromethyl)phenyl)sulfonyl)amino)butanamide | C34 H39 F3 N4 O3 S | 640.767 | 641 |
| eq | 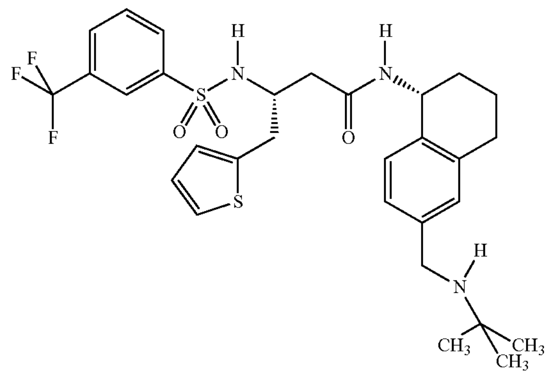 | (3R)-N-((1R)-6-(((1,1-dimethylethyl)amino)methyl)-1,2,3,4-tetrahydro-1-naphthalenyl)-4-((2-thienyl)-3-(((3-(trifluoromethyl)phenyl)sulfonyl)amino)butanamide | C30 H36 F3 N3 O3 S2 | 607.758 | 608 |
| er | 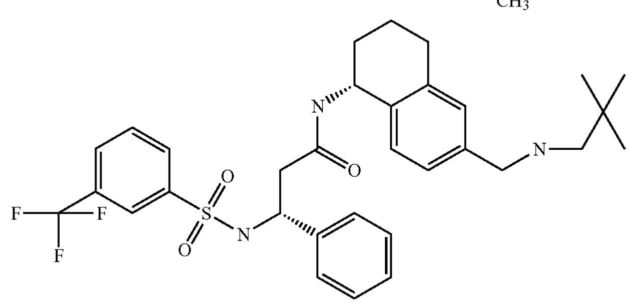 | N-{6-[((2,2-Dimethyl-propylamino)-methyl]-1,2,3,4-tetrahydro-naphthalen-1-yl}-3-phenyl-3-(3-trifluoromethyl-benzenesulfonylamino)-propionamide | C32 H38 F3 N3 O3 S | 601.73 | 602 |

-continued
| Example | Structure | Name | Formula | MW | M + H |
|---|---|---|---|---|---|
| es | 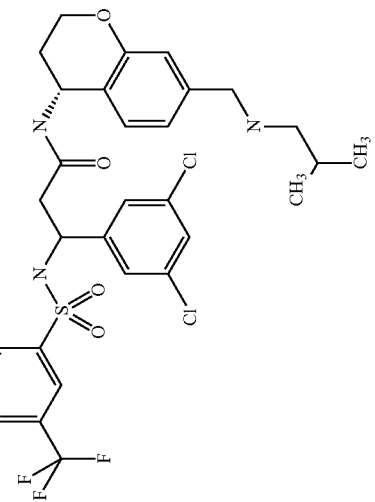 | 3-(3,5-Dichloro-phenyl)-N-[7-(isobutylamino-methyl)-chroman-4-yl]-3-(3-trifluoromethyl-benzenesulfonylamino)-propionamide | C30 H32 Cl2 F3 N3 O4 S | 658.56 | 659 |
| et | 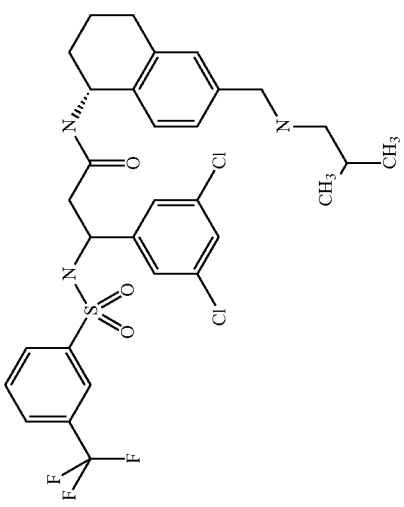 | 3-(3,5-Dichloro-phenyl)-N-[6-(isobutylamino-methyl)-1,2,3,4-tetrahydro-naphthalen-1-yl]-3-(3-trifluoromethyl-benzenesulfonylamino)-propionamide | C31 H34 Cl2 F3 N3 O3 S | 656.59 | 657 |

| Example | Structure | Name | Formula | MW | M + H |
|---|---|---|---|---|---|
| eu | 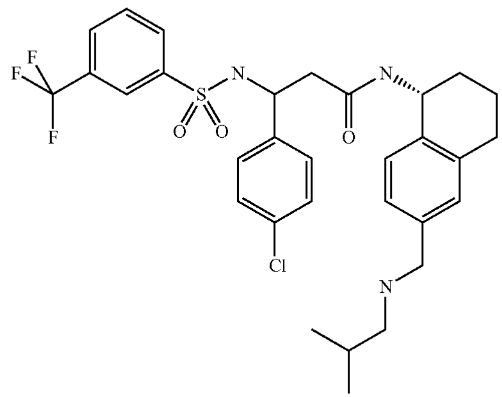 | 3-(4-Chloro-phenyl)-N-[6-(isobutylamino-methyl)-1,2,3,4-tetrahydro-naphthalen-1-yl]-3-(3-trifluoromethyl-benzenesulfonylamino)-propionamide | C31 H35 Cl F3 N3 O3 S | 622.15 | 623 |
| ev | 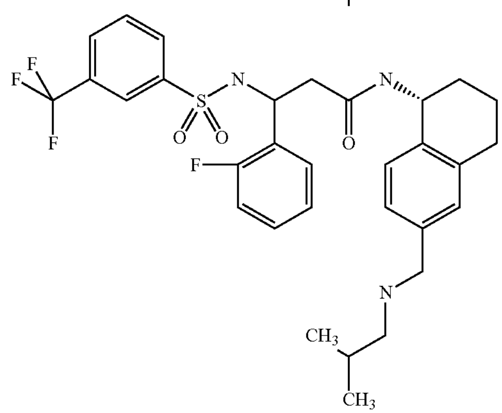 | 3-(2-Fluoro-phenyl)-N-[6-(isobutylamino-methyl)-1,2,3,4-tetrahydro-naphthalen-1-yl]-3-(3-trifluoromethyl-benzenesulfonylamino)-propionamide | C31 H35 F4 N3 O3 S | 605.7 | 606 |

-continued

| Example | Structure | Name | Formula | MW | M+H |
|---|---|---|---|---|---|
| ew | 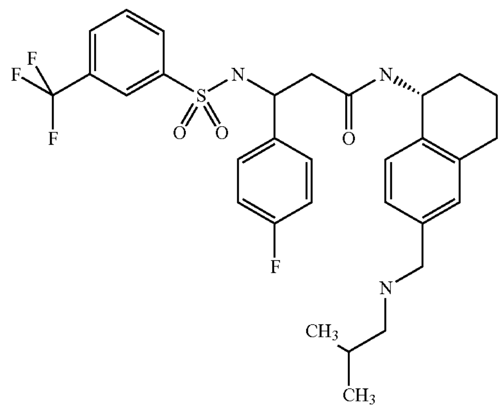 | 3-(4-Fluoro-phenyl)-N-[6-(isobutylamino-methyl)-1,2,3,4-tetrahydro-naphthalen-1-yl]-3-(3-trifluoromethyl-benzenesulfonylamino)-propionamide | C31 H35 F4 N3 O3 S | 605.7 | 606 |
| ex | 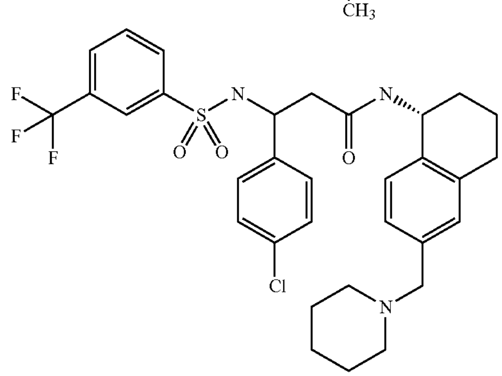 | 3-(4-Chloro-phenyl)-N-(6-piperidin-1-ylmethyl-1,2,3,4-tetrahydro-naphthalen-1-yl)-3-(3-trifluoromethyl-benzenesulfonylamino)-propionamide | C32 H35 Cl F3 N3 O3 S | 634.16 | 635 |

-continued

| Example | Structure | Name | Formula | MW | M + H |
|---|---|---|---|---|---|
| ey | 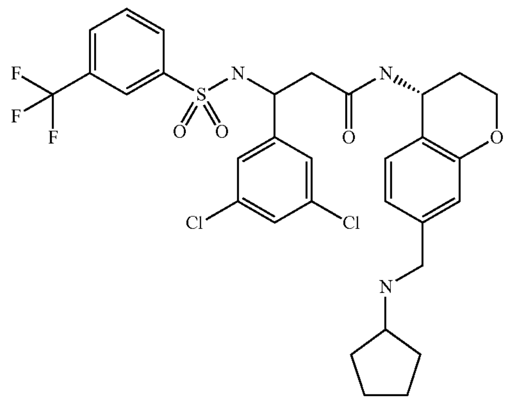 | N-(7-Cyclopentylaminomethyl-chroman-4-yl)-3-(3,5-dichloro-phenyl)-3-(3-trifluoromethyl-benzenesulfonylamino)-propionamide | C31 H32 Cl2 F3 N3 O4 S | 670.57 | 671 |
| ez | 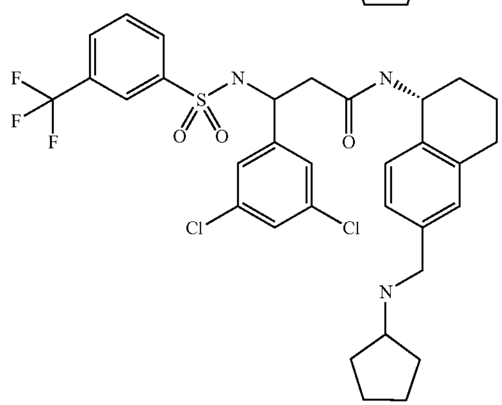 | N-(6-Cyclopentylaminomethyl-1,2,3,4-tetrahydro-naphthalen-1-yl)-3-(3,5-dichloro-phenyl)-3-(3-trifluoromethyl-benzenesulfonylamino)-propionamide | C32 H34 Cl2 F3 N3 O3 S | 668.6 | 669 |

| Example | Structure | Name | Formula | MW | M + H |
|---|---|---|---|---|---|
| fa | 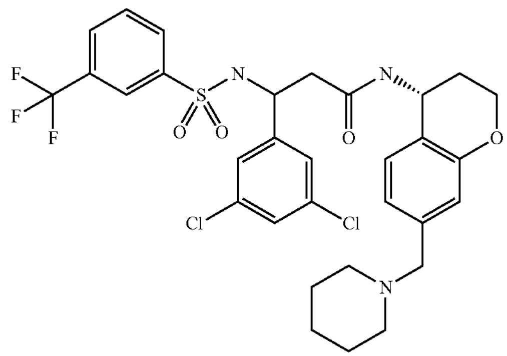 | 3-(3,5-Dichloro-phenyl)-N-(7-piperidin-1-ylmethyl-chroman-4-yl)-3-(34-trifluoromethyl-benzenesulfonylamino)-propionamide | C31 H32 Cl2 F3 N3 O4 S | 670.55 | 671 |
| fb | 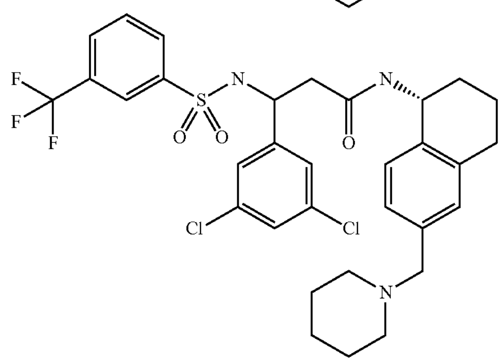 | 3-(3,5-Dichloro-phenyl)-N-(6-piperidin-1-ylmethyl-1,2,3,4-tetrahydro-naphthalen-1-yl)-3-(3-trifluoromethyl-benzenesulfonylamino)-propionamide | C32 H34 Cl2 F3 N3 O3 S | 668.6 | 669 |

| Example | Structure | Name | Formula | MW | M + H |
|---|---|---|---|---|---|
| fc | 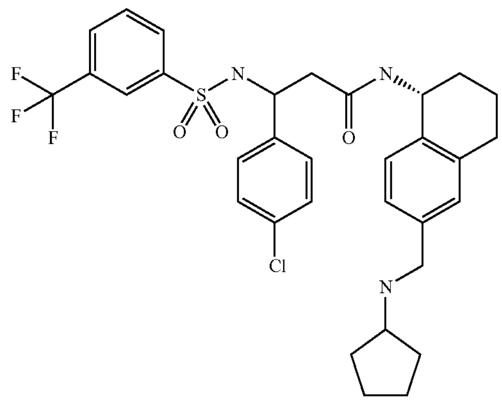 | 3-(4-Chloro-phenyl)-N-(6-cyclopentylaminomethyl-1,2,3,4-tetrahydro-naphthalen-1-yl)-3-(3-trifluoromethyl-benzenesulfonylamino)-propionamide | C32 H35 Cl F3 N3 O3 S | 634.16 | 643 |
| fd | 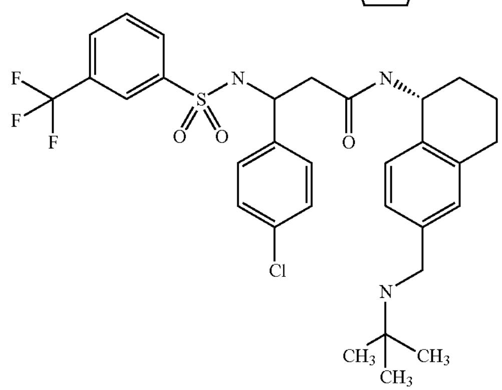 | N-[6-((tert-Butylamino-methyl)-1,2,3,4-tetrahydro-naphthalen-1-yl]-3-(4-chloro-phenyl)-3-(3-trifluoromethyl-benzenesulfonylamino)-propionamide | C31 H35 Cl F3 N3 O3 S | 622.15 | 622 |

| Example | Structure | Name | Formula | MW | M + H |
|---|---|---|---|---|---|
| fe | 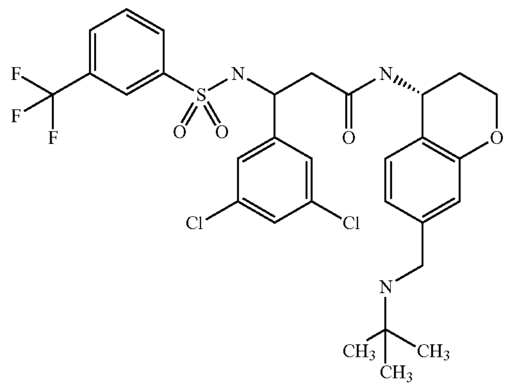 | N-[7-(tert-Butylamino-methyl)-chroman-4-yl]-3-(3,5-dichloro-phenyl)-3-(3-trifluoromethyl-benzenesulfonylamino)-propionamide | C30 H32 Cl2 F3 N3 O4 S | 658.56 | 657 |
| ff | 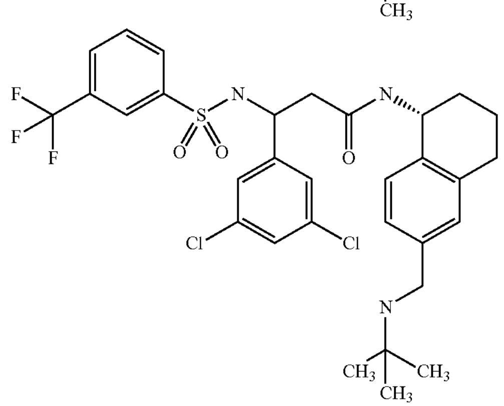 | N-[6-(tert-Butylamino-methyl)-1,2,3,4-tetrahydro-naphthalen-1-yl]-3-(3,5-dichloro-phenyl)-3-(3-trifluoromethyl-benzenesulfonylamino)-propionamide | C31 H34 Cl2 F3 N3 O3 S | 656.59 | 657 |

-continued

| Example | Structure | Name | Formula | MW | M + H |
|---|---|---|---|---|---|
| fg | 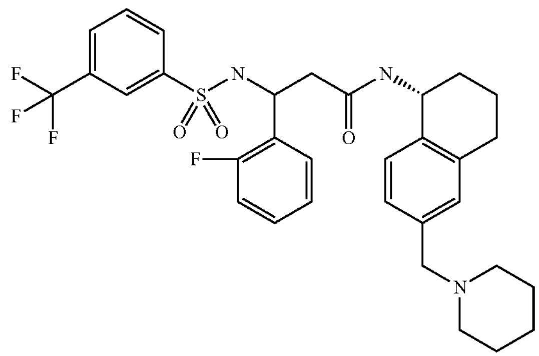 | 3-(2-Fluoro-phenyl)-N-(6-piperidin-1-ylmethyl-1,2,3,4-tetrahydro-naphthalen-1-yl)-3-(3-trifluoromethyl-benzenesulfonylamino)-propionamide | C32 H35 F4 N3 O3 S | 617.71 | 618 |
| fh | 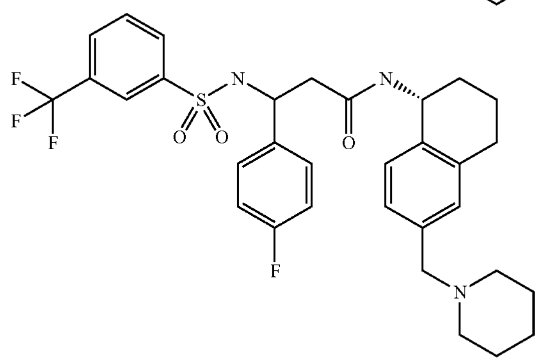 | 3-(4-Fluoro-phenyl)-N-(6-piperidin-1-ylmethyl-1,2,3,4-tetrahydro-naphthalen-1-yl)-3-(3-trifluoromethyl-benzenesulfonylamino)-propionamide | C32 H35 F4 N3 O3 S | 617.71 | 618 |

| Example | Structure | Name | Formula | MW | M + H |
|---|---|---|---|---|---|
| fi | 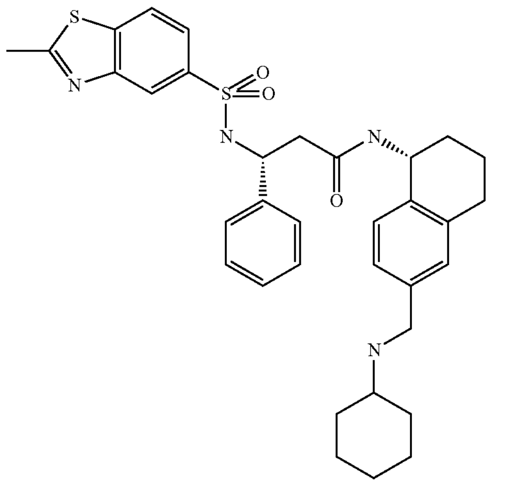 | N-(6-Cyclohexylaminomethyl-1,2,3,4-tetrahydro-naphthalen-1-yl)-3-(2-methyl-benzothiazole-5-sulfonylamino)-3-phenyl-propionamide | C34 H40 N4 O3 S2 | 616.847 | 617 |
| fj | 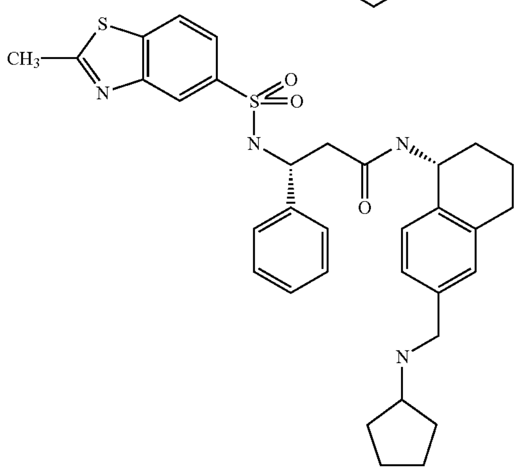 | N-(6-Cyclopentylaminomethyl-1,2,3,4-tetrahydro-naphthalen-1-yl)-3-(2-methyl-benzothiazole-5-sulfonylamino)-3-phenyl-propionamide | C33 H38 N4 O3 S2 | 602.82 | 603 |

| Example | Structure | Name | Formula | MW | M + H |
|---|---|---|---|---|---|
| fk | 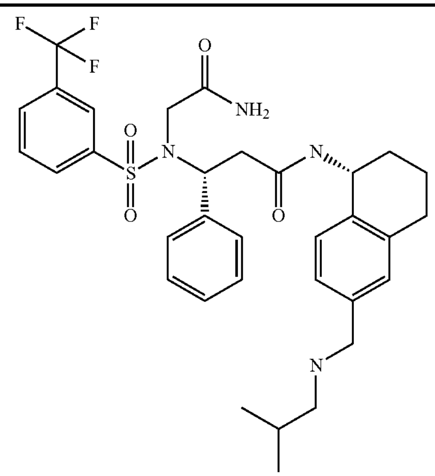 | 3-[Carbamoylmethyl-(3-trifluoromethyl-benzenesulfonyl)-amino]-N-[6-(isobutylamino-methyl)-1,2,3,4-tetrahydro-naphthalen-1-yl]-3-phenyl-propionamide | C33 H39 F3 N4 O4 S | 644.755 | 645 |
| fl | 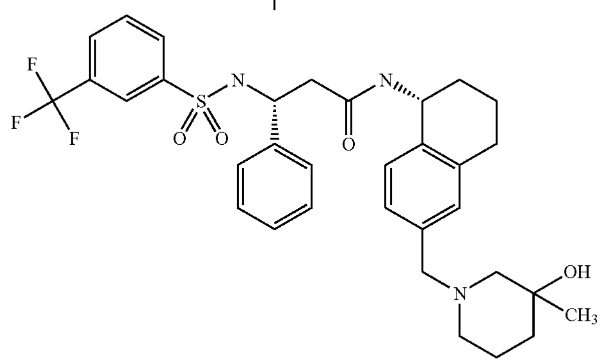 | N-[6-(3-Hydroxy-3-methyl-piperidin-1-ylmethyl)-1,2,3,4-tetrahydro-naphthalen-1-yl]-3-phenyl-3-(3-trifluoromethyl-benzenesulfonylamino)-propionamide | C33 H38 F3 N3 O4 S | 629.74 | 630 |

| Example | Structure | Name | Formula | MW | M + H |
|---|---|---|---|---|---|
| fm | 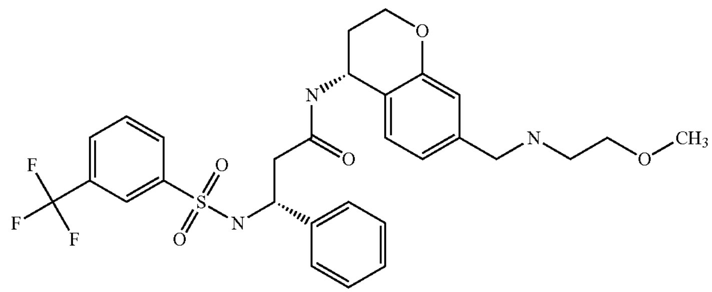 | N-{7-[(2-Methoxy-ethylamino)-methyl]-chroman-4-yl}-3-phenyl-3-(3-trifluoromethyl-benzenesulfonylamino)-propionamide | C29 H32 F3 N3 O5 S | 591.648 | 592 |
| fn | 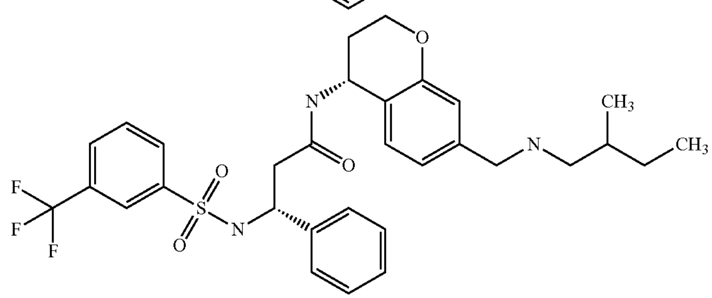 | N-{7-[(2-Methyl-butylamino)-methyl]-chroman-4-yl}-3-phenyl-3-(3-trifluoromethyl-benzenesulfonylamino)-propionamide | C31 H36 F3 N3 O4 S | 603.702 | 605 |
| fo | 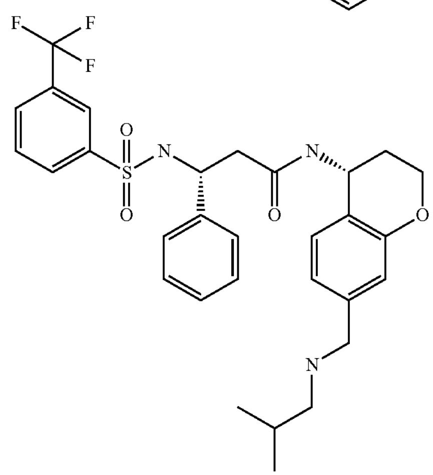 | N-[7-(Isobutylamino-methyl)-chroman-4-yl]-3-phenyl-3-(3-trifluoromethyl-benzenesulfonylamino)-propionamide | C30 H34 F3 N3 O4 S | 589.676 | 590 |

-continued

| Example | Structure | Name | Formula | MW | M + H |
|---|---|---|---|---|---|
| fp | 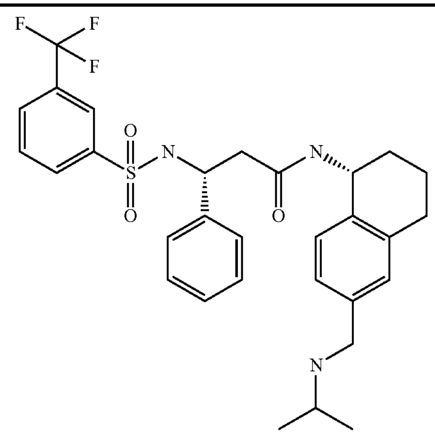 | N-[6-(Isopropylamino-methyl)-1,2,3,4-tetrahydro-naphthalen-1-yl]-3-phenyl-3-(3-trifluoromethyl-benzenesulfonylamino)-propionamide | C30 H34 F3 N3 O3 S | 573.677 | 574 |
| fq | 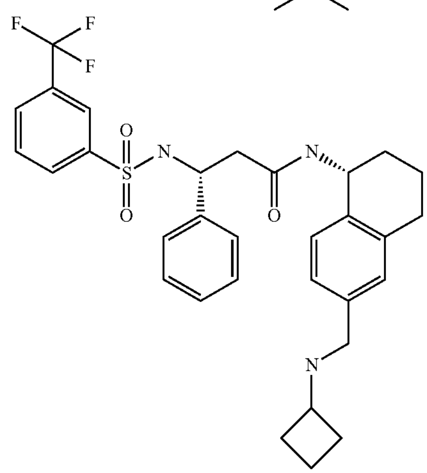 | N-(6-Cyclobutylaminomethyl-1,2,3,4-tetrahydro-naphthalen-1-yl)-3-phenyl-3-(3-trifluoromethyl-benzenesulfonylamino)-propionamide | C31 H34 F3 N3 O3 S | 585.688 | 586 |

-continued

| Example | Structure | Name | Formula | MW | M + H |
|---|---|---|---|---|---|
| fr | 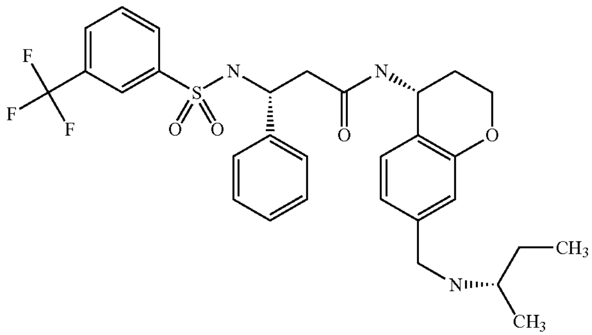 | N-[7-(sec-Butylamino-methyl)-chroman-4-yl]-3-phenyl-3-(3-trifluoromethyl-benzenesulfonylamino)-propionamide | C30 H34 F3 N3 O4 S | 589.676 | 600 |
| fs | 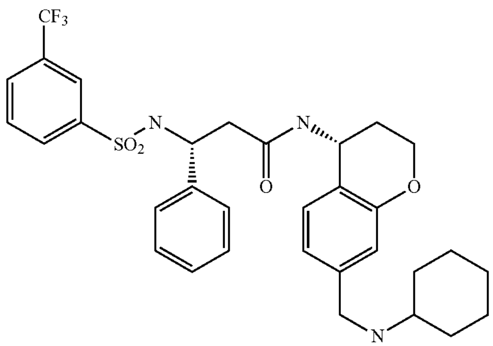 | N-(7-Cyclohexylaminomethyl-chroman-4-yl)-3-phenyl-3-(3-trifluoromethyl-benzenesulfonylamino)-propionamide | C32 H36 F3 N3 O4 S | 615.713 | 616 |
| ft | 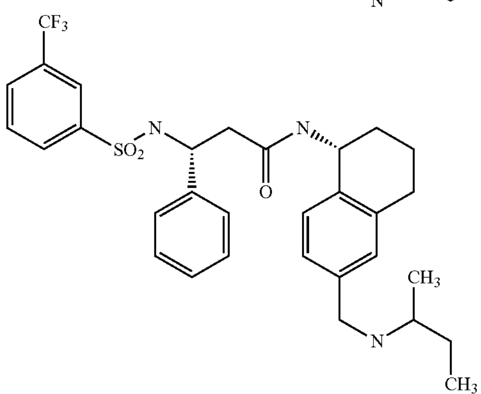 | N-[7-(sec-Butylamino-methyl)-chroman-4-yl]-3-phenyl-3-(3-trifluoromethyl-benzenesulfonylamino)-propionamide | C30 H34 F3 N3 O4 S | 589.676 | 590 |

-continued

| Example | Structure | Name | Formula | MW | M + H |
|---|---|---|---|---|---|
| fu | 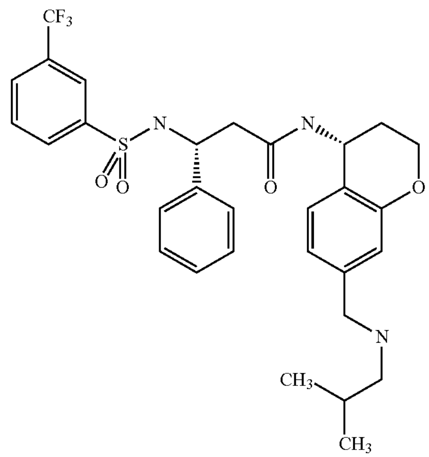 | N-[7-(Isobutylamino-methyl)-chroman-4-yl]-3-phenyl-3-(3-trifluoromethyl-benzenesulfonylamino)-propionamide | C30 H34 F3 N3 O4 S | 589.676 | 590 |
| fv | 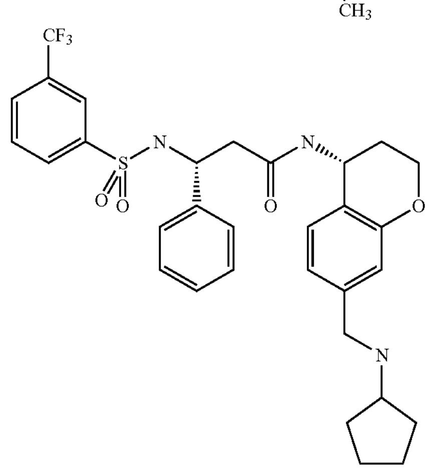 | N-(7-Cyclopentylaminomethyl-chroman-4-yl)-3-phenyl-3-(3-trifluoromethyl-benzenesulfonylamino)-propionamide | C31 H34 F3 N3 O4 S | 601.687 | 602 |

-continued

| Example | Structure | Name | Formula | MW | M + H |
|---|---|---|---|---|---|
| fx | 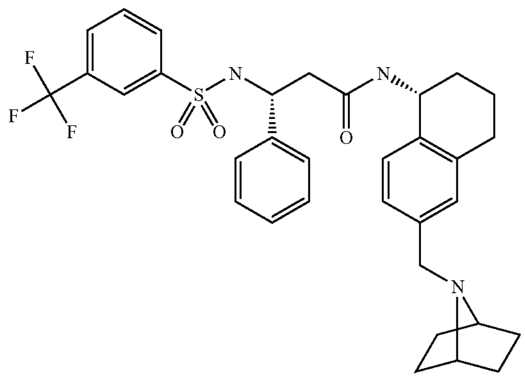 | N-[6-(7-Aza-bicyclo[2.2.1]hept-7-ylmethyl)-1,2,3,4-tetrahydro-naphthalen-1-yl]-3-phenyl-3-(3-trifluoromethyl-benzenesulfonylamino)-propionamide | C33 H36 F3 N3 O3 S | 611.725 | 612 |
| fy | 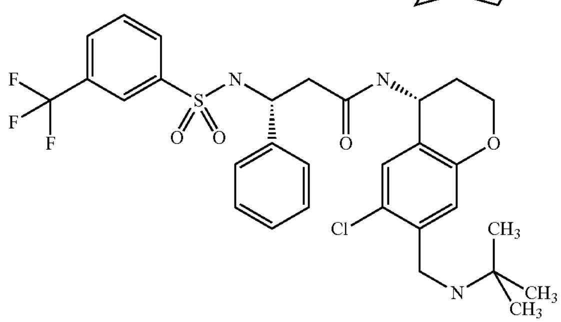 | 3-(3,4-Dichloro-benzenesulfonylamino)-N-[6-(2-dimethylamino-ethoxy)-1,2,3,4-tetrahydro-naphthalen-1-yl]-3-phenyl-propionamide | C29 H33 Cl2 N3 O4 S | 590.57 | 591 |

| Example | Structure | Name | Formula | MW | M + H |
|---|---|---|---|---|---|
| fz | 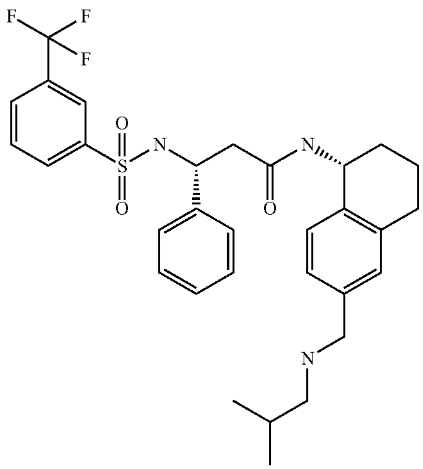 | (3R)-N-((1R)-6-(((2-methylpropyl)amino)methyl)-1,2,3,4-tetrahydro-1-naphthalenyl)-3-phenyl-3-(((3-(trifluoromethyl)phenyl)sulfonyl)amino)propanamide | C31H36F3N3O3S | 584.67 | |
| ga | 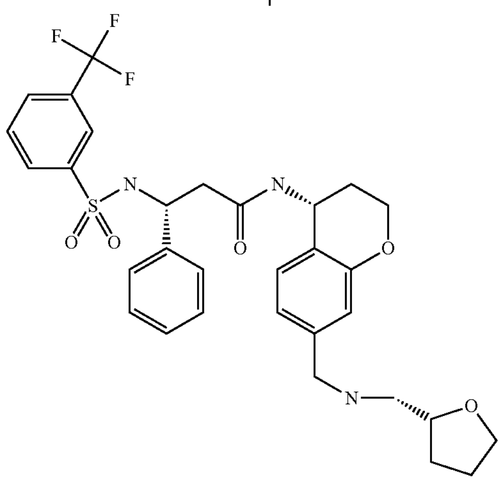 | (3R)-3-phenyl-N-((4R)-7-((((2R)-tetrahydro-2-furanylmethyl)amino)methyl)-3,4-dihydro-2H-chromen-4-yl)-3-(((3-(trifluoromethyl)phenyl)sulfonyl)amino)propanamide | C31 H34 F3 N3 O5 S | 617.69 | |

Other compounds included in this invention are set forth in Tables 1-7 below and Examples 166-227.

TABLE 1

| # | R¹ |
|---|---|
| 16. | cyclohexyl |
| 17. | 3,4-dimethylphenyl |
| 18. | benzodioxolyl-5-yl |
| 19. | 2,3-dihydro-benzo[1,4]dioxin-6-yl |
| 20. | 3-chlorophenyl |
| 21. | 3-fluorophenyl |
| 22. | 3-methoxyphenyl |
| 23. | 4-methoxyphenyl |
| 24. | 3-hydroxyphenyl |
| 25. | 3-CF₃-phenyl |
| 26. | 3-methylphenyl |
| 27. | 4-methylphenyl |
| 28. | 3,4-dichlorophenyl |
| 29. | 4-chlorophenyl |
| 30. | 3-pyridyl |
| 31. | 3,4-dimethoxyphenyl |
| 32. | 3-phenyloxyphenyl |
| 33. | 3-furyl |
| 34. | 3-benzyloxyphenyl |
| 35. | 3-thienyl |
| 36. | 3-isopropylphenyl |
| 37. | 3,4-difluorophenyl |
| 38. | benzo[1,2,5]thiadiazol-5-yl |
| 39. | thiazol-2-yl |
| 40. | 4-bromophenyl |
| 41. | 2-benzofuryl |
| 42. | 5-benzofuryl |
| 43. | 4-isopropylphenyl |
| 44. | 6-benzofuryl |
| 45. | 4-CF₃-phenyl |
| 46. | 5-benzothienyl |
| 47. | 4-benzofuryl |
| 48. | 2,3-dihydrofur-6-yl |
| 49. | benzo[1,2,5]oxadiazol-5-yl |
| 50. | 2,3-dihydrofur-4-yl |
| 51. | 3-methylbenzofur-5-yl |

TABLE 2

| # | R² |
|---|---|
| 52. | 5,6,7,8-tetrahydronaphth-2-yl |
| 53. | 2,4-dichloro-3-methylphenyl |
| 54. | 2-quinolyl |
| 55. | phenyl |
| 56. | 2-chlorophenyl |
| 57. | 3-chlorophenyl |
| 58. | 4-chlorophenyl |
| 59. | 4-methoxyphenyl |
| 60. | 3,5-dichlorophenyl |
| 61. | 3-methoxyphenyl |
| 62. | 3-fluorophenyl |
| 63. | 3-biphenyl |
| 64. | 4-biphenyl |
| 65. | 3-methylphenyl |
| 66. | 3-CF₃-phenyl |
| 67. | 2,4,6-trichlorphenyl |
| 68. | 2,3,4-trichlorphenyl |
| 69. | 2,4,5-trichlorphenyl |
| 70. | 3,4-dichlorophenyl |
| 71. | 1-naphthyl |
| 72. | phenyl-ethenyl |
| 73. | benzo[1,2,5]oxadiazol-5-yl |
| 74. | 5-(dimethylamino)naphth-1-yl |
| 75. | 5-chloro-3-methylphenyl |
| 76. | benzothiazol-2-yl |
| 77. | 2,3,4,5,6-pentamethylphenyl |
| 78. | 6-methoxy-2-naphthyl |
| 79. | 4-t-butylphenyl |
| 80. | 3-chloro-4-methylphenyl |
| 81. | 5-methoxy-3-methylbenzothien-2-yl |
| 82. | 6-methoxy-3-methylbenzothien-2-yl |
| 83. | 5-chloro-3-methylbenzothien-2-yl |
| 84. | 3-methylbenzothien-2-yl |
| 85. | 2,4-dichloro-5-methylphenyl |
| 86. | 7-methoxy-2-naphthyl |
| 87. | 6-fluoroethoxy-2-naphthyl |
| 88. | 3-methyl-5-trifluoromethoxybenzofur-2-yl |
| 89. | 3-methyl-5-methoxybenzofur-2-yl |
| 90. | 5-chloro-benzo[1,2,5]oxadiazol-4-yl |
| 91. | 3-methyl-5-trifluoromethoxybenzothien-2-yl |
| 92. | 6-ethoxy-2-naphthyl |
| 93. | 2-Cl-4-CF₃-phenyl |
| 94. | 6-bromonaphthyl |
| 95. | 3-methylbenzofur-2-yl |
| 96. | 3-chlorobenzothien-2-yl |
| 97. | 5-chloro-benzo[1,2,5]thiadiazol-4-yl |
| 98. | 5-chloro-1,3-dimethyl-1H-pyrazol-4-yl |
| 99. | 2,3-dichlorothien-5-yl |
| 100. | 2,5-dichlorothien-3-yl |
| 101. | 5-chloro-2-naphthyl |
| 102. | 4-butoxyphenyl |
| 103. | 3,5-di(trifluoromethyl)phenyl |
| 104. | 5-(isoxazol-3-yl)thien-2-yl |
| 105. | 2-chlorothien-5-yl |
| 106. | 4-chloro-benzo[1,2,5]oxadiazol-7-yl |
| 107. | 2,4-dichloro-6-methylphenyl |
| 108. | 2,4,6-trimethylphenyl |
| 109. | 4-chloro-2,5-dimethylphenyl |
| 110. | 2,5-dichlorophenyl |
| 111. | 3,4-difluorophenyl |
| 112. | 3-chloro-4-fluorophenyl |
| 113. | 4-methylcyclohexyl |

TABLE 2-continued

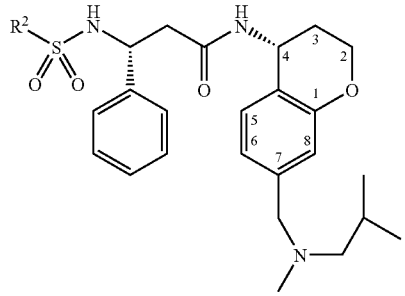

| # | R² |
|---|---|
| 114. | 3,5-dimethylbenzothien-2-yl |
| 115. | 5-fluoro-3-methylbenzothien-2-yl |
| 116. | 5-methylbenzothien-2-yl |
| 117. | 5-chloro-3-methylbenzofur-2-yl |
| 118. | 3-pyridyl |

TABLE 3

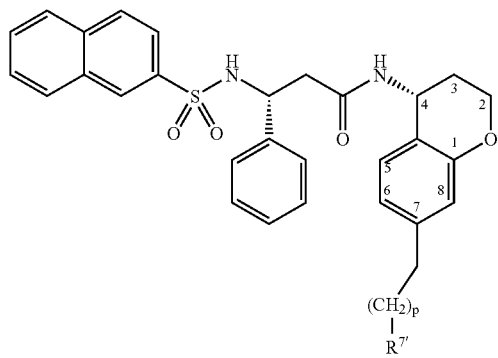

| # | R⁷' | p |
|---|---|---|
| 119. | piperidin-1-yl | 1 |
| 120. | (CH₃)₂N— | 1 |
| 121. | piperazin-1-yl | 1 |
| 122. | 4-CH₃-piperazin-1-yl | 1 |
| 123. | (Et₂)N— | 1 |
| 124. | (CH₃)(Et)N— | 2 |
| 125. | piperazin-1-yl | 2 |

TABLE 4

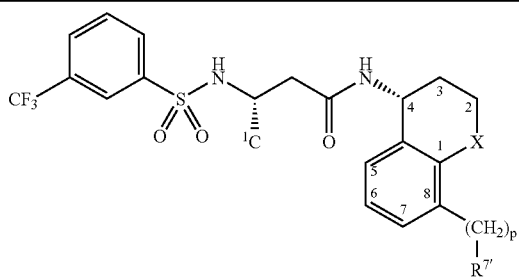

| # | R1 | R2 |
|---|---|---|
| 126. | 3-pyridyl | 1 |
| 127. | 4-methoxy-3-pyridyl | 1 |
| 128. | 4-fluorophenyl | 1 |
| 129. | 4-CH₃-piperazin-1-yl | 1 |
| 130. | (Et₂)N— | 1 |

TABLE 4-continued

| 131. | (CH₃)(Et)N— | 2 |
|---|---|---|
| 132. | piperazin-1-yl | 2 |

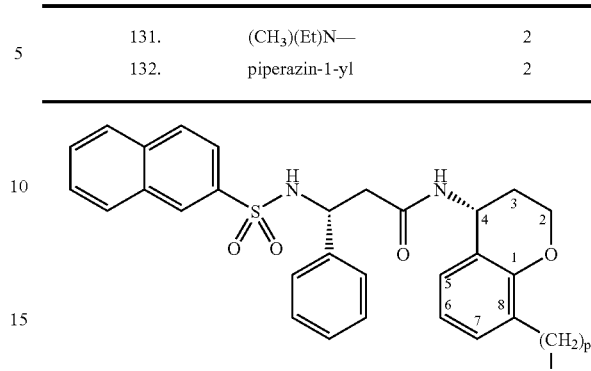

| # | R⁷' | p |
|---|---|---|
| 133. | piperidin-1-yl | 1 |
| 134. | (CH₃)₂N— | 1 |
| 135. | piperazin-1-yl | 1 |
| 136. | 4-CH₃-piperazin-1-yl | 1 |
| 137. | (Et₂)N— | 1 |
| 138. | (CH₃)(Et)N— | 2 |

TABLE 5

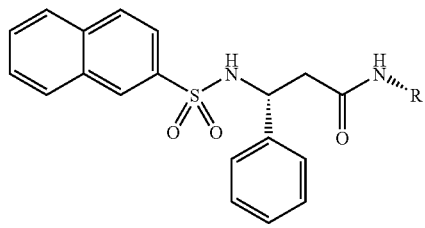

| # | R |
|---|---|
| 139. | 3-isopropyl-7-(1-methylpiperidin-2-yl)chroman-4-yl |
| 140. | 2,2-dimethyl-7-(1-methylpiperidin-2-yl)chroman-4-yl |
| 141. | 7-(piperidin-2-yl)chroman-4-yl |
| 142. | 2,2-dimethyl-7-(methylaminomethyl)chroman-4-yl |
| 143. | 7-(dimethylaminomethyl)-1,2,3,4-tetrahydronaphth-4-yl |
| 144. | 7-(piperidin-1-ylaminomethyl)-1,2,3,4-tetrahydronaphth-2-yl |
| 145. | 5-(piperidin-1-yl)methylindan-1-yl |
| 146. | 6-(4-methylpiperazin-1-yl)methylindan-1-yl |
| 147. | 4-(piperazin-1-yl)methylindan-1-yl |
| 148. | 2-(di-ethylaminomethyl)-5,6,7,8-tetrahydroquinolin-5-yl |
| 149. | 2-(isopropylaminomethyl)-5,6,7,8-tetrahydroquinolin-8-yl |
| 150. | 2-(t-butylaminomethyl)-5,6,7,8-tetrahydoisoquinolin-8-yl |
| 151. | 7-(morpholin-4-ylmethyl)-quinolin-4-yl |
| 152. | 1-methyl-2-oxo-6-(piperidin-1-yl)methylindol-3-yl |

TABLE 6

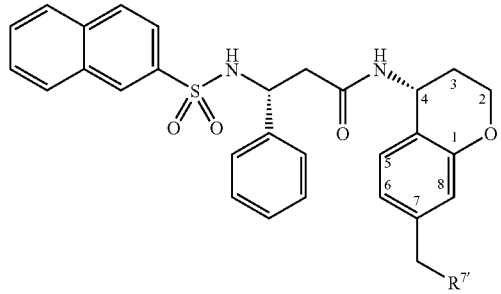

| # | R⁷' |
|---|---|
| 153. | cyclohexylamino |
| 154. | cyclohexylmethylamino |
| 155. | phenylamino |
| 156. | benzylamino |
| 157. | pyridylmethylamino |
| 158. | furylamino |

TABLE 7

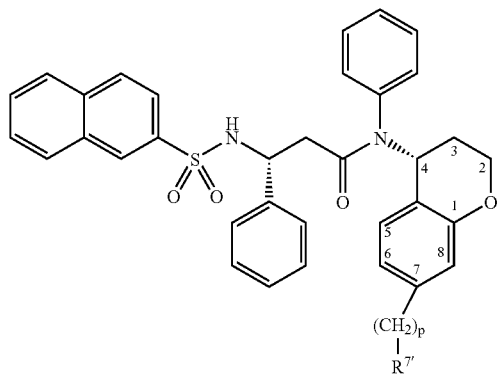

| # | R⁷' | p |
|---|---|---|
| 159. | piperidin-1-yl | 1 |
| 160. | (CH₃)₂N— | 1 |
| 161. | piperazin-1-yl | 1 |
| 162. | 4-CH₃-piperazin-1-yl | 1 |
| 163. | (Et₂)N— | 1 |
| 164. | (CH₃)(Et)N— | 2 |
| 165. | piperazin-1-yl | 2 |

TABLE 8

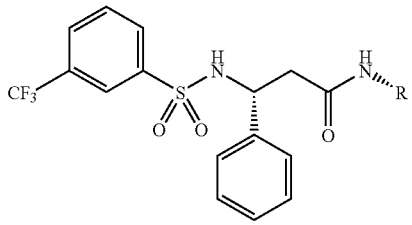

| # | R |
|---|---|
| 233. | 6-(1-isobutylamino-ethyl)-1,2,3,4-tetrahydro-naphthalen-1-ylamine |
| 234. | 6-(isobutylamino-methyl)-1,2,3,4-tetrahydro-naphthalen-1-ylamine |

TABLE 8-continued

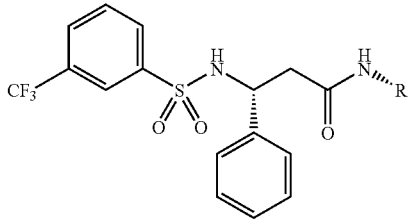

| # | R |
|---|---|
| 235. | 6-(1-Cyclobutylamino-vinyl)-1,2,3,4-tetrahydro-naphthalen-1-ylamine |
| 236. | 5-Piperidin-1-ylmethyl-indan-1-ylamine |
| 237. | 7-[(Cyclopropylmethyl-amino)-methyl]-chroman-4-ylamine |
| 238. | 6-[(Cyclopropylmethyl-amino)-methyl]-1,2,3,4-tetrahydro-naphthalen-1-ylamine |
| 239. | 6-Piperidin-1-ylmethyl-1,2,3,4-tetrahydro-naphthalen-1-ylamine |
| 240. | 1-(5-Amino-5,6,7,8-tetrahydro-naphthalen-2-ylmethyl)-piperidin-3-ol |
| 241. | 6-(4-Fluoro-piperidin-1-ylmethyl)-1,2,3,4-tetrahydro-naphthalen-3-ylamine |
| 242. | 7-Cyclobutaminomethyl-chroman-4-ylamine |
| 243. | 7-tert-butylaminomethyl-chroman-4-ylamine |
| 244. | 7-[(Cyclopropylmethyl-amino)-methyl]-chroman-4-ylamine |
| 245. | 6-[(Cyclopropylmethyl-amino)-methyl]-1,2,3,4-tetrahydro-naphthalen-1-ylamine |
| 246. | 5-(4-Fluoro-piperidin-1-ylmethyl)-indan-1-ylamine |
| 247. | 6-(1-Cyclopentylamino-vinyl)-1,2,3,4-tetrahydro-naphthalen-1-ylammine |
| 248. | 6-(1-tert-Butylamino-vinyl)-1,2,3,4-tetrahydro-naphthalen-1-ylamine |
| 249. | 6-(1-Cyclopentylamino-ethyl)-1,2,3,4-tetrahydro-naphthalen-1-ylamine |
| 250. | 6-[1-(2,2-Dimethyl-propylamino)-vinyl]-1,2,3,4-tetrahydro-naphthalen-1-ylamine |
| 251. | 1-(4-Amino-chroman-7-ylmethyl)-piperidin-4-ol |
| 252. | 7-{[(Tetrahydro-furan-2-ylmethyl)-amino]-methyl}-chroman-4-ylamine |
| 253. | 3-[(4-Amino-chroman-7-ylmethyl)-amino]-2,2-dimethyl-propan-1-ol |
| 254. | 6-(4,4-Difluoro-piperidin-1-ylmethyl)-1,2,3,4-tetrahydro-naphthalen-1-ylamine |
| 255. | 5-Piperidin-1-ylmethyl-indan-1-ylamine |
| 256. | 7-Phenylaminomethyl-chroman-4-ylamine |
| 257. | (4-Amino-chroman-7-ylmethyl)-pyridin-2-yl-amine |
| 258. | 2-[(4-Amino-chroman-7-ylmethyl)-amino]-2-methyl-propan-1-ol |
| 259. | 7-[(3-Methyl-butylamino)-methyl]-chroman-4-ylamine |
| 260. | 6-[(3-Methyl-butylamino)-methyl]-1,2,3,4-tetrahydro-naphthalen-1-ylamine |
| 261. | 5-Piperidin-1-ylmethyl-indan-1-ylamine |
| 262. | 7-Cyclopropylaminomethyl-chroman-4-ylamine |
| 263. | 6-(1-Piperidin-1-yl-ethyl)-1,2,3,4-tetrahydro-naphthalen-1-ylamine |
| 264. | Methyl-(6-piperidin-1-ylmethyl-1,2,3,4-tetrahydro-naphthalen-1-yl)-amine |
| 265. | 1-(5-Amino-5,6,7,8-tetrahydro-naphthalen-2-yl)-ethanone |
| 266. | 6-(1-Piperidin-1-ylmethyl-vinyl)-1,2,3,4-tetrahydro-naphthalen-1-ylamine |
| 267. | 6-(1-Isobutylamino-ethyl)-1,2,3,4-tetrahydro-naphthalen-1-ylamine |
| 268. | 1-(4-Amino-chroman-7-ylmethyl)-piperidin-3-ol |
| 269. | 6-[(1,2,2-Trimethyl-propylamino)-methyl]-1,2,3,4-tetrahydro-naphthalen-1-ylamine |
| 270. | 7-(3,6-Dihydro-2H-pyridin-1-ylmethyl)-chroman-4-ylamine |
| 271. | 7-[(Allyl-but-3-enyl-amino)-methyl]-chroman-4-ylamine |
| 272. | 6-(1-Cyclopentylaminomethyl-vinyl)-1,2,3,4-tetrahydro-naphthalen-1-ylamine |
| 273. | 2-[(5-Amino-5,6,7,8-tetrahydro-naphthalen-2-ylmethyl)-amino]-acetamide |
| 274. | [(5-Amino-5,6,7,8-tetrahydro-naphthalen-2-ylmethyl)-amino]-acetic acid |
| 275. | 2-[(5-Amino-5,6,7,8-tetrahydro-naphthalen-2-ylmethyl)-amino]-acetamide |

TABLE 8-continued

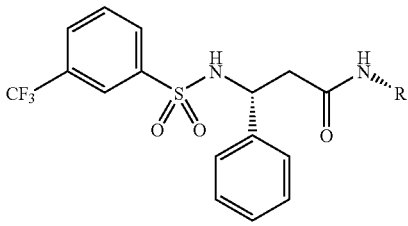

| # | R |
|---|---|
| 276. | 6-[(2-Methoxy-ethylamino)-methyl]-1,2,3,4-tetrahydro-naphthalen-1-ylamine |
| 277. | 6-[(2-Methoxy-ethylamino)-methyl]-1,2,3,4-tetrahydro-naphthalen-1-ylamine |
| 278. | 6-(1-Cyclobutylamino-ethyl)-1,2,3,4-tetrahydro-naphthalen-1-ylamine |
| 279. | 6-[1-(Cyclopropylmethyl-amino)-ethyl]-1,2,3,4-tetrahydro-naphthalen-1-ylamine |
| 280. | 1-(4-Amino-chroman-7-ylmethyl)-piperidine-3-carboxylic acid amide |
| 281. | 7-(2,5-Dihydro-pyrrol-1-ylmethyl)-chroman-4-ylamine |
| 282. | 7-Allylaminomethyl-chroman-4-ylamine |
| 283. | 6-[1-(2-Methoxy-ethylamino)-ethyl]-1,2,3,4-tetrahydro-naphthalen-1-ylamine |
| 284. | 6-(1-Cyclopropylamino-ethyl)-1,2,3,4-tetrahydro-naphthalen-1-ylamine |
| 285. | 6-[1-(2,2-Dimethyl-propylamino)-ethyl]-1,2,3,4-tetrahydro-naphthalen-1-ylamine |
| 286. | 6-(1-Isopropylamino-ethyl)-1,2,3,4-tetrahydro-naphthalen-1-ylamine |
| 287. | 6-{1-[(2-Methoxy-ethylamino)-methyl]-vinyl}-1,2,3,4-tetrahydro-naphthalen-1-ylamine |
| 288. | 2-[2-(5-Amino-5,6,7,8-tetrahydro-naphthalen-2-yl)-allylamino]-ethanol |
| 289. | 1-[2-(5-Amino-5,6,7,8-tetrahydro-naphthalen-2-yl)-allyl]-pyrrolidin-3-ol |
| 290. | 1-[2-(5-Amino-5,6,7,8-tetrahydro-naphthalen-2-yl)-allyl]-pyrrolidin-2-carboxylic acid |
| 291. | 6-[1-(Isobutylamino-methyl)-vinyl]-1,2,3,4-tetrahydro-naphthalen-1-ylamine |
| 292. | 6-[1-(Isopropylamino-methyl)-vinyl]-1,2,3,4-tetrahydro-naphthalen-1-ylamine |
| 293. | 6-{1-[(Cyclopropylmethyl-amino)-methyl]-vinyl}-1,2,3,4-tetrahydro-naphthalen-1-ylamine |
| 294. | 1-[2-(5-Amino-5,6,7,8-tetrahydro-naphthalen-2-yl)-allyl]-poyrrolidin-2-carboxylic acid methyl ester |
| 295. | 6-(1-Pyrrolidin-1-ylmethyl-vinyl)-1,2,3,4-tetrahydro-naphthalen-1-ylamine |
| 296. | 6-[(2,2-Dimethyl-propylamino)-methyl]-1,2,3,4-tetrahydro-naphthalen-1-ylamine |
| 297. | 6-(3,3-Dimethyl-piperidin-1-ylmethyl)-1,2,3,4-tetrahydro-naphthalen-1-ylamine |
| 298. | 1-(5-Amino-5,6,7,8-tetrahydro-naphthalen-2-ylmethyl)-3-methyl-piperidin-3-ol |
| 299. | 7-[(2-Methoxy-ethylamino)-methyl]-chroman-4-ylamine |
| 300. | 6-[(2-Methyl-butylamino)-methyl]-1,2,3,4-tetrahydro-naphthalen-1-ylamine |
| 301. | 7-[(2-Methyl-butylamino)-methyl]-chroman-4-ylamine |
| 302. | 7-[(2,2,2-Trifluoro-ethylamino)-methyl]-chroman-4-ylamine |
| 303. | 6-(1-Piperidin-1-ylmethyl-vinyl)-1,2,3,4-tetrahydro-naphthalen-1-ylamine |
| 304. | 7-Cyclopentylaminomethyl-chroman-4-ylamine |
| 305. | 6-(7-Aza-bicyclo[2.2.1]hept-7-ylmethyl)-1,2,3,4-tetrahydro-naphthalen-1-ylamine |

The following compounds were prepared using essentially as described above.

EXAMPLE 166

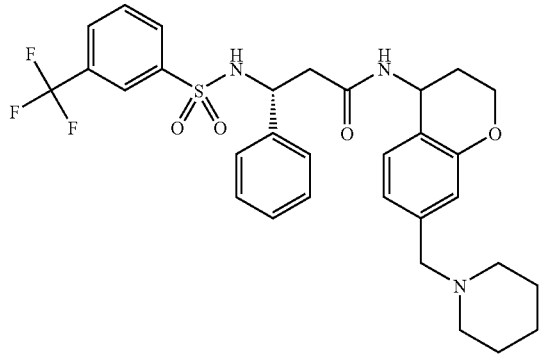

(3R)-3-Phenyl-N-((4R)-7-(1-piperidinylmethyl)-3,4-dihydro-2H-chromen-4-yl)-3-(((3-(trifluoromethyl)phenyl)sulfonyl)amino)propanamide

EXAMPLE 167

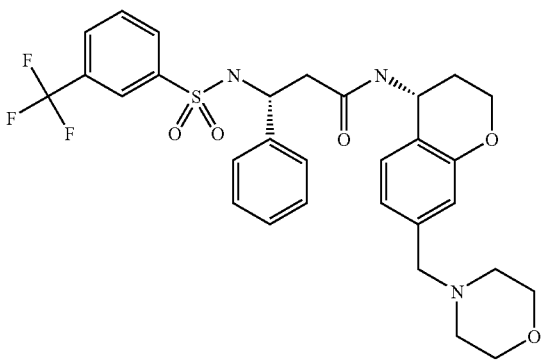

(3R)-N-((4R)-7-(4-Morpholinylmethyl)-3,4-dihydro-2H-chromen-4-yl)-3-phenyl-3-(((3-(trifluoromethyl)phenyl)sulfonyl)amino)propanamide

EXAMPLE 168

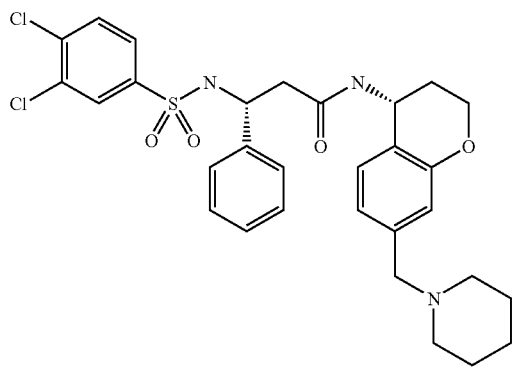

(3R)-3-(((3,4-Dichlorophenyl)sulfonyl)amino)-3-phenyl-N-((4R)-7-(1-piperidinylmethyl)-3,4-dihydro-2H-chromen-4-yl)propanamide

267

EXAMPLE 169

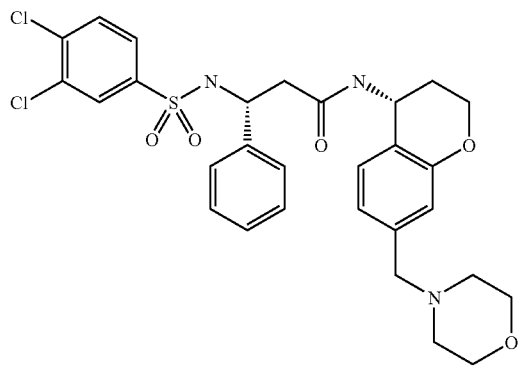

(3R)-3-(((3,4-Dichlorophenyl)sulfonyl)amino)-N-
((4R)-7-(4-morpholinylmethyl)-3,4-dihydro-2H-
chromen-4-yl)-3-phenylpropanamide

EXAMPLE 170

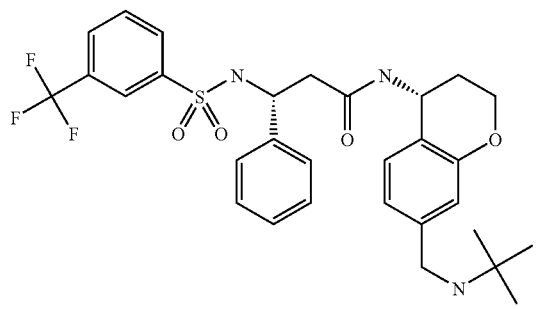

(3R)-N-((4R)-7-(((1,1-Dimethylethyl)amino)me-
thyl)-3,4-dihydro-2H-chromen-4-yl)-3-phenyl-3-
(((3-(trifluoromethyl)phenyl)sulfonyl)amino)pro-
panamide

EXAMPLE 171

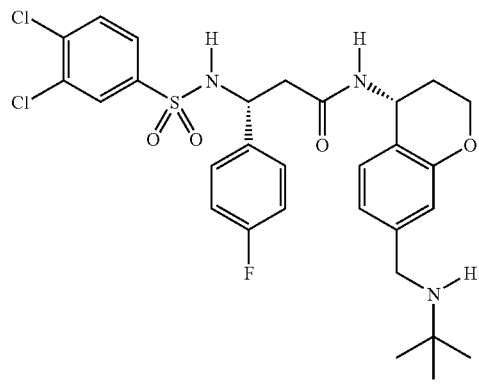

(3R)-3-(((3,4-Dichlorophenyl)sulfonyl)amino)-N-
((4R)-7-(((1,1-dimethylethyl)amino)methyl)-3,4-
dihydro-2H-chromen-4-yl)-3-phenylpropanamide

268

EXAMPLE 172

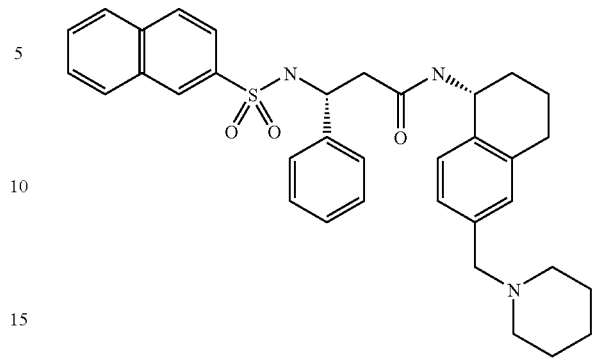

(3R)-3-((2-Naphthalenylsulfonyl)amino)-3-phenyl-
N-((1R)-6-(1-piperidinylmethyl)-1,2,3,4-tetrahydro-
1-naphthalenyl)propanamide

EXAMPLE 173

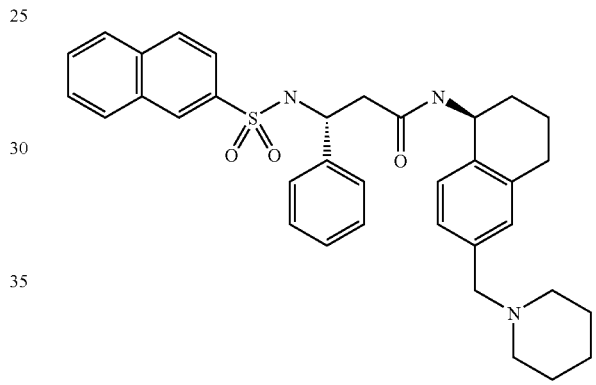

(3R)-3-((2-Naphthalenylsulfonyl)amino)-3-phenyl-
N-((1S)-6-(1-piperidinylmethyl)-1,2,3,4-tetrahydro-
1-naphthalenyl)propanamide

EXAMPLE 174

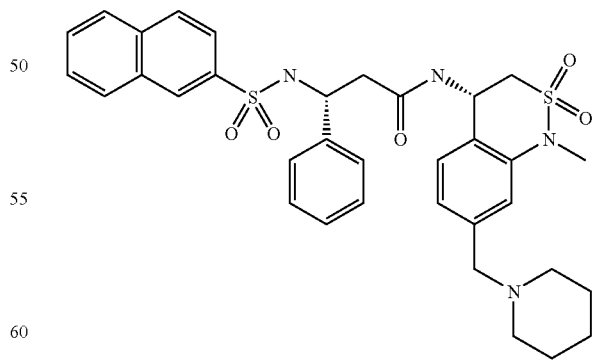

(3R)-N-((4S)-1-Methyl-2,2-dioxido-7-(1-piperidinyl-
methyl)-3,4-dihydro-1H-2,1-benzothiazin-4-yl)-3-
((2-naphthalenylsulfonyl)amino)-3-phenylpropana-
mide

EXAMPLE 175

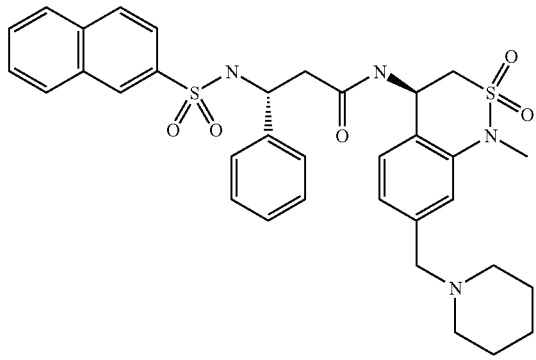

(3R)-N-((4R)-1-Methyl-2,2-dioxido-7-(1-piperidinylmethyl)-3,4-dihydro-1H-2,1-benzothiazin-4-yl)-3-((2-naphthalenylsulfonyl)amino)-3-phenylpropanamide

EXAMPLE 176

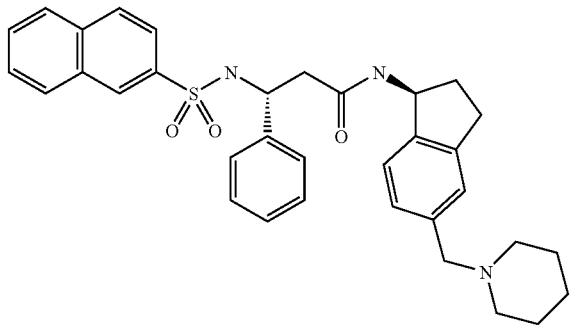

(3R)-3-((2-Naphthalenylsulfonyl)amino)-3-phenyl-N-((1S)-5-(1-piperidinylmethyl)-2,3-dihydro-1H-inden-1-yl)propanamide

EXAMPLE 177

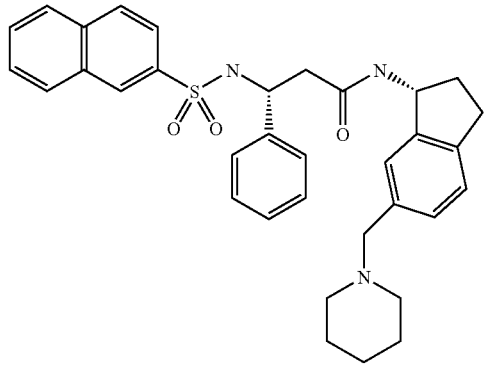

(3R)-3-((2-Naphthalenylsulfonyl)amino)-3-phenyl-N-((1R)-6-(1-piperidinylmethyl)-2,3-dihydro-1H-inden-1-yl)propanamide

EXAMPLE 178

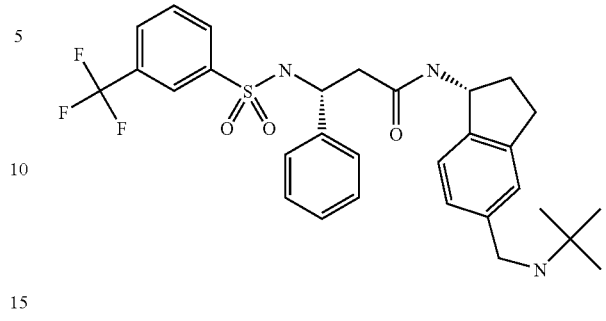

(3R)-N-((1R)-5-(((1,1-Dimethylethyl)amino)methyl)-2,3-dihydro-1H-inden-1-yl)-3-phenyl-3-(((3-(trifluoromethyl)phenyl)sulfonyl)amino)propanamide

EXAMPLE 179

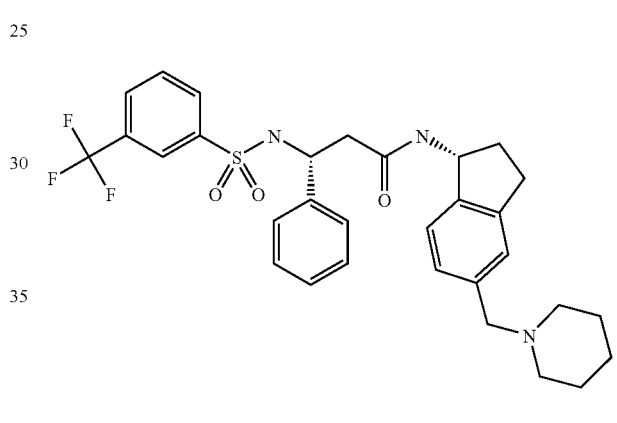

(3R)-3-Phenyl-N-((1R)-5-(1-piperidinylmethyl)-2,3-dihydro-1H-inden-1-yl)-3-(((3-(trifluoromethyl)phenyl)sulfonyl)amino)propanamide

EXAMPLE 180

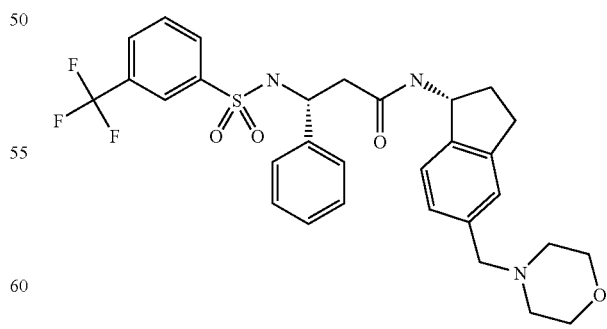

(3R)-N-((1R)-5-(4-Morpholinylmethyl)-2,3-dihydro-1H-inden-1-yl)-3-phenyl-3-(((3-(trifluoromethyl)phenyl)sulfonyl)amino)propanamide

EXAMPLE 181

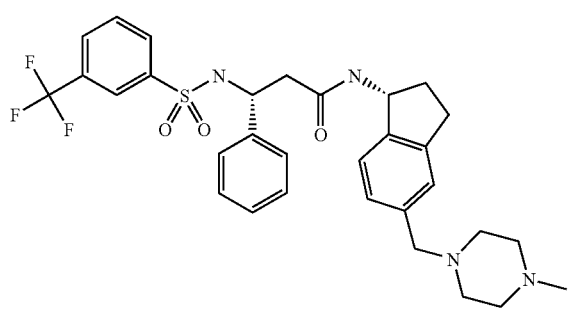

(3R)-N-((1R)-5-((4-Methyl-1-piperazinyl)methyl)-2,
3-dihydro-1H-inden-1-yl)-3-phenyl-3-(((3-(trifluo-
romethyl)phenyl)sulfonyl)amino)propanamide

EXAMPLE 182

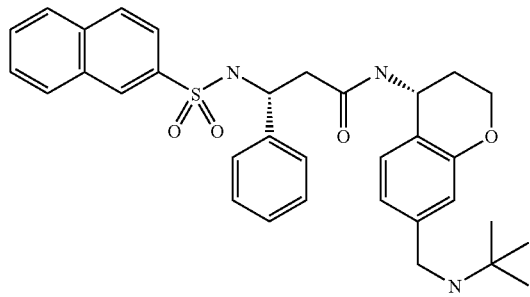

(3R)-N-((4R)-7-(((1,1-Dimethylethyl)amino)me-
thyl)-3,4-dihydro-2H-chromen-4-yl)-3-((2-naphtha-
lenylsulfonyl)amino)-3-phenylpropanamide

EXAMPLE 183

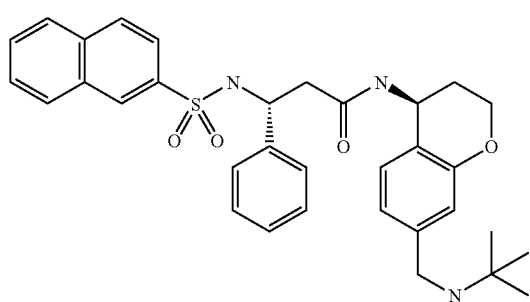

(3R)-N-((4S)-7-(((1,1-dimethylethyl)amino)methyl)-
3,4-dihydro-2H-chromen-4-yl)-3-((2-naphthalenyl-
sulfonyl)amino)-3-phenylpropanamide

EXAMPLE 184

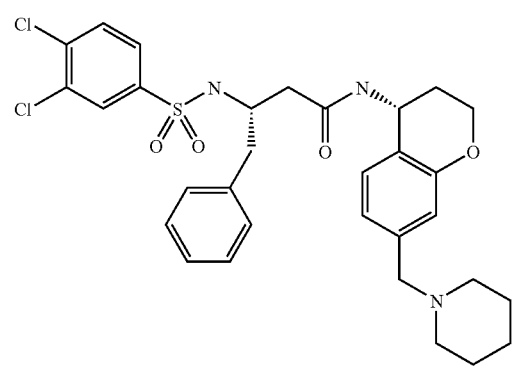

(3S)-3-(((3,4-Dichlorophenyl)sulfonyl)amino)-4-
phenyl-N-((4R)-7-(1-piperidinylmethyl)-3,4-dihy-
dro-2H-chromen-4-yl)butanamide

EXAMPLE 185

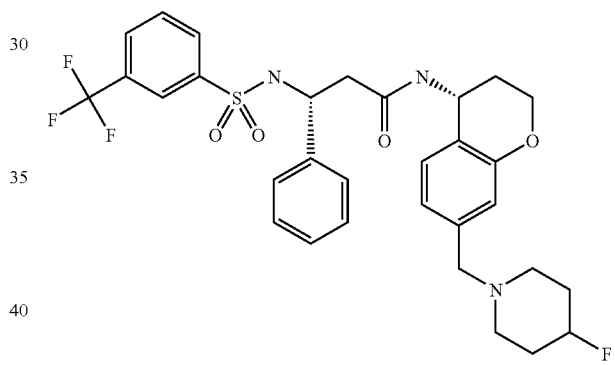

(3R)-N-((4R)-7-((4-Fluoro-1-piperidinyl)methyl)-3,
4-dihydro-2H-chromen-4-yl)-3-phenyl-3-(((3-(trif-
luoromethyl)phenyl)sulfonyl)amino)propanamide

EXAMPLE 186

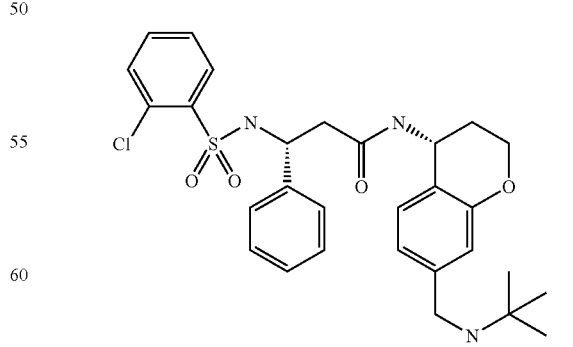

(3R)-3-(((2-Chlorophenyl)sulfonyl)amino)-N-((4R)-
7-(((1,1-dimethylethyl)amino)methyl)-3,4-dihydro-
2H-chromen-4-yl)-3-phenylpropanamide

EXAMPLE 187

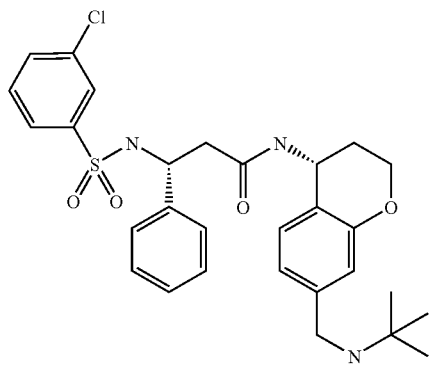

(3R)-3-(((3-Chlorophenyl)sulfonyl)amino)-N-((4R)-7-(((1,1-dimethylethyl)amino)methyl)-3,4-dihydro-2H-chromen-4-yl)-3-phenylpropanamide

EXAMPLE 188

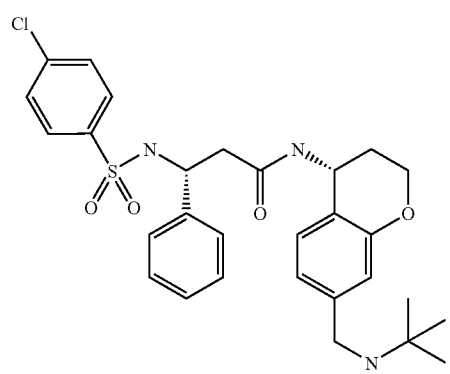

(3R)-3-(((4-Chlorophenyl)sulfonyl)amino)-N-((4R)-7-(((1,1-dimethylethyl)amino)methyl)-3,4-dihydro-2H-chromen-4-yl)-3-phenylpropanamide

EXAMPLE 189

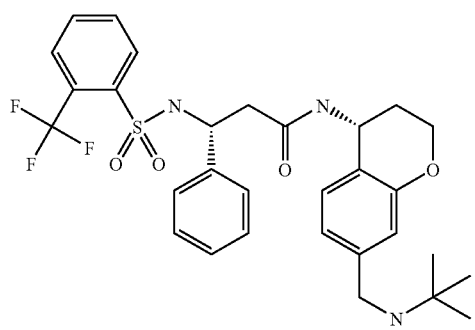

(3R)-N-((4R)-7-(((1,1-Dimethylethyl)amino)methyl)-3,4-dihydro-2H-chromen-4-yl)-3-phenyl-3-(((2-(trifluoromethyl)phenyl)sulfonyl)amino)propanamide

EXAMPLE 190

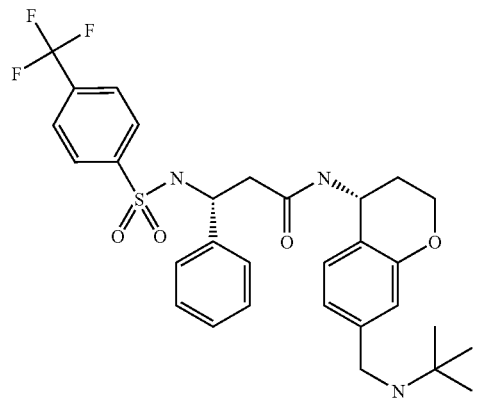

(3R)-N-((4R)-7-(((1,1-Dimethylethyl)amino)methyl)-3,4-dihydro-2H-chromen-4-yl)-3-phenyl-3-(((4-(trifluoromethyl)phenyl)sulfonyl)amino)propanamide

EXAMPLE 191

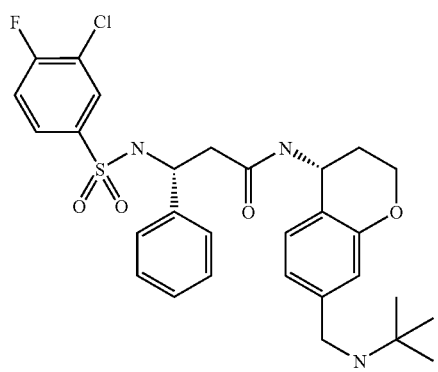

(3R)-3-(((3-Chloro-4-fluorophenyl)sulfonyl)amino)-N-((4R)-7-(((1,1-dimethylethyl)amino)methyl)-3,4-dihydro-2H-chromen-4-yl)-3-phenylpropanamide

EXAMPLE 192

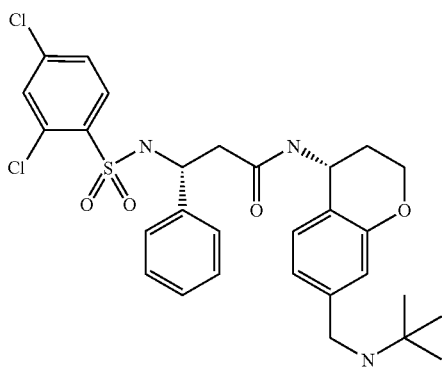

(3R)-3-(((2,4-Dichlorophenyl)sulfonyl)amino)-N-((4R)-7-(((1,1-dimethylethyl)amino)methyl)-3,4-dihydro-2H-chromen-4-yl)-3-phenylpropanamide

EXAMPLE 193

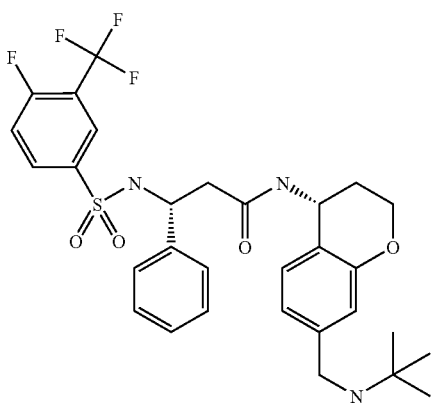

(3R)-N-((4R)-7-(((1,1-Dimethylethyl)amino)methyl)-3,4-dihydro-2H-chromen-4-yl)-3-(((4-fluoro-3-(trifluoromethyl)phenyl)sulfonyl)amino)-3-phenyl-propanamide

EXAMPLE 194

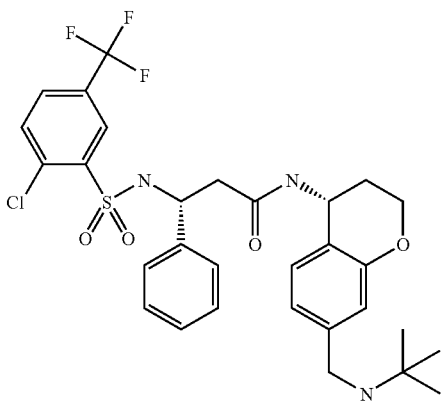

(3R)-3-(((2-Chloro-5-(trifluoromethyl)phenyl)sulfonyl)amino)-N-((4R)-7-(((1,1-dimethylethyl)amino)methyl)-3,4-dihydro-2H-chromen-4-yl)-3-phenylpropanamide

EXAMPLE 195

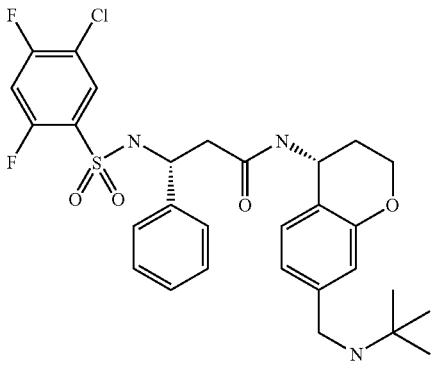

(3R)-3-(((5-Chloro-2,4-difluorophenyl)sulfonyl)amino)-N-((4R)-7-(((1,1-dimethylethyl)amino)methyl)-3,4-dihydro-2H-chromen-4-yl)-3-phenylpropanamide

EXAMPLE 196

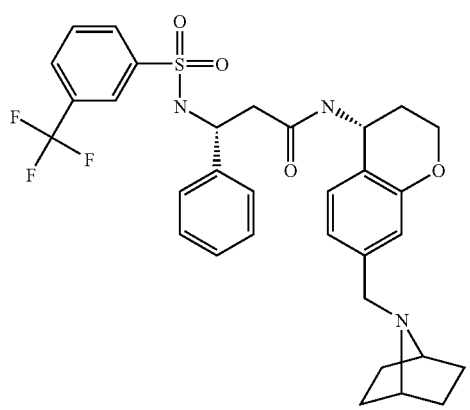

(3R)-N-((4R)-7-(7-Azabicyclo[2.2.1]hept-7-ylmethyl)-3,4-dihydro-2H-chromen-4-yl)-3-phenyl-3-(((3-(trifluoromethyl)phenyl)sulfonyl)amino)propanamide

EXAMPLE 197

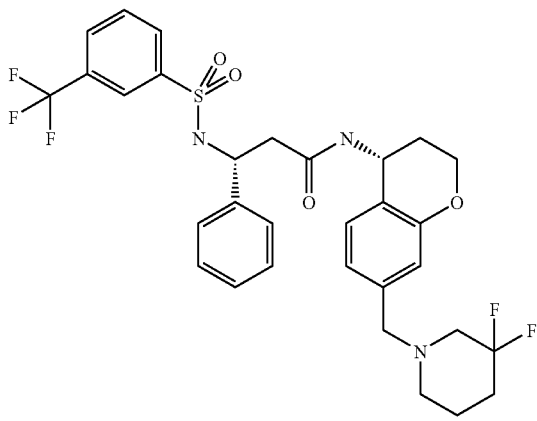

(3R)-N-((4R)-7-((3,3-Difluoro-1-piperidinyl)methyl)-3,4-dihydro-2H-chromen-4-yl)-3-phenyl-3-(((3-(trifluoromethyl)phenyl)sulfonyl)amino)propanamide

EXAMPLE 198

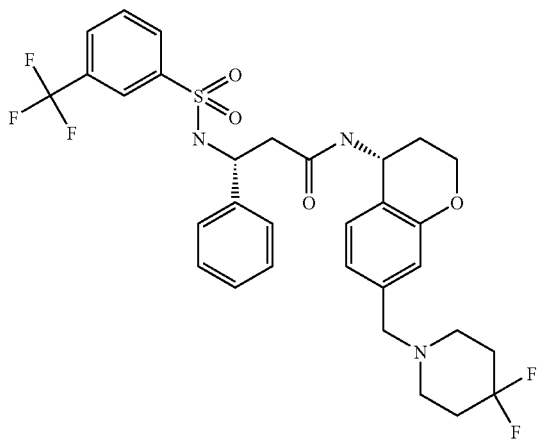

(3R)-N-((4R)-7-((4,4-Difluoro-1-piperidinyl)methyl)-3,4-dihydro-2H-chromen-4-yl)-3-phenyl-3-(((3-(trifluoromethyl)phenyl)sulfonyl)amino)propanamide

EXAMPLE 199

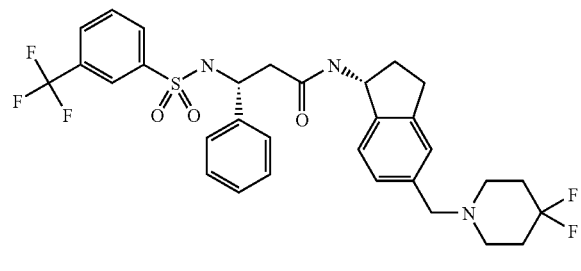

(3R)-N-((1R)-5-((4,4-Difluoro-1-piperidinyl)methyl)-2,3-dihydro-1H-inden-1-yl)-3-phenyl-3-(((3-(trifluoromethyl)phenyl)sulfonyl)amino)propanamide

EXAMPLE 200

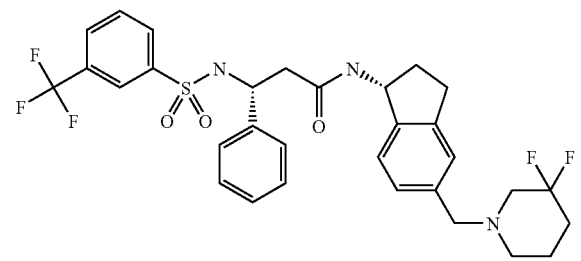

(3R)-N-((1R)-5-((3,3-Difluoro-1-piperidinyl)methyl)-2,3-dihydro-1H-inden-1-yl)-3-phenyl-3-(((3-(trifluoromethyl)phenyl)sulfonyl)amino)propanamide

EXAMPLE 201

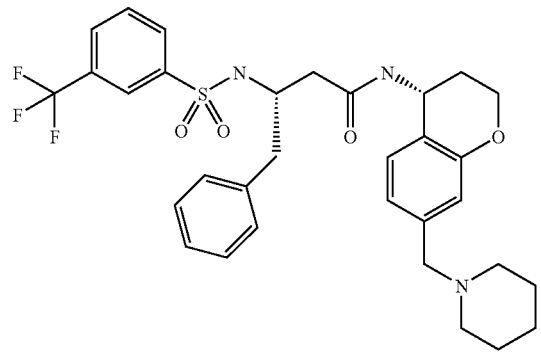

(3S)-4-Phenyl-N-((4R)-7-(1-piperidinylmethyl)-3,4-dihydro-2H-chromen-4-yl)-3-(((3-(trifluoromethyl)phenyl)sulfonyl)amino)butanamide

EXAMPLE 202

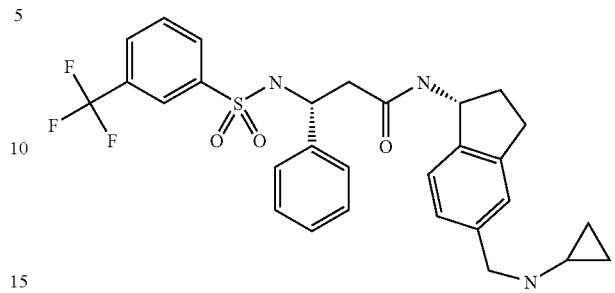

(3R)-N-((1R)-5-(((Cyclopropylamino)methyl)-2,3-dihydro-1H-inden-1-yl)-3-phenyl-3-(((3-(trifluoromethyl)phenyl)sulfonyl)amino)propanamide

EXAMPLE 203

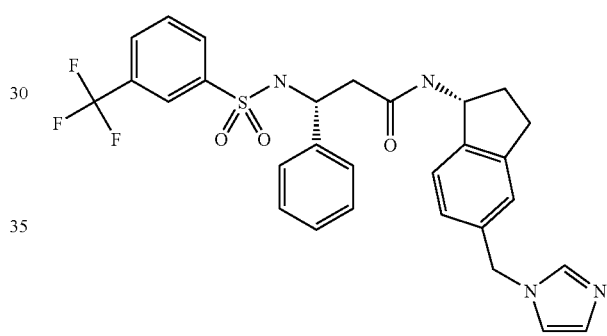

(3R)-N-((1R)-5-(1H-imidazol-1-ylmethyl)-2,3-dihydro-1H-inden-1-yl)-3-phenyl-3-(((3-(trifluoromethyl)phenyl)sulfonyl)amino)propanamide

EXAMPLE 204

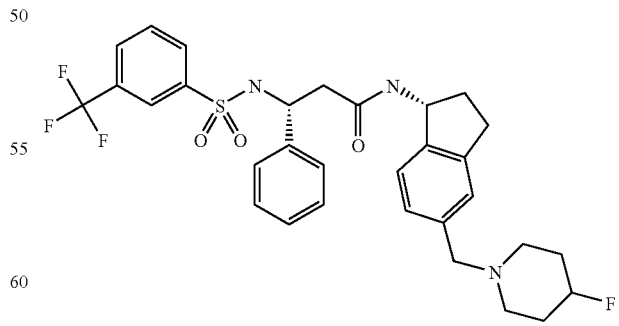

(3R)-N-((1R)-5-((4-Fluoro-1-piperidinyl)methyl)-2,3-dihydro-1H-inden-1-yl)-3-phenyl-3-(((3-(trifluoromethyl)phenyl)sulfonyl)amino)propanamide

EXAMPLE 205

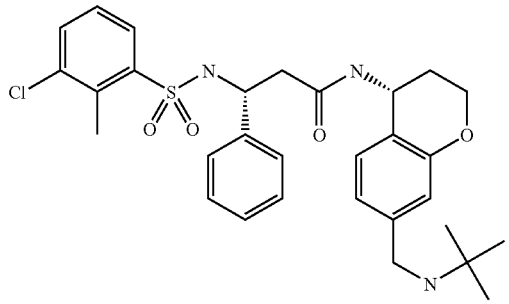

(3R)-3-(((3-Chloro-2-methylphenyl)sulfonyl)
amino)-N-((4R)-7-(((1,1-dimethylethyl)amino)me-
thyl)-3,4-dihydro-2H-chromen-4-yl)-3-phenylpro-
panamide

EXAMPLE 206

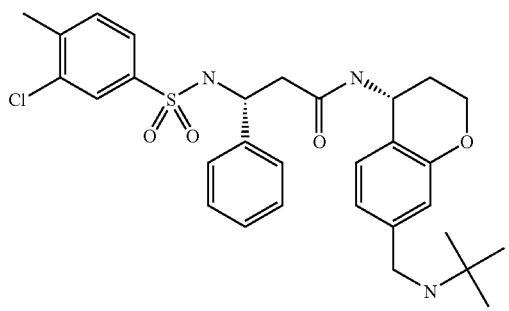

(3R)-3-(((3-Chloro-4-methylphenyl)sulfonyl)
amino)-N-((4R)-7-(((1,1-dimethylethyl)amino)me-
thyl)-3,4-dihydro-2H-chromen-4-yl)-3-phenylpro-
panamide

EXAMPLE 207

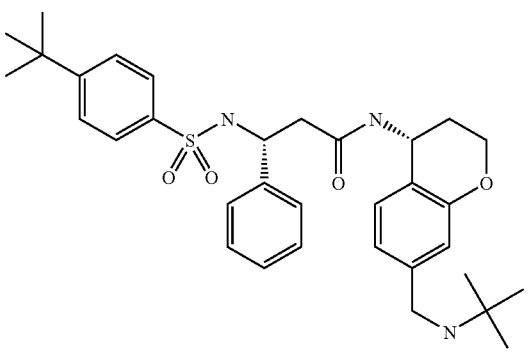

(3R)-N-((4R)-7-(((1,1-Dimethylethyl)amino)me-
thyl)-3,4-dihydro-2H-chromen-4-yl)-3-(((4-(1,1-
dimethylethyl)phenyl)sulfonyl)amino)-3-phenylpro-
panamide

EXAMPLE 208

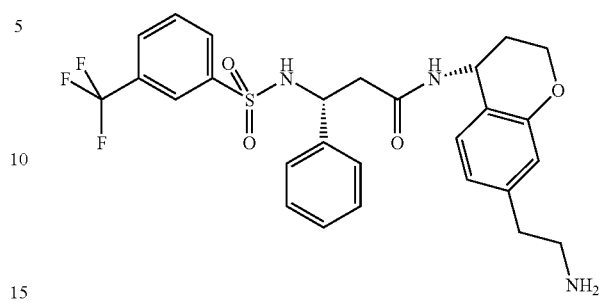

N-[7-(2-Aminoethyl)-chroman-4-yl]-3-phenyl-3-(3-
trifluoromethylbenzenesulfonylamino)-propionamide Step A. Preparation of
(4-amino-chroman-7-yl)-acetonitrile.

To a 125 mL flame dry 3-neck round bottom flask was added P(Ph)$_3$ (4.4 g, 16.74 mmol) and THF (50 mL). After cooling to −20° C., DEAD (3.3 mL, 16.74 mmol) was added dropwise via the addition funnel. After stirring for 20 min at −20° C., (4-aminochroman-7-yl)-methanol (2.0 g, 11.16 mmol) in THF (75 mL) was added dropwise via the addition funnel. It was stirred for another 30 min. acetone cyanohydrin (3.1 mL, 33.48 mmol) was then added dropwise via the addition funnel. The resulting mixture was warmed to RT and stirred for 18 h. Solvent was evaporated in vacuo. The residue was purified by chromatography on silica gel. Elution with CH$_2$Cl$_2$:MeOH mixture (95:5) gave final compound. MS m/z: 189.12 (M+H). Calc'd. for C$_{11}$H$_{12}$N$_2$O-188.23.

Step B. Preparation of N-(7-cyanomethyl-chroman-
4-yl)-3-phenyl-3-(3-trifluoromethyl-benzenesulfony-
lamino)-propionamide To a solution of (4-amino-chroman-7-yl)-acetonitrile (Step A, 400 mg, 2.15 mmol) in CH$_2$Cl$_2$ (15 mL) was added 3-phe-nyl-3-(3-trifluoromethyl-benzenesulfonylamino)-propionic acid (802 mg, 2.15 mmol), HATU (408 mg, 1.07 mmol), EDC (453 mg, 2.36 mmol), and DIEA (0.7 mL, 4.29 mmol). The resulting mixture was stirred at RT for 18 h. Solvent was evaporated in vacuo. The residue was purified by chromatography on silica gel. Elution with CH$_2$Cl$_2$:MeOH mixture (95:5) gave final compound. MS m/z: 544.12 (M+H). Calc'd. for C$_{27}$H$_{24}$F$_3$N$_3$O$_4$S-543.56.

Step C. Preparation of N-[7-(2-amino-ethyl)-chro-
man-4-yl]-3-phenyl-3-(3-trifluoromethyl-benzene-
sulfonylamino)-propionamide To a solution of N-(7-cyanomethyl-chroman-4-yl)-3-phe-nyl-3-(3-trifluoromethyl-benzenesulfonylamino)-propiona-mide (790 mg, 1.45 mmol) in MeOH (20 mL) in the Parr-bottle was added Pd/C (80 mg) while flushed under N$_2$. The reaction mixture bottle was placed in Parr-shaker. The H$_2$ was filled up the bottle then released-this was done 3 times. After last release, the fresh H$_2$ (50 psi) was then filled up the bottle. The reaction was under hydrogenation for 18 h. Solvent was separated from the Pd/C by passing through the Celite®. Solvent was evaporated in vacuo to give the final product. MS m/z: 548.12 (M+H). Calc'd. for C$_{27}$H$_{28}$F$_3$N$_3$O$_4$S-547.06.

The following compound, 208a, was prepared similar to the method described in Example 208.

| # | Structure | formula | MW | M + H |
|---|-----------|---------|-----|-------|
| 208a | (3R)-N-((4R)-7-(2-aminoethyl)-3,4-dihydro-2H-chromen-4-yl)-3-phenyl-3-(((3-(trifluoromethyl)-phenyl)sulfonyl)amino)-propanamide | C27 H28 F3 N3 O4 S | 547.595 | 548 |

EXAMPLE 209

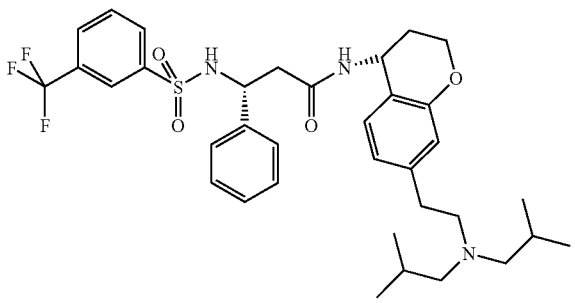

N-[7-(2-Di-isobutylamino-ethyl)-chroman-4-yl]-3-phenyl-3-(3-trifluoromethylbenzenesulfonylamino)-propionamide To a solution of N-[7-(2-aminoethyl)-chroman-4-yl]-3-phenyl-3-(3-trifluoromethylbenzenesulfonylamino)-propionamide (Example 208, 50 mg, 0.09 mmol) in dry $CH_2Cl_2$ (8 mL) was added isobutyraldehyde (83 L, 0.9 mmol) and HOAc (1 drop). The resulting mixture was stirred at RT under $N_2$ After 3 h, MS showed the formation of imine; $NaBH_4$ (17 mg, 0.45 mmol) was then added. The resulting mixture was stirred for 18 h. Quenched with minimum amount of sat. $NaHCO_3$. The organic layer was isolated, dried over $MgSO_4$ and evaporated in vacuo. The crude product was purified by chromatography on silica gel. Elution with $CH_2Cl_2$:MeOH mixture (97:3) gave final compound. MS m/z: 660.31 (M+H). Calc'd. for Calc'd. for $C_{35}H_{44}F_3N_3O_4S$-659.82.

The following compounds (#209 a-i) were prepared similar to the method described in Example 209.

| # | Structure | formula | MW | M + H |
|---|-----------|---------|-----|-------|
| A | (3R)-N-((4R)-7-(2-(bis(2-methylpropyl)amino)ethyl)-3,4-dihydro-2H-chromen-4-yl)-3-phenyl-3-(((3-(trifluoromethyl)phenyl)sulfonyl)amino)propanamide | C35 H44 F3 N3 O4 S | 659.81 | 660 |

-continued

| # | Structure | formula | MW | M + H |
|---|---|---|---|---|
| b | 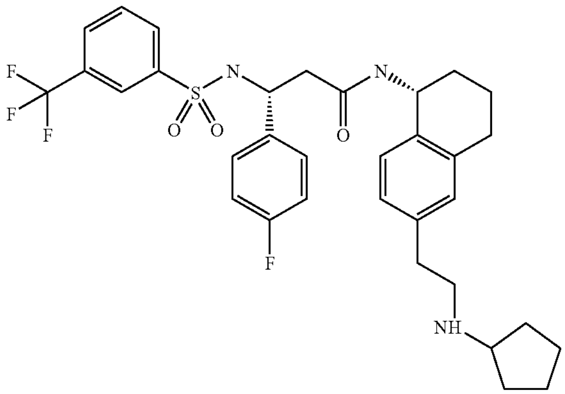 | C33 H37 F4 N3 O3 S | 631.731 | 632 |

(3R)-N-((1R)-6-(2-(cyclopentylamino)ethyl)-1,2,3,4-tetrahydro-1-naphthalenyl)-
3-(4-fluorophenyl)-3-(((3-(trifluoromethyl)phenyl)sulfonyl)amino)propanamide

| c | | C32 H35 F4 N3 O3 S | 617.705 | 618 |

(3R)-N-((1R)-6-(2-(cyclobutylamino)ethyl)-1,2,3,4-tetrahydro-1-naphthalenyl)-3-
(4-fluorophenyl)-3-(((3-(trifluoromethyl)phenyl)sulfonyl)amino)propanamide

| d | | C32 H37 F4 N3 O3 S | 619.72 | 619 |

(3R)-3-(4-fluorophenyl)-N-((1R)-6-(2-((2-methylpropyl)amino)ethyl)-1,2,3,4-
tetrahydro-1-naphthalenyl)-3-(((3-(trifluoromethyl)phenyl)sulfonyl)amino)
propanamide -continued

| # | Structure | formula | MW | M + H |
|---|---|---|---|---|
| E | 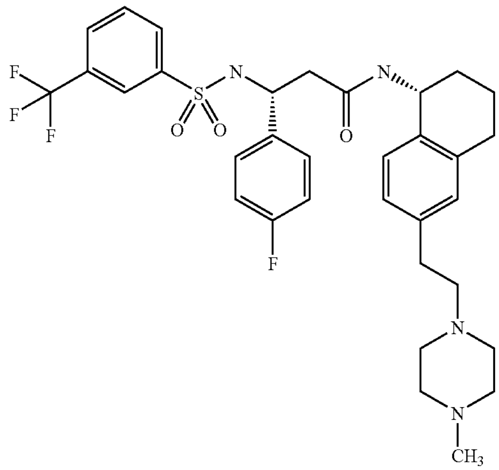 | C33 H38 F4 N4 O3 S | 646.746 | 647 |

(3R)-3-(4-fluorophenyl)-N-((1R)-6-(2-(4-methyl-1-piperazinyl)ethyl)-1,2,3,4-tetrahydro-1-naphthalenyl)-3-(((3-(trifluoromethyl)phenyl)sulfonyl)amino)propanamide

| F | | C32 H35 F4 N3 O3 S | 617.705 | 618 |

(3R)-3-(4-fluorophenyl)-N-((1R)-6-(2-(1-pyrrolidinyl)ethyl)-1,2,3,4-tetrahydro-1-naphthalenyl)-3-(((3-(trifluoromethyl)phenyl)sulfonyl)amino)propanamide

| g | | C32 H35 F4 N3 O4 S | 633.703 | 634 |

(3R)-3-(4-fluorophenyl)-N-((1R)-6-(2-(4-morpholinyl)ethyl)-1,2,3,4-tetrahydro-1-naphthalenyl)-3-(((3-(trifluoromethyl)phenyl)sulfonyl)amino)propanamide -continued

| # | Structure | formula | MW | M + H |
|---|---|---|---|---|
| h | 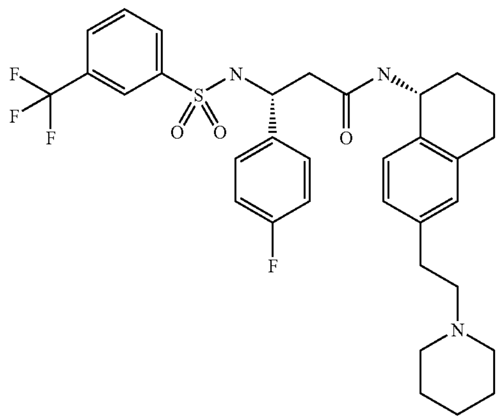 | C33 H37 F4 N3 O3 S | 631.731 | 632 |

(3R)-3-(4-fluorophenyl)-N-((1R)-6-(2-(1-piperidinyl)ethyl)-1,2,3,4-tetrahydro-1-naphthalenyl)-3-(((3-(trifluoromethyl)phenyl)sulfonyl)amino)propanamide

| i | | C33 H36 F5 N3 O3 S | 649.721 | 650 |

(3R)-3-(4-fluorophenyl)-N-((1R)-6-(2-(4-fluoro-1-piperidinyl)ethyl)-1,2,3,4-tetrahydro-1-naphthalenyl)-3-(((3-(trifluoromethyl)phenyl)sulfonyl)amino)propanamide

EXAMPLE 210

N-[6-(3-Amino-propyl)-1,2,3,4-tetrahydro-naphthalen-1-yl]-3-(3,4-dichloro-benzenesulfonylamino)-3-(4-fluoro-phenyl)-

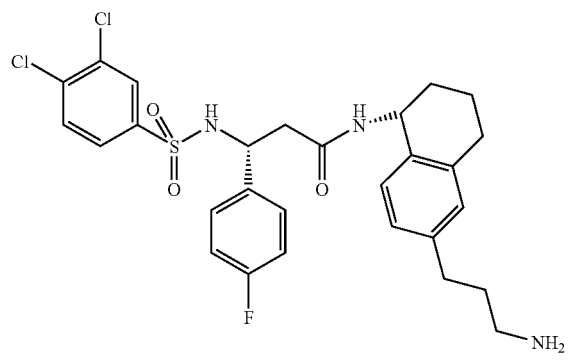

step A. Preparation of (6-Hydroxymethyl-1,2,3,4-tetrahydro-naphthalen-1-yl)-carbamic acid tert-butyl Ester To a solution of (5-amino-5,6,7,8-tetrahydro-naphthalen-2-yl)-methanol (2.0 g, 11.28 mmol) in CH$_2$Cl$_2$ (20 mL) was added (BOC)$_2$O (2.7 g, 12.41 mmol). The resulting mixture was stirred at RT under N$_2$ gas for 2 h. Reaction mixture was quenched with sat. NH$_4$Cl, the organic layer was isolated and washed with water, brine, dried over MgSO$_4$ and evaporated in vacuo to give the final product. MS m/z: 278.12 (M+H). Calc'd. for C$_{16}$H$_{23}$NO$_3$-277.36.

Step B. Preparation of (6-formyl-1,2,3,4-tetrahydro-naphthalen-1-yl)-carbamic acid tert-butyl Ester To a solution of (6-hydroxymethyl-1,2,3,4-tetrahydro-naphthalen-1-yl)-carbamic acid tert-butyl ester (3.1 g, 11.18 mmol) in $CH_2Cl_2$ (30 mL) was added $MnO_2$ (4.85 g, 55.9 mmol). The resulting mixture was stirred at RT under $N_2$ gas for 18 h. Solvent was separated from $MnO_2$ by passing through the Celite®. Solvent was evaporated in vacuo to give the final product. MS m/z: 276.5 (M+H). Calc'd. for $C_{16}H_{21}NO_3$-275.34.

Step C. Preparation of [6-(2-cyano-vinyl)-1,2,3,4-tetrahydro-naphthalen-1-yl]-carbamic acid tert-butyl Ester To a solution of diethyl cyanophosphate (6.62 g, 37.36 mmol) in dry THF (25 mL) at 0° C. was added sodium bis(trimethylsilyl)amide (32 mL, 32.03 mmol) dropwise via the addition funnel. The temp. was kept between 0° C. to 5° C. for 30 min. The resulting mixture was then cooled to −78° C. followed by adding (6-formyl-1,2,3,4-tetrahydro-naphthalen-1-yl)-carbamic acid tert-butyl ester (2.94 g, 10.67 mmol) in THF (40 mL) dropwise via the addition funnel. After the addition, it was stirred for 18 h and slowly warmed to RT. The reaction mixture was quenched with sat. $NH_4Cl$. Solvent was removed. The residue was partitioned between EtOAc and water. The organic layer was washed with water, brine, dried over $MgSO_4$ and evaporated in vacuo. The crude product was purified by chromatography on silica gel. Elution with Hex:EtOAc mixture (85:15) gave final compound MS m/z: 299.12 (M+H). Calc'd. for $C_{18}H_{22}N_2O_2$-298.38.

Step D. Preparation of 3-(5-amino-5,6,7,8-tetrahydro-naphthalen-2-yl)-acrylonitrile To a solution of [6-(2-cyano-vinyl)-1,2,3,4-tetrahydro-naphthalen-1-yl]-carbamic acid tert-butyl ester (2.7 g, 9.05 mmol) in DCM (40 mL) was added TFA (15 mL). The resulting mixture was stirred at RT for 1 h. Solvent was removed. The residue was redissolved in EtOAc. The organic layer was washed with sat. $NaHCO_3$, $H_2O$, brine, dried over $MgSO_4$ and removed solvent. The crude product was purified by chromatography on silica gel. Elution with $CH_2Cl_2$:MeOH (2M $NH_3$) mixture (97:3) gave final compound (1.6 g, 89%). MS m/z: 199.3 (M+H). Calc'd. for $C_{13}H_{14}N_2$-198.26.

Step E. Preparation of N-[6-(2-Cyano-vinyl)-1,2,3,4-tetrahydro-naphthalen-1-yl]-3-(3,4-dichloro-benzenesulfonylamino)-3-(4-fluoro-phenyl)-propionamide To a solution of 3-(5-amino-5,6,7,8-tetrahydro-naphthalen-2-yl)-acrylonitrile (100 mg, 0.504 mmol) in $CH_2Cl_2$ (10 mL) was added 3-(3,4-dichlorobenzene-sulfonylamino)-3-(4-fluoro-phenyl)-propionic acid (210 mg, 0.554 mmol), HATU (96 mg, 0.252 mmol), EDC (106 mg, 0.55 mmol), and DIEA (0.17 mL, 1.008 mmol). The resulting mixture was stirred at RT for 18 h. Solvent was evaporated in vacuo. The residue was purified by chromatography on silica gel. Elution with Hex:Acetone mixture (75:25) gave final compound. MS m/z: 573.12 (M+H). Calc'd. for $C_{28}H_{24}Cl_2FN_3O_3S$-572.48.

Step F. Preparation of N-[6-(3-aminopropyl)-1,2,3,4-tetrahydro-naphthalen-1-yl]-3-(3,4-dichlorobenzene-sulfonylamino)-3-(4-fluoro-phenyl)-propionamide To a solution of N-[6-(2-Cyano-vinyl)-1,2,3,4-tetrahydro-naphthalen-1-yl]-3-(3,4-dichloro-benzenesulfonylamino)-3-(4-fluoro-phenyl)-propionamide (150 mg, 0.26 mmol) in EtOH:$CHCl_3$ mixture (75:25, 10 mL) was added $PtO_2$ (18 mg, 0.078 mmol). The resulting mixture was flushed under $N_2$ gas followed by evacuating—this was done 3 times. After last evacuation, the hydrogen balloon was inserted. The reaction mixture was stirred under $H_2$ at RT for 2 h. Solvent was separated from the $PtO_2$ by passing through the Celite®. Solvent was evaporated in vacuo to give the final product. MS m/z: 579.11 (M+H). Calc'd. for $C_{28}H_{30}Cl_2FN_3O_3S$-578.53.

The following compounds (#210 a-b) were prepared similar to the method described in Example 210.

| # | Structure | formula | MW | M+H |
|---|---|---|---|---|
| a | 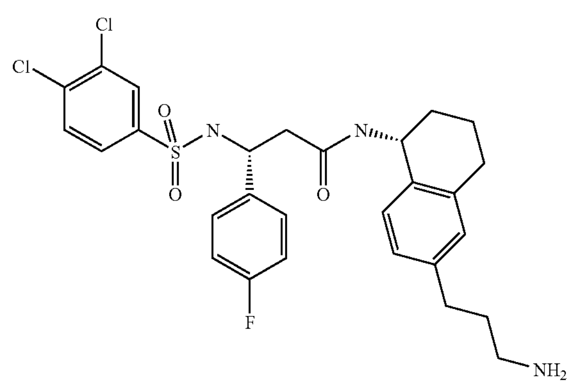 | C28 H30 Cl2 F N3 O3S | 578.533 | 579 |

(3R)-N-((1R)-6-(3-aminopropyl)-1,2,3,4-tetrahydro-1-naphthalenyl)-3-(((3,4-dichlorophenyl)sulfonyl)amino)-3-(4-fluorophenyl)propanamide

| # | Structure | formula | MW | M+H |
|---|---|---|---|---|
| b | (3R)-N-((1R)-6-(3-aminopropyl)-1,2,3,4-tetrahydro-1-naphthalenyl)-3-phenyl-3-(((3-(trifluoromethyl)phenyl)sulfonyl)amino)propanamide | C29 H32 F3 N3 O3 S | 559.65 | 560 |

EXAMPLE 211

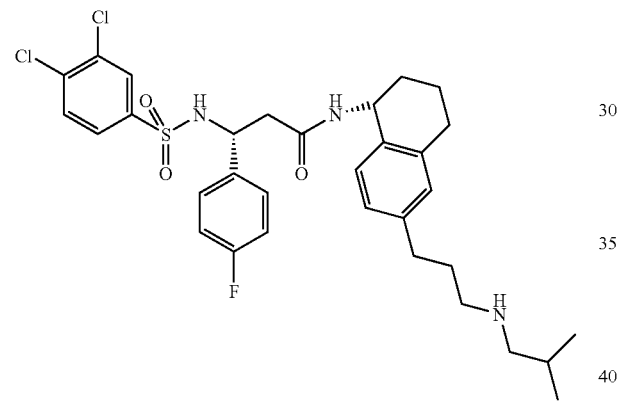

3-(3,4-Dichloro-benzenesulfonylamino)-3-(4-fluoro-phenyl)-N-[6-(3-isobutylamino-propyl)-1,2,3,4-tetrahydro-naphthalen-1-yl]-propionamide To a solution of N-[6-(3-aminopropyl)-1,2,3,4-tetrahydro-naphthalen-1-yl]-3-(3,4-dichloro-benzenesulfonylamino)-3-(4-fluoro-phenyl)-propionamide(63 mg, 0.109 mmol) in dry CH$_2$Cl$_2$ (5 mL) was added isobutyraldehyde (10 µL, 0.109 mmol) and HOAc (1 drop). The resulting mixture was stirred at RT under N$_2$ After 1 h, MS showed the formation of imine; NaBH(OAc)$_3$ (46 mg, 0.218 mmol) was then added. The resulting mixture was stirred for 10 min. The reaction mixture was quenched with sat. NaHCO$_3$. The organic layer was dried over MgSO$_4$ and evaporated in vacuo. The crude solid was purified by chromatography on silica gel. Elution with CH$_2$Cl$_2$:MeOH(2M NH$_3$) mixture (95:5) gave final compound. MS m/z: 635.11 (M+H). Calc'd. for C$_{32}$H$_{38}$Cl$_2$FN$_3$O$_3$S-634.63.

The following compounds (#212-217 and 217 a-f) were prepared similar to the method described in Example 211.

EXAMPLE 212

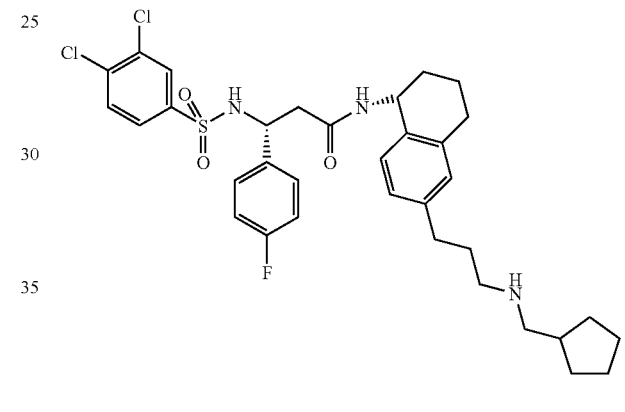

N-{6-[3-(Cyclopentylmethylamino)-propyl]-1,2,3,4-tetrahydro-naphthalen-1-yl}-3-(3,4-dichloro-benzenesulfonylamino)-3-(4-fluoro-phenyl)-propionamide MS m/z: 661.32 (M+H). Calc'd. for C$_{34}$H$_{40}$Cl$_2$FN$_3$O$_3$S-660.67.

EXAMPLE 213

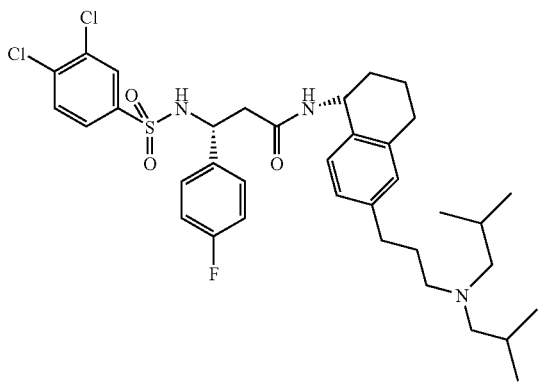

3-(3,4-Dichloro-benzenesulfonylamino)-N-[6-(3-diisobutylamino-propyl)-1,2,3,4-tetrahydro-naphthalen-1-yl]-3-(4-fluoro-phenyl)-propionamide MS m/z: 691.32 (M+H). Calc'd. for $C_{36}H_{46}Cl_2FN_3O_3S$-690.74.

EXAMPLE 214

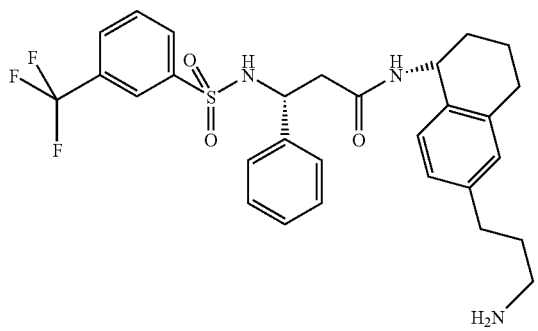

N-[6-(3-Amino-propyl)-1,2,3,4-tetrahydro-naphthalen-1-yl]-3-phenyl-3-(3-trifluoromethyl-benzenesulfonylamino)-propionamide MS m/z: 560.32 (M+H). Calc'd. for $C_{29}H_{32}F_3N_3O_3S$-559.64.

EXAMPLE 215

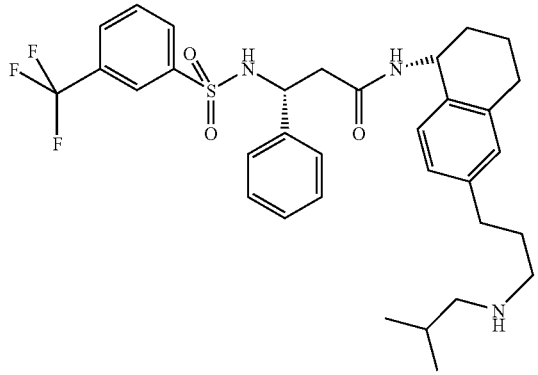

N-[6-(3-Isobutylamino-propyl)-1,2,3,4-tetrahydro-naphthalen-1-yl]-3-phenyl-3-(3-trifluoromethyl-benzenesulfonylamino)-propionamide MS m/z: 616.31 (M+H). Calc'd. for $C_{33}H_{40}F_3N_3O_3S$-615.75

EXAMPLE 216

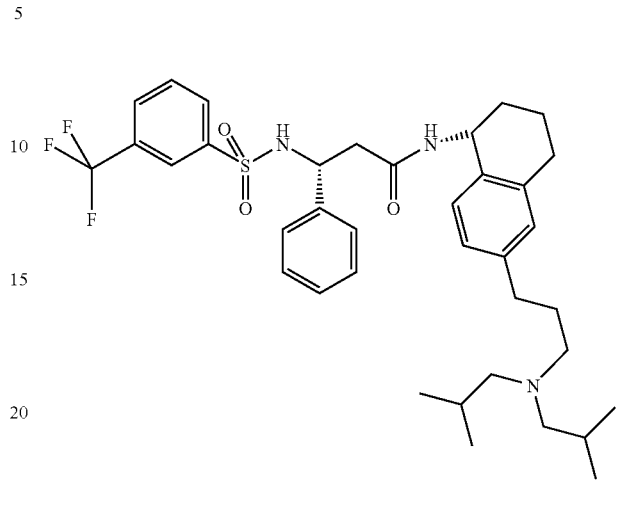

N-[6-(3-Di-isobutylamino-propyl)-1,2,3,4-tetrahydro-naphthalen-1-yl]-3-phenyl-3-(3-trifluoromethyl-benzenesulfonylamino)-propionamide MS m/z: 672.4 (M+H). Calc'd. for $C_{37}H_{48}F_3N_3O_3S$-671.86

EXAMPLE 217

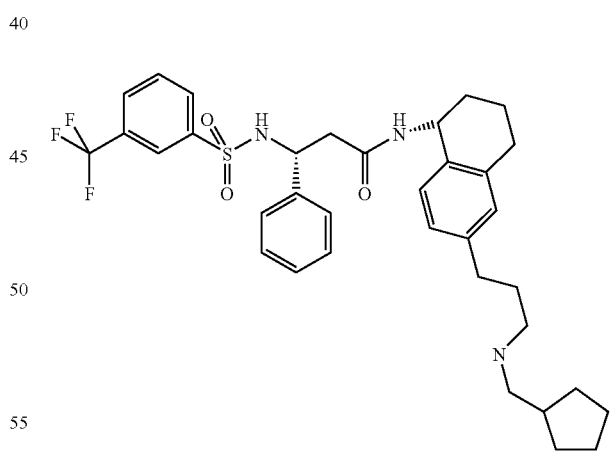

N-{6-[3-(Cyclopentylmethyl-amino)-propyl]-1,2,3,4-tetrahydro-naphthalen-1-yl}-3-phenyl-3-(3-trifluoromethyl-benzenesulfonylamino)-propionamide MS m/z: 642.11 (M+H). Calc'd. for $C_{35}H_{42}F_3N_3O_3S$-641.79.

| # | Structure | formula | MW | M+H |
|---|---|---|---|---|
| a | (3R)-3-(((3,4-dichlorophenyl)sulfonyl)amino)-3-(4-fluoro-phenyl)-N-((1R)-6-(3-((2-methylpropyl)amino)-propyl)-1,2,3,4-tetrahydro-1-naphthalenyl)propanamide | C32H38 Cl2FN3O3S | 634.64 | 635 |
| b | (3R)-N-((1R)-6-(3-((cyclopentylmethyl)-amino)propyl)-1,2,3,4-tetrahydro-1-naphthalenyl)-3-((((1E,2E)-1-ethylidene-3-(trifluoromethyl)-2,4-pentadienyl)sulfonyl)amino)-3-phenylpropanamide | C36 H46 F3 N3 O3 S | 657.837 | 658 |
| c | (3R)-N-((1R)-6-(3-((cyclopentylmethyl)amino)propyl)-1,2,3,4-tetrahydro-1-naphthalenyl)-3-(((3,4-dichlorophenyl)sulfonyl)amino)-3-(4-fluorophenyl)propanamide | C34 H40 Cl2 F N3O3 S | 660.67 | 661 |

| # | Structure | formula | MW | M+H |
|---|---|---|---|---|
| d | (3R)-N-((1R)-6-(3-(bis(2-methylpropyl)amino)propyl)-1,2,3,4-tetrahydro-1-naphthalenyl)-3-(((3,4-dichlorophenyl)sulfonyl)amino)-3-(4-fluorophenyl)propanamide | C36 H46 Cl2 F N3O3 S | 690.747 | 691 |
| E | (3R)-N-((1R)-6-(3-((2-methylpropyl)amino)propyl)-1,2,3,4-tetrahydro-1-naphthalenyl)-3-((((1E,2E)-1-ethylidene-3-(trifluoromethyl)-2,4-pentadienyl)sulfonyl)amino)-3-phenylpropanamide | C34 H44 F3 N3 O3 S | 631.8 | 632 |
| f | (3R)-N-((1R)-6-(3-(bis(2-methylpropyl)amino)propyl)-1,2,3,4-tetrahydro-1-naphthalenyl)-3-(((((1E,2E)-1-ethylidene-3-(trifluoromethyl)-2,4-pentadienyl)sulfonyl)amino)-3-phenylpropanamide | C38 H52 F3 N3 O3 S | 687.9 | 688 |

EXAMPLE 218

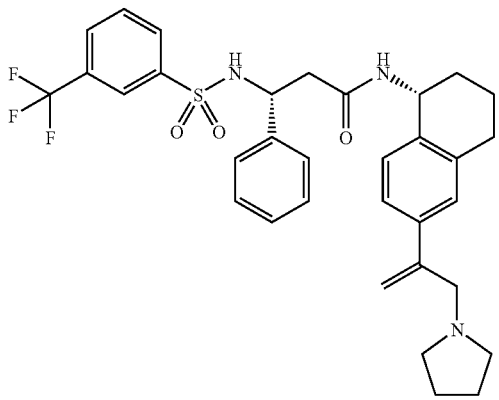

3-(R)-Phenyl-N-[6-(R)-(1-pyrrolidin-1-ylmethyl-vinyl)-1,2,3,4-tetrahydro-naphthalen-1-yl]-3-(3-trifluoromethyl-benzenesulfonylamino)-propionamide Step A. Preparation of trifluoro-methanesulfonic acid 5-oxo-5,6,7,8-tetrahydro-naphthalen-2-yl Ester To a 1 L round-bottomed flask charged with 6-hydroxy-1-tetralone (Aldrich, 21.97 g, 0.136 mol) was added CH$_2$Cl$_2$ (500 mL) and pyridine (Aldrich, 11 mL, 0.136 mol) at 0° C. Triflic anhydride (Aldrich, 23 mL, 0.136 mmol) was then added through an additional funnel over 12 min. The reaction mixture was gradually warmed to RT and stirred overnight. The mixture was treated with water. The organic phase was separated, washed with 1 N HCl (100 mL×2), saturated NaHCO$_3$, and brine, dried over Na$_2$SO$_4$, and concentration in vacuo. The crude was purified by flash chromatography (5-11% EtOAc-hexane) to provide the title compound as yellow oil. MS (ESI): 295 (M+H)$^+$.

Step B. Preparation of trifluoro-methanesulfonic acid 5-hydroxy-5,6,7,8-tetrahydro-naphthalen-2-yl Ester To a dry three-necked flask containing (R)-2-methyl-CBS-oxazaborolidine (Aldrich, 1.94 mL, 1.0 M in toluene, 1.93 mmol, 0.05 eq) under N$_2$ was added a solution of borane-methylsulfide (BMS) (Aldrich, 3.30 mL, 34.80 mmol, 0.9 eq) in toluene (200 mL) through an additional funnel at RT. After the addition, the reaction was cooled to 0° C. A solution of trifluoro-methanesulfonic acid 5-oxo-5,6,7,8-tetrahydro-naphthalen-2-yl ester (11.37 g, 38.67 mmol, 1.0 eq) in THF (180 mL) was added drop-wise through an additional funnel. Following the addition, the reaction mixture was warmed to RT and stirred for additional 40 min, then quenched with MeOH. The solvent was removed in vacuo. The residue was treated with H$_2$O (50 mL), and extracted with ether (3×150 mL). The combined organic layers were washed with brine, dried over Na$_2$SO$_4$, filtered and concentrated in vacuo. The title compound was obtained as an off-white solid after flash chromatography purification (16-22% EtOAc-hexane).

Step C. Preparation of trifluoro-methanesulfonic acid 5-azido-5,6,7,8-tetrahydro-naphthalen-2-yl Ester To a solution of trifluoro-methanesulfonic acid 5-hydroxy-5,6,7,8-tetrahydro-naphthalen-2-yl ester (Step B, 11.2 g, 37.9 mmol, 1.0 eq) in THF (150 mL) at RT was added DPPA (Aldrich, 11.1 mL, 51.6 mmol, 1.36 eq). The resulting mixture was cooled to 0° C. and then DBU (Aldrich, 7.7 mL, 51.6 mmol, 1.36 eq) was added slowly through a syringe. The reaction was warmed to RT and stirred over the weekend. The mixture was concentrated in vacuo. The residue was dissolved in EtOAc (400 mL), washed with saturated NH$_4$Cl (twice), H$_2$O, and brine, dried over Na$_2$SO$_4$ and concentrated in vacuo. The crude was purified by flash chromatography (5% EtOAc-hexane) to provide the title compound.

Step D. Preparation of trifluoro-methanesulfonic acid 5-amino-5,6,7,8-tetrahydro-naphthalen-2-yl Ester A solution of trifluoro-methanesulfonic acid 5-azido-5,6,7,8-tetrahydro-naphthalen-2-yl ester (Step C, 10.3 g, 32.1 mmol, 1.0 eq) in THF (70 mL) was added PPh$_3$ (Aldrich, 8.4 g, 32.1 mmol, 1.0 eq), and H$_2$O (30 mL) at 0° C. The mixture was warmed to RT and stirred overnight. 2 N HCl was added until the mixture was acidic (pH ~1-2). The mixture was extracted with toluene (3×100 mL). The aqueous phase was neutralized with 5 N NaOH to pH around 12-13, and extracted with ether (3×150 mL). The ether solution was dried over Na$_2$SO$_4$ filtered and concentrated in vacuo. The crude was purified by flash chromatography (6% MeOH—CH$_2$Cl$_2$) to provide the title compound.

Step E. Preparation of—Trifluoro-methanesulfonic acid 5-[3-phenyl-3-(3-trifluoromethyl-benzenesulfonylamino)-propionylamino]-5,6,7,8-tetrahydro-naphthalen-2-yl Ester To a solution of 3-phenyl-3-(3-trifluoromethyl-benzenesulfonylamino)-propionic acid (4.31 g, 11.56 mmol), trifluoro-methanesulfonic acid 5-amino-5,6,7,8-tetrahydro-naphthalen-2-yl ester (Step D, 3.10 g, 10.51 mmol), HOBt (Aldrich, 1.28 g, 9.46 mmol), and CH$_2$Cl$_2$ (30 mL) was added EDC (Aldrich, 3.02 g, 15.76 mmol). The reaction was stirred at RT overnight and diluted with CH$_2$Cl$_2$ (100 mL). The organic phase was washed with saturated NaHCO$_3$, water and brine, dried over Na$_2$SO$_4$, filtered and concentrated in vacuo. The crude was purified by silica gel chromatography (16-30% EtOAc-hexane) to afford the title compound as an off-white solid. MS (ESI): 651 (M+H)$^+$.

Step F. Preparation of N-[6 (R)-(1-Hydroxymethyl-vinyl)-1,2,3,4-tetrahydro-naphthalen-1-yl]-3-(R)-phenyl-3-(3-trifluoromethyl-benzenesulfonylamino)-propionamide A solution of trifluoro-methanesulfonic acid 5-[3-phenyl-3-(3-trifluoromethyl-benzenesulfonylamino)-propionylamino]-5,6,7,8-tetrahydro-naphthalen-2-yl ester (Step E, 221 mg, 0.34 mmol) in DMF (1.5 mL) was purged with N$_2$, and then added palladium (II) acetate (Strem Chemicals, 7.6 mg, 0.034 mmol, 0.1 eq), dppf (Aldrich, 38 mg, 0.068 mmol, 0.2 eq), Et$_3$N (0.05 mL, 0.376 mmol, 1.1 eq) and allyl alcohol (Aldrich, 0.07 mL, 1.02 mmol, 3.0 eq). The mixture was heated to 80° C. overnight, cooled to RT, diluted with EtOAc, and washed with H$_2$O (twice) and brine. The organic solution was dried over Na$_2$SO$_4$, filtered and concentrated in vacuo. The crude was purified by silica gel chromatography (50% EtOAc-Hexane) to provide the title compound as an off-white solid. MS (ESI): 559 (M+H)$^+$.

Step G. Preparation of Methanesulfonic acid 2-{5-[3-phenyl-3-(3-trifluoromethyl-benzenesulfonylamino)-propionylamino]-5,6,7,8-tetrahydro-naphthalen-2-yl}-allyl Ester To a flask charged with N-[6-(1-hydroxymethyl-vinyl)-1,2,3,4-tetrahydro-naphthalen-1-yl]-3-phenyl-3-(3-trifluoromethyl-benzenesulfonylamino)-propionamide (Step F, 558 mg, 1.0 mmol, 1.0 eq) was added $CH_2Cl_2$ (7 mL) and $Et_3N$ (0.18 mL, 1.3 mmol, 1.3 eq). The suspension was cooled to 0° C., purged with $N_2$, and then added the $CH_2Cl_2$ solution (1 mL) of methanesulfonyl chloride (Aldrich, 0.1 mL, 1.3 mmol, 1.3 eq). The mixture was concentrated in vacuo after 1 h. The crude was dried on vacuum and used for next step directly.

Step H. Preparation of 3-(R)-Phenyl-N-[6-(R)-(1-pyrrolidin-1-ylmethyl-vinyl)-1,2,3,4-tetrahydro-naphthalen-1-yl]-3-(3-trifluoromethyl-benzenesulfonylamino)-propionamide To a solution of methanesulfonic acid 2-{5-[3-phenyl-3-(3-trifluoromethyl-benzenesulfonylamino)-propionylamino]-5,6,7,8-tetrahydro-naphthalen-2-yl}-allyl ester (Step G, 0.2 mmol, 1.0 eq) in $CH_2Cl_2$ (1 mL) was added pyrrolidine (0.08 mL, 1.0 mmol, 5.0 eq). The reaction mixture was stirred at RT, diluted with $CH_2Cl_2$ (30 mL) and washed with saturated $NaHCO_3$, $H_2O$ and brine. The organic phase was dried over $Na_2SO_4$, filtered and concentrated in vacuo. The crude product was purified by silica gel chromatography (7% MeOH—$CH_2Cl_2$) to provide the title compound as a white solid. MS (ESI): 612 (M+H)$^+$.

The following compounds were prepared by a similar method:

a)

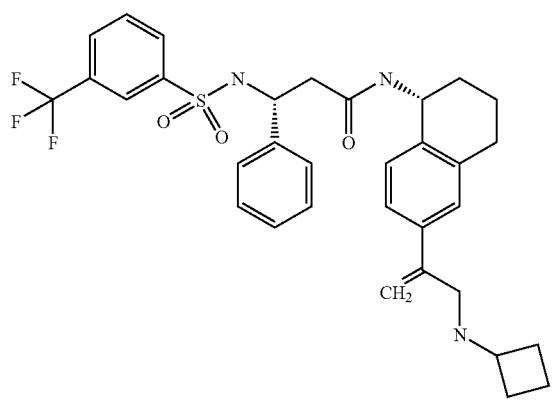

(3R)-N-((1R)-6-(1-((cyclobutylamino)methyl)-ethenyl)-1,2,3,4-tetrahydro-1-naphthalenyl)-3-phenyl-3-(((3-(trifluoromethyl)phenyl)sulfonyl)-amino)propanamide
M+H 612; MW Calc'd for C33 H36 F3 N3 O3 S-611.725.

b)

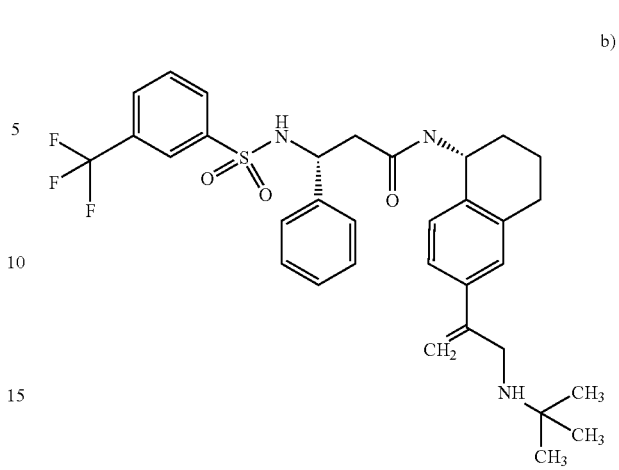

(3R)-N-((1R)-6-(1-(((1,1-dimethylethyl)amino)methyl)ethenyl)-1,2,3,4-tetrahydro-1-naphthalenyl)-3-phenyl-3-(((3-(trifluoromethyl)phenyl)sulfonyl)amino)propanamide;
M+H 614; MW Calc'd for C33 H38 F3 N3 O3 S-613.74.

c)

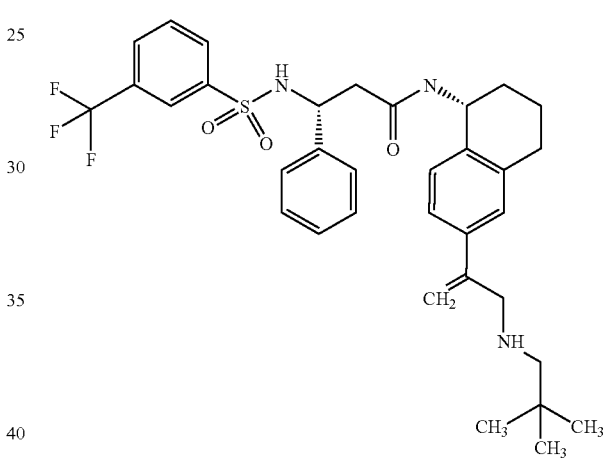

(3R)-N-((1R)-6-(1-(((2,2-dimethylpropyl)amino)methyl)ethenyl)-1,2,3,4-tetrahydro-1-naphthalenyl)-3-phenyl-3-(((3-(trifluoromethyl)phenyl)sulfonyl)amino)propanamide;
M+H 628; MW Calc'd for C34 H40 F3 N3 O3 S-627.77.

d)

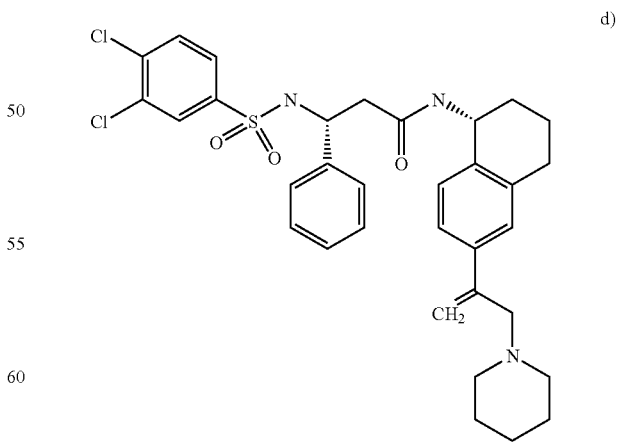

(3R)-3-(((3,4-dichlorophenyl)sulfonyl)amino)-3-phenyl-N-((1R)-6-(1-(1-piperidinylmethyl)ethenyl)-1,2,3,4-tetrahydro-1-naphthalenyl)propanamide; M+H 627; Calc'd for C33 H37 Cl2 N3 O3 S-626.65.

e)

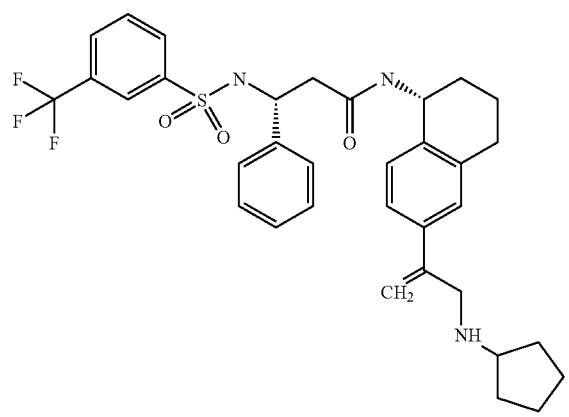

(3R)-N-((1R)-6-(1-((cyclopentylamino)methyl)ethenyl)-1,2,3,4-tetrahydro-1-naphthalenyl)-3-phenyl-3-(((3-(trifluoromethyl)phenyl)sulfonyl)amino)propanamide; M+H 626; MW Calc'd for C34 H38 F3 N3 O3 S-625.75.

h)

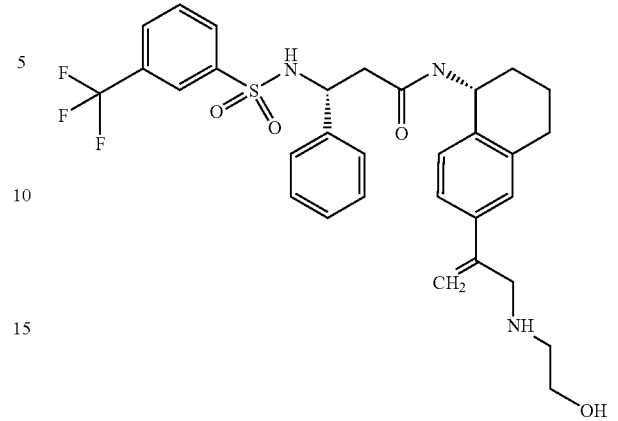

methyl 1-(2-((5R)-5-(((3R)-3-phenyl-3-(((3-(trifluoromethyl)phenyl)sulfonyl)amino)propanoyl)amino)-5,6,7,8-tetrahydro-2-naphthalenyl)-2-propenyl)-L-prolinate; M+H 602; MW Calc'd for C31 H34 F3 N3 O4 S-601.69.

f)

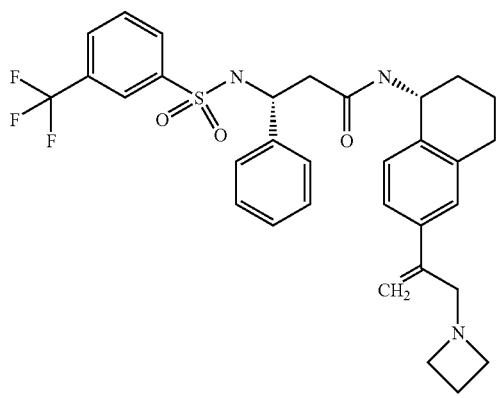

(3R)-N-((1R)-6-(1-(1-azetidinylmethyl)ethenyl)-1,2,3,4-tetrahydro-1-naphthalenyl)-3-phenyl-3-(((3-(trifluoromethyl)phenyl)sulfonyl)amino)propanamide; M+H 598; MW Calc'd for C32 H34 F3 N3 O3 S-597.7.

i)

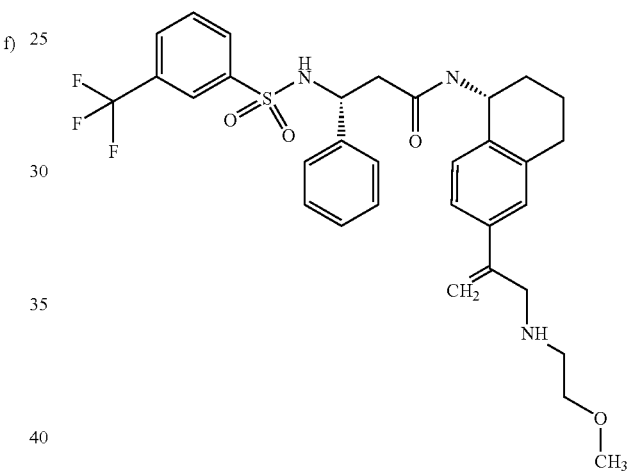

methyl 1-(2-((5R)-5-(((3R)-3-phenyl-3-(((3-(trifluoromethyl)phenyl)sulfonyl)amino)propanoyl)amino)-5,6,7,8-tetrahydro-2-naphthalenyl)-2-propenyl)-L-prolinate; M+H 616; MW Calc'd for C32 H36 F3 N3 O4 S-615.71.

g)

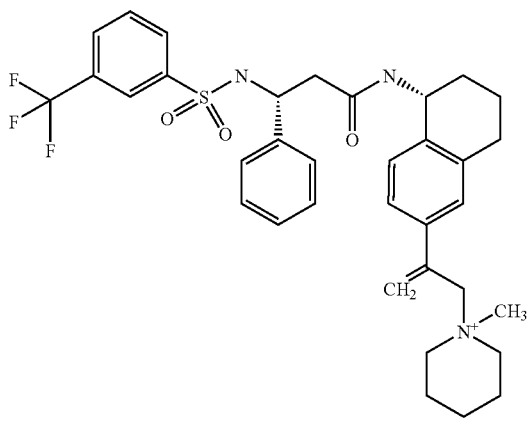

1-methyl-1-(2-((5R)-5-(((3R)-3-phenyl-3-(((3-(trifluoromethyl)phenyl)sulfonyl)amino)propanoyl)amino)-5,6,7,8-tetrahydro-2-naphthalenyl)-2-propenyl)piperidinium, TFA salt; M+H 641; MW Calc'd for C35 H41 F3 N3 O3 S-640.79.

j)

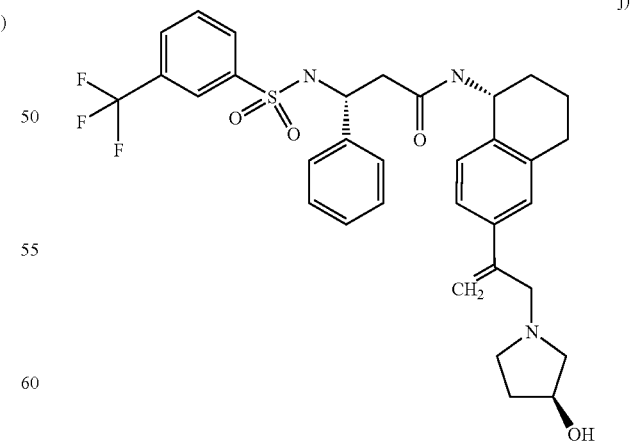

(3R)-N-((1R)-6-(1-(((3S)-3-hydroxy-1-pyrrolidinyl)methyl)ethenyl)-1,2,3,4-tetrahydro-1-naphthalenyl)-3-phenyl-3-(((3-(trifluoromethyl)phenyl)sulfonyl)amino)propanamide; M+H 628; MW Calc'd for C33 H36 F3 N3 O4 S-627.72.

k)

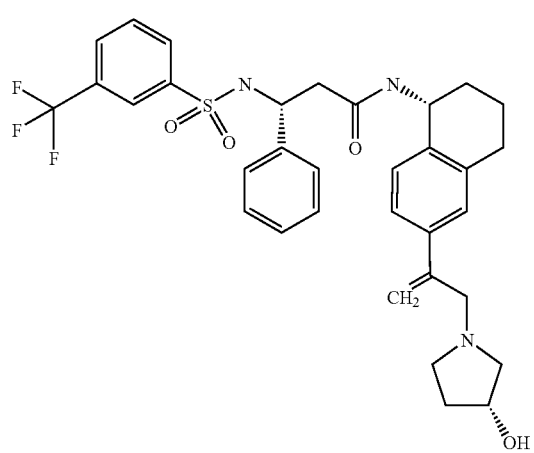

(3R)-N-((1R)-6-(1-(((3R)-3-hydroxy-1-pyrrolidinyl)methyl)ethenyl)-1,2,3,4-tetrahydro-1-naphthalenyl)-3-phenyl-3-(((3-(trifluoromethyl)phenyl)sulfonyl)amino)propanamide; M+H 628; MW Calc'd for C33 H36 F3 N3 O4 S-627.72.

l)

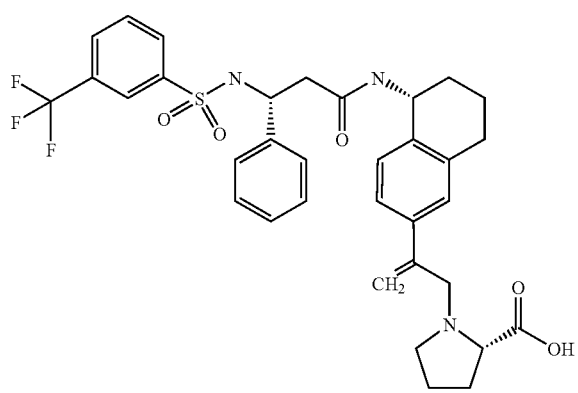

1-(2-((5R)-5-(((3R)-3-phenyl-3-(((3-(trifluoromethyl)phenyl)sulfonyl)amino)propanoyl)amino)-5,6,7,8-tetrahydro-2-naphthalenyl)-2-propenyl)-L-proline; M+H 656; Calc'd for C34 H36 F3 N3 O5 S-655.73.

m)

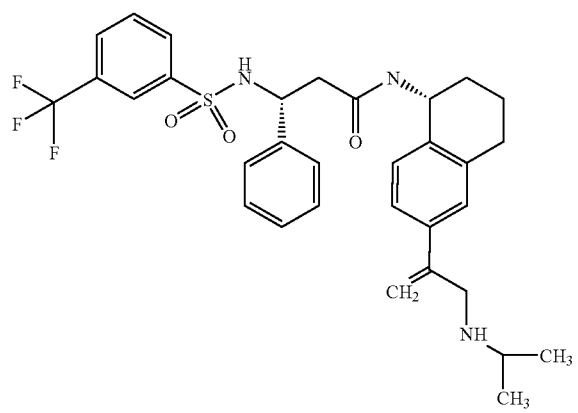

(3R)-N-((1R)-6-(1-(((1-methylethyl)amino)methyl)ethenyl)-1,2,3,4-tetrahydro-1-naphthalenyl)-3-phenyl-3-(((3-(trifluoromethyl)phenyl)sulfonyl)amino)propanamide; M+H 600; MW Calc'd for C32 H36 F3 N3 O3 S-599.71.

n)

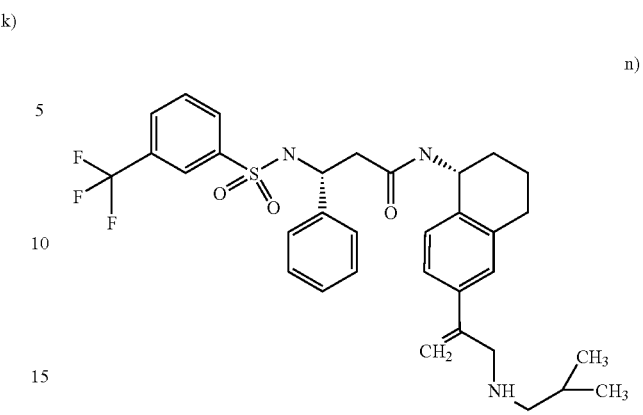

(3R)-N-((1R)-6-(1-(((2,2-dimethylpropyl)amino)methyl)ethenyl)-1,2,3,4-tetrahydro-1-naphthalenyl)-3-phenyl-3-(((3-(trifluoromethyl)phenyl)sulfonyl)amino)propanamide; M+H 614; MW Calc'd for C33 H38 F3 N3 O3 S-613.471.

o)

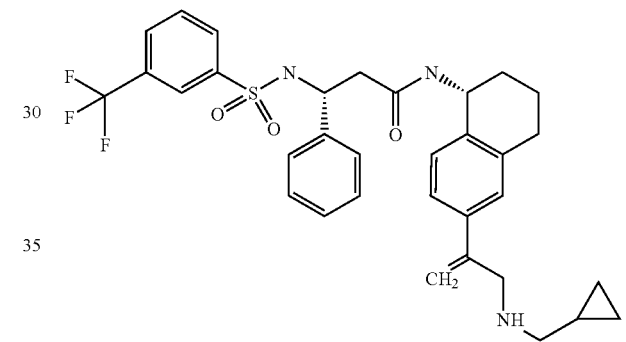

(3R)-N-((1R)-6-(1-(((cyclopropylmethyl)amino)methyl)ethenyl)-1,2,3,4-tetrahydro-1-naphthalenyl)-3-phenyl-3-(((3-(trifluoromethyl)phenyl)sulfonyl)amino)propanamide; M+H 612; MW Calc'd for C33 H36 F3 N3 O3 S-611.72.

p)

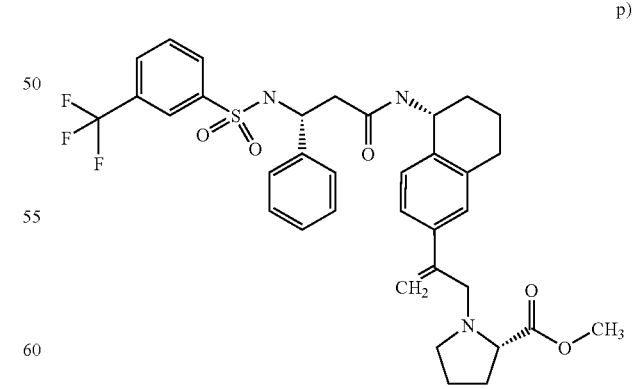

methyl 1-(2-((5R)-5-(((3R)-3-phenyl-3-(((3-(trifluoromethyl)phenyl)sulfonyl)amino)propanoyl)amino)-5,6,7,8-tetrahydro-2-naphthalenyl)-2-propenyl)-L-prolinate; M+H 670; MW Calc'd for C35 H38 F3 N3 O5 S-669.76.

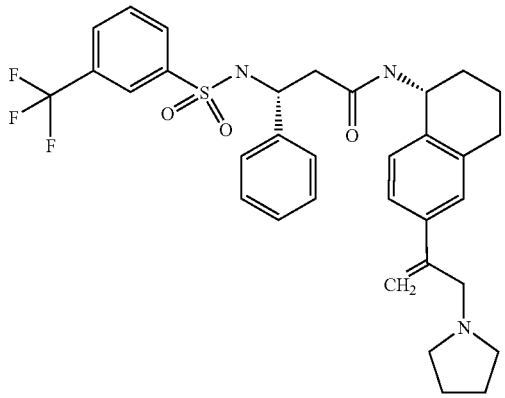

(3R)-3-phenyl-N-((1R)-6-(1-(1-pyrrolidinylmethyl)ethenyl)-1,2,3,4-tetrahydro-1-naphthalenyl)-3-(((3-(trifluoromethyl)phenyl)sulfonyl)amino)propanamide; M+H 612; MW Calc'd for C33 H36 F3 N3 O3 S-611.725.

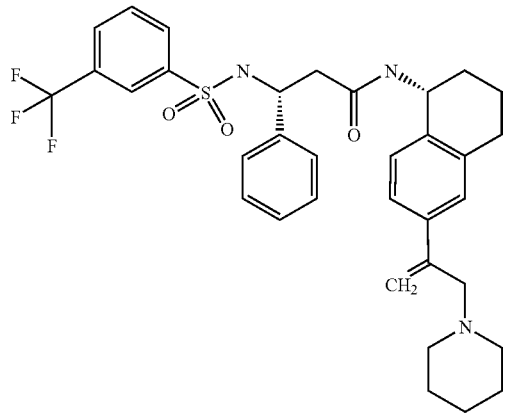

(3R)-3-phenyl-N-((1R)-6-(1-(1-piperidinylmethyl)ethenyl)-1,2,3,4-tetrahydro-1-naphthalenyl)-3-(((3-(trifluoromethyl)phenyl)sulfonyl)amino)propanamide; M+H 626; MW Calc'd for C34 H38 F3 N3 O3 S-625.75.

EXAMPLE 219

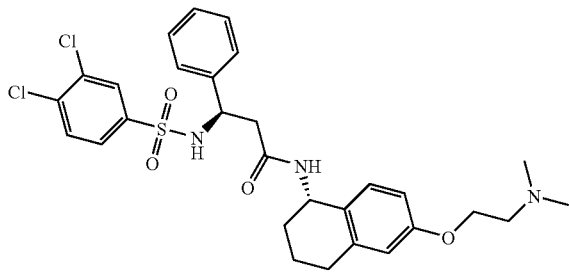

(3R)-3-(((3,4-Dichlorophenyl)sulfonyl)amino)-N-((1S)-6-((2-(dimethylamino)ethyl)oxy)-1,2,3,4-tetrahydro-1-naphthalenyl)-3-phenylpropanamide Step A. Preparation of 6-(2-dimethylamino-ethoxy)-3,4-dihydro-2H-naphthalen-1-one To a mixture of 6-hydroxy-1-tetralone (Aldrich, 1.0 g, 6.17 mmol, 1.0 eq), N,N-dimethylethanolamine (Aldrich, 0.93 mL, 9.26 mmol, 1.5 eq), and triphenylphosphine (Aldrich, 2.43 g, 9.26 mmol, 1.5 eq) in THF (10 mL) was added diethyl azodicarboxylate (Aldrich, 1.94 mL, 12.34 mmol, 2.0 eq) at 0° C. The reaction mixture was gradually warmed to RT and continued to stir overnight. The solvent was evaporated in vacuo. The residue was purified by silica gel chromatography (3%-5% MeOH—CH$_2$Cl$_2$) to provide the product as orange oil. MS (ESI): 234 (M+H)$^+$.

Step B. Preparation of 6-(2-dimethylamino-ethoxy)-3,4-dihydro-2H-naphthalen-1-one Oxime A solution of 6-(2-dimethylamino-ethoxy)-3,4-dihydro-2H-naphthalen-1-one (0.53 g, 2.3 mmol), hydroxylamine hydrochloride (Riedel DeHaen, 0.69 g, 10.0 mmol), and Et$_3$N (Aldrich, 1.4 mL, 10.0 mmol) in MeOH (6 mL) was heated to reflux overnight. The reaction mixture was diluted with EtOAc (70 mL) and washed with 10% Na$_2$CO$_3$, brine. The organic solution was dried over Na$_2$SO$_4$, filtered and concentrated in vacuo to afford the product as an off-white solid. MS (ESI): 249 (M+H)$^+$.

Step C. Preparation of 6-(2-dimethylamino-ethoxy)-1,2,3,4-tetrahydro-naphthalen-1-ylamine A mixture of 6-(2-dimethylamino-ethoxy)-3,4-dihydro-2H-naphthalen-1-one oxime (0.3 g, 1.2 mmol), EtOH (12 mL), Pd/C (Aldrich, 0.13g, 0.12 mmol), and concentrated HCl (0.24 mL) was purged with H$_2$ and connected to a H$_2$ balloon overnight at RT. The catalyst was filtered through Celite® and washed with MeOH. The filtrate was concentrated in vacuo. The residue was added saturated NaHCO$_3$ and extracted with CH$_2$Cl$_2$. The organic solution was dried over Na$_2$SO$_4$, filtered and concentrated in vacuo. The crude product was purified by silica gel chromatography (5%-10% MeOH—CH$_2$Cl$_2$) to afford the compound as a colorless oil. MS (ESI): 235 (M+H)$^+$.

Step D. Preparation of—3-(3,4-dichloro-benzenesulfonylamino)-N-[6-(2-dimethylamino-ethoxy)-1,2,3,4-tetrahydro-naphthalen-1-yl]-3-phenyl-propionamide To a 20 mL vial equipped with stirring was added 3-(3,4-dichloro-benzenesulfonylamino)-3-phenyl-propionic acid (128 mg, 0.34 mmol), 6-(2-dimethylamino-ethoxy)-1,2,3,4-tetrahydro-naphthalen-1-ylamine (40 mg, 0.17 mmol), EDC (Aldrich, 49 mg, 0.26 mmol), HOBt (Aldrich, 23 mg, 0.17 mmol), and CH$_2$Cl$_2$ (1 mL). The reaction was stirred at RT overnight and diluted with CH$_2$Cl$_2$ (50 mL). The organic phase was washed with saturated NaHCO$_3$, and brine, dried over Na$_2$SO$_4$, filtered and concentrated in vacuo. The crude was purified by silica gel chromatography (4%-6% MeOH—CH$_2$Cl$_2$) to afford the title compound as a white solid. MS (ESI): 590 (M+H)$^+$.

EXAMPLE 220

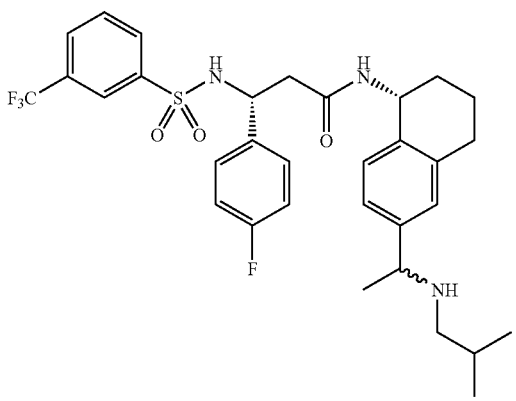

3-(R)-(4-Fluoro-phenyl)-N-[6-(R)-1 (R,S)-isobutylamino-ethyl)-1,2,3,4-tetrahydro-naphthalen-1-yl]-3-(3-trifluoromethyl-benzenesulfonylamino)-propionamide Step A. Preparation of (5-amino-5,6,7,8-tetrahydro-naphthalen-2-yl)-methanol To a three-necked round-bottom flask equipped with a mechanical stirrer was added anhydrous THF (1 L), followed by the addition of LAH (Aldrich, 1.0 M in THF, 302 mL, 302 mmol, 2.0 eq). The resulting solution was cooled to −10° C. A solution of 5-azido-5,6,7,8-tetrahydro-naphthalene-2-carboxylic acid methyl ester (35 g, 151 mmol, 1.0 eq) in THF (100 mL) was added dropwise in 30 min. The reaction was warmed to RT spontaneously and stirred at RT overnight. The reaction was quenched with THF and $H_2O$ mixture (30 mL, $THF:H_2O=2:1$), followed by the sequential addition of 5 N NaOH (10 mL) and $H_2O$ (100 mL) while keeping the temperature of the reaction lower than 5° C. The reaction was stirred at RT for additional 5 h. The precipitate was filtered and washed with THF. The concentration of the filtrate afforded the title compound as a light yellow solid. MS (ESI, pos. ion) m/z: 161 (M−$NH_3$+1).

Step B. Preparation of (6-hydroxymethyl-1,2,3,4-tetrahydro-naphthalen-1-yl)-carbamic acid tert-butyl Ester A mixture of (5-amino-5,6,7,8-tetrahydro-naphthalen-2-yl)-methanol (2.50 g, 14.1 mmol, 1.0 eq) and di-tert-butyl dicarbonate (Aldrich, 3.69 g, 16.9 mmol, 1.2 eq) and $Et_3N$ (Aldrich, 2.85 g, 28.2 mmol, 2.0 eq) in $CH_2Cl_2$ (60 mL) was stirred at RT overnight. The reaction was quenched with $H_2O$ (100 mL) and extracted with $CH_2Cl_2$ (100 mL×3). The extract phase was washed with saturated NaCl, dried over $Na_2SO_4$, filtered and concentrated. Flash column chromatography (silica gel, 0-35% EtOAc-Hexane) afforded the title compound as a white solid (3.19 g, 82%). MS (ESI, pos. ion) m/z: 278 (M+1).

Step C. Preparation of (6-formyl-1,2,3,4-tetrahydro-naphthalen-1-yl)-carbamic acid tert-butyl Ester A mixture of (6-hydroxymethyl-1,2,3,4-tetrahydro-naphthalen-1-yl)-carbamic acid tert-butyl ester (3.16 g, 11.4 mmol, 1.0 eq) and $MnO_2$ (Aldrich, 12.9 g, 148.3 mmol, 13 eq) in $CH_2Cl_2$ (110 mL) was stirred at RT overnight. The mixture was passed through a pad of Celite® and the pad was washed with $CH_2Cl_2$ (100 mL×2). The concentration of the filtrate afforded the title compound as a white sticky semi-solid. MS (ESI, pos. ion) m/z: 298 (M+Na).

Step D. Preparation of [6-(1-hydroxy-ethyl)-1,2,3,4-tetrahydro-naphthalen-1-yl]-carbamic acid tert-butyl Ester To a solution of (6-formyl-1,2,3,4-tetrahydro-naphthalen-1-yl)-carbamic acid tert-butyl ester (Step c, 2.80 g, 10.2 mmol, 1.0 eq) in THF (100 mL) at −78° C. was added a solution of MeMgBr (Aldrich, 1.4 M in toluene/THF (3:1), 29 mL, 40.7 mmol, 4.0 eq) slowly. The reaction was stirred at −78° C. for 20 min, warmed to RT and stirred at RT for 2 h. The reaction was quenched with saturated $NaHCO_3$ (120 mL), and the crude was extracted with EtOAc (100 mL×3). The extract phase was washed with saturated NaCl, dried over $Na_2SO_4$, filtered and concentrated. The title compound was obtained as a white solid. MS (ESI, pos. ion) m/z: 292 (M+1).

Step E. Preparation of (6-acetyl-1,2,3,4-tetrahydro-naphthalen-1-yl)-carbamic acid tert-butyl Ester A mixture of [6-(1-hydroxy-ethyl)-1,2,3,4-tetrahydro-naphthalen-1-yl]-carbamic acid tert-butyl ester (2.63 g, 9.04 mmol, 1.0 eq) and $MnO_2$ (Aldrich, 10.2 g, 117.5 mmol, 13 eq) in $CH_2Cl_2$ (100 mL) was stirred at RT overnight. The mixture was passed through a pad of Celite® and the pad was washed with $CH_2Cl_2$ (100 mL×2). The concentration of the filtrate afforded the title compound as a white sticky semi-solid. MS (ESI, pos. ion) m/z: 290 (M+1).

Step F. Preparation of N-(6-acetyl-1,2,3,4-tetrahydro-naphthalen-1-yl)-3-(4-fluoro-phenyl)-3-(3-trifluoromethyl-benzenesulfonylamino)-propionamide A mixture of (6-acetyl-1,2,3,4-tetrahydro-naphthalen-1-yl)-carbamic acid tert-butyl ester (Step e, 543 mg, 1.88 mmol, 1.0 eq) in HCl/EtOAc (4.7 M, 20 mL) was stirred at RT for 200 min. The solvent was removed with a rotary evaporator, and the resulting 1-(5-amino-5,6,7,8-tetrahydro-naphthalen-2-yl)-ethanone hydrogen chloride was dried in vacuo. A mixture of 1-(5-amino-5,6,7,8-tetrahydro-naphthalen-2-yl)-ethanone hydrogen chloride, 3-(4-fluoro-phenyl)-3-(3-trifluoromethyl-benzenesulfonylamino)-propionic acid (882 mg, 2.26 mmol, 1.2 eq), EDC (Aldrich, 649 mg, 3.38 mmol, 1.8 eq), HOBt (Aldrich, 51 mg, 0.376 mmol, 0.2 eq) and DIEA (Aldrich, 486 mg, 3.76 mmol, 2.0 eq) in $CH_2Cl_2$ (20 mL) and DMF (5 mL) was stirred at RT overnight. The reaction was quenched with $H_2O$ (100 mL). The crude was extracted with $CH_2Cl_2$ (150 mL×3). The extract phase was washed with saturated NaCl, dried over $Na_2SO_4$, filtered and concentrated. Flash column chromatography (silica gel, 0-5% MeOH—$CH_2Cl_2$) afforded the title compound as an off-white solid. MS (ESI, pos. ion) m/z: 563 (M+1).

Step G. Preparation of 3-(4-fluoro-phenyl)-N-[6-(1-isobutylamino-ethyl)-1,2,3,4-tetrahydro-naphthalen-1-yl]-3-(3-trifluoromethyl-benzenesulfonylamino)-propionamide A mixture of N-(6-acetyl-1,2,3,4-tetrahydro-naphthalen-1-yl)-3-(4-fluoro-phenyl)-3-(3-trifluoromethyl-benzenesulfonylamino)-propionamide (161 mg, 0.286 mmol, 1.0 eq), isobutylamine (Aldrich, 126 mg, 1.72 mmol, 6.0 eq), NaBH(OAc)$_3$ (Aldrich, 182 mg, 0.858 mmol, 3.0 eq) and glacial HOAc (J, T. Baker, 34 mg, 0.572 mmol, 2.0 eq) in ClCH$_2$—CH$_2$Cl (3 mL) was stirred at RT for 5 days. The reaction was quenched with saturated NaHCO$_3$ (60 mL). The crude was extracted with CH$_2$Cl$_2$ (60 mL×3). The extract phase was washed with saturated NaCl, dried over Na$_2$SO$_4$, filtered and concentrated. Flash column chromatography (silica gel, 0-10% MeOH—CH$_2$Cl$_2$) afforded the title compound as a colorless thin film. MS (ESI, pos. ion) m/z: 620 (M+1).

The following compounds were prepared by a similar method:

a)

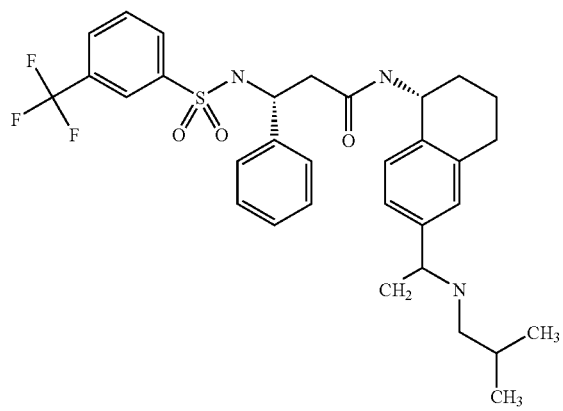

(3R)-3-((hydroxy(oxido)(3-(trifluoromethyl)phenyl)-lambda-4—sulfanyl)amino)-N-((1R)-6-((1R)-1-((2-methylpropyl)amino)ethyl)-1,2,3,4-tetrahydro-1-naphthalenyl)-3-phenylpropanamide;

M+H 603; MW Calc'd for C32 H38 F3 N3 O3 S-601.7.

b)

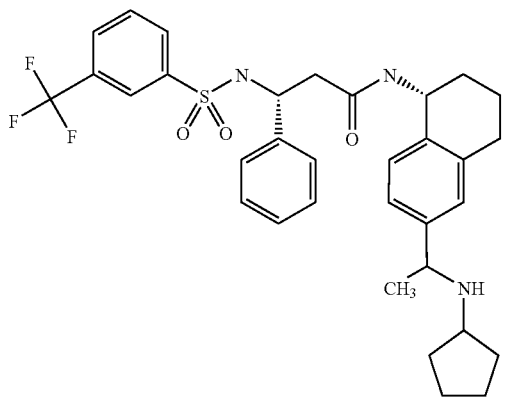

(3R)-N-((1R)-6-((1R)-1-(cyclopentylamino)ethyl)-1,2,3,4-tetrahydro-1-naphthalenyl)-3-phenyl-3-(((3-(trifluoromethyl)phenyl)sulfonyl)amino)propanamide; M+H 614, MW Calc'd for C33 H38 F3 N3 O3 S-613.7 c)

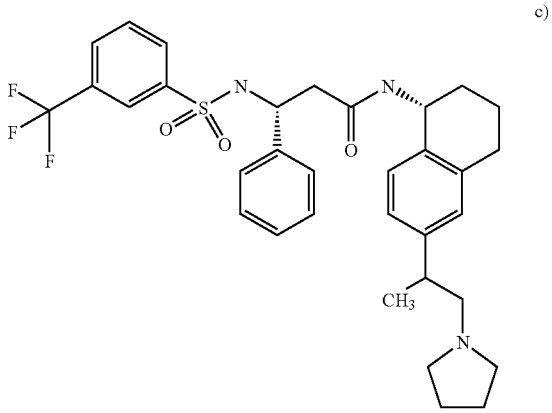

(3R)-N-((1R)-6-((1S)-1-methyl-2-(1-pyrrolidinyl)ethyl)-1,2,3,4-tetrahydro-1-naphthalenyl)-3-phenyl-3-(((3-(trifluoromethyl)phenyl)sulfonyl)amino)propanamide; M+H 614, MW Calc'd for C33 H38 F3 N3 O3 S-613.7.

e)

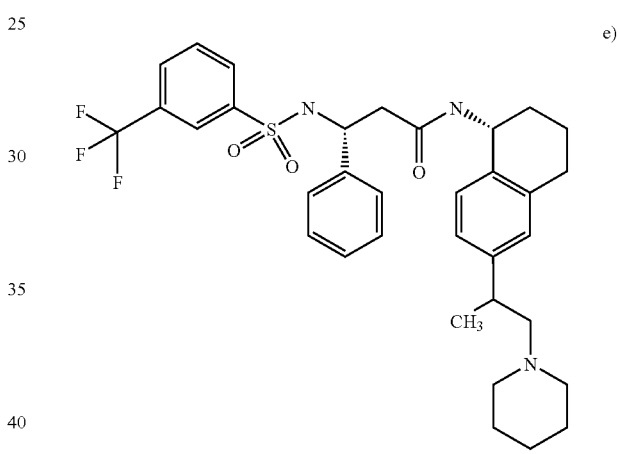

(3R)-N-((1R)-6-((1S)-1-methyl-2-(1-piperidinyl)ethyl)-1,2,3,4-tetrahydro-1-naphthalenyl)-3-phenyl-3-(((3-(trifluoromethyl)phenyl)sulfonyl)amino)propanamide; M+H 628; MW Calc'd for C34 H40 F3 N3 O3 S-627.8.

f)

(3R)-N-((1R)-6-((1S)-2-(dimethylamino)-1-methylethyl)-1,2,3,4-tetrahydro-1-naphthalenyl)-3-phenyl-3-(((3-(trifluoromethyl)phenyl)sulfonyl)amino)propanamide; M+H 588; MW Calc'd for C31 H36 F3 N3 O3 S-587.7.

g)

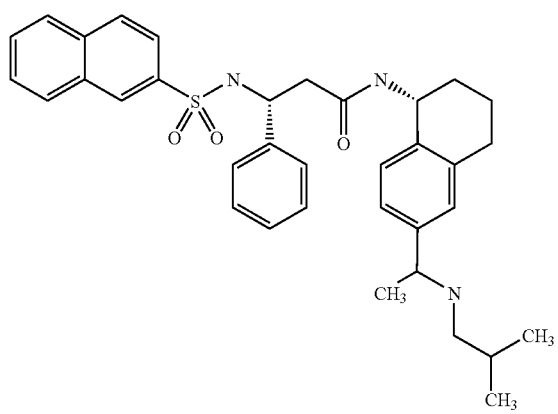

(3R)-N-((1R)-6-((1R)-1-((2-methylpropyl)amino)ethyl)-1,2,3,4-tetrahydro-1-naphthalenyl)-3-((2-naphthalenylsulfonyl)amino)-3-phenylpropanamide; M+H 584; MW Calc'd for C35 H41 N3 O3 S-583.78.

h)

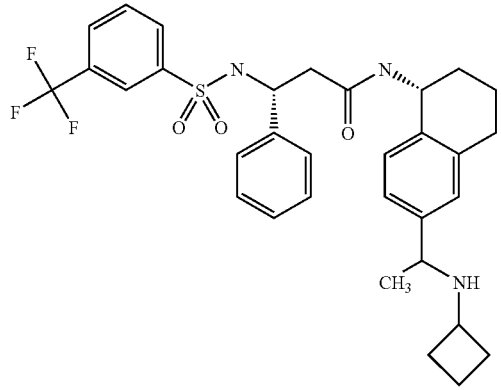

(3R)-N-((1R)-6-((1S)-1-(cyclobutylamino)ethyl)-1,2,3,4-tetrahydro-1-naphthalenyl)-3-phenyl-3-(((3-(trifluoromethyl)phenyl)sulfonyl)amino)propanamide; M+H 600; MW Calc'd for C32 H36 F3 N3 O3 S-599.7.

i)

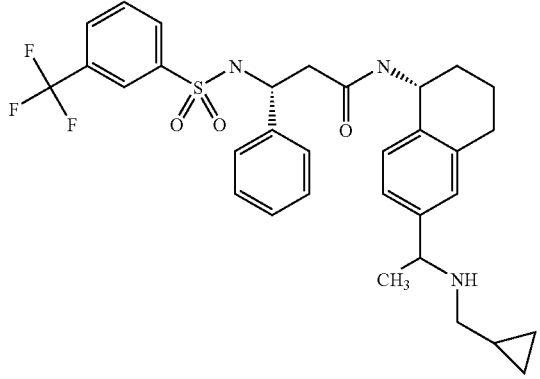

(3R)-N-((1R)-6-((1S)-1-((cyclopropylmethyl)amino)ethyl)-1,2,3,4-tetrahydro-1-naphthalenyl)-3-phenyl-3-(((3-(trifluoromethyl)phenyl)sulfonyl)amino)propanamide; M+H 600; MW Calc'd for C32 H36 F3 N3 O3 S-599.7.

j)

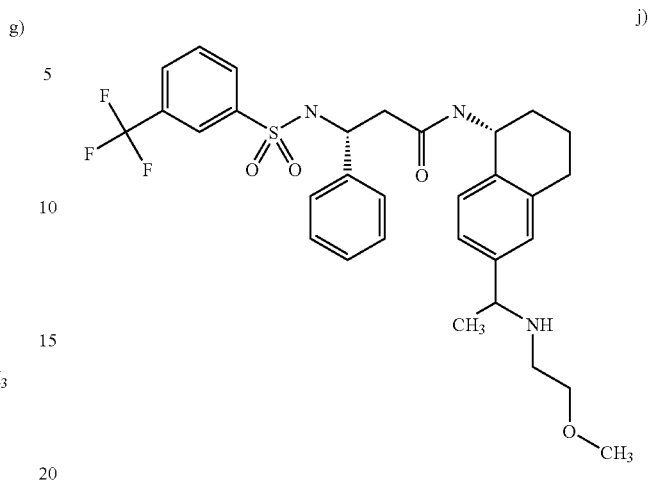

(3R)-N-((1R)-6-((1R)-1-((2-(methyloxy)ethyl)amino)ethyl)-1,2,3,4-tetrahydro-1-naphthalenyl)-3-phenyl-3-(((3-(trifluoromethyl)phenyl)sulfonyl)amino)propanamide; M+H 603; MW Calc'd for C31 H36 F3 N3 O4 S-603.7.

k)

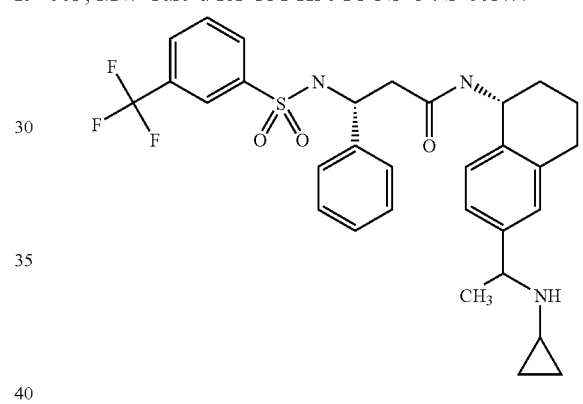

(3R)-N-((1R)-6-((1R)-1-(cyclopropylamino)ethyl)-1,2,3,4-tetrahydro-1-naphthalenyl)-3-phenyl-3-(((3-(trifluoromethyl)phenyl)sulfonyl)amino)propanamide; M+H 586; MW Calc'd for C31 H34 F3 N3 O3 S-585.69.

l)

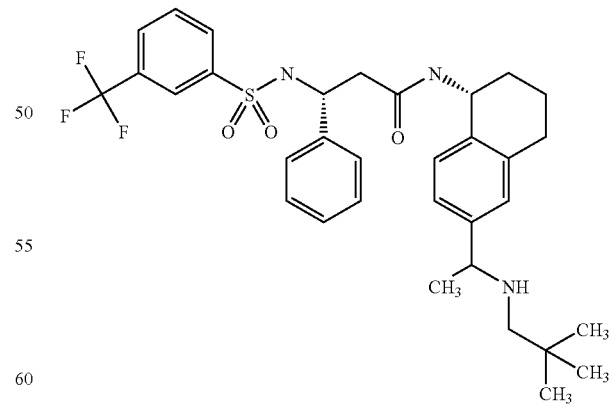

(3R)-N-((1R)-6-((1R)-1-((2,2-dimethylpropyl)amino)ethyl)-1,2,3,4-tetrahydro-1-naphthalenyl)-3-phenyl-3-(((3-(trifluoromethyl)phenyl)sulfonyl)amino)propanamide; M+H 616; MW Calc'd for C33 H40 F3 N3 O3 S-615.75.

m)

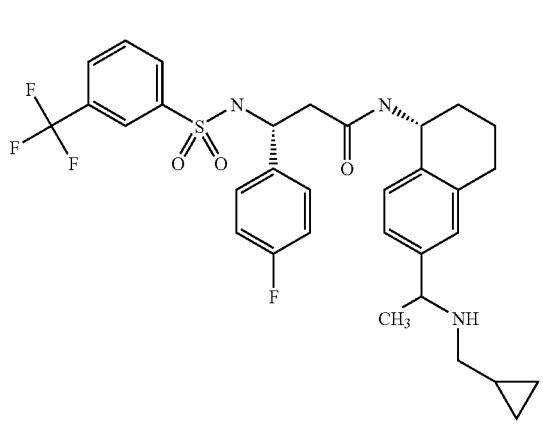

(3R)-N-((1R)-6-((1S)-1-((cyclopropylmethyl)amino)ethyl)-1,2,3,4-tetrahydro-1-naphthalenyl)-3-(4-fluorophenyl)-3-(((3-(trifluoromethyl)phenyl)sulfonyl)amino)propanamide; M+H 618; Calc'd for C32 H35 F4 N3 O3 S-617.7 n)

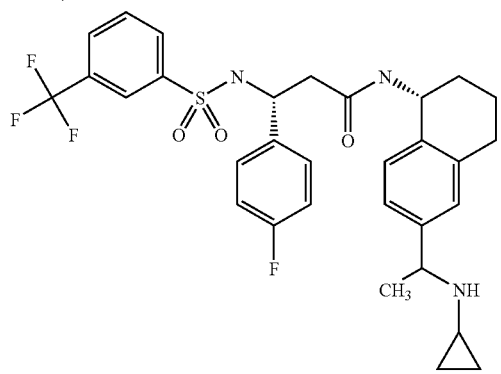

(3R)-N-((1R)-6-((1S)-1-(cyclopropylamino)ethyl)-1,2,3,4-tetrahydro-1-naphthalenyl)-3-(4-fluorophenyl)-3-(((3-(trifluoromethyl)phenyl)sulfonyl)amino)propanamide; M+H 604; Calc'd for C31 H33 F4 N3 O3 S-603.68.

o)

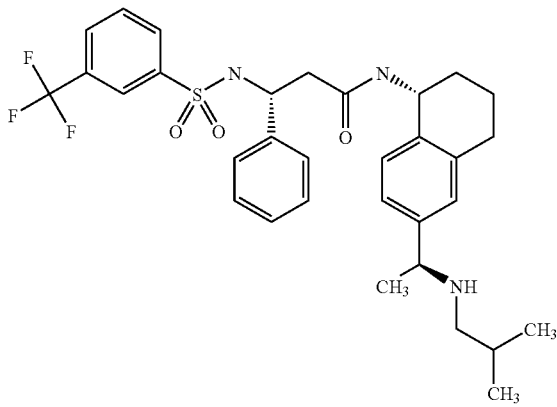

(3R)-3-((hydroxy(oxido)(3-(trifluoromethyl)phenyl)-lambda~4~-sulfanyl)amino)-N-((1R)-6-((1S)-1-((2-methyl-propyl)amino)ethyl)-1,2,3,4-tetrahydro-1-naphthalenyl)-3-phenylpropanamide; M+H 602; MW Calc'd for C32 H38 F3 N3 O3 S-601.73.

p)

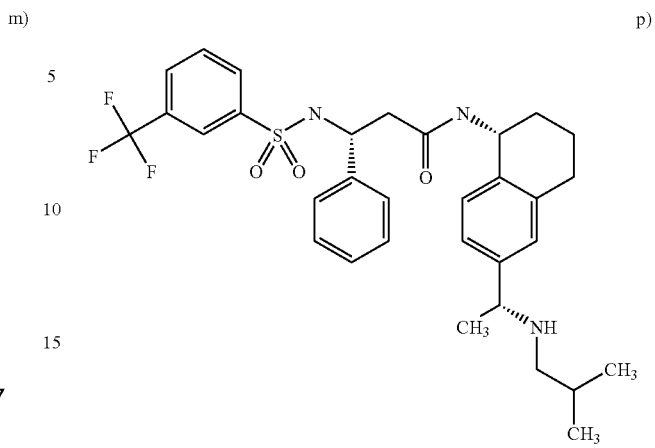

(3R)-3-((hydroxy(oxido)(3-(trifluoromethyl)phenyl)-lambda~4~-sulfanyl)amino)-N-((1R)-6-((1R)-1-((2-methyl-propyl)amino)ethyl)-1,2,3,4-tetrahydro-1-naphthalenyl)-3-phenylpropanamide; M+H 602; MW Calc'd for C32 H38 F3 N3 O3 S-601.73.

q)

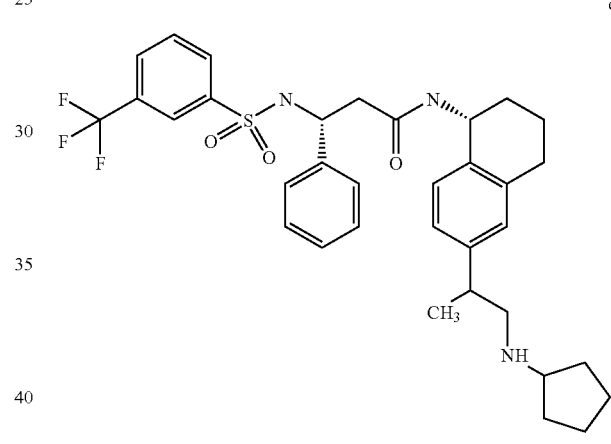

(3R)-N-((1R)-6-((1S)-2-(cyclopentylamino)-1-methyl-ethyl)-1,2,3,4-tetrahydro-1-naphthalenyl)-3-phenyl-3-(((3-(trifluoromethyl)phenyl)sulfonyl)amino)propanamide; M+H 628; MW Calc'd for C34 H40 F3 N3 O3 S-627.77.

r)

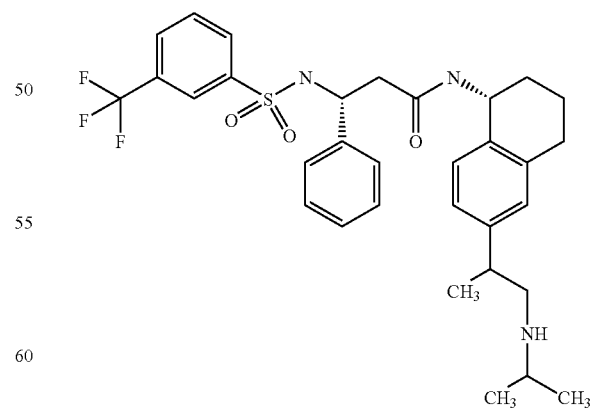

(3R)-N-((1R)-6-((1S)-1-methyl-2-((1-methylethyl)amino)ethyl)-1,2,3,4-tetrahydro-1-naphthalenyl)-3-phenyl-3-(((3-(trifluoromethyl)phenyl)sulfonyl)-amino)propanamide; M+H 602; MW Calc'd for C32 H38 F3 N3 O3 S-601.73.

EXAMPLE 221

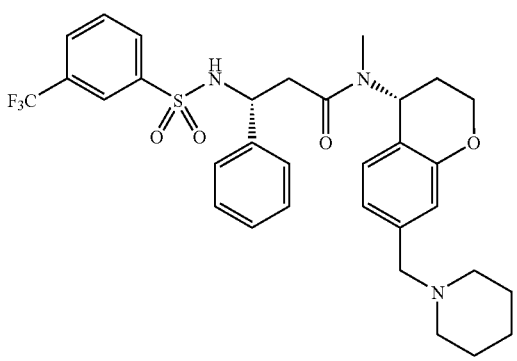

N-Methyl-3-(R)-phenyl-N-(7-piperidin-1-ylmethyl-chroman-4-(R)-yl)-3-(3-trifluoromethyl-benzenesulfonylamino)-propionamide

Step A. Preparation of (7-cyano-chroman-4-yl)-carbamic acid tert-butyl ester A solution of 4-amino-chroman-7-carbonitrile (600 mg, 3.44 mmol, 1.0 eq), di-tert-butyl dicarbonate (Aldrich, 902 mg, 4.13 mmol, 1.2 eq) and Et$_3$N (Aldrich, 696 mg, 6.88 mmol, 2.0 eq) in CH$_2$Cl$_2$ (10 mL) was stirred at RT overnight. The reaction was quenched with H$_2$O (50 mL). The crude was extracted with CH$_2$Cl$_2$ (60 mL×3). The extract phase was washed with saturated NaCl, dried over Na$_2$SO$_4$, filtered and concentrated. Flash column chromatography (silica gel, 0-15% EtOAc-Hexane) afforded the title compound as a white solid. MS (ESI, pos. ion) m/z: 275 (M+1).

Step B. Preparation of (7-cyano-chroman-4-yl)-methyl-carbamic acid tert-butyl ester A mixture of (7-cyano-chroman-4-yl)-carbamic acid tert-butyl ester (769 mg, 2.81 mmol, 1.0 eq), NaH (Aldrich, 449 mg (60% by weight), 11.2 mmol, 4.0 eq) in DMF (15 mL) was stirred at RT for 3 h. Iodomethane (Aldrich, 1.99 g, 14.1 mmol, 5.0 eq) was added slowly. The resulting mixture was stirred at RT for 21 h. The reaction was quenched with saturated NH$_4$Cl (40 mL) DMF was removed with a rotary evaporator at 70° C. The crude was diluted with H$_2$O (100 mL), extracted with EtOAc (80 mL×4). The extract phase was washed with saturated NaCl, dried over Na$_2$SO$_4$, filtered and concentrated. Flash column chromatography (silica gel, 0-15% EtOAc-Hexane) afforded the title compound as an off-white solid. MS (ESI, pos. ion) m/z: 289 (M+1).

Step C. Preparation of (7-formyl-chroman-4-yl)-methyl-carbamic acid tert-butyl ester To a solution of (7-cyano-chroman-4-yl)-methyl-carbamic acid tert-butyl ester (299 mg, 1.04 mmol, 1.0 eq) in anhydrous toluene (5 mL) under N$_2$ at −20° C. was added diisobutylaluminum hydride (Aldrich, 1.50 M in toluene, 1.38 mL, 2.08 mmol, 2.0 eq) slowly. The reaction was stirred at −20° C. for 1 h. Glacial HOAc (1 mL) and H$_2$O (5 mL) was added sequentially. The reaction was warmed to RT spontaneously and stirred at this temperature for an additional 1.5 h. A solution of saturated sodium potassium tartrate (50 mL) was added and the mixture was extracted with EtOAc (60 mL). The aqueous layer was adjusted to pH-10 with 2N NaOH, and extracted with EtOAc (60 mL×2). Combined organic phase was washed with saturated NaCl, dried over Na$_2$SO$_4$, filtered and concentrated. Flash column chromatography (silica gel, 0-8% EtOAc-Hexane) afforded the title compound as a colorless sticky solid.

Step D. Preparation of methyl-(7-piperidin-1-ylmethyl-chroman-4-yl)-carbamic acid tert-butyl ester A mixture of (7-formyl-chroman-4-yl)-methyl-carbamic acid tert-butyl ester (554 mg, 1.90 mmol, 1.0 eq), piperidine (Aldrich, 195 mg, 2.28 mmol, 1.2 eq), NaBH(OAc)$_3$ (Aldrich, 805 mg, 3.8 mmol, 2.0 eq) and glacial HOAc (J. T. Baker, 114 mg, 1.90 mmol, 1.0 eq) in ClCH$_2$—CH$_2$Cl (8 mL) was stirred at RT for 4 h. The reaction was quenched with saturated Na$_2$CO$_3$ (50 mL) The crude was extracted with CH$_2$Cl$_2$ (60 mL×3). The extract phase was washed with saturated NaCl, dried over Na$_2$SO$_4$, filtered and concentrated. Flash column chromatography (silica gel, 0-5% MeOH—CH$_2$Cl$_2$) afforded the title compound as colorless sticky solid. MS (ESI, pos. ion) m/z: 361 (M+1).

Step E. Preparation of methyl-(7-piperidin-1-ylmethyl-chroman-4-yl)-amine

A mixture of methyl-(7-piperidin-1-ylmethyl-chroman-4-yl)-carbamic acid tert-butyl ester (567 mg, 1.58 mmol, 1.0 eq) in saturated HCl/EtOAc (15 mL) was stirred at RT for 7 h. The solvent was removed with a rotary evaporator. The crude was diluted with saturated Na$_2$CO$_3$ (60 mL), and extracted with EtOAc (60 mL×3). The extract phase was washed with saturated NaCl, dried over Na$_2$SO$_4$, filtered and concentrated. The title compound was obtained as orange oil. MS (ESI, pos. ion) m/z: 261 (M+1).

Step F. Preparation of N-methyl-3-phenyl-N-(7-piperidin-1-ylmethyl-chroman-4-yl)-3-(3-trifluoromethyl-benzenesulfonylamino)-propionamide To a solution of 3-phenyl-3-(3-trifluoromethyl-benzenesulfonylamino)-propionic acid (100 mg, 0.268 mmol, 1.0 eq) and DMF (one small drop) in CH$_2$Cl$_2$ (2.5 mL) was added oxalyl chloride (68 mg, 0.536 mmol, 2.0 eq). The reaction was stirred at 0° C. for 1 h. It was warmed to RT and stirred at RT for additional 15 min. Solvent was removed with a rotary evaporator. The newly formed acid chloride was dissolved in CH$_2$Cl$_2$ (2 mL) and the solution was cooled down to 0° C. A solution of methyl-(7-piperidin-1-ylmethyl-chroman-4-yl)-amine (70 mg, 0.268 mmol, 1.0 eq) in CH$_2$Cl$_2$ (0.95 mL) was added slowly. The resulting mixture was stirred at 0° C. for 20 min. The mixture was warmed to RT and stirred at this temperature for additional 20 min. The reaction was quenched with saturated Na$_2$CO$_3$ (60 mL) The crude was extracted with CH$_2$Cl$_2$ (60 mL×3). The extract phase was washed with saturated NaCl, dried over Na$_2$SO$_4$, filtered and concentrated. Flash column chromatography (silica gel, 0-4% MeOH—CH$_2$Cl$_2$) afforded the title compound as a colorless thin film. MS (ESI, pos. ion) m/z: 616 (M+1).

EXAMPLE 222

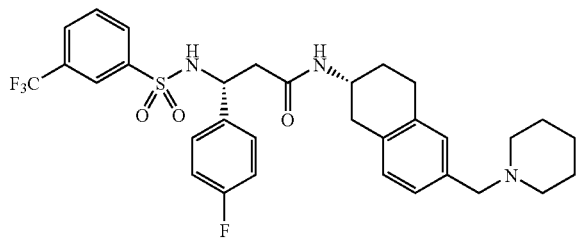

3-(R)-(4-Fluoro-phenyl)-N-(6-piperidin-1-ylmethyl-1,2,3,4-tetrahydro-naphthalen-2-(R)-yl)-(3-trifluoromethyl-benzenesulfonylamino)-propionamide

Step A. Preparation of (6-Bromo-1,2,3,4-tetrahydro-naphthalen-2-(R)-yl)-carbamic acid tert-butyl ester.

To a solution of (t-Boc)$_2$O (3.28 g, 15 mmol) and 2-amino-6-bromo-1,2,3,4-tetrahydronaphthalene (3.94 g, 15 mmol) in DMF (10 mL) was added dropwise Et$_3$N (3.0 g, 30 mmol) at 0° C. After stirring 3 h at RT, the reaction solution was diluted with EtOAc/Hexane (2:1), washed with H$_2$O, dried over Na$_2$SO$_4$ and evaporated to afford the title compound as a white solid.

Step B. Preparation of (6-vinyl-1,2,3,4-tetrahydro-naphthalen-2-(R)-yl)-carbamic acid tert-butyl ester.

A mixture of (6-bromo-1,2,3,4-tetrahydro-naphthalen-2-(R)-yl)-carbamic acid tert-butyl ester (1.63 g, 5 mmol), vinyltributyltin (2.2 g, 7 mmol), tri-t-butylphosphine (101 mg, 0.5 mmol), Et$_3$N (1.0 g, 10 mmol) and Pd$_2$(dba)$_3$ (229 mg, 0.25 mmol) in toluene (2 mL) was heated at 80° C. in microwave for 20 min. After cooling to RT, the reaction was quenched with Sat. NH$_4$Cl, extracted with EtOAc, dried, and evaporated to dryness. Flash chromatography (SiO$_2$, hexane to hexane/CH$_2$Cl$_2$=2:1 to 1:1 to pure CH$_2$Cl$_2$) afforded the title compound as a white solid.

Step C. Preparation of (6-vinyl-1,2,3,4-tetrahydro-naphthalen-2-(R)-yl)-amine.

TFA (0.7 mL, 9.07 mmol) was added dropwise to a solution of (6-vinyl-1,2,3,4-tetrahydro-naphthalen-2-(R)-yl)-carbamic acid tert-butyl ester (620 mg, 2.27 mmol) in CH$_2$Cl$_2$ (10 mL). After stirring at RT for 4 h, the mixture was evaporated to dryness. Et$_3$N (1 mL) was added to the residue and evaporated again to give the crude which was directly used in the next step.

Step D. Preparation of 3-(R)-(4-fluoro-phenyl)-3-(3-trifluoromethyl-benzenesulfonylamino)-N-(6-vinyl-1,2,3,4-tetrahydro-naphthalen-2-(R)-yl)-propionamide.

A solution of 3-(R)-(4-fluoro-phenyl)-N-(6-formyl-1,2,3,4-tetrahydro-naphthalen-2-(R)-yl)-3-(3-trifluoromethyl-benzenesulfonylamino)-propionamide (391 mg, 1 mmol), crude (6-vinyl-1,2,3,4-tetrahydro-naphthalen-2-(R)-yl)-amine (190 mg, 1.1 mmol), HOBt (135 mg, 1 mmol) and EDC (191 mg, 1 mmol) in 2 mL of DMF was stirred overnight at RT. After quenching with Sat. NaHCO$_3$ solution, the reaction mixture was extracted with EtOAc. The combined organic phase was washed brine, dried over Na2SO4, and evaporated in vacuo. Flash chromatography (SiO2, hexane/EtOAc=1:2) gave the desired compound as a white solid.

Step E. Preparation of 3-(R)-(4-fluoro-phenyl)-N-(6-formyl-1,2,3,4-tetrahydro-naphthalen-2-(R)-yl)-3-(3-trifluoromethyl-benzenesulfonylamino)-propionamide.

To a solution of 3-(R)-(4-fluoro-phenyl)-3-(3-trifluoromethyl-benzenesulfonylamino)-N-(6-vinyl-1,2,3,4-tetrahydro-naphthalen-2-(R)-yl)-propionamide (314 mg, 0.575 mmol) in 13 mL of a mixture solvent t-butanol/THF/water (10:2:1) was added NMO (135 mg, 1.15 mmol), followed by OsO$_4$ (2.5% w/w in t-butanol, 175 mg, 0.017 mmol). After stirring overnight at RT, 4 mL of pH=7.2 phosphate buffer was added, followed by NaIO$_4$ (615 mg, 2.875 mmol). After stirring for 5 h at RT, the solution was diluted with EtOAc and washed with brine. The organic phase was dried over Na$_2$SO$_4$ and evaporated to dryness in vacuo. Flash chromatography (SiO$_2$, EtOAc/hexane=1:1) afforded the desired compound as a white solid.

Step F. Preparation of 3-(R)-(4-fluoro-phenyl)-N-(6-piperidin-1-ylmethyl-1,2,3,4-tetrahydro-naphthalen-2-(R)-yl)-(3-trifluoromethyl-benzenesulfonylamino)-propionamide.

To a solution of 3-(R)-(4-fluoro-phenyl)-N-(6-formyl-1,2,3,4-tetrahydro-naphthalen-2-(R)-yl)-3-(3-trifluoromethyl-benzenesulfonylamino)-propionamide (70 mg, 0.128 mmol) and pyperidine (20 mg, 0.23 mmol) in 1 mL of dichloroethane was added sodium triacetoxyborohydride (49 mg, 0.23 mmol). After stirring overnight at RT, the solution was diluted with EtOAc and washed with sat. NaHCO$_3$ and brine. The organic phase was dried over Na$_2$SO$_4$ and evaporated to dryness in vacuo. Flash chromatography (SiO$_2$, EtOAc to EtOAc/MeOH=100:10 to 100:12) afforded the desired compound as a white solid. MS: 618.2 (M+1).

EXAMPLE 223

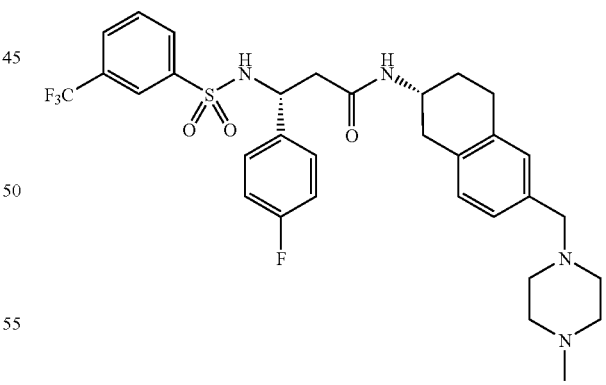

3-(4-Fluoro-phenyl)-N-[6-(4-methyl-piperazin-1-ylmethyl)-1,2,3,4-tetrahydro-naphthalen-2-yl]-3-(3-trifluoromethyl-benzenesulfonylamino)-propionamide Prepared from 3-(R)-(4-fluoro-phenyl)-N-(6-formyl-1,2,3,4-tetrahydro-naphthalen-2-(R)-yl)-3-(3-trifluoromethyl-benzenesulfonylamino)-propionamide as described in Example 222 and isolated as a white solid. MS: 633.2 (M+1).

EXAMPLE 224

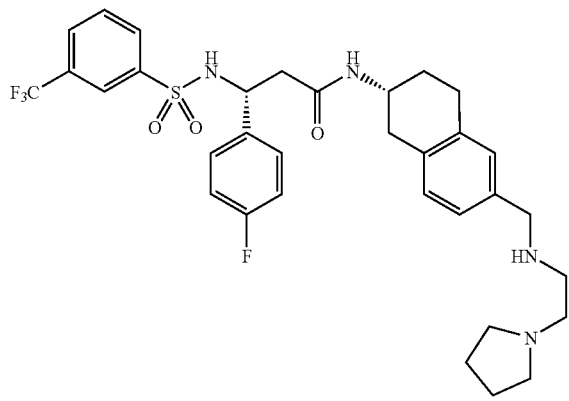

3-(4-Fluoro-phenyl)-N-{6-[(2-pyrrolidin-1-yl-ethylamino)-methyl]-1,2,3,4-tetrahydro-naphthalen-2-yl}-3-(3-trifluoromethyl-benzenesulfonylamino)-propionamide Prepared from 3-(R)-(4-fluoro-phenyl)-N-(6-formyl-1,2,3,4-tetrahydro-naphthalen-2-(R)-yl)-3-(3-trifluoromethyl-benzenesulfonylamino)-propionamide as described above isolated as a white solid. MS: 647.1 (M+1).

EXAMPLE 225

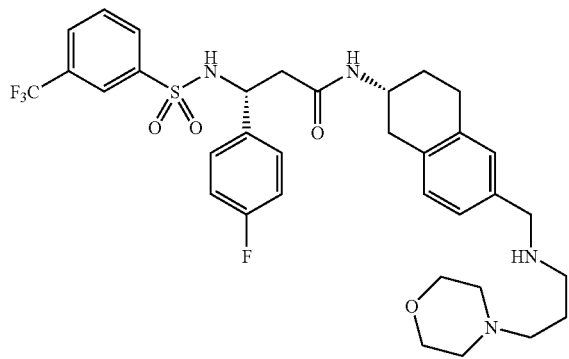

3-(4-Fluoro-phenyl)-N-{6-[(3-morpholin-4-yl-propylamino)-methyl]-1,2,3,4-tetrahydro-naphthalen-2-yl}-3-(3-trifluoromethyl-benzenesulfonylamino)-propionamide Prepared from 3-(R)-(4-fluoro-phenyl)-N-(6-formyl-1,2,3,4-tetrahydro-naphthalen-2-(R)-yl)-3-(3-trifluoromethyl-benzenesulfonylamino)-propionamide as described above isolated as a white solid MS: 677.1 (M+1).

EXAMPLE 226

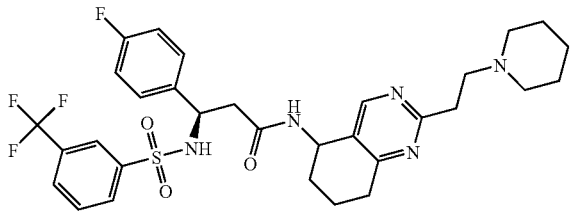

(3R)-3-(4-Fluorophenyl)-N-((5S,R)-2-(2-(1-piperidinyl)ethyl)-5,6,7,8-tetrahydro-5-quinazolinyl)-3-(((3-(trifluoromethyl)phenyl)sulfonyl)amino)propanamide

Step A. Preparation of 3-(tert-Butyl-diphenyl-silanyloxy)-propionitrile.

To a solution of 3-hydroxy-propionitrile (7.1 g, 0.1 mmol) and DMAP (1.22 g, 0.01 mmol) in 30 mL of dry $CH_2Cl_2$ at RT was added Et3N (30.3 g, 0.3 mmol), followed by PBDPSCl (27.5 g, 0.1 mol). A lot of white solid appeared. After stirring at RT overnight, the reaction was quenched with Sat. NH4Cl solution, extracted with $CH_2Cl_2$, dried over $Na_2SO_4$, and evaporated in vacuo. Flash chromatography ($SiO_2$, hexane/EtOAc=100:2 to 100:5 to 100:10) gave the desired compound as a white solid.

Step B. Preparation of 3-(tert-Butyl-diphenyl-silanyloxy)-propionamidine.

To a suspension of NH4Cl (5.35 g, 0.1 mmol) in 60 mL of dry benzend at 0 C was slowly added 50 mL of 2 M solution of trimethylaluminum in toluene. After the addition was complete, the reaction was warmed to RT and was stirred for 2 h until gas evolution had ceased. A solution of 3-(tert-butyl-diphenyl-silanyloxy)-propionitrile (9.27 g, 0.03 mol) in 20 mL of dry benzene was added to the aluminum amide reagent and the resulting was heated up to 80° C. for 20 h. The reaction was slowly cooled to RT and then carefully poured into a slurry of 300 mL of $Ch_2Cl_2$ and 200 g of silica gel. It was then filtered and washed thoroughly with MeOH/$CH_2Cl_2$ (1:2). After concentration, flash chromatography ($SiO_2$, EtOAc to EtOAc/MeOH=100:20 to 100:30 to EtOAc/2 M $NH_3$ in MeOH=100:30) gave the desired compound as a white solid.

Step C. Preparation of 2-[2-(tert-Butyl-diphenyl-silanyloxy)-ethyl]-7,8-dihydro-6H-quinazolin-5-one.

A solution of 3-(tert-butyl-diphenyl-silanyloxy)-propionamidine (25 g, 77 mmol) and 2-dimethylaminomethylene-cyclohexane-1,3-dione (12.8 g, 77 mmol) in 400 mL of dry EtOH was heated at 80° C. for 3 h. After cooling to RT, the solvent was evaporated. Flash chromatography ($SiO_2$, EtOAc/hexane=1:1) gave the desired compound as a white solid.

Step D. Preparation of 2-[2-(tert-butyl-diphenyl-silanyloxy)-ethyl]-5,6,7,8-tetrahydro-quinazolin-5-ol.

A solution of 2-[2-(tert-butyl-diphenyl-silanyloxy)-ethyl]-7,8-dihydro-6H-quinazolin-5-one_(2.16 g, 5 mmol) in 30 mL of dry MeOH was treated with NaBH4 (189 mg, 5 mmol). After 5 min, the reaction was quenched with 5 mL of sat. NH4Cl solution. The MeOH was evaporated and the residue was extracted with $CH_2Cl_2$, dried over $Na_2SO_4$ and evaporated. Flash chromatography ($SiO_2$, $CH_2Cl_2$ to EtOAc) gave the desired compound as a white solid.

Step E. Preparation of 5-amino-2-[2-(tert-butyl-diphenyl-silanyloxy)-ethyl]-5,6,7,8-tetrahydro-quinazoline.

To a solution of 2-[2-(tert-butyl-diphenyl-silanyloxy)-ethyl]-5,6,7,8-tetrahydro-quinazolin-5-ol (2.0 g, 4.63 mmol) in 25 mL of toluene at −10° C. was added DPPA (1.2 mL, 5.56 mmol). To this stirred solution was then added DBU (0.83 mL, 5.56 mmol) dropwise while keeping the temperature below 0° C. After stirring at RT for 16 h, the reaction was evaporated to dryness and directly submitted to flash chromatography (SiO$_2$, hexane/DCM=1:2) to afford the azide (1.5 g, 71%) as a white solid. A suspension of 80 mg of Pd/C (10% w/w) in a solution of the above azide (800 mg, 1.75 mmol) in 30 mL of EtOAc was stirred under H$_2$ atomosphere overnight. The reaction mixture was then directly submitted to flash chromatograph (SiO$_2$, EtOAc to EtOAc/MeOH=100: 15 to EtOAc/2 M NH$_3$ in MeOH=2:1) to give compound as a white solid.

Step G. Preparation of 2-(5-amino-5,6,7,8-tetrahydro-quinazolin-2-yl)-ethanol.

A solution of 5-amino-2-[2-(tert-butyl-diphenyl-silanyloxy)-ethyl]-5,6,7,8-tetrahydro-quinazoline (570 mg, 1.32 mmol) in 10 mL of THF at 0° C. was treated with a 1 M TBAF solution in THF (1.56 mL, 1.56 mmol). After stirring at RT overnight, the reaction mixture was directly submitted to flash chromatograph (SiO$_2$, EtOAc to EtOAc/MeOH=100:15 to EtOAc/2 M NH$_3$ in MeOH=1:1) to give crude compound as a white solid.

Step H. Preparation of 3-(4-fluorophenyl)-N-[2-(2-hydroxy-ethyl)-5,6,7,8-tetrahydro-quinazolin-5-yl]-3-(3-trifluoromethyl-benzenesulfonylamino)-propionamide.

A solution of 3-(4-fluorophenyl)-3-(3-trifluoromethyl-benzenesulfonylamino)-propionic acid (172 mg, 0.44 mmol), crude 2-(5-amino-5,6,7,8-tetrahydro-quinazolin-2-yl)-ethanol (Step G, 85 mg, 0.44 mmol), HOBt (65.5 mg, 0.484 mmol) and EDC (93 mg, 0.484 mmol) in 1.5 mL of DMF was stirred overnight at RT. After quenching with Sat. NaHCO$_3$ solution, the mixture was extracted with EtOAc. The combined organic phase was washed brine, dried over Na$_2$SO$_4$, and evaporated in vacuo. Flash chromatography (SiO$_2$, EtOAc/MeOH=100:5 to 100:10 to 100:12) gave the title compound as a white solid. MS: 567.0 (M+1).

Step I. Preparation of methanesulfonic acid 2-{5-[3-(4-fluoro-phenyl)-3-(3-trifluoromethyl-benzenesulfonylamino)-propionylamino]-5,6,7,8-tetrahydroquinazolin-2-yl}-ethyl ester To a solution of 3-(4-fluorophenyl)-N-[2-(2-hydroxyethyl)-5,6,7,8-tetrahydro-quinazolin-5-yl]-3-(3-trifluoromethyl-benzenesulfonylamino)-propionamide (56.6 mg, 0.1 mmol) in dry CH$_2$Cl$_2$ at 0 C was added MsCl (34 mg, 0.3 mmol), followed by Et$_3$N (50 mg, 0.5 mmol). After stirring at 0° C. for 20 min, the reaction was quenched with Sat. NaHCO$_3$ solution, extracted with EtOAc, dried over Na$_2$SO$_4$, and evaporated in vacuo. Flash chromatography (SiO$_2$, EtOAc/MeOH=100:3 to 100:5 to 100:7) gave the title compound as a white solid. MS: 645.0 (M+1).

Step J. Preparation of (3R)-3-(4-fluorophenyl)-N-((5S,R)-2-(2-(1-piperidinyl)ethyl)-5,6,7,8-tetrahydro-5-quinazolinyl)-3-(((3-(trifluoromethyl)phenyl)sulfonyl)amino)propanamide A solution of the above mesylate (58 mg, 0.09 mmol) and piperidine (77 mg, 0.9 mmol) in dry CH$_2$Cl$_2$ at RT was stirred overnight. The reaction was quenched with Sat. NaHCO$_3$ solution, extracted with EtOAc, dried over Na$_2$SO$_4$, and evaporated in vacuo. Flash chromatography (SiO$_2$, EtOAc/MeOH=100:7 to 100:10 to 100:12 to 100:15) gave the title compound as a white solid. MS: 634.2 (M+1). MW Calc'd for C31 H35 F4 N5 O3 S-633.71.

The following compound was prepared by a method similar to that described above:

EXAMPLE 226a

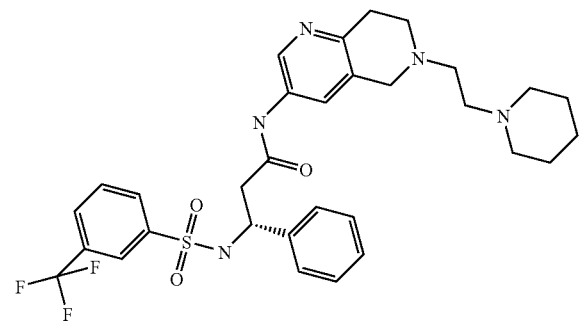

(3R)-3-phenyl-N-(6-(2-(1-piperidinyl)ethyl)-5,6,7,8-tetrahydro-1,6-naphthyridin-3-yl)-3-(((3-(trifluoromethyl)phenyl)sulfonyl)amino)propanamide M+H 616; Calc'd for C$_{31}$H$_{36}$F$_3$N$_5$O$_3$S-615.25.

EXAMPLE 227

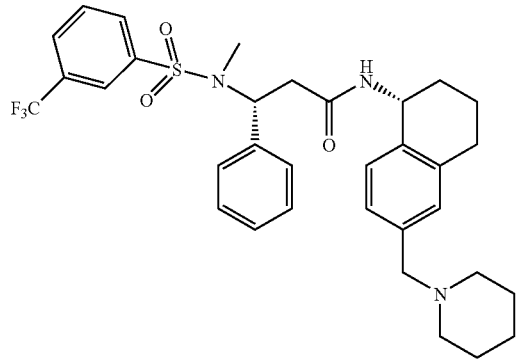

3-[Methyl-(3-trifluoromethyl-benzenesulfonyl)-amino]-3-phenyl-N-(6-piperidin-1-ylmethyl-1,2,3,4-tetrahydro-naphthalen-1-yl)-propionamide The aldehyde, N-(6-formyl-1,2,3,4-tetrahydro-naphthalen-1-yl)-3-phenyl-3-(3-trifluoromethyl-benzenesulfonylamino)-propionamide (0.11 g), was stirred in dry DMF (5 mL) with sodium carbonate (0.2 g) and methyl iodide (0.2 mL) at RT for 3 days. Aqueous workup gave the crude product, N-(6-formyl-1,2,3,4-tetrahydro-naphthalen-1-yl)-3-[methyl-(3-trifluoromethyl-benzenesulfonyl)-amino]-3-phenyl-propionamide (0.12 g). MS: 545.1 (M+1). This aldehyde (0.12 g) was converted to 3-[methyl-(3-trifluoromethyl-benzenesulfonyl)-amino]-3-phenyl-N-(6-piperidin-1-ylmethyl-1,2,3,4-tetrahydro-naphthalen-1-yl)-propionamide using the general reductive amination conditions (amine, NaBH(OAc)$_3$, RT, DCE) described earlier in this application. MS: 614.1 (M+1).

Although the pharmacological properties of the compounds of Formula I-VI vary with structural change, in general, activity possessed by compounds of Formula I-VI may be demonstrated in vivo. The pharmacological properties of the compounds of this invention may be confirmed by a number of pharmacological in vitro assays. The exemplified pharmacological assays which follow have been carried out with the compounds according to the invention and their salts. Compounds of the present invention showed binding IC$_{50}$'s of B1 at doses less than 10 μm.

Biological Testing

Human Bradykinin B1 Receptor and human B2 Receptor In Vitro Binding Assay Supporting Methods:

Preparation of membranes expressing human B1 and human B2 bradykinin receptor. Membranes were prepared from CHO-d⁻AQN cells stably transfected with human bradykinin B1 receptor cDNA. For large-scale production of membranes, cells were grown in 100 L suspension culture to 1.0E8 cells/mL then harvested using the Viafuge at continuous centrifugation of 1000 g. For pilot studies, cells were grown in 2 L spinner culture and harvested by centrifugation (1900 g, 10 min, 4° C.). The cell pellet was washed with PBS, centrifuged (1900 g, 10 min, 4° C.), then the cells resuspended in lysis buffer (25 mM HEPES, pH 7.4, 5 mM EDTA, 5 mM EGTA, 3 mM MgCl$_2$, 10% (w/v) sucrose, Complete Protease Inhibitor tablets (EDTA-free)) to a density of 14% w/v for passage through a microfluidizer (Microfluidics 110S, 3 passes, 6,000 psi). The resulting cell lysate was centrifuged (1900 g, 10 min, 4° C.), and the crude particulate fraction isolated by centrifugation (142,000 g, 1 h, 4° C.) of the low-speed supernatant. The resulting pellet was resuspended in ⅓ the original lysis buffer volume, homogenized, and recentrifuged as above. The membrane pellet was resuspended by homogenization in storage buffer (25 mM HEPES, pH 7.4, 3 mM MgCl$_2$, 10% (w/v) sucrose and Complete Protease Inhibitor tablets (EDTA-free)). Single-use aliquots were made and flash-frozen in liquid N$_2$ prior to storage at −80° C.

Membranes containing human bradykinin B2R were purchased from Receptor Biology (now Perkin Elmer Life Sciences). They were derived from a CHO-K1 line stably expressing the human B2 receptor developed by Receptor Biology and subsequently purchased by Amgen. For some studies, membranes were prepared in-house from this same cell line using the method described for human B1 receptor membranes, except cells were grown in roller bottles and harvested using Cellmate.

Radioligand Binding Assay for human B1 and human B2 bradykinin receptor. Human B1 receptor binding assay was performed in 96-well polypropylene plates (Costar 3365) by adding 50 μL [$^3$H]des-arg$^{10}$ kallidin (NET1064; Perkin Elmer Life Sciences) to 10 μL test compound diluted in 90 μl assay buffer (24 mM TES, pH 6.8, 1 mM 1,10 o-phenanthroline, 0.3% BSA, 0.5 mM Pefabloc SC, 2 μg/ml aprotinin, 5 μg/mL leupeptin, and 0.7 μg/mL pepstatin A). Membranes (50 μL) were added last. [$^3$H] des-arg$^{10}$ kallidin was diluted from stock into assay buffer to yield a final concentration of ~0.3 nM in the assay but was adjusted as needed to ensure a concentration at or below the K$_d$ determined for each batch of receptor membranes. Nonspecific binding was defined with 2 μM des-Arg$^{10}$Leu$^9$ kallidin. Membranes were diluted in assay buffer to yield a final concentration of 0.068 nM hB1 receptor in the assay. Compounds were solubilized in either DMSO or ddH$_2$O, plated into polypropylene plates (Costar 3365), then serially diluted in either DMSO or dilution buffer (20 mM Hepes, pH 7.6, 0.1% BSA) to yield a final concentration of either 5% DMSO or no DMSO in the assay. The assay mixture was incubated with shaking for 1 hr at RT and then filtered through GF/C plates presoaked in 0.5% polyethyleneimine (Unifilter; Perkin Elmer Life Sciences) using a Filtermate 96-well harvester (Perkin Elmer Life Sciences). Filter plates were rapidly washed 6 times with 200 μl ice-cold buffer (50 mM Tris, pH 7.4), dried in a vacuum oven at 55C for 15-20 min, backed, and 40 μL per well of Microscint 20 was added. The plates were sealed and activity read on Topcount (Perkin Elmer Life Sciences) using a count time of 3 min per channel.

For human B2 bradykinin receptor, the same procedure was followed with the following exceptions: [$^3$H] bradykinin (NET706; Perkin Elmer Life Sciences) was used at a final concentration of ~0.2 nM and non specific binding was defined with 2 μM bradykinin. Human B2 receptor concentration was 0.068 nM final in the assay.

Data analysis. Data was analyzed in XLFit with the four-parameter logistic y=A+((B-A)/(1+((C/x)^D))) and fit with the Levenburg-Marquardt algorithm. Raw cpm were converted to percent of control values prior to analysis (POC= ((compound cpm−nonspecfic cpm)/(no-compound cpm−nonspecific cpm)*100)). K$_i$ values were determined from the IC$_{50}$ using the Cheng-Prusoff equation and K$_d$ values determined by direct saturation binding of the radioligands.

The compounds of examples 1, 1a, 1d-1f, 1 h, 3, 3b-3f, 3h-3j, 3l, 4a, 5a, 8, 13, and 15, have binding Ki's to the hB1 receptor at a level below 100 nm. The compounds of examples 1-15, have binding Ki's to the hB2 receptor at a level above 1 μM.

In vitro B1-Inhibition Activity

A. In vitro Assay of human B1 Receptor Function using Calcium Flux:

Activation of the G$_q$ linked B1 receptor results in an increase in intracellular calcium. The calcium sensitive photoprotein aequorin can, therefore, be used as an indicator of B1 receptor activation. Aequorin is a 21-kDa photoprotein that forms a bioluminescent complex when linked to the chromophore cofactor coelenterazine. Following the binding of calcium to this complex, an oxidation reaction of coelenterazine results in the production of apoaequorin, coelenteramide, CO$_2$, and light that can be detected by conventional luminometry.

A stable CHO D-/hB1/Aequorin cell line was established and the cells were maintained in suspension in spinner bottles containing a 1:1 ratio of DMEM and HAM F12 (Gibco 11765-047), high glucose (Gibco 11965-084), 10% Heat Inactivated Dialyzed serum (Gibco 26300-061), 1X Non-Essential Amino acids (Gibco 11140-050), 1X Glutamine-Pen-Strep (Gibco 10378-016), and Hygromycin, 300 μg/mL (Roche 843555). 15-24 h prior to the luminometer assay, 25,000 cells/well (2.5E6 cells/10 mL/plate) were plated in 96-well black-sided clear bottom assay plates (Costar #3904).

Media was removed from the wells and replaced with 60 μl of serum free HAM's F12 with 30 mM HEPES (pH 7.5) and 15μM coelenterazine (Coelenterazine h Luciferin #90608 from Assay Designs). The plates were incubated for 1.5-2 h. Ten point IC$_{50}$ compound plates containing 1:3 or 1:5 dilutions of antagonist compounds and an agonist activator plate (20 nM des-Arg10-Kallidin final concentration, EC$_{80}$) were prepared using Ham's F12 with 30 mM HEPES, pH 7.5. Following coelenterazine incubation, an automated flash-luminometer platform was used to dispense the B1 antagonist compounds (dissolved in DMSO and diluted with buffer to the desired concentration (final DMSO concentration <1% DMSO)) to the cell plate, a CCD camera situated underneath the cell plate took 12 images of the cell plate at 5 second intervals to determine if there was any agonist activity with the compounds. The hB1 agonist, des-$Arg_{10}$-Kallidin, was added to the cell plate and another 12 images were recorded to determine the $IC_{50}$ of the antagonist(s). The compounds of Examples 1, 1e-1f, 1h, 3, 3b, 3d, 3e, 3f, 3h, 3i, 3j, 3l, 5a, 8, 13, 15, a-i, k-p, t, x-y, aa-ae, ah-an, au-ba, bd-bg, bl-bm, bo, bq-br, bt, by-bz, cb-cv, cv-cz, db, de-dh, dj, dl-dr, dt, dw-dz, eb-em, er-ex, ez-fd, ff-fh, fn-fr, fu, fw, fz-ga, 166-176, 180, 182, 184, 185, 191, 193-196, 198-199, 206-207, 209c, 209f-209h, 215, 218a-218b, 218d-218f, 218h, 218j-218k, 218m, 218o, 218q-218r, 220a-c, 220e, 220f-220k, and 220m-220n have binding $IC_{50}$'s to hB1 receptor function at a level below 100 nm.

The compounds of Examples 1, 1f, 5a, 8, a, g-h, 1, n-o, t, aa, ad-ae, am, aw, ay, ba, be-bg, bm, by-bz, cb, ce-cj, cl, co-ct, cx-cy, de, dh, dj, do, dq, dx-dy, eb, ed-ej, em, ex, fb, fg-fh, 166, 168-170, 173, 175, 176, 185, 198, 218d, 218j, 218q-218r, 220a and 220g have binding $IC_{50}$'s to hB1 receptor function at a level below 10 nm.

B. In Vitro Assay of hB2 Receptor Function using Calcium Flux:

The intracellular calcium flux induced by hB2 receptor activation was analyzed using a hB2 recombinant cell line (CHO-K1) purchased from PerkinElmer (Catalog Number: RBHB2C000EA) on a fluorometric imaging plate reader (FLIPR). The cells were cultured in T225 flask containing Ham's F12 Nutrient Mixture (Invitrogen Corp., Cat # 11765-047), 10% Fetal Clone II Bovine Serum (HyClone, Cat # SH3006603), 1 mM Sodium pyruvate (100 mM stock, Invitrogen Corp., Cat# 12454-013), and 0.4 mg/mL Geneticin (G418; 50 mg/mL active geneticin, Invitrogen, Cat# 10131-207). Culture medium was changed every other day. 24 h prior to the FLIPR assay, the hB2/CHO cells were washed once with PBS (Invitrogen, Cat. #) and 10 mL of Versene (1:5000, Invitrogen, Cat# 15040-066) was added to each flask. After 5 min incubation at 37° C., Versene was removed and cells were detached from the flask and resuspended in culture medium. Cells were counted and 25,000 cells/well were plated in 96-well black-sided clear bottom assay plates (Costar #3904). Cells were incubated in a 37° C. $CO_2$ incubator overnight.

The media was aspirated from the cells and replaced with 65 µL of dye-loading buffer. The loading buffer was prepared by diluting a stock solution of 0.5 mM Fluo-4 AM (Molecular Probes, dissolved in DMSO containing 10% [w/v] pluronic acid) to a concentration of 1 µM in Clear Dulbecco's Modified Eagle Medium (DMEM) containing 0.1% BSA, 20 mM HEPES, and 2.5 mM probenecid. The cells were dye-loaded for 1 h at RT. The excess dye was removed by washing the cells 2× with assay buffer. The assay buffer consists of Hank's Balanced Salt Solution (HBSS) containing 20 mM HEPES, 0.1% BSA, and 2.5 mM probenecid. After the wash cycles, a volume of 100 µL was left in each well, and the plate was ready to be assayed in the FLIPR System. Single point (10 µM final concentration) POC antagonist compound plates or ten point $IC_{50}$ compound plates containing 1:3 or 1:5 dilutions of antagonist compounds (dissolved in DMSO and diluted with buffer to the desired concentration (final DMSO concentration <1% DMSO)) and an agonist activator plate (0.3 nM bradykinin final concentration, $EC_{80}$) were prepared using assay buffer. The cell plate and the compound plates were loaded onto the FLIPR and during the assay, fluorescence readings are taken simultaneously from all 96 wells of the cell plate. Ten 1-second readings were taken to establish a stable baseline for each well, then 25 µL from the B1 antagonist plate was rapidly (50 µL/sec.) added. The fluorescence signal was measured in 1-second (1 min) followed by 6-second (2 min) intervals for a total of 3 min to determine if there is any agonist activity with the compounds. The B2 agonist, bradykinin, was added to the cell plate and another 3 min were recorded to determine the percent inhibition at 10 µM (POC plates) or the $IC_{50}$ of the antagonist.

C. Cell and Tissue based In Vitro Assays of hB1 Receptor Binding:

These studies established the antagonist activity of several compounds at the bradykinin B1 receptors in in vitro cell-based and isolated organ assays.

1. Rabbit endothelial cell B1-specific $PGI_2$ secretion Assay
2. B1 and B2 umblical vein Assay D. In vitro B1-Inhibition Activity The effectiveness of the compounds as inhibitors of B1 activity (i.e., B1 "neutralization") can be evaluated by measuring the ability of each compound to block B1 stimulated CGRP and substance P release and calcium signaling in Dorsal Root Ganglion (DRG) neuronal cultures.

Dorsal Root Ganglion Neuronal Cultures. Dorsal root ganglia are dissected one by one under aseptic conditions from all spinal segments of embryonic 19-day old (E19) rats that are surgically removed from the uterus of timed-pregnant, terminally anesthetized Sprague-Dawley rats (Charles River, Wilmington, Mass.). DRG are collected in ice-cold L-15 media (GibcoBRL, Grand Island, N.Y.) containing 5% heat inactivated horse serum (GibcoBRL), and any loose connective tissue and blood vessels are removed. The DRG are rinsed twice in $Ca^{2+}$- and $Mg^{2+}$-free Dulbecco's phosphate buffered saline (DPBS), pH 7.4 (GibcoBRL). The DRG are dissociated into single cell suspension using a papain dissociation system (Worthington Biochemical Corp., Freehold, N.J.). Briefly, DRG are incubated in a digestion solution containing 20 U/mL of papain in Earle's Balanced Salt Solution (EBSS) at 37° C. for fifty minutes. Cells are dissociated by trituration through fire-polished Pasteur pipettes in a dissociation medium consisting of MEM/Ham's F12, 1:1, 1 mg/mL ovomucoid inhibitor and 1 mg/mL ovalbumin, and 0.005% deoxyribonuclease I (DNase). The dissociated cells are pelleted at 200×g for five min and re-suspended in EBSS containing 1 mg/mL ovomucoid inhibitor, 1 mg/mL ovalbumin and 0.005% DNase. Cell suspension is centrifuged through a gradient solution containing 10 mg/mL ovomucoid inhibitor, 10 mg/ml ovalbumin at 200×g for six min to remove cell debris, then filtered through a 88 µM nylon mesh (Fisher Scientific, Pittsburgh, Pa.) to remove any clumps. Cell number is determined with a hemocytometer, and cells are seeded into poly-ornithine 100 µg/mL (Sigma, St. Louis, Mo.) and mouse 1 aminin 1 µg/mL (GibcoBRL)-coated 96-well plates at $10\times10^3$ cells/well in complete medium. The complete medium consists of minimal essential medium (MEM) and Ham's F12, 1:1, penicillin (100 U/ml), streptomycin (100 µg/mL), and 10% heat inactivated horse serum (GibcoBRL). The cultures are kept at 37° C., 5% $CO_2$ and 100% humidity. For controlling the growth of non-neuronal cells, 5-fluoro-2'-deoxyuridine (75 µM) and uridine (180 µM) are included in the medium. 2 h after plating, cells are treated with recombinant human β-B1 or recombinant rat β-B1 at a concentration of 10 ng/mL (0.38 nM). Positive controls comprising serial-diluted anti-B1 antibody (R&D Systems, Minneapolis, Minn.) are applied to each culture plate. Compounds are added at ten concentrations using 3.16-fold serial dilutions. All samples are diluted in complete medium before being added to the cultures. Incubation time is generally around 40 h prior to measurement of VR1 expression.

Measurement of VR1 Expression in DRG Neurons. Cultures are fixed with 4% paraformaldehyde in Hanks' balanced salt solution for 15 min, blocked with Superblock (Pierce, Rockford, Ill.), and permeabilized with 0.25% Nonidet P-40 (Sigma) in Tris.HCl (Sigma)-buffered saline (TBS) for 1 h at RT. Cultures are rinsed once with TBS containing 0.1% Tween 20 (Sigma) and incubated with rabbit anti-VR1 IgG (prepared at Amgen) for 1.5 h at RT, followed by incubation of Eu-labeled anti-rabbit second antibody (Wallac Oy, Turku, Finland) for 1 h at RT. Washes with TBS (3×5 min with slow shaking) are applied after each antibody incubation. Enhance solution (150 µL/well, Wallac Oy) is added to the cultures. The fluorescence signal is measured in a time-resolved fluorometer (Wallac Oy). VR1 expression in samples treated with the compounds is determined by comparing to a standard curve of B1 titration from 0-1000 ng/mL. Percent inhibition (compared to maximum possible inhibition) of B1 effect on VR1 expression in DRG neurons is determined by comparing to controls that are not B1-treated.

In Vivo Antinociceptive Activity in Rat and Monkey Pain models

A. Rat Neuropathic Pain Model. Male Sprague-Dawley rats (200 g) are anesthetized with isoflurane inhalant anesthesia and the left lumbar spinal nerves at the level of L5 and L6 are tightly ligated (4-0 silk suture) distal to the dorsal root ganglion and prior to entrance into the sciatic nerve, as first described by Kim and Chung (Kim, S. H.; Chung, J. M. An experimental model for peripheral neuropathy produced by segmental spinal nerve ligation in the rat. Pain 50:355-363, (1992)). The incisions are closed and the rats are allowed to recover. This procedure results in mechanical (tactile) allodynia in the left hind paw as assessed by recording the pressure at which the affected paw (ipsilateral to the site of nerve injury) was withdrawn from graded stimuli (von Frey filaments ranging from 4.0 to 148.1 mN) applied perpendicularly to the plantar surface of the paw (between the footpads) through wire-mesh observation cages. A paw withdrawal threshold (PWT) was determined by sequentially increasing and decreasing the stimulus strength and analyzing withdrawal data using a Dixon non-parametric test, as described by Chaplan et al. (Chaplan, S. R.; Bach, F. W.; Pogrel, J. W.; Chung, J. M.; Yaksh, T. L. Quantitative assessment of tactile allodynia in the rat paw. J. Neurosci. Meth, 53:55-63 (1994)).

Normal rats and sham surgery rats (nerves isolated but not ligated) withstand at least 148.1 mN (equivalent to 15 g) of pressure without responding. Spinal nerve ligated rats respond to as little as 4.0 mN (equivalent to 0.41 g) of pressure on the affected paw. Rats are included in the study only if they did not exhibit motor dysfunction (e.g., paw dragging or dropping) and their PWT was below 39.2 mN (equivalent to 4.0 g). At least seven days after surgery rats are treated with compounds (usually a screening dose of 60 mg/kg) or control diluent (PBS) once by s.c. injection and PWT was determined each day thereafter for 7 days.

B. Rat CFA Inflammatory Pain Model. Male Sprague-Dawley rats (200 g) are lightly anesthetized with isoflurane inhalant anesthesia and the left hindpaw is injected with complete Freund's adjuvant (CFA), 0.15 mL. This procedure results in mechanical (tactile) allodynia in the left hind paw as assessed by recording the pressure at which the affected paw is withdrawn from graded stimuli (von Frey filaments ranging from 4.0 to 148.1 mN) applied perpendicularly to the plantar surface of the paw (between the footpads) through wire-mesh observation cages. PWT is determined by sequentially increasing and decreasing the stimulus strength and analyzing withdrawal data using a Dixon non-parametric test, as described by Chaplan et al. (1994). Rats are included in the study only if they do not exhibit motor dysfunction (e.g., paw dragging or dropping) or broken skin and their PWT is below 39.2 mN (equivalent to 4.0 g). At least seven days after CFA injection rats are treated with compounds (usually a screening dose of 60 mg/kg) or control solution (PBS) once by s.c. injection and PWT is determined each day thereafter for 7 days. Average paw withdrawal threshold (PWT) is converted to percent of maximum possible effect (% MPE) using the following formula: % MPE=100*(PWT of treated rats −PWT of control rats)/(15−PWT of control rats). Thus, the cutoff value of 15 g (148.1 mN) is equivalent to 100% of the MPE and the control response is equivalent to 0% MPE.

At the screening dose of 60 mg/kg, compounds in vehicle are expected to produce an antinociceptive effect with a PD relationship.

B. Green Monkey LPS Inflammation Model. The effectiveness of the compounds as inhibitors of B1 activity are evaluated in Male green monkeys (*Cercopithaecus aethiops* St Kitts) challenged locally with B1 agonists essentially as described by deBlois and Horlick (British Journal of Pharmacology. 132:327-335 (2002), which is hereby incorporated by reference in its entirety).

In order to determine whether compounds of the present invention inhibit B1 induced oedema the studies described below are conducted on male green monkeys (*Cercopithaecus aethiops* St Kitts) at the Caribbean Primates Ltd. experimental farm (St Kitts, West Indies). Procedures are reviewed and accepted by the Animal Care Committees of the CR-CHUM (Montreal, Canada) and of Caribbean Primates Ltd. (St Kitts, West Indies). Animals weighing 6.0±0.5 kg (n=67) were anaesthetized (50 mg ketamine $kg^{-1}$) and pretreated with a single intravenous injection of LPS (90 µg $kg^{-1}$) or saline (1 ml) via the saphenous vein.

1. Inflammation Studies

Kinin-induced oedema is evaluated by the ventral skin fold assay (Sciberras et al., 1987). Briefly, anaesthetized monkeys were injected with captopril (1 mg $kg^{-1}$ 30 min before assay). A single subcutaneous injection of dKD, BK or the vehicle (2 mM amastatin in 100 µL Ringer's lactate) is given in the ventral area and the increase in thickness of skin folds is monitored for 30-45 min using a calibrated caliper. The results are expressed as the difference between the skin fold thickness before and after the subcutaneous injection. Captopril and amastatin are used to reduce degradation of kinins at the carboxyl- and amino-terminus, respectively.

Antagonist Schild Analysis

The dose-response relationship for dKD (1-100 nmol)-induced oedema is determined at 24 h post-LPS in the absence or presence of different concentrations of antagonist. BK (30 nmol) is used as a positive control.

Antagonst Time Course

The time course of inhibition by antagonist is determined at 4, 24 and 48 h, 72 and/or 96 h after single bolus administration. BK (30 nmol) is used as a positive control.

Drugs

Ketamine hydrochloride, LPS, amastatin and captopril are from Sigma (MO, U.S.A). All peptides are from Phoenix Pharmaceuticals (CA, U.S.A.).

Statistics

Values are presented as mean±standard error of the mean (s.e. mean). In edema studies, the pre-injection thickness of the skin folds was subtracted from the values after subcutaneous challenge. Curve fitting and $EC_{50}$ calculations were obtained using the Delta Graph 4.0 software for Apple Computers. Data were compared by two-way analysis of variance followed by unpaired, one tail Student's t-test with Bonferroni correction. $P<0.05$ was considered statistically significant.

Formulations

Also embraced within this invention is a class of pharmaceutical compositions comprising the active compounds of Formula I-VI in association with one or more non-toxic, pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, preferably from about 1 to 500 mg or 5 to 1000 mg. A suitable daily dose for a human or other mammal may vary widely depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, preferably between about 0.1 and about 50 mg/kg, and more preferably about 0.1 and about 20 mg/kg body weight may be appropriate. The daily dose can be administered in one to four doses per day.

For therapeutic purposes, the active compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of psoriasis and other skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include DMSO and related analogs.

The compounds of this invention can also be administered by a transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

All mentioned references, patents, applications and publications, are hereby incorporated by reference in their entirety, as if here written.

What is claimed is:

1. A compound of formula II'

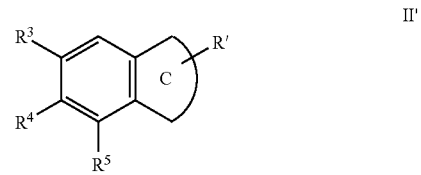

wherein the C ring is a 5 to 6-membered saturated carbocyclic moiety;

wherein R' is in the 1-position relative to the fused phenyl ring and is

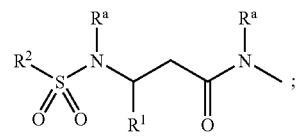

wherein R' is phenyl or pyridinyl optionally substituted with one to five groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, haloalkoxy, ($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$, and ($C_1$-$C_6$)alkyl, aryl, heteroaryl, cycloalkyl and heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

wherein $R^2$ is phenyl, benzothienyl or naphthyl optionally substituted with one to five groups independently selected from halo, —$NH_2$, —OH, —CN, —$CF_3$, ($C_1$-$C_6$)alkylamino, oxo, ($C_1$-$C_6$)alkoxy, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, —N$R^8$C(O)$R^{8'}$, and ($C_1$-$C_6$)alkyl, aryl, heteroaryl, cycloalkyl or heterocyclyl, each of which is optionally substituted with one to three groups independently selected from halo, —$NH_2$, —OH, —CN, —$CF_3$, ($C_1$-$C_6$)alkylamino, halo($C_1$-$C_6$)alkyl, oxo, ($C_1$-$C_6$)alkoxy, ($C_1$-$C_6$)alkoxy($C_1$-$C_6$)alkyl, ($C_1$-$C_6$)alkyl, ($C_2$-$C_6$)alkenyl, ($C_2$-$C_6$)alkynyl, di($C_1$-$C_6$)alkylamino, —C(O)$R^8$, —COO$R^8$, —C(O)N$R^8R^{8'}$, and —N$R^8$C(O)$R^{8'}$;

wherein $R^a$ is H;

wherein $R^4$ and $R^5$ are hydrogen;

wherein $R^3$ represents a basic moiety; and wherein $R^8$ and $R^{8'}$ independently are selected from H, and lower alkyl, aryl and heteroaryl, each of which is optionally substituted with one, two or three groups independently selected from lower alkyl, halogen, lower alkoxy, hydroxy, amino, mono- or dialkylamino, and trifluoromethyl;

provided at least one of $R^3$, $R^4$ and $R^5$ is a basic moiety; and pharmaceutically acceptable derivatives thereof.

2. The compound of claim 1 wherein $R^3$ is selected from —NH$_2$, aminomethyl, aminoethyl, aminopropyl, isopropylaminomethyl, t-butylaminomethyl, iso-butylaminomethyl, 1-methylpropylaminomethyl, 2-methylbutylaminomethyl, 2,2'-dimethylpropylamnomethyl, 2,2',3-trimethylpropylaminomethyl, allyl-aminomethyl, isopropylaminopropyl, 1-(isobutylamino)ethyl, 1-(isopropylamino)-1-methylethyl, N-isopropyl-N-ethylaminomethyl, N-isopropyl-N-methylaminomethyl, N-t-butyl-N-methylaminomethyl, N-iso-butyl-N-methylaminomethyl, N-t-butyl-N-ethylaminomethyl, N-isobutyl-N-methylaminomethyl, N-t-butyl-N-isopropylylaminomethyl, N,N-di(isopropyl)aminomethyl, N,N-dimethylaminomethyl, N,N-diethylaminomethyl, N,N-di(t-butyl)-aminomethyl, N,N-di(allyl)-aminomethyl, cyclopropylaminomethyl, 1-(cyclopropylamino)ethyl, cyclobutylaminomethyl, 2-(cyclobutylamino)ethyl, 1-(cyclobutylamino)ethyl, cyclopentylaminomethyl, 1-cyclopentylaminoethyl, cyclopropylmethylaminomethyl, hydroxyethylamino-allyl, isopropylamino-allyl, t-butylamino-allyl, cyclopropylmethylamino-allyl, piperidin-1-yl-allyl, pyrrolidin-1-yl-allyl, azetidin-1-yl-allyl, 3-hydroxypyrrolidin-1-yl-allyl, aminocarbonylethylaminomethyl, methoxyethylaminomethyl, 1-(methoxyethylamino)ethyl, 1-piperidinylmethyl, 2-(piperidin-1-yl)ethyl, 3,4-dihydropiperidin-1-ylmethyl, 4-fluoropiperidinylmethyl, 4,4'-difluoropiperidinylmethyl, 4-(piperidin-1-yl)piperidinylmethyl, 3-aminocarbonylpiperidin-1-ylmethyl, 4-(dimethylamino)piperidin-1-ylmethyl, 2,6-dimethylpiperidin-1-ylmethyl, 3,3-dimethylpiperidin-1-ylmethyl, piperidin-1-yl-2-methylethyl, 3-hydroxypiperidin-1-yl, 4-morpholinylmethyl, 4-morpholinylethyl, 1-pyrrolidinylmethyl, 2-methylpyrrolidin-1-ylmethyl, 1-(methylpyrrolidin-1-yl)ethyl, 2,5-dimethylpyrrolidin-1-ylmethyl, 1-azetidinylmethyl, 7-aza-bicyclo[2.2.1]heptyl, piperazin-1-ylmethyl, 4-methylpiperazin-1-ylmethyl, and 1-pyrrolidinylethylaminomethyl; and pharmaceutically acceptable derivatives thereof.

3. The compound of claim 1 wherein $R^2$ is 2-naphthyl.

4. The compound of claim 1 wherein $R^2$ is 3,4-dichiorophenyl.

5. The compound of claim 1 wherein $R^2$ is 3-trifluoromethyiphenyl.

6. The compound of claim 1 and/or pharmaceutically acceptable derivatives thereof selected from 3-(Naphthalen-2-yl-sulfonylamino)-3-phenyl-N-(5-piperidin-1-ylmethyl-indan-1-yl)-propionamide;

3-(Naphthalen-2-yl-sulfonylamino)-3-phenyl-N-(6-piperidin-1-ylmethyl-1,2,3,4-tetrahydro-naphthalen-1-yl)-propionamide;

(3S)-N-((1R)-6-(((1,1-dimethylethyl)amino)-methyl)-1,2,3,4-tetrahydro-1-naphthalenyl)-3-(4-fluorophenyl)-3-(((3-(trifluoromethyl)phenyl)-sulfonyl)amino)propanamide;

(3R)-3-phenyl-N-((1R)-6-(1-piperidinylmethyl)-1,2,3,4-tetrahydro-1-naphthalenyl)-3-(((3-(trifluoromethyl)phenyl)sulfonyl) amino)propanamide;

(3R)-N-((1R)-6-((4-fluoro-1-piperidinyl)methyl)-1,2,3,4-tetrahydro-1-naphthalenyl)-3-phenyl-3-(((3-(trifluoromethyl)phenyl)-sulfonyl)amino)propanamide;

(3R)-N-((1R)-5-((4,4-difluoro-1-piperidinyl)methyl)-2,3-dihydro-1H-inden-1-yl)-3-phenyl-3-(((3-(trifluoromethyl)phenyl)sulfonyl)amino)propanamide;

(3R)-N-((1R)-6-((cyclopentylamino)methyl)-1,2,3,4-tetrahydro-1-naphthalenyl)-3-(4-fluorophenyl)-3-(((3-(trifluoromethyl)phenyl)sulfonyl)-amino)propanamide;

(3R)-3-(4-fluorophenyl)-N-((1R)-6-(1-pyrrolidinylmethyl)-1,2,3,4-tetrahydro-1-naphthalenyl)-3-(((3-(trifluoromethyl)phenyl)sulfonyl)-amino)propanamide;

(3R)-N-((1R)-6-((4,4-difluoro-1-piperidinyl)methyl)-1,2,3,4-tetrahydro-1-naphthalenyl)-3-phenyl-3-(((3-(trifluoromethyl)phenyl)-sulfonyl)amino)propanamide;

(3R)-3-(methyl((3-(trifluoromethyl)phenyl)sulfonyl)amino)-3-phenyl-N-((1R)-6-(1-piperidinylmethyl)-1,2,3,4-tetrahydro-1-naphthalenyl)propanamide;

(3R)-3-(((5-chloro-3-methyl-1-benzothien-2-yl)sulfonyl)amino)-N-(6-(((1,1-dimethylethyl)amino)methyl)-1,2,3,4-tetrahydro-1-naphthalenyl)-3-phenylpropanamide;

(3R)-3-(((5-chloro-3-methyl-1-benzothien-2-yl)sulfonyl)amino)-3-phenyl-N-(6-(1-piperidinylmethyl)-1,2,3,4-tetrahydro-1-naphthalenyl)propanamide;

(3R)-N-((1R)-6-(3,6-dihydro-1(2H)-pyridinylmethyl)-1,2,3,4-tetrahydro-1-naphthalenyl)-3-phenyl-3-(((3-(trifluoromethyl)phenyl)sulfonyl) amino)propanamide;

(3R)-3-(((5-chloro-1-benzothien-2-yl)sulfonyl)amino)-3-(6-(methyloxy)-3-pyridinyl)-N-((1R)-6-(1-piperidinylmethyl)-1,2,3,4-tetrahydro-1-naphthalenyl)propanamide;

(3R)-3-(6-(methyloxy)-3-pyridinyl)-N-((1R)-6-(1-piperidinylmethyl)-1,2,3,4-tetrahydro-1-naphthalenyl)-3-(((3-(trifluoromethyl)phenyl)sulfonyl)amino)propanamide;

(3S)-3-(4-fluorophenyl)-N-((1R)-6-(1-piperidinylmethyl)-1,2,3,4-tetrahydro-1-naphthalenyl)-3-(((3-(trifluoromethyl)phenyl)sulfonyl)amino)propanamide;

(3R)-3-(((3,4-dichlorophenyl)sulfonyl)amino)-N-((1R)-6-(((1,1-dimethylethyl)amino)methyl)-1,2,3,4-tetrahydro-1-naphthalenyl)-3-phenylpropanamide;

(3R)-N-((1R)-6-((cyclopentylamino)methyl)-1,2,3,4-tetrahydro-1-naphthalenyl)-3-(((3,4-dichlorophenyl)sulfonyl)amino)-3-phenylpropanamide;

(3R)-3-(((3,4-dichlorophenyl)sulfonyl)amino)-N-((1R)-6-(((2-methylpropyl)amino)methyl)-1,2,3,4-tetrahydro-1-naphthalenyl)-3-phenylpropanamide;

3-(3,4-Dichloro-benzenesulfonylamino)-3-(4-fluoro-phenyl)-N-[6-(isobutylamino-methyl)-1,2,3,4-tetrahydro-naphthalen-1-yl]-propionamide;

3-(3,4-Dichloro-benzenesulfonylamino)-3-(4-fluoro-phenyl)-N-[6-(isopropylamino-methyl)-1,2,3,4-tetrahydro-naphthalen-1-yl]-propionamide;

3-(3,4-Dichloro-benzenesulfonylamino)-3-(4-fluoro-phenyl)-N-{6-[(2-methoxy-ethylamino)-methyl]-1,2,3,4-tetrahydro-naphthalen-1-yl}-propionamide;

N-[6-(tert-Butylamino-methyl)-1,2,3,4-tetrahydro-naphthalen-1-yl]-3-(3,4-dichloro-benzenesulfonylamino)-3-(4-fluoro-phenyl)-propionamide;

N-(6-Cyclobutylaminomethyl-1,2,3,4-tetrahydro-naphthalen-1-yl)-3-(4-fluoro-phenyl)-3-(3-trifluoromethyl-benzenesulfonylamino)-propionamide;

3-(4-Fluoro-phenyl)-N-[6-(isobutylamino-methyl)-1,2,3,4-tetrahydro-naphthalen-1-yl]-3-(3-trifluoromethyl-benzenesulfonylamino)-propionamide;

3-(4-Fluoro-phenyl)-N-[6-(isopropylamino-methyl)-1,2,3,4-tetrahydro-naphthalen-1-yl]-3-(3-trifluoromethyl-benzenesulfonylamino)-propionamide;

3-(4-Fluoro-phenyl)-N-{6-[(2-methoxy-ethylamino)-methyl]-1,2,3,4-tetrahydro-naphthalen-1-yl}-3-(3-trifluoromethyl-benzenesulfonylamino)-propionamide;

N-[6-(tert-Butylamino-methyl)-1,2,3,4-tetrahydro-naphthalen-1-yl]-3-(3-nitro-phenyl)-3-(3-trifluoromethyl-benzenesulfonylamino)-propionamide;

N-[6-(tert-Butylamino-methyl)-1,2,3,4-tetrahydro-naphthalen-1-yl]-3-(3-cyano-phenyl)-3-(3-trifluoromethyl-benzenesulfonylamino)-propionamide;

3-(4-tert-Butyl-benzenesulfonylamino)-N-(6-cyclobutylaminomethyl-1,2,3,4-tetrahydro-naphthalen-1-yl)-3-(4-fluoro-phenyl)-propionamide;

3-(4-tert-Butyl-benzenesulfonylamino)-3-(4-fluoro-phenyl)-N-(6-piperidin-1-ylmethyl-1,2,3,4-tetrahydro-naphthalen-1-yl)-propionamide;

3-(4-tert-Butyl-benzenesulfonylamino)-3-(4-fluoro-phenyl)-N-[6-(isobutylamino-methyl)-1,2,3,4-tetrahydro-naphthalen-1-yl]-propionamide;

N-[6-(tert-Butylamino-methyl)-1,2,3,4-tetrahydro-naphthalen-1-yl]-3-(4-tert-butyl-benzenesulfonylamino)-3-(4-fluoro-phenyl)-propionamide;

3-(3-Fluoro-phenyl)-N-(6-piperidin-1-ylmethyl-1,2,3,4-tetrahydro-naphthalen-1-yl)-3-(3-trifluoromethyl-benzenesulfonylamino)-propionamide;

N-(6-Cyclopentylaminomethyl-1,2,3,4-tetrahydro-naphthalen-1-yl)-3-(3,4-dichloro-benzenesulfonylamino)-3-(3-fluoro-phenyl)-propionamide;

3-(4-Fluoro-phenyl)-N-[6-(4-fluoro-piperidin-1-ylmethyl)-1,2,3,4-tetrahydro-naphthalen-1-yl]-3-(3-trifluoromethyl-benzenesulfonylamino)-propionamide;

3-(3-Chloro-phenyl)-3-(3,4-dichloro-benzenesulfonylamino)-N-(6-piperidin-1-ylmethyl-1,2,3,4-tetrahydro-naphthalen-1-yl)-propionamide;

3-(3,4-Dichloro-benzenesulfonylamino)-3-(3-fluoro-phenyl)-N-(6-piperidin-1-ylmethyl-1,2,3,4-tetrahydro-naphthalen-1-yl)-propionamide;

N-[6-(tert-Butylamino-methyl)-1,2,3,4-tetrahydro-naphthalen-1-yl]-3-(3,4-dichloro-benzenesulfonylamino)-3-(3-fluoro-phenyl)-propionamide;

N-[6-(tert-Butylamino-methyl)-1,2,3,4-tetrahydro-naphthalen-1-yl]-3-(3,4-dichloro-benzenesulfonylamino)-3-(3-fluoro-phenyl)-propionamide;

N-{6-[(Cyclopropylmethyl-amino)-methyl]-1,2,3,4-tetrahydro-naphthalen-1-yl}-3-(4-fluoro-phenyl)-3-(3-trifluoromethyl-benzenesulfonylamino)-propionamide;

N-[6-(tert-Butylamino-methyl)-1,2,3,4-tetrahydro-naphthalen-1-yl]-3-(4-nitro-phenyl)-3-(3-trifluoromethyl-benzenesulfonylamino)-propionamide;

3-(4-Chloro-phenyl)-N-(6-piperidin-1-ylmethyl-1,2,3,4-tetrahydro-naphthalen-1-yl)-3-(3-trifluoromethyl-benzenesulfonylarnino)-propionamide;

3-(3,5-Dichloro-phenyl)-N-(6-piperidin-1-ylmethyl-1,2,3,4-tetrahydro-naphthalen-1-yl)-3-(3-trifluoromethyl-benzenesulfonylarnino)-propionamide;

3-(2-Fluoro-phenyl)-N-(6-piperidin-1-ylmethyl-1,2,3,4-tetrahydro-naphthalen-1-yl)-3-(3-trifluoromethyl-benzenesulfonylamino)-propionamide;

3-(4-Fluoro-phenyl)-N-(6-piperidin-1-ylmethyl-1,2,3,4-tetrahydro-naphthalen-1-yl)-3-(3-trifluoromethyl-benzenesulfonylamino)-propionamide;

(3R)-3-((2-Naphthalenylsulfonyl)amino)-3-phenyl-N-((1S)-6-(1-piperidinylmethyl)-1,2,3,4-tetrahydro-1-naphthalenyl)propanamide;

(3R)-3-((2-Naphthalenylsulfonyl)amino)-3-phenyl-N-((1S)-5-(1-piperidinylmethyl)-2,3-dihydro-1H-inden-1-yl)propanamide;

(3R)-3-(((3,4-dichlorophenyl)sulfonyl)amino)-3-phenyl-N-((1R)-6-(1-(1-piperidinylmethyl)ethenyl)-1,2,3,4-tetrahydro-1-naphthalenyl)propanamide;

(3R)-N-((1R)-6-( 1-(((3S)-3-hydroxy-1-pyrrolidinyl)methyl)ethenyl)-1,2,3,4-tetrahydro-1-naphthalenyl)-3-phenyl-3-(((3-(trifluoromethyl)phenyl)sulfonyl)amino)propanamide;

(3R)-3-phenyl-N-((1R)-6-(1-(1-pyrrolidinylmethyl)ethenyl)-1,2,3,4-tetrahydro-1-naphthalenyl)-3-(((3-(trifluoromethyl)phenyl)sulfonyl)amino)propanamide;

(3R)-3-phenyl-N-((1R)-6-(1-(1-piperidinylmethyl)ethenyl)-1,2,3,4-tetrahydro-1-naphthalenyl)-3-(((3-(trifluoromethyl)phenyl)sulfonyl)amino)propanamide;

(3R)-3-((hydroxy(oxido(3-(trifluoromethyl)phenyl)-lambda~-4~-sulfanyl)amino)-N-((1R)-6-((1R)-1-((2-methylpropyl)amino)ethyl)-1,2,3,4-tetrahydro-1-naphthalenyl)-3-phenylpropanamide; and (3R)-N-((1R)-6-((1R)-1-((2-methylpropyl)amino)ethyl)-1,2,3,4-tetrahydro-1-naphthalenyl)-3-((2-naphthalenylsulfonyl)amino)-3-phenylpropanamide.

* * * * *

UNITED STATES PATENT AND TRADEMARK OFFICE
CERTIFICATE OF CORRECTION

PATENT NO.        : 7,425,631 B2
APPLICATION NO.   : 10/823377
DATED             : September 16, 2008
INVENTOR(S)       : Robert D. Groneberg et al.

It is certified that error appears in the above-identified patent and that said Letters Patent is hereby corrected as shown below:

Claim 1 Line 34 the term "R'" should read --R1--; lines 37-38 the term "(C1-C6)alkyl" should read --(C1-C6)alkoxy(C1-C6)alkyl--

Claim 4 lines 45-46 the term "3,4-di-chiorophenyl" should read --3,4-di-chlorophenyl--

Claim 5 lines 47-48 the term "3-trifluorom-ethyiphenyl" should read --trifluorom-ethylphenyl--

Claim 6 Column 336 line 46 please insert --(3R)-3-(((3,4-dichlorophenyl)sulfonyl) amino)-N-((1R)-6-(((1,1-dimethylethyl)amino)methyl-1,2,3,4-tetrahydro-1-naphthalenyl)-3-phenylpropanamide--

Signed and Sealed this

Sixteenth Day of December, 2008

JON W. DUDAS
*Director of the United States Patent and Trademark Office*

UNITED STATES PATENT AND TRADEMARK OFFICE
CERTIFICATE OF CORRECTION

PATENT NO. : 7,425,631 B2  
APPLICATION NO. : 10/823377  
DATED : September 16, 2008  
INVENTOR(S) : Robert D. Groneberg et al.

Page 1 of 1

It is certified that error appears in the above-identified patent and that said Letters Patent is hereby corrected as shown below:

Column 334, Claim 1 Line 34 the term "R'" should read --R1--; lines 37-38 the term "(C1-C6)alkyl" should read --(C1-C6)alkoxy(C1-C6)alkyl--

Column 335, Claim 4 lines 45-46 the term "3,4-di-chiorophenyl" should read --3,4-di-chlorophenyl--

Column 335, Claim 5 lines 47-48 the term "3-trifluorom-ethyiphenyl" should read --trifluorom-ethylphenyl--

Claim 6 Column 336 line 46 please insert --(3R)-3-(((3,4-dichlorophenyl)sulfonyl)amino)-N-((1R)-6-(((1,1-dimethylethyl)amino)methyl-1,2,3,4-tetrahydro-1-naphthalenyl)-3-phenylpropanamide--

This certificate supersedes the Certificate of Correction issued December 16, 2008.

Signed and Sealed this

Sixth Day of January, 2009

JON W. DUDAS  
*Director of the United States Patent and Trademark Office*

UNITED STATES PATENT AND TRADEMARK OFFICE
CERTIFICATE OF CORRECTION

PATENT NO. : 7,425,631 B2
APPLICATION NO. : 10/823377
DATED : September 16, 2008
INVENTOR(S) : Groneberg et al.

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 442 days.

Delete the phrase "by 442 days" and insert -- by 965 days --

Signed and Sealed this

First Day of June, 2010

David J. Kappos
*Director of the United States Patent and Trademark Office*